United States Patent
Hepperle et al.

(10) Patent No.: US 7,951,801 B2
(45) Date of Patent: *May 31, 2011

(54) BETA-CARBOLINES USEFUL FOR TREATING INFLAMMATORY DISEASE

(75) Inventors: Michael E. Hepperle, Boston, MA (US); Julie Fields Liu, Lexington, MA (US); Francois Soucy, Stoneham, MA (US); Prakash Raman, Acton, MA (US); Jeremy D. Little, Wakefield, MA (US); Paul E. Fleming, Wellesley, MA (US); Dominic Reynolds, Cambridge, MA (US); Geraldine C. B. Harriman, Charlestown, RI (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 35 days.

This patent is subject to a terminal disclaimer.

(21) Appl. No.: 11/101,998

(22) Filed: Apr. 8, 2005

(65) Prior Publication Data

US 2005/0239781 A1  Oct. 27, 2005

Related U.S. Application Data

(60) Provisional application No. 60/560,892, filed on Apr. 9, 2004.

(51) Int. Cl.
*A61K 31/535* (2006.01)
*C07D 413/14* (2006.01)

(52) U.S. Cl. ............. 514/232.5; 514/232.8; 514/235.2; 544/121; 544/127; 544/130; 544/131; 544/132; 544/140; 544/142

(58) Field of Classification Search .......... 544/142, 544/130, 131, 121, 140, 132, 127; 514/232.5, 514/235.2, 232.8

See application file for complete search history.

(56) References Cited

U.S. PATENT DOCUMENTS

| 6,627,637 B2 | 9/2003 | Ritzeler et al. |
| 2004/0110759 A1 | 6/2004 | Ritzeler et al. |
| 2004/0235839 A1* | 11/2004 | Hepperle et al. ........... 514/227.8 |

FOREIGN PATENT DOCUMENTS

| DE | 19951360 A1 | 5/2001 |
| WO | WO 00/09492 A1 | 2/2000 |
| WO | WO 01/68648 A1 | 9/2001 |
| WO | WO 03/024936 A1 | 3/2003 |
| WO | WO 03/039545 A2 | 5/2003 |
| WO | WO 2004/092167 A1 | 10/2004 |

OTHER PUBLICATIONS

International Search Report issued in PCT Application No. PCT/US05/013812, which corresponds to U.S. Appl. No. 11/101,998, (2005).
Castro, Alfredo C. et al., "Novel IKK Inhibitors: β-Carbolines," *Bioorganic & Medicinal Chemistry Letters*, vol. 13, No. 14 (2003), pp. 2419-2422.
Hottelet, M. et al., "Development of IκB Kinase Inhibitors as Anti-Inflammatory Therapeutics," *Inflammation Research*, Birkhaeuser Verlag, vol. 49, No. Supplement 2 (Sep. 24, 2000), p. S91 (Abstract).
Lee, Michael et al., "Down-Regulation of Protein Kinase C in Murine Splenocytes: A Potential Mechanism for 2-Acetylaminofluorene-Mediated Immunosuppression," *Cancer Letters*, vol. 101, No. 1 (1996), pp. 53-57.
Palanki, Moorthy S.S., "Inhibitors of AP-1 and NF-κB Mediated Transcriptional Activation Therapeutic Potential in Autoimmune Diseases and Structural Diversity," *Current Medicinal Chemistry*, vol. 9, No. 2 (Jan. 2002), pp. 219-227.

* cited by examiner

*Primary Examiner* — Rebecca L Anderson

(57) ABSTRACT

This invention provides beta-carboline compounds of formula III-A-aa:

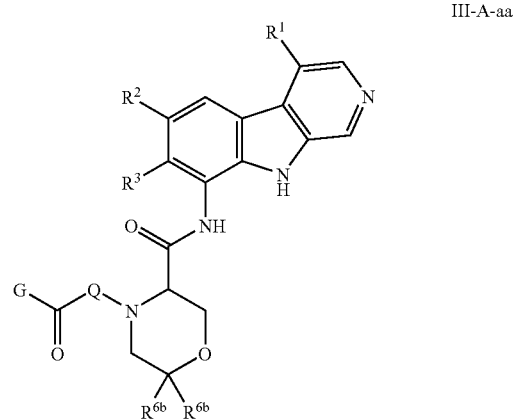

wherein Q, G, $R^1$, $R^2$, $R^3$, and $R^{6b}$ are as described in the specification. The compounds are useful for treating diseases such as inflammatory diseases and cancer.

6 Claims, No Drawings

BETA-CARBOLINES USEFUL FOR TREATING INFLAMMATORY DISEASE

PRIORITY INFORMATION

The present application claims priority under 35 U.S.C. §119(e) to U.S. Provisional Application No. 60/560,892 filed Apr. 9, 2004 entitled "Beta-Carbolines Useful for Treating Inflammatory Disease", the entire contents of which are hereby incorporated by reference.

FIELD OF THE INVENTION

This invention relates to beta-carboline compounds, pharmaceutical compositions thereof, and methods of using the compositions for treating disease. The compounds are particularly useful for treating inflammatory disease and cancer.

BACKGROUND OF THE INVENTION

The transcription (nuclear) factor NF-κB is a member of the Rel protein family, and is typically a heterodimer composed of p50 and p65 subunits. NF-κB is constitutively present in the cytosol, and is inactivated by its association with one of the IκB family of inhibitors. Palombella et al., WO 95/25533, teaches that the ubiquitin-proteasome pathway plays an essential role in the regulation of NF-κB activity, being responsible for the processing of p105 to p50 and the degradation of the inhibitor protein IκB-α. Chen et al., Cell 84:853 (1996), teaches that prior to degradation, IκB-α undergoes selective phosphorylation at serine residues 32 and 36 by the multisubunit IκB kinase complex (IKK). IκB-α is phosphorylated by IKK, which has two catalytic subunits, IKK-1 (IκB kinase α or IKK-α) and IKK-2 (IκB kinase β or IKK-β). Once phosphorylated, IκB is targeted for ubiquitination and degradation by the 26S proteasome, allowing translocation of NF-κB into the nucleus, where it binds to specific DNA sequences in the promoters of target genes and stimulates their transcription. Inhibitors of IKK can block the phosphorylation of IκB and its further downstream effects, particularly those associated with NF-κB transcription factors.

The protein products of genes under the regulatory control of NF-κB include cytokines, chemokines, cell adhesion molecules, and proteins mediating cellular growth and control. Importantly, many of these proinflammatory proteins also are able to act, either in an autocrine or paracrine fashion, to further stimulate NF-κB activation. In addition, NF-κB plays a role in the growth of normal and malignant cells. Furthermore, NF-κB is a heterodimeric transcription factor which can activate a large number of genes which code, inter alia, for proinflammatory cytokines such as IL-1, IL-2, TNFα or IL-6. NF-κB is present in the cytosol of cells, building a complex with its naturally occurring inhibitor IκB. The stimulation of cells, for example by cytokines, leads to the phosphorylation and subsequent proteolytic degradation of IκB. This proteolytic degradation leads to the activation of NF-κB, which subsequently migrates into the nucleus of the cell and activates a large number of proinflammatory genes.

Rinehart et al., U.S. Pat. No. 4,631,149 (1986), discloses beta-carboline compounds useful as antiviral, antibacterial, and antitumor agents.

Ritzeler et al., WO 01/68648, discloses beta-carboline compounds with IκB kinase inhibitory activity for use in the treatment of inflammatory disorders (e.g., rheumatoid arthritis), osteoarthritis, asthma, cardiac infarct, Alzheimer's disease, carcinomatous disorders (potentiation of cytotoxic therapies) and atherosclerosis.

It would be beneficial to provide novel IKK inhibitors that possess good therapeutic properties, especially for the treatment of inflammatory diseases and cancer.

DETAILED DESCRIPTION OF THE INVENTION

1. General Description of Compounds of the Invention:

This invention provides compounds that are inhibitors of IKK-2, and accordingly are useful for the treatment of inflammatory diseases and cancer. The compounds of this invention are represented by formula I:

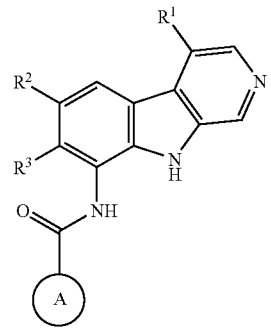

or a pharmaceutically acceptable salt thereof, wherein:

Ring A is selected from the group consisting of:
(a) a pyridinyl or pyrimidinyl ring that is substituted by (i) —CH$_2$C(O)-G and 0-1 R$^{6a}$ or (ii) 1-2 R$^{6a}$, and
(b) a morpholinyl, piperidinyl, piperazinyl, pyrrolidinyl, pyranyl, tetrahydrofuranyl, cyclohexyl, cyclopentyl or thiomorpholinyl ring that is substituted by (i) —C(R$^9$)$_3$, —W-G, or -G, (ii) 0-4 R$^{6b}$ and (iii) 0-1 oxo groups on a ring carbon or 0-2 oxo groups on a ring sulfur;

each R$^{6a}$ is independently selected from C$_{1-6}$ aliphatic, halo, C$_{1-6}$ alkoxy, or amino;

each R$^{6b}$ is independently selected from C$_{1-3}$ aliphatic or —N(R$^7$)$_2$, and two R$^{6b}$ on the same carbon or on adjacent carbons optionally are taken together with the intervening carbon(s) to form a 5-6 membered ring having 1-2 ring heteroatoms selected from N, O or S;

W is -Q-, Q-C(O)—, —C(R$^9$)$_2$—C(R$^9$)(R$^{12}$)—, or —C(R$^9$)$_2$—[C(R$^9$)(R$^{12}$)]$_2$—;

Q is —C(R$^9$)$_2$— or —C(R$^9$)$_2$C(R$^9$)$_2$—;

G is —OH, —NR$^4$R$^5$, —N(R$^9$)CONR$^4$R$^5$, —N(R$^9$)SO$_2$(C$_{1-3}$ aliphatic), —N(R$^9$)COCF$_3$, —N(R$^9$)CO(C$_{1-6}$ aliphatic), —N(R$^9$)CO(heterocyclyl), —N(R$^9$)CO(heteroaryl), —N(R$^9$)CO(aryl), 3-10 membered monocyclic or bicyclic heterocyclyl ring, or a 5-6 membered heteroaryl ring, wherein each of the heteroaryl, aryl and heterocyclyl moieties of G is optionally substituted by 1-4 R$^{10}$;

R$^1$ is hydrogen, halo, C$_{1-3}$ aliphatic, amino, cyano, (C$_{1-3}$ alkyl)$_{1-2}$ amino, C$_{1-3}$ alkoxy, —CONH$_2$, —NHCOCF$_3$, or —CH$_2$NH$_2$;

R$^2$ is hydrogen, halo, C$_{1-4}$ aliphatic, C$_{1-2}$alkoxy, or C$_{1-2}$haloalkyl;

R$^3$ is hydrogen, halo, C$_{1-6}$ haloalkyl, hydroxy, amino, cyano, or an optionally substituted group selected from C$_{1-6}$ aliphatic, C$_{1-6}$ alkoxy, (C$_{1-6}$ alkyl)$_{1-2}$ amino, C$_{1-6}$thioalkyl, morpholinyl, piperazinyl, piperidinyl, or pyrrolidinyl;

R⁴ is hydrogen, 3-7 membered heterocyclyl, or $C_{1-6}$ aliphatic;

R⁵ is: a) hydrogen;
b) an optionally substituted group selected from aryl, heteroaryl, heterocyclyl, or carbocyclyl, or
c) a $C_{1-6}$ aliphatic group that is optionally substituted by: halo, —OR⁷, —CN, —SR⁸, —S(O)₂R⁸, —C(O)R⁷, —CO₂R⁷, —N(R⁷)₂, —C(O)N(R⁷)₂, —N(R⁷)C(O)R⁷, —N(R⁷)CO₂R⁸, —SO₂N(R⁷)₂, —NR⁷SO₂R⁷, —N(R⁷)C(O)N(R⁷)₂, or an aryl, heteroaryl, heterocyclyl, or carbocyclyl group that is optionally further substituted by $C_{1-6}$aliphatic, —CF₃, halo, —OR⁷, —CN, —SR⁸, —S(O)₂R⁸, —C(O)R⁷, —CO₂R⁷, —N(R⁷)₂, —C(O)N(R⁷)₂, —N(R⁷)C(O)R⁷, —N(R⁷)CO₂R⁸, —SO₂N(R⁷)₂, —NR⁷SO₂R⁷, —N(R⁷)C(O)N(R⁷)₂;

each R⁷ is independently selected from hydrogen or an optionally substituted $C_{1-4}$ aliphatic, or two R⁷ on the same nitrogen atom are taken together with the nitrogen to form an optionally substituted 3-6 membered heteroaryl or heterocyclyl ring;

each $R^{7a}$ is independently selected from hydrogen or an optionally substituted group selected from $C_{1-4}$ aliphatic, aryl, heteroaryl, heterocyclyl, or carbocyclyl, or two $R^{7a}$ on the same nitrogen atom are taken together with the nitrogen to form an optionally substituted 3-6 membered heteroaryl or heterocyclyl ring;

each R⁸ is independently an optionally substituted $C_{1-4}$ aliphatic;

each $R^{8a}$ is independently an optionally substituted group selected from $C_{1-4}$ aliphatic, aryl, heteroaryl, heterocyclyl, or carbocyclyl;

each R⁹ is independently selected from hydrogen or $C_{1-3}$ aliphatic;

each R¹⁰ is independently selected from oxo, —R¹¹, -T-R¹¹, or —V-T-R¹¹, or two occurrences of R¹⁰, taken together with the atom(s) to which they are bound, form an optionally substituted monocyclic or bicyclic 3-8-membered aryl, heteroaryl, heterocyclyl, or carbocyclyl ring;

each R¹¹ is independently selected from —CF₃, halo, —OR⁷ᵃ, —CN, —SR⁸ᵃ, —S(O)₂R⁸ᵃ, —C(O)R⁷ᵃ, —CO₂R⁷ᵃ, —N(R⁷ᵃ)₂, —C(O)N(R⁷ᵃ)₂, —N(R⁷)C(O)R⁷ᵃ, —N(R⁷)CO₂R⁷ᵃ, —SO₂N(R⁷ᵃ)₂, —N(R⁷)SO₂R⁷ᵃ, —N(R⁷)C(O)N(R⁷ᵃ)₂ or an optionally substituted group selected from $C_{6-4}$aliphatic, aryl, heteroaryl, heterocyclyl or carbocyclyl;

T is a straight or branched $C_{1-4}$ alkylene chain;

V is —O—, —N(R⁷)—, —S—, —S(O)—, —S(O)₂—, —C(O)—, or —CO₂—; and

R¹² is hydrogen or an amino acid side chain.

In another embodiment, the compounds of this invention are represented by formula I:

I or a pharmaceutically acceptable salt thereof, wherein:

Ring A is selected from the group consisting of:
(a) a pyridinyl or pyrimidinyl ring that is substituted by (i) —CH₂C(O)-G and 0-1 R⁶ᵃ or (ii) 1-2 R⁶ᵃ, and
(b) a morpholinyl, piperidinyl, piperazinyl, pyrrolidinyl, pyranyl, tetrahydrofuranyl, cyclohexyl, cyclopentyl or thiomorpholinyl ring that is substituted by (i) —C(R⁹)₃, —W-G, or -G, (ii) 0-4 R⁶ᵇ and (iii) 0-1 oxo groups on a ring carbon or 0-2 oxo groups on a ring sulfur;

each R⁶ᵃ is independently selected from $C_{1-6}$ aliphatic, halo, $C_{1-6}$ alkoxy, or amino;

each R⁶ᵇ is independently selected from $C_{1-3}$ aliphatic or —N(R⁷)₂, and two R⁶ᵇ on the same or an adjacent carbon optionally are taken together with the intervening carbon(s) to form a 5-6 membered ring having 1-2 ring heteroatoms selected from N, O or S;

W is -Q-, -Q-C(O)—, —C(R⁹)₂—C(R⁹)(R¹²)—, or —C(R⁹)₂—[C(R⁹)(R¹²)]₂—;

Q is —C(R⁹)₂— or —C(R⁹)₂C(R⁹)₂—;

G is —OH, —NR⁴R⁵, —N(R⁹)CONR⁴R⁵, —N(R⁹)SO₂(C_{1-3} aliphatic), —N(R⁹)COCF₃, —N(R⁹)CO(C_{1-6} aliphatic), —N(R⁹)CO(heterocyclyl), —N(R⁹)CO(heteroaryl), —N(R⁹)CO(aryl), a 3-7 membered heterocyclyl ring, or a 5-6 membered heteroaryl, wherein each of the heteroaryl, aryl and heterocyclyl moieties of G is optionally substituted by 1-3 R¹⁰;

R¹ is hydrogen, halo, $C_{1-3}$ aliphatic, amino, cyano, ($C_{1-3}$ alkyl)$_{1-2}$ amino, $C_{1-3}$ alkoxy, —CONH₂, —NHCOCF₃, or —CH₂NH₂;

R² is hydrogen, halo, $C_{1-3}$ aliphatic, —CF₃;

R³ is hydrogen, halo, $C_{1-6}$ aliphatic, $C_{1-6}$ haloalkyl, $C_{1-6}$ alkoxy, hydroxy, amino, cyano, or ($C_{1-6}$ alkyl)$_{1-2}$ amino;

R⁴ is hydrogen, 3-7 membered heterocyclyl, or $C_{1-6}$ aliphatic;

R⁵ is hydrogen, $C_{1-6}$ aliphatic group or a 3-7 membered heterocyclic ring having 1-2 ring heteroatoms selected from N, O, or S, wherein R⁵ is optionally substituted by halo, —OR⁷, —CN, —SR⁸, —S(O)₂R⁸, —S(O)₂N(R⁷)₂, —C(O)R⁷, —CO₂R⁷, —N(R⁷)₂, —C(O)N(R⁷)₂, —N(R⁷)C(O)R⁷, —N(R⁷)CO₂R⁸, or —N(R⁷)C(O)N(R⁷)₂;

each R⁷ is independently selected from hydrogen or $C_{1-4}$ aliphatic, or two R⁷ on the same nitrogen atom are taken together with the nitrogen to form a 5-6 membered heteroaryl or heterocyclyl ring;

each R⁸ is independently selected from $C_{1-4}$ aliphatic;

each R⁹ is independently selected from hydrogen or $C_{1-3}$ aliphatic;

each R¹⁰ is independently selected from oxo, —R¹¹, -T-R¹¹, or —V-T-R¹¹;

each R¹¹ is independently selected from $C_{1-6}$ aliphatic, halo, —S(O)₂N(R⁷)₂, —OR⁷, —CN, —SR⁸, —S(O)₂R⁸, —C(O)R⁷, —CO₂R⁷, —N(R⁷)₂, —C(O)N(R⁷)₂, —N(R⁷)C(O)R⁷, —N(R⁷)CO₂R⁷, or —N(R⁷)C(O)N(R⁷)₂;

T is a straight or branched $C_{1-4}$ alkylene chain;

V is —O—, —N(R⁷)—, —S—, —S(O)—, —S(O)₂—, —C(O)—, or —CO₂—; and

R¹² is hydrogen or an amino acid side chain.

2. Compounds and Definitions:

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001.

The term "aliphatic" as used herein means straight-chain, branched or cyclic $C_1$-$C_{12}$ hydrocarbons which are completely saturated or which contain one or more units of unsaturation but which are not aromatic. For example, suitable aliphatic groups include substituted or unsubstituted linear, branched or cyclic alkyl, alkenyl, alkynyl groups and hybrids thereof such as (cycloalkyl)alkyl, (cycloalkenyl)alkyl or (cycloalkyl)alkenyl. The terms "alkyl", "alkoxy", "hydroxyalkyl", "alkoxyalkyl", and "alkoxycarbonyl", used alone or as part of a larger moiety, include both straight and branched chains containing one to twelve carbon atoms. The terms "alkenyl" and "alkynyl", used alone or as part of a larger moiety, include both straight and branched chains containing two to twelve carbon atoms. The term "cycloalkyl, used alone or as part of a larger moiety, includes cyclic $C_3$-$C_{12}$ hydrocarbons which are completely saturated or which contain one or more units of unsaturation, but which are not aromatic.

The terms "haloalkyl", "haloalkenyl" and "haloalkoxy", mean alkyl, alkenyl or alkoxy, as the case may be, substituted with one or more halogen atoms. The term "halogen" means F, Cl, Br, or I.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0-3 heteroatoms selected from oxygen, sulfur or nitrogen, the nitrogen may be N (as in 3,4-dihydro-2-pyrrolyl), NH (as in pyrrolidinyl) or $NR^+$ (as in N-substituted pyrrolidinyl).

The terms "carbocycle", "carbocyclyl", "carbocyclo", or "carbocyclic" as used herein means an aliphatic ring system having three to fourteen members. The terms "carbocycle", "carbocyclyl", "carbocyclo", or "carbocyclic" whether saturated or partially unsaturated, also refers to rings that are optionally substituted. The terms "carbocycle", "carbocyclyl", "carbocyclo", or "carbocyclic" also include aliphatic rings that are fused to one or more aromatic or nonaromatic rings, such as in a decahydronaphthyl or tetrahydronaphthyl, where the radical or point of attachment is on the aliphatic ring. Bridged ring systems are also included in the scope of the term "carbocycle", "carbocyclyl", "carbocyclo", or "carbocyclic".

The term "aryl" used alone or as part of a larger moiety as in "aralkyl", "aralkoxy", or "aryloxyalkyl", refers to aromatic ring groups having five to fourteen members, such as phenyl, benzyl, phenethyl, 1-naphthyl, 2-naphthyl, 1-anthracyl and 2-anthracyl. The term "aryl" also refers to rings that are optionally substituted. The term "aryl" may be used interchangeably with the term "aryl ring". "Aryl" also includes fused polycyclic aromatic ring systems in which an aromatic ring is fused to one or more rings. Examples include 1-naphthyl, 2-naphthyl, 1-anthracyl and 2-anthracyl. Also included within the scope of the term "aryl", as it is used herein, is a group in which an aromatic ring is fused to one or more non-aromatic rings, such as in an indanyl, phenanthridinyl, or tetrahydronaphthyl, where the radical or point of attachment is on the aromatic ring.

The term "heterocycle", "heterocyclyl", or "heterocyclic" as used herein includes non-aromatic ring systems having three to fourteen members, preferably five to ten, in which one or more ring carbons, preferably one to four, are each replaced by a heteroatom such as N, O, or S. Examples of heterocyclic rings include 3-1H-benzimidazol-2-one, (1-substituted)-2-oxo-benzimidazol-3-yl, 2-tetrahydrofuranyl, 3-tetrahydrofuranyl, 2-tetrahydropyranyl, 3-tetrahydropyranyl, 4-tetrahydropyranyl, [1,3]-dioxalanyl, [1,3]-dithiolanyl, [1,3]-dioxanyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-hiazolidinyl, diazolonyl, N-substituted diazolonyl, 1-phthalimidinyl, benzoxanyl, benzopyrrolidinyl, benzopiperidinyl, benzoxolanyl, benzothiolanyl, and benzothianyl. Also included within the scope of the term "heterocyclyl" or "heterocyclic", as it is used herein, is a group in which a non-aromatic heteroatom-containing ring is fused to one or more aromatic or non-aromatic rings, such as in an indolinyl, chromanyl, phenanthridinyl, or tetrahydroquinolinyl, where the radical or point of attachment is on the non-aromatic heteroatom-containing ring. Bridged ring systems are also included within the scope of the term "heterocyclyl" or "heterocyclic". The term "heterocycle", "heterocyclyl", or "heterocyclic" whether saturated or partially unsaturated, also refers to rings that are optionally substituted.

The term "heteroaryl", used alone or as part of a larger moiety as in "heteroaralkyl" or "heteroarylalkoxy", refers to heteroaromatic ring groups having five to fourteen members. Examples of heteroaryl rings include 2-furanyl, 3-furanyl, 3-furazanyl, N-imidazolyl, 2-imidazolyl, 4 -imidazolyl, 5-imidazolyl, 3-isoxazolyl, 4-isoxazolyl, 5-isoxazolyl, 2-oxadiazolyl, 5-oxadiazolyl, 2 -oxazolyl, 4-oxazolyl, 5-oxazolyl, 1-pyrrolyl, 2-pyrrolyl, 3-pyrrolyl, 1 -pyrazolyl,2-pyrazolyl, 3 -pyrazolyl, 2-pyridyl, 3-pyridyl, 4-pyridyl, 2-pyrimidyl, 4-pyrimidyl, 5-pyrimidyl, 3-pyridazinyl, 2 -thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, or benzoisoxazolyl. Also included within the scope of the term "heteroaryl", as it is used herein, is a group in which a heteroatomic ring is fused to one or more aromatic or nonaromatic rings where the radical or point of attachment is on the heteroaromatic ring. Examples include tetrahydroquinolinyl, tetrahydroisoquinolinyl, and pyrido[3,4-d]pyrimidinyl. The term "heteroaryl" also refers to rings that are optionally substituted. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Unless otherwise stated, examples of suitable substituents on the unsaturated carbon atom of an aryl, heteroaryl, aralkyl, or heteroaralkyl group generally include a halogen, —$R^°$, —$OR^°$, —$SR^°$, 1,2-methylene-dioxy, 1,2-ethylene-dioxy, protected OH (such as acyloxy), phenyl (Ph), substituted Ph, —O(Ph), substituted —O(Ph), —$CH_2$(Ph), substituted —$CH_2$(Ph), —$CH_2CH_2$(Ph), substituted —$CH_2CH_2$(Ph), —$NO_2$, —CN, —N($R^°$)$_2$, —$NR^°$C(O)$R^°$, —$NR^°$C(O)N($R^°$)$_2$, —$NR^°CO_2R^°$, —$NR^°NR^°$C(O)$R^°$, —$NR^°NR^°$C(O)N($R^°$)$_2$, —$NR^°NR^°CO_2R^°$, —C(O)C(O)$R^°$, —C(O)$CH_2$C(O)$R^°$, —$CO_2R^°$, —C(O)$R^°$, —C(O)N($R^°$)$_2$, —OC(O)N($R^°$)$_2$, —S(O)$_2R^°$, —$SO_2$N($R^°$)$_2$, —S(O)$R^°$, —$NR^°SO_2$N($R^°$)$_2$, —$NR^°SO_2R^°$, —C(=S)N($R^°$)$_2$, —C(=NH)—N($R^°$)$_2$, —($CH_2$)$_y$NHC(O)$R^°$, —($CH_2$)$_y$NHC(O)CH(V—$R^°$)($R^°$); wherein each $R^°$ is independently selected from hydrogen, a substituted or unsubstituted aliphatic group, an unsubstituted heteroaryl or heterocyclic ring, phenyl (Ph), substituted Ph, —O(Ph), substituted —O(Ph), —$CH_2$(Ph), or substituted —$CH_2$(Ph), or two independent occurrences of $R^°$, taken together with their intervening atom(s), form an optionally substituted 3-12-membered saturated, partially unsaturated, or fully unsaturated monocyclic or bicyclic ring having 0-4 heteroatoms independently selected from nitrogen, oxygen, or sulfur; y is 0-6; and V is a linker group. Unless otherwise stated, examples of substituents on the aliphatic group or the phenyl ring of R° generally include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

An aliphatic group or a non-aromatic heterocyclic ring may contain one or more substituents. Unless otherwise stated, examples of suitable substituents on the saturated carbon of an aliphatic group or of a non-aromatic heterocyclic ring generally include those listed above for the unsaturated carbon of an aryl or heteroaryl group and the following: =O, =S, =NNHR*, =NN(R*)$_2$, =N—, =NNHC(O)R*, =NNHCO$_2$(alkyl), =NNHSO$_2$(alkyl), or =NR*, where each R* is independently selected from hydrogen, an unsubstituted aliphatic group or a substituted aliphatic group. Examples of substituents on the aliphatic group include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

Unless otherwise stated, suitable substituents on the nitrogen of a non-aromatic heterocyclic ring generally include —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, and —NR$^+$SO$_2$R$^+$; wherein each R$^+$ is independently selected from hydrogen, an aliphatic group, a substituted aliphatic group, phenyl (Ph), substituted Ph, —O(Ph), substituted —O(Ph), CH$_2$(Ph), substituted CH$_2$(Ph), or an unsubstituted heteroaryl or heterocyclic ring, or two independent occurrences of R+, taken together with their intervening atom(s), form an optionally substituted 3-12-membered saturated, partially unsaturated, or fully unsaturated monocyclic or bicyclic ring having 0-4 heteroatoms independently selected from nitrogen, oxygen, or sulfur. Unless otherwise stated, examples of substituents on the aliphatic group or the phenyl ring generally include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

As detailed above, in some embodiments, two independent occurrences of R° (or R$^+$ or any other variable similarly defined in the specification and claims herein), are taken together with their intervening atom(s) to form an optionally substituted 3-12 membered saturated, partially unsaturated, or fully unsaturated monocyclic or bicyclic ring having 0-4 heteroatoms independently selected from nitrogen, oxygen, or sulfur.

Exemplary rings that are formed when two independent occurrences of R° (or R$^+$, or any other variable similarly defined in the specification and claims herein), are taken together with their intervening atom(s) include, but are not limited to the following: a) two independent occurrences of R° (or R$^+$, or any other variable similarly defined in the specification or claims herein) that are bound to the same atom and are taken together with that atom to form a ring, for example, N(R°)$_2$, where both occurrences of R° are taken together with the nitrogen atom to form a piperidin-1-yl, piperazin-1-yl, or morpholin-4-yl group; and b) two independent occurrences of R° (or R$^+$, or any other variable similarly defined in the specification or claims herein) that are bound to different atoms and are taken together with both of those atoms to form a ring, for example where a phenyl group is substituted with two occurrences of OR°

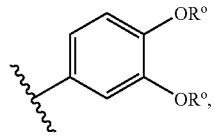

these two occurrences of R° are taken together with the oxygen atoms to which they are bound to form a fused 6-membered oxygen containing ring:

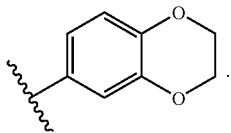

It will be appreciated that a variety of other rings (e.g., also spiro, and bridged rings) can be formed when two independent occurrences of R° (or R$^+$, or any other variable similarly defined in the specification and claims herein) are taken together with their intervening atom(s) and that the examples detailed above are not intended to be limiting.

Unless otherwise stated the term "linker group" or "linker" means an organic moiety that connects two parts of a compound. Linkers are typically comprised of an atom such as oxygen or sulfur, a unit such as —NH—, —CH$_2$—, —C(O)—, —C(O)NH—, or a chain of atoms, such as an alkylidene chain. The molecular mass of a linker is typically in the range of about 14 to 200, preferably in the range of 14 to 96 with a length of up to about six atoms. Examples of linkers include a saturated or unsaturated C$_{1-6}$ alkylidene chain which is optionally substituted, and wherein one or two saturated carbons of the chain are optionally replaced by —C(O)—, —C(O)C(O)—, —CONH—, —CONHNH—, —CO$_2$—, —OC(O)—, —NHCO$_2$—, —O—, —NHCONH—, —OC(O)NH—, —NHNH—, —NHCO—, —S—, —SO—, —SO$_2$—, —NH—, —SO$_2$NH—, or —NHSO$_2$—.

The term "alkylidene chain" or "alkylene chain" refers to an optionally substituted, straight or branched carbon chain that may be fully saturated or have one or more units of unsaturation. The optional substituents are as described above for an aliphatic group.

A combination of substituents or variables is permissible only if such a combination results in a stable or chemically feasible compound. A stable compound or chemically feasible compound is one in which the chemical structure is not substantially altered when kept at a temperature of 40° C. or less, preferably 25° C. or less, in the absence of moisture or other chemically reactive conditions, for at least a week.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen atom by a deuterium or tritium, or the replacement of a carbon by a $^{13}$C- or $^{14}$C-enriched carbon are within the scope of this invention.

3. Description of Exemplary Compounds:

In one embodiment of the formula I compounds, Ring A is selected from a pyridinyl or a pyrimidinyl ring that is substituted by 1-2 $R^{6a}$ groups. In this embodiment, preferred Ring A include a 3-pyridinyl or a 5-pyrimidinyl ring, shown below by the compounds of formula II-A and II-B, respectively.

TABLE 1

Compounds where Ring A is Pyridyl or Pyrimidinyl

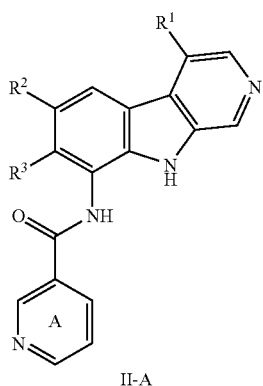

II-A

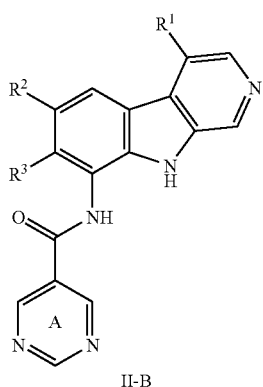

II-B

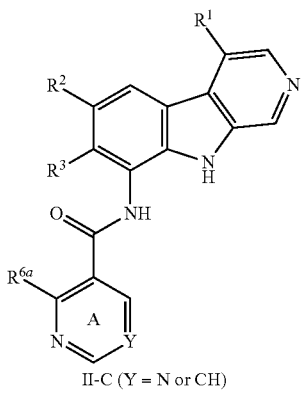

II-C (Y = N or CH)

Preferably, $R^{6a}$ is selected from halo or a $C_{1-6}$ aliphatic, such as chloro or methyl. When $R^{6a}$ is an aliphatic group such as methyl, a favorable position for the $R^{6a}$ group is at the 2-position of the pyridinyl ring or the 4-position of the pyrimidinyl ring, as shown in II-C above. Particular Ring A moieties are 2-methyl-3-pyridinyl and 4-methyl-5-pyrimidinyl. It has been found that compounds of formula II-C where $R^{6a}$ is a methyl group are surprisingly more potent in biological testing for IKK inhibition than analogous compounds that have an unsubstituted Ring A pyridine, such as those described in the aforementioned Ritzeler et al. PCT application WO 01/68648.

In some embodiments, $R^1$ is hydrogen, halo, $C_{1-2}$alkyl, amino, or $(C_{1-2}alkyl)_{1-2}$amino. Preferred $R^1$ groups are small groups such as hydrogen, methyl, amino and fluoro.

Preferred $R^2$ groups include hydrogen and halo. Chloro is a preferred $R^2$ halo group.

Preferred $R^3$ groups include hydrogen, halo (especially chloro) and alkoxy. Examples of suitable alkoxy groups include $C_{1-4}$ alkoxy groups such as methoxy, ethoxy, propoxy and cyclopropylmethoxy.

In another embodiment, Ring A is selected from a 5-6 membered non-aromatic ring having 0-2 ring heteroatoms selected from nitrogen, oxygen and sulfur. These are designated generally as compounds of formula III. Examples of non-aromatic Ring A groups include a morpholinyl, piperidinyl, piperazinyl, pyrrolidinyl, pyranyl, tetrahydrofuranyl, cyclohexyl, cyclopentyl and a thiomorpholinyl ring. Preferably, such non-aromatic rings are substituted by (i) —C(R$^9$)$_3$ or —W-G, (ii) 0-4 $R^{6b}$, and (iii) 0-1 oxo groups on a ring carbon or 0-2 oxo groups on a ring sulfur. More preferably, such non-aromatic rings are substituted by (i) —W-G, (ii) 0-2 $R^{6b}$, and (iii) 0-1 oxo groups on a ring carbon or 0-2 oxo groups on a ring sulfur.

A preferred G is —NR$^4$R$^5$ or a 3-7 membered heterocyclyl ring. Preferably G is —NR$^4$R$^5$ or a 5-6 membered heterocyclyl ring, where G is substituted by 1-4 $R^{10}$. More preferably G is —NR$^4$R$^5$ or a 5-6 membered heterocyclyl ring, where G is substituted by 1-2 $R^{10}$.

A preferred $R^4$ is a hydrogen, 5-6 membered heterocyclyl ring, or $C_{1-6}$ aliphatic, more preferably hydrogen or $C_{1-6}$ aliphatic. $R^4$ may also be a $C_{1-6}$ alkoxy.

A preferred $R^5$ is hydrogen, an optionally substituted 5-6 membered aryl, heteroaryl, carbocyclyl, or heterocyclyl ring, or optionally substituted $C_{1-6}$ aliphatic, more preferably hydrogen or optionally substituted $C_{1-6}$ aliphatic. In other preferred embodiments, $R^5$ is hydrogen, 5-6 membered heterocyclyl ring, or $C_{1-6}$ aliphatic, more preferably hydrogen or $C_{1-6}$ aliphatic.

Various formula III compounds where Ring A is a non-aromatic ring are shown in Table 2. For ease of viewing, substituents on these non-aromatic Ring A compounds, except for the oxo group in some cases, are not shown.

TABLE 2

Compounds where Ring A is Non-Aromatic

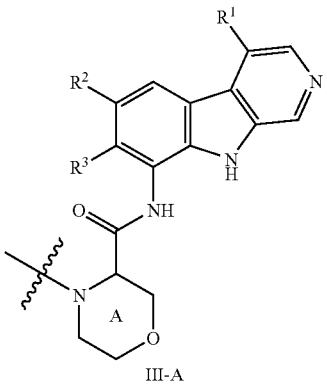

III-A

TABLE 2-continued
Compounds where Ring A is Non-Aromatic
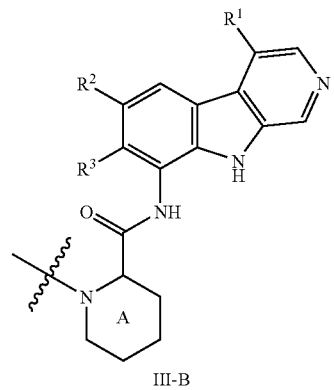
III-B
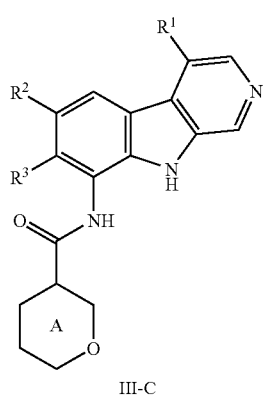
III-C
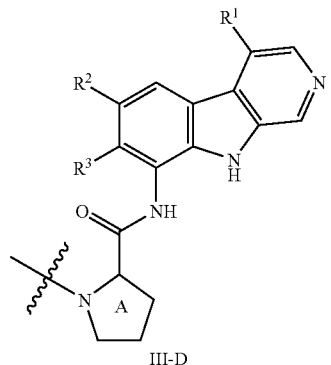
III-D
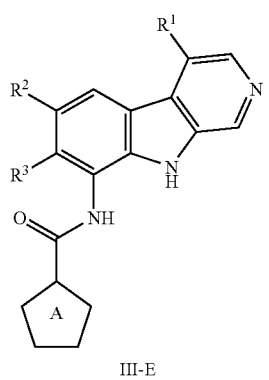
III-E
TABLE 2-continued
Compounds where Ring A is Non-Aromatic
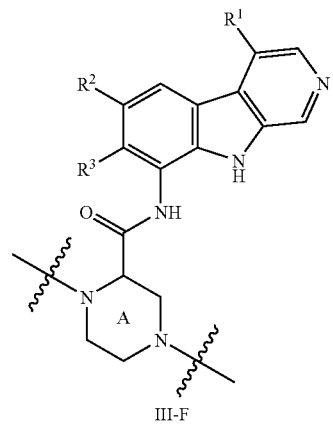
III-F
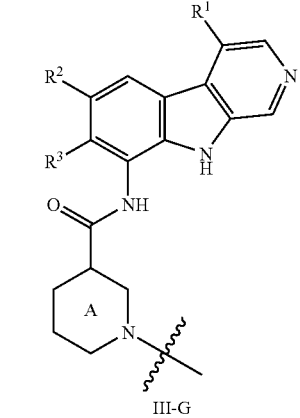
III-G
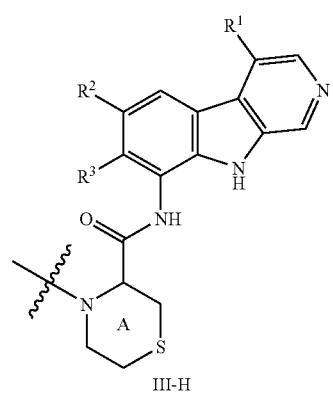
III-H
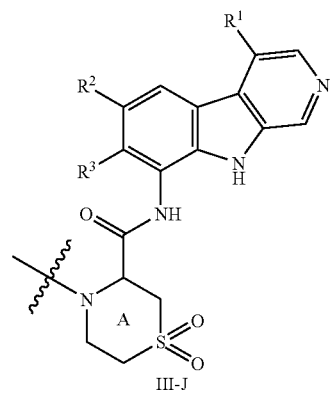
III-J TABLE 2-continued Compounds where Ring A is Non-Aromatic

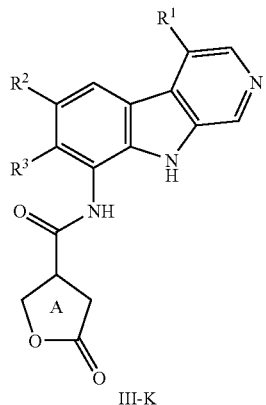

III-K

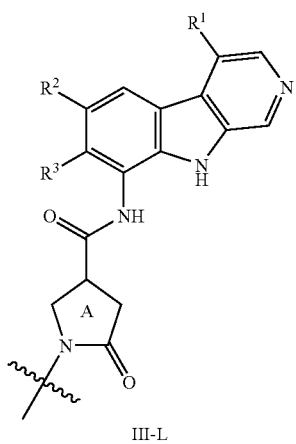

III-L

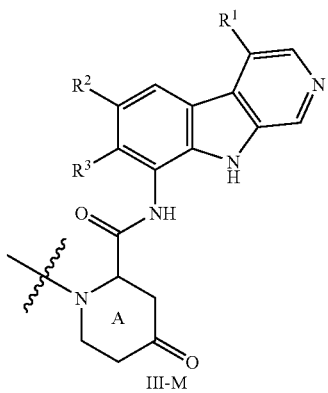

III-M

When Ring A is a non-aromatic, six-membered heterocylic ring, a favorable position for the —W-G and —C(R⁹)₃ substituents on Ring A is ortho to the position where the beta-carboline portion is attached. For example, in compounds III-A, III-B, III-D, III-H, III-J and III-M, a preferred position for attachment of —W-G and —C(R⁹)₃ is at the Ring A nitrogen or at N-1 in the case of compound III-F.

Preferably, W is -Q-, -Q-C(O)—, —C(R⁹)₂—C(R⁹)(R¹²)—, or —C(R⁹)₂—[C(R⁹)(R¹²)]₂— where R⁹ is hydrogen. More preferably, W is -Q-, -Q-C(O)—, or —C(R⁹)₂—C(R⁹)(R¹²)—. R¹² is hydrogen, $C_{1-6}$ aliphatic, substituted or unsubstituted phenyl, substituted or unsubstituted benzyl or an amino acid side chain, particularly the side chain of a natural amino acid. Examples of particular natural amino acid side chains include the side chains of alanine, phenylalanine, valine, leucine, isoleucine, serine, tyrosine, aspartic acid and glutamic acid.

In one embodiment, W is Q-C(O)—. In this embodiment, a preferred Q is —CH₂— or —CH₂—CH₂—, more preferably —CH₂—.

In another embodiment, Ring A is substituted by 0-2 $R^{6b}$. A preferred $R^{6b}$ group is methyl. When Ring A is a non-aromatic six membered ring, one embodiment provides compounds of formula III where there are two methyl groups on the Ring A position para to the position where the beta carboline portion is attached. An example of this embodiment is a compound where Ring A is a 6,6-dimethyl-morpholinyl ring. Preferably, such compounds are further substituted by —W-G as described above.

When Ring A is a morpholinyl ring, it has been found that compounds having the "S" stereochemistry at position 3 of the morpholine ring are preferred, as shown below by compounds of formula (S)-III-A.

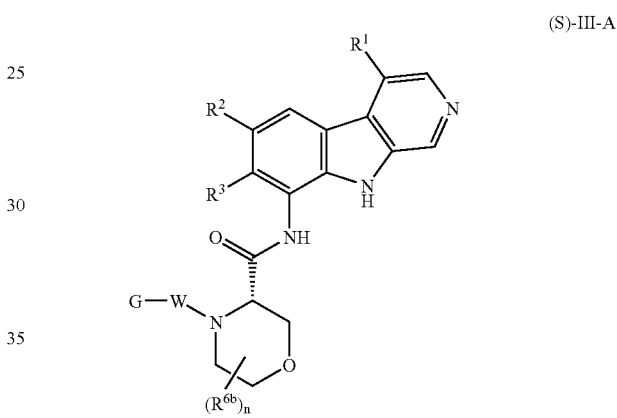

(S)-III-A where n is 0-4 and $R^1$, $R^2$, $R^3$, W, G and $R^{6b}$ are as defined above. By analogy, it is expected that "S" stereochemistry is also preferred for other six-membered non-aromatic Ring A compounds of formula III.

One embodiment of the formula I compounds relates to compounds of formula III-A or (S)-III-A where:
  $R^1$ is hydrogen, halo, methyl or amino;
  $R^2$ is hydrogen, methyl or halo;
  $R^3$ is hydrogen, halo, alkoxy, or ($C_{1-6}$ aliphatic)₂amino;
  Ring A is substituted by 0-2 $R^{6b}$;
  $R^{6b}$ is $C_{1-3}$ aliphatic;
  W is -Q-, -Q-C(O)—, —C(R⁹)₂—C(R⁹)(R¹²)—, or —C(R⁹)₂—[C(R⁹)(R¹²)]₂—;
  Q is —C(R⁹)₂— or —C(R⁹)₂C(R⁹)₂—;
  G is —NR⁴R⁵, —N(R⁹)CONR⁴R⁵, —N(R⁹)SO₂(C₁₋₃ aliphatic), —N(R⁹)COCF₃, —N(R⁹)CO(C₁₋₆ aliphatic), —N(R⁹)CO(heterocyclyl), —N(R⁹)CO(heteroaryl), —N(R⁹)CO(aryl), 3-10 membered monocyclic or bicyclic heterocyclyl ring, or a 5-6 membered heteroaryl ring, wherein each of the heteroaryl, aryl and heterocyclyl moieties of G is optionally substituted by 1-4 $R^{10}$;
  $R^4$ is hydrogen or $C_{1-6}$ aliphatic;
  $R^5$ is: a) hydrogen;
    b) an optionally substituted group selected from aryl, heteroaryl, heterocyclyl, or carbocyclyl, or
    c) a $C_{1-6}$ aliphatic group that is optionally substituted by: halo, —OR⁷, —CN, —SR⁸, —S(O)₂R⁸, —C(O)R⁷, —CO₂R⁷, —N(R⁷)₂, —C(O)N(R⁷)₂, —N(R⁷)C(O)

$R^7$, —$N(R^7)CO_2R^8$, —$SO_2N(R^7)_2$, —$NR^7SO_2R^7$, —$N(R^7)C(O)N(R^7)_2$, or an aryl, heteroaryl, heterocyclyl, or carbocyclyl group that is optionally further substituted by $C_{1-6}$aliphatic, —$CF_3$, halo, —$OR^7$, —CN, —$SR^8$, —$S(O)_2R^8$, —$C(O)R^7$, —$CO_2R^7$, —$N(R^7)_2$, —$C(O)N(R^7)_2$, —$N(R^7)C(O)R^7$, —$N(R^7)CO_2R^8$, —$SO_2N(R^7)_2$, —$NR^7SO_2R^7$, —$N(R^7)C(O)N(R^7)_2$;

each $R^7$ is independently selected from hydrogen or an optionally substituted $C_{1-4}$ aliphatic, or two $R^7$ on the same nitrogen atom are taken together with the nitrogen to form an optionally substituted 3-6 membered heteroaryl or heterocyclyl ring;

each $R^{7a}$ is independently selected from hydrogen or an optionally substituted group selected from $C_{1-4}$ aliphatic, aryl, heteroaryl, heterocyclyl, or carbocyclyl, or two $R^{7a}$ on the same nitrogen atom are taken together with the nitrogen to form an optionally substituted 3-6 membered heteroaryl or heterocyclyl ring;

each $R^8$ is independently an optionally substituted $C_{1-4}$ aliphatic;

each $R^{8a}$ is independently an optionally substituted group selected from $C_{1-4}$ aliphatic, aryl, heteroaryl, heterocyclyl, or carbocyclyl;

$R^9$ is hydrogen;

each $R^{10}$ is independently selected from oxo, —$R^{11}$, -T-$R^{11}$, or —V-T-$R^{11}$, or two occurrences of $R^{10}$, taken together with the atom(s) to which they are bound, form an optionally substituted monocyclic or bicyclic 3-8-membered aryl, heteroaryl, heterocyclyl, or carbocyclyl ring;

each $R^{11}$ is independently selected from —$CF_3$, halo, —$OR^{7a}$, —CN, —$SR^{8a}$, $S(O)_2R^{8a}$, —$C(O)R^{7a}$, —$CO_2R^{7a}$, —$N(R^{7a})_2$, —$C(O)N(R^{7a})_2$, —$N(R^7)C(O)R^{7a}$, —$N(R^7)CO_2R^{7a}$, —$SO_2N(R^{7a})_2$, —$N(R^7)SO_2R^{7a}$, —$N(R^7)C(O)N(R^{7a})_2$ or an optionally substituted group selected from $C_{1-6}$aliphatic, aryl, heteroaryl, heterocyclyl or carbocyclyl;

T is a straight or branched $C_{1-4}$ alkylene chain;

V is —O—, —$N(R^7)$—, —S—, —S(O)—, —$S(O)_2$—, —C(O)—, or —$CO_2$—; and $R^{12}$ is hydrogen, $C_{1-6}$ aliphatic, substituted or unsubstituted phenyl, or substituted or unsubstituted benzyl.

Another embodiment of the formula I compounds relates to compounds of formula III-A or (S)-III-A where:

$R^1$ is hydrogen, halo, methyl or amino;

$R^2$ is hydrogen, methyl or halo;

$R^3$ is hydrogen, halo, alkoxy, or $(C_{1-6}$ aliphatic$)_2$ amino;

Ring A is substituted by 0-2 $R^{6b}$;

$R^{6b}$ is $C_{1-3}$ aliphatic;

W is -Q-, -Q-C(O)—, —$C(R^9)_2$—$C(R^9)(R^{12})$—, or —$C(R^9)_2$—$[C(R^9)(R^{12})]_2$—;

Q is —$C(R^9)_2$— or —$C(R^9)_2C(R^9)_2$—;

G is —$NR^4R^5$, —$N(R^9)C(O)NR^4R^5$, —$N(R^9)SO_2(C_{1-3}$ aliphatic), —$N(R^9)C(O)CF_3$, —$N(R^9)CO(C_{1-6}$ aliphatic), and —$N(R^9)CO$(heterocyclyl), —$N(R^9)CO$(heteroaryl), —$N(R^9)CO$(aryl), a 5-6 membered heterocyclyl ring, or a 5-6 membered heteroaryl, wherein each of the heteroaryl, aryl and heterocyclyl moieties of G is optionally substituted by 1-3 $R^{10}$;

$R^4$ is hydrogen or $C_{1-6}$ aliphatic;

$R^5$ is hydrogen or a $C_{1-6}$ aliphatic group that is optionally substituted by halo, —$OR^7$, —CN, —$SR^8$, —$S(O)_2R^8$, —$S(O)_2N(R^7)_2$, —$C(O)R^7$, —$CO_2R^7$, —$N(R^7)_2$, —$C(O)N(R^7)_2$, —$N(R^7)C(O)R^7$, —$N(R^7)CO_2R^8$, or —$N(R^7)C(O)N(R^7)_2$;

each $R^7$ is independently selected from hydrogen or $C_{1-4}$ aliphatic, or two $R^7$ on the same nitrogen atom are taken together with the nitrogen to form a 5-6 membered heteroaryl or heterocyclyl ring;

each $R^8$ is independently selected from $C_{1-4}$ aliphatic;

$R^9$ is hydrogen;

each $R^{10}$ is independently selected from oxo, $R^{11}$, T-$R^{11}$, or V-T-$R^{11}$;

each $R^{11}$ is independently selected from $C_{1-6}$ aliphatic, halo, —$S(O)_2N(R^7)_2$, —$OR^7$, —CN, —$SR^8$, —$S(O)_2R^8$, —$C(O)R^7$, —$CO_2R^7$, —$N(R^7)_2$, —$C(O)N(R^7)_2$, —$N(R^7)C(O)R^7$, —$N(R^7)CO_2R^7$, or —$N(R^7)C(O)N(R^7)_2$;

T is a straight or branched $C_{1-4}$ alkylene chain;

V is —O—, —$N(R^7)$—, —S—, —S(O)—, —$S(O)_2$—, —C(O)—, or —$CO_2$—; and $R^{12}$ is hydrogen, $C_{1-6}$ aliphatic, substituted or unsubstituted phenyl, or substituted or unsubstituted benzyl.

Another embodiment relates to compounds of formula III-A or (S)-III-A where:

$R^1$ is hydrogen, methyl, fluoro or amino;

$R^2$ is chloro;

$R^3$ is hydrogen or alkoxy;

Ring A is substituted by —W-G and 0-2 $R^{6b}$;

$R^{6b}$ is methyl;

W is -Q-, Q-C(O)— or —$C(R^9)_2$—$C(R^9)(R^{12})$—;

Q is —$C(R^9)_2$— or —$C(R^9)_2C(R^9)_2$—;

G is —$NR^4R^5$, —$N(R^9)C(O)NR^4R^5$, —$N(R^9)C(O)CF_3$, —$N(R^9)CO(C_{1-6}$ aliphatic), and —$N(R^9)CO$(heterocyclyl), —$N(R^9)CO$(heteroaryl), 3-10 membered monocyclic or bicyclic heterocyclyl ring, or a 5-6 membered heteroaryl ring, wherein each of the heteroaryl and heterocyclyl moieties of G is optionally substituted by 1-4 $R^{10}$;

$R^4$ is hydrogen or $C_{1-6}$ aliphatic;

$R^5$ is: a) hydrogen;

b) an optionally substituted group selected from aryl, heteroaryl, heterocyclyl, or carbocyclyl, or c) a $C_{1-6}$ aliphatic group that is optionally substituted by: halo, —$OR^7$, —CN, —$SR^8$, —$S(O)_2R^8$, —$C(O)R^7$, —$CO_2R^7$, —$N(R^7)_2$, —$C(O)N(R^7)_2$, —$N(R^7)C(O)R^7$, —$N(R^7)CO_2R^8$, —$SO_2N(R^7)_2$, —$NR^7SO_2R^7$, —$N(R^7)C(O)N(R^7)_2$, or an aryl, heteroaryl, heterocyclyl, or carbocyclyl group that is optionally further substituted by $C_{1-6}$aliphatic, —$CF_3$, halo, —$OR^7$, —CN, —$SR^8$, —$S(O)_2R^8$, —$C(O)R^7$, —$CO_2R^7$, —$N(R^7)_2$, —$C(O)N(R^7)_2$, —$N(R^7)C(O)R^7$, —$N(R^7)CO_2R^8$, —$SO_2N(R^7)_2$, —$NR^7SO_2R^7$, —$N(R^7)C(O)N(R^7)_2$;

each $R^7$ is independently selected from hydrogen or an optionally substituted $C_{1-4}$ aliphatic, or two $R^7$ on the same nitrogen atom are taken together with the nitrogen to form an optionally substituted 3-6 membered heteroaryl or heterocyclyl ring;

each $R^{7a}$ is independently selected from hydrogen or an optionally substituted group selected from $C_{1-4}$ aliphatic, aryl, heteroaryl, heterocyclyl, or carbocyclyl, or two $R^{7a}$ on the same nitrogen atom are taken together with the nitrogen to form an optionally substituted 3-6 membered heteroaryl or heterocyclyl ring;

each $R^8$ is independently an optionally substituted $C_{1-4}$ aliphatic;

each $R^{8a}$ is independently an optionally substituted group selected from $C_{1-4}$ aliphatic, aryl, heteroaryl, heterocyclyl, or carbocyclyl;

$R^9$ is hydrogen;

each $R^{10}$ is independently selected from oxo, —$R^{11}$, -T-$R^{11}$, or —V-T-$R^{11}$, or two occurrences of $R^{10}$, taken together with the atom(s) to which they are bound, form an optionally substituted monocyclic or bicyclic 3-8-membered aryl, heteroaryl, heterocyclyl, or carbocyclyl ring;

each $R^{11}$ is independently selected from —$CF_3$, halo, —$OR^{7a}$, —CN, —$SR^{8a}$, —$S(O)_2R^{7a}$, —$C(O)R^{7a}$, —$CO_2R^{7a}$, —$N(R^{7a})_2$, —$C(O)N(R^{7a})_2$, —$N(R^7)C(O)R^{7a}$, —$N(R^7)CO_2R^{7a}$, —$SO_2N(R^{7a})_2$, —$N(R^7)SO_2R^{7a}$, —$N(R^7)C(O)N(R^{7a})_2$ or an optionally substituted group selected from $C_{1-6}$ aliphatic, aryl, heteroaryl, heterocyclyl or carbocyclyl;

T is a straight or branched $C_{1-4}$ alkylene chain;

V is —O—, —$N(R^7)$—, —S—, —S(O)—, —$S(O)_2$—, —C(O)—, or —$CO_2$—; and $R^{12}$ is hydrogen, $C_{1-6}$ aliphatic, phenyl, or benzyl.

Yet another embodiment relates to compounds of formula III-A or (S)-III-A where:

$R^1$ is hydrogen, methyl, fluoro or amino;
$R^2$ is chloro;
$R^3$ is hydrogen or alkoxy;
Ring A is substituted by —W-G and 0-2 $R^{6b}$;
$R^{6b}$ is methyl;
W is -Q-, Q-C(O)— or —$C(R^9)_2$—$C(R^9)(R^{12})$—;
Q is —$C(R^9)_2$— or —$C(R^9)_2C(R^9)_2$—;
G is —$NR^4R^5$, —$N(R^9)C(O)NR^4R^5$, —$N(R^9)C(O)CF_3$, —$N(R^9)CO(C_{1-6}$ aliphatic), and —$N(R^9)CO$(heterocyclyl), —$N(R^9)CO$(heteroaryl), a 5-6 membered heterocyclyl ring, or a 5-6 membered heteroaryl, wherein each of the heteroaryl and heterocyclyl moieties of G is optionally substituted by 1-3 $R^{10}$;
$R^4$ is hydrogen or $C_{1-6}$ aliphatic;
$R^5$ is hydrogen or $C_{1-6}$ aliphatic;
each $R^7$ is independently selected from hydrogen or $C_{1-4}$ aliphatic, or two $R^7$ on the same nitrogen atom are taken together with the nitrogen to form a 5-6 membered heteroaryl or heterocyclyl ring;
each $R^5$ is independently selected from $C_{1-4}$ aliphatic;
$R^9$ is hydrogen;
each $R^{10}$ is independently selected from oxo, $R^{11}$, T-$R^{11}$, or V-T-$R^{11}$;
each $R^{11}$ is independently selected from $C_{1-6}$ aliphatic, halo, —$S(O)_2N(R^7)_2$, —$OR^7$, —CN, —$SR^8$, —$S(O)_2R^8$, —$C(O)R^7$, —$CO_2R^7$, —$N(R^7)_2$, —$C(O)N(R^7)_2$, —$N(R^7)C(O)R^7$, —$N(R^7)CO_2R^7$, or —$N(R^7)C(O)N(R^7)_2$;
T is a straight or branched $C_{1-4}$ alkylene chain;
V is —O—, —$N(R^7)$—, —S—, —S(O)—, —$S(O)_2$—, —C(O)—, or —$CO_2$—; and
$R^{12}$ is hydrogen, $C_{1-4}$ aliphatic, phenyl, or benzyl.

Preferred compounds of formula III-A are the compounds of formula (S)-III-A':

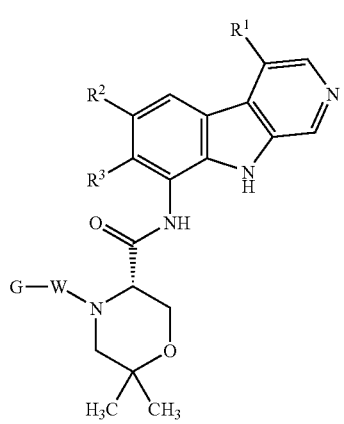

(S)-III-A' where $R^1$, $R^2$, $R^3$, W and G are as defined above for (S)-III-A.

Another embodiment relates to compounds of formula III-A-a:

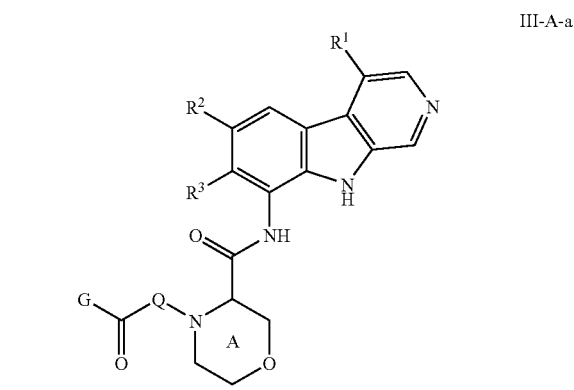

III-A-a or a pharmaceutically acceptable salt thereof, wherein:
Q is —$CH_2$—, —$CH(R^9)$—, or —$C(R^9)_2$—;
G is —$NR^4R^5$ or a 3-7 membered heterocyclyl or heteroaryl ring that is optionally substituted by 1-4 $R^{10}$;
$R^1$ is hydrogen, halo, $C_{1-3}$ aliphatic, amino, cyano, ($C_{1-3}$ alkyl)$_{1-2}$ amino, $C_{1-3}$ alkoxy, ($C_{1-3}$ aliphatic)-C(O)—, ($C_{1-6}$ aliphatic)-$CO_2$—, or ($C_{1-3}$ aliphatic)-C(O)NH—;
$R^2$ is hydrogen, halo, $C_{1-3}$ aliphatic, $C_{1-3}$ alkoxy, $C_{1-3}$ haloalkoxy, or $C_{1-3}$ haloalkyl;
$R^3$ is hydrogen, halo, $C_{1-6}$ aliphatic, $C_{1-6}$ haloalkyl, $C_{1-6}$ alkoxy, hydroxy, amino, cyano, or ($C_{1-6}$ alkyl)$_{1-2}$ amino;
$R^4$ is hydrogen or $C_{1-6}$ aliphatic;
$R^5$ is:
a) an optionally substituted group selected from aryl, heteroaryl, heterocyclyl, or carbocyclyl, or
b) a $C_{1-6}$ aliphatic group that is optionally substituted by: halo, —$OR^7$, —CN, —$SR^8$, —$S(O)_2R^8$, —$C(O)R^7$, —$CO_2R^7$, —$N(R^7)_2$, —$C(O)N(R^7)_2$, —$N(R^7)C(O)R^7$, —$N(R^7)CO_2R^8$, —$SO_2N(R^7)_2$, —$NR^7SO_2R^7$, —$N(R^7)C(O)N(R^7)_2$, or an aryl, heteroaryl, heterocyclyl, or carbocyclyl group that is optionally further substituted by $C_{1-6}$ aliphatic, —$CF_3$, halo, —$OR^7$, —CN, —$SR^8$, —$S(O)_2R^8$, —$C(O)R^7$, —$CO_2R^7$, —$N(R^7)_2$, —$C(O)N(R^7)_2$, —$N(R^7)C(O)R^7$, —$N(R^7)CO_2R^8$, —$SO_2N(R^7)_2$, —$NR^7SO_2R^7$, —$N(R^7)C(O)N(R^7)_2$;
Ring A is substituted by 0-4 $R^{6b}$;
each $R^{6b}$ is independently selected from a $C_{1-6}$ aliphatic group;
each $R^7$ is independently selected from hydrogen or an optionally substituted $C_{1-4}$ aliphatic, or two $R^7$ on the same nitrogen atom are taken together with the nitrogen to form an optionally substituted 3-6 membered heteroaryl or heterocyclyl ring;
each $R^{7a}$ is independently selected from hydrogen or an optionally substituted group selected from $C_{1-4}$ aliphatic, aryl, heteroaryl, heterocyclyl, or carbocyclyl, or two $R^{7a}$ on the same nitrogen atom are taken together with the nitrogen to form an optionally substituted 3-6 membered heteroaryl or heterocyclyl ring;
each $R^8$ is independently an optionally substituted $C_{1-4}$ aliphatic;
each $R^{8a}$ is independently an optionally substituted group selected from $C_{1-4}$ aliphatic, aryl, heteroaryl, heterocyclyl, or carbocyclyl;
each $R^9$ is independently selected from a $C_{1-3}$ aliphatic;

each $R^{10}$ is independently selected from oxo, —$R^{11}$, -T-$R^{11}$, or —V-T-$R^{11}$, or two occurrences of $R^{10}$, taken together with the atom(s) to which they are bound, form an optionally substituted monocyclic or bicyclic 3-8-membered aryl, heteroaryl, heterocyclyl, or carbocyclyl ring;

each $R^{11}$ is independently selected from —$CF_3$, halo, —$OR^{7a}$, —CN, —$SR^{8a}$, $S(O)_2R^{8a}$, —$C(O)R^{7a}$, —$CO_2R^{7a}$, —$N(R^{7a})_2$, —$C(O)N(R^{7a})_2$, —$N(R^7)C(O)R^{7a}$, —$N(R^7)CO_2R^{7a}$, —$SO_2N(R^{7a})_2$, —$N(R^7)SO_2R^{7a}$, —$N(R^7)C(O)N(R^{7a})_2$ or an optionally substituted group selected from $C_{1-6}$aliphatic, aryl, heteroaryl, heterocyclyl or carbocyclyl;

T is a straight or branched $C_{1-4}$ alkylene chain; and
V is —O—, —$N(R^7)$—, —S—, —S(O)—, —$S(O)_2$—, —C(O)—, or —$CO_2$—.

Still another embodiment relates to compounds of formula III-A-a:

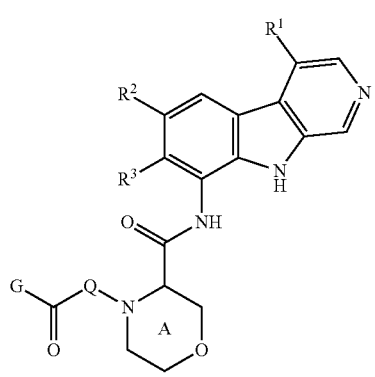

III-A-a or a pharmaceutically acceptable salt thereof, wherein:
Q is —$CH_2$—, —$CH(R^9)$—, or —$C(R^9)_2$—;
G is —$NR^4R^5$ or a 3-7 membered heterocyclyl or heteroaryl ring that is optionally substituted by 1-2 $R^{10}$;
$R^1$ is hydrogen, halo, $C_{1-3}$ aliphatic, amino, cyano, ($C_{1-3}$ alkyl)$_{1-2}$ amino, $C_{1-3}$ alkoxy, ($C_{1-3}$ aliphatic)-C(O)—, ($C_{1-6}$ aliphatic)-$CO_2$—, or ($C_{1-3}$ aliphatic)-C(O)NH—;
$R^2$ is hydrogen, halo, $C_{1-3}$ aliphatic, $C_{1-3}$ alkoxy, $C_{1-3}$ haloalkoxy, or $C_{1-3}$ haloalkyl;
$R^3$ is hydrogen, halo, $C_{1-6}$ aliphatic, $C_{1-6}$ haloalkyl, $C_{1-6}$ alkoxy, hydroxy, amino, cyano, or ($C_{1-6}$ alkyl)$_{1-2}$ amino;
$R^4$ is hydrogen or $C_{1-6}$ aliphatic;
$R^5$ is a $C_{1-6}$ aliphatic group that is optionally substituted by halo, —$OR^7$, —CN, —$SR^8$, —$S(O)_2R^8$, —$C(O)R^7$, —$CO_2R^7$, —$N(R^7)_2$, —$C(O)N(R^7)_2$, —$N(R^7)C(O)R^7$, —$N(R^7)CO_2R^8$, or —$N(R^7)C(O)N(R^7)_2$;
Ring A is substituted by 0-4 $R^{6b}$;
each $R^{6b}$ is independently selected from a $C_{1-4}$ aliphatic group;
each $R^7$ is independently selected from hydrogen or $C_{1-4}$ aliphatic, or two $R^7$ on the same nitrogen atom are taken together with the nitrogen to form a 5-6 membered heteroaryl or heterocyclyl ring;
each $R^8$ is independently selected from $C_{1-4}$ aliphatic;
each $R^9$ is independently selected from a $C_{1-3}$ aliphatic;
each $R^{10}$ is independently selected from $R^{11}$, T-$R^{11}$, or V-T-$R^{11}$;
each $R^{11}$ is independently selected from $C_{1-6}$ aliphatic, halo, —$OR^7$, —CN, —$SR^8$, —$S(O)_2R^8$, —$C(O)R^7$, —$CO_2R^7$, —$N(R^7)_2$, —$C(O)N(R^7)_2$, —$N(R^7)C(O)R^7$, —$N(R^7)CO_2R^7$, or —$N(R^7)C(O)N(R^7)_2$;

T is a straight or branched $C_{1-4}$ alkylene chain; and
V is —O—, —$N(R^7)$—, —S—, —S(O)—, —$S(O)_2$—, —C(O)—, or —$CO_2$—.

One embodiment relates to compounds of formula III-A-a where:
Q is —$CH_2$—, or —$CH(R^9)$—;
G is —$NR^4R^5$ or a 5-6 membered heterocyclyl or heteroaryl ring that is optionally substituted by 1-4 $R^{10}$;
$R^1$ is hydrogen, halo, $C_{1-2}$ alkyl, amino, or ($C_{1-2}$ alkyl)$_{1-2}$ amino;
$R^2$ is hydrogen, halo, $C_{1-2}$ aliphatic, $C_{1-2}$ alkoxy, or $C_{1-2}$ haloalkyl;
$R^3$ is hydrogen, halo, $C_{1-2}$ aliphatic, $C_{1-2}$ alkoxy, or $C_{1-2}$ haloalkyl;
$R^4$ is hydrogen or $C_{1-6}$ aliphatic;
$R^5$ is:
a) an optionally substituted group selected from aryl, heteroaryl, heterocyclyl, or carbocyclyl, or
b) a $C_{1-6}$ aliphatic group that is optionally substituted by: halo, —$OR^7$, —CN, —$SR^8$, —$S(O)_2R^5$, —$C(O)R^7$, —$CO_2R^7$, —$N(R^7)_2$, —$C(O)N(R^7)_2$, —$N(R^7)C(O)R^7$, —$N(R^7)CO_2R^8$, —$SO_2N(R^7)_2$, —$NR^7SO_2R^7$, —$N(R^7)C(O)N(R^7)_2$, or an aryl, heteroaryl, heterocyclyl, or carbocyclyl group that is optionally further substituted by $C_{1-6}$aliphatic, —$CF_3$, halo, —$OR^7$, —CN, —$SR^8$, —$S(O)_2R^8$, —$C(O)R^7$, —$CO_2R^7$, —$N(R^7)_2$, —$C(O)N(R^7)_2$, —$N(R^7)C(O)R^7$, —$N(R^7)CO_2R^8$, —$SO_2N(R^7)_2$, —$NR^7SO_2R^7$, —$N(R^7)C(O)N(R^7)_2$;
Ring A is substituted by 0-2 $R^{6b}$;
each $R^{6b}$ is independently selected from a $C_{1-3}$ aliphatic group;
each $R^7$ is independently selected from hydrogen or an optionally substituted $C_{1-4}$ aliphatic, or two $R^7$ on the same nitrogen atom are taken together with the nitrogen to form an optionally substituted 3-6 membered heteroaryl or heterocyclyl ring;
each $R^{7a}$ is independently selected from hydrogen or an optionally substituted group selected from $C_{1-4}$ aliphatic, aryl, heteroaryl, heterocyclyl, or carbocyclyl, or two $R^{7a}$ on the same nitrogen atom are taken together with the nitrogen to form an optionally substituted 3-6 membered heteroaryl or heterocyclyl ring;
each $R^8$ is independently an optionally substituted $C_{1-4}$ aliphatic;
each $R^{8a}$ is independently an optionally substituted group selected from $C_{1-4}$ aliphatic, aryl, heteroaryl, or carbocyclyl;
$R^9$ is independently selected from $C_{1-3}$ aliphatic;
each $R^{10}$ is independently selected from oxo, —$R^{11}$, -T-$R^{11}$, or —V-T-$R^{11}$, or two occurrences of $R^{10}$, taken together with the atom(s) to which they are bound, form an optionally substituted monocyclic or bicyclic 3-8-membered aryl, heteroaryl, heterocyclyl, or carbocyclyl ring;
each $R^{11}$ is independently selected from —$CF_3$, halo, —$OR^{7a}$, —CN, —$SR^{8a}$, —$S(O)_2R^{8a}$, —$C(O)R^{7a}$, —$CO_2R^{7a}$, —$N(R^{7a})_2$, —$C(O)N(R^{7a})_2$, —$N(R^7)C(O)R^{7a}$, —$N(R^7)CO_2R^{7a}$, —$SO_2N(R^{7a})_2$, —$N(R^7)SO_2R^{7a}$, —$N(R^7)C(O)N(R^{7a})_2$ or an optionally substituted group selected from $C_{1-6}$aliphatic, aryl, heteroaryl, heterocyclyl or carbocyclyl;
T is a straight or branched $C_{1-4}$ alkylene chain; and
V is —O—, —$N(R^7)$—, —S—, —S(O)—, —$S(O)_2$—, —C(O)—, or —$CO_2$—.

Another embodiment relates to compounds of formula III-A-a where:
Q is —$CH_2$—, or —$CH(R^9)$—;
G is —$NR^4R^5$ or a 5-6 membered heterocyclyl or heteroaryl ring that is optionally substituted by 1-2 $R^{10}$;

$R^1$ is hydrogen, halo, $C_{1-2}$ alkyl, amino, or $(C_{1-2}$ alkyl$)_{1-2}$ amino;

$R^2$ is hydrogen, halo, $C_{1-2}$ aliphatic, $C_{1-2}$ alkoxy, or $C_{1-2}$ haloalkyl;

$R^3$ is hydrogen, halo, $C_{1-2}$ aliphatic, $C_{1-2}$ alkoxy, or $C_{1-2}$ haloalkyl;

$R^4$ is hydrogen or $C_{1-6}$ aliphatic;

$R^5$ is a $C_{1-6}$ aliphatic group that is optionally substituted by halo, —$OR^7$, —CN, —$SR^8$, —$S(O)_2R^8$, —$C(O)R^7$, —$CO_2R^7$, —$N(R^7)_2$, —$C(O)N(R^7)_2$, —$N(R^7)C(O)R^7$, —$N(R^7)CO_2R^8$, or —$N(R^7)C(O)N(R^7)_2$;

Ring A is substituted by 0-2 $R^{6b}$;

each $R^{6b}$ is independently selected from a $C_{1-3}$ aliphatic group;

each $R^7$ is independently selected from hydrogen or $C_{1-4}$ aliphatic, or two $R^7$ on the same nitrogen atom are taken together with the nitrogen to form a 5-6 membered heteroaryl or heterocyclyl ring;

$R^8$ is $C_{1-4}$ aliphatic;

$R^9$ is independently selected from a $C_{1-3}$ aliphatic;

each $R^{10}$ is independently selected from $R^{11}$, T-$R^{11}$, or V-T-$R^{11}$;

each $R^{11}$ is independently selected from $C_{1-6}$ aliphatic, halo, —$OR^7$, —CN, —$SR^8$, —$S(O)_2R^8$, —$C(O)R^7$, —$CO_2R^7$, —$N(R^7)_2$, —$C(O)N(R^7)_2$, —$N(R^7)C(O)R^7$, —$N(R^7)CO_2R^7$, or —$N(R^7)C(O)N(R^7)_2$;

T is a straight or branched $C_{1-4}$ alkylene chain; and

V is —O—, —$N(R^7)$—, —S—, —S(O)—, —$S(O)_2$—, —C(O)—, or —$CO_2$—.

Another embodiment relates to compounds of formula III-A-a where:

Q is —$CH_2$—, or —$CH(R^9)$—;

G is —$NR^4R^5$ or a 5-6 membered heterocyclyl ring, having 1-2 ring heteroatoms selected from oxygen or nitrogen, that is optionally substituted by 1-4 $R^{10}$;

$R^1$ is hydrogen, halo, methyl, amino, or $(C_{1-2}$ alkyl$)_{1-2}$ amino;

$R^2$ is hydrogen, halo, $C_{1-2}$ aliphatic, or $C_{1-2}$ haloalkyl;

$R^3$ is hydrogen, halo, or $C_{1-2}$ aliphatic;

$R^4$ is hydrogen or $C_{1-6}$ aliphatic;

$R^5$ is:
a) an optionally substituted group selected from aryl, heteroaryl, heterocyclyl, or carbocyclyl, or
b) a $C_{1-6}$ aliphatic group that is optionally substituted by: halo, —$OR^7$, —CN, —$SR^8$, —$S(O)_2R^8$, —$C(O)R^7$, —$CO_2R^7$, —$N(R^7)_2$, —$C(O)N(R^7)_2$, —$N(R^7)C(O)R^7$, —$N(R^7)CO_2R^8$, —$SO_2N(R^7)_2$, —$NR^7SO_2R^7$, —$N(R^7)C(O)N(R^7)_2$, or an aryl, heteroaryl, heterocyclyl, or carbocyclyl group that is optionally further substituted by $C_{1-6}$ aliphatic, —$CF_3$, halo, —$OR^7$, —CN, —$SR^8$, —$S(O)_2R^8$, —$C(O)R^7$, —$CO_2R^7$, —$N(R^7)_2$, —$C(O)N(R^7)_2$, —$N(R^7)C(O)R^7$, —$N(R^7)CO_2R^8$, —$SO_2N(R^7)_2$, —$NR^7SO_2R^7$, —$N(R^7)C(O)N(R^7)_2$;

Ring A is substituted by 0-2 $R^{6b}$;

each $R^{6b}$ is independently selected from a $C_{1-3}$ aliphatic group;

each $R^7$ is independently selected from hydrogen or $C_{1-4}$ aliphatic, or two $R^7$ on the same nitrogen atom are taken together with the nitrogen to form a 5-6 membered heteroaryl or heterocyclyl ring;

each $R^8$ is independently $C_{1-4}$ aliphatic;

$R^9$ is independently selected from $C_{1-3}$ aliphatic;

each $R^{10}$ is independently selected from oxo, —$R^{11}$, T-$R^{11}$, or —V-T-$R^{11}$;

each $R^{11}$ is independently selected from $C_{1-6}$ aliphatic halo, —$OR^7$, —CN, —$SR^8$, —$S(O)_2R^8$, —$C(O)R^7$, —$CO_2R^7$, —$N(R^7)_2$, $C(O)N(R^7)_2$, —$N(R^7)C(O)R^7$, —$N(R^7)C(O)N(R^7)_2$; —$N(R^7)C(O)N(R^7)_2$;

T is a straight or branched $C_{1-4}$ alkylene chain; and

V is —O—, —$N(R^7)$—, —S—, —S(O)—, —$S(O)_2$—, —C(O)—, or —$CO_2$—.

Still another embodiment relates to compounds of formula III-A-a where:

Q is —$CH_2$—, or —$CH(R^9)$—;

G is —$NR^4R^5$ or a 5-6 membered heterocyclyl ring, having 1-2 ring heteroatoms selected from oxygen or nitrogen, that is optionally substituted by 1-2 $R^{10}$;

$R^1$ is hydrogen, halo, methyl, amino, or $(C_{1-2}$ alkyl$)_{1-2}$ amino;

$R^2$ is hydrogen, halo, $C_{1-2}$ aliphatic, or $C_{1-2}$ haloalkyl;

$R^3$ is hydrogen, halo, or $C_{1-2}$ aliphatic;

$R^4$ is hydrogen or $C_{1-6}$ aliphatic;

$R^5$ is a $C_{1-6}$ aliphatic group that is optionally substituted by halo, —$OR^7$, —CN, —$SR^8$, —$S(O)_2R^8$, —$C(O)R^7$, —$CO_2R^7$, —$N(R^7)_2$, —$C(O)N(R^7)_2$, —$N(R^7)C(O)R^7$, —$N(R^7)CO_2R^8$, or —$N(R^7)C(O)N(R^7)_2$;

Ring A is substituted by zero or two $R^{6b}$;

each $R^{6b}$ is independently selected from a $C_{1-3}$ aliphatic group;

each $R^7$ is independently selected from hydrogen or $C_{1-4}$ aliphatic, or two $R^7$ on the same nitrogen atom are taken together with the nitrogen to form a 5-6 membered heteroaryl or heterocyclyl ring;

each $R^8$ is independently $C_{1-4}$ aliphatic;

each $R^9$ is independently selected from a $C_{1-3}$ aliphatic;

each $R^{10}$ is independently selected from $R^{11}$, T-$R^{11}$, or V-T-$R^{11}$;

each $R^{11}$ is independently selected from $C_{1-6}$ aliphatic, halo, —$OR^7$, —CN, —$SR^8$, —$S(O)_2R^8$, —$C(O)R^7$, —$CO_2R^7$, —$N(R^7)_2$, —$C(O)N(R^7)_2$, —$N(R^7)C(O)R^7$, —$N(R^7)CO_2R^7$, or —$N(R^7)C(O)N(R^7)_2$;

T is a straight or branched $C_{1-4}$ alkylene chain; and

V is —O—, —$N(R^7)$—, —S—, —S(O)—, —$S(O)_2$—, —C(O)—, or —$CO_2$—.

In preferred compounds of formula III-A-a, Q is —$CH_2$—; G is selected from an optionally substituted piperidinyl, piperazinyl, morpholinyl, pyrrolidinyl, or —$NR^4R^5$; $R^4$ is hydrogen or $C_{1-6}$ aliphatic; and $R^5$ is $C_{1-6}$ aliphatic, 5-6 membered heterocyclyl, or $C_{1-6}$ hydroxyalkyl. In other preferred compounds of formula III-A-a, Q is —$CH_2$—; G is selected from an optionally substituted piperidinyl, piperazinyl, morpholinyl, pyrrolidinyl, or —$NR^4R^5$; $R^4$ is hydrogen or $C_{1-6}$ aliphatic; and $R^5$ is $C_{1-6}$ aliphatic, 5-6 membered heterocyclyl, $C_{1-6}$ hydroxyalkyl, aminoalkyl, or mono- or dialkylaminoalkyl. In preferred compounds of formula III-A-a, G is unsubstituted or substituted by 1-4 groups independently selected from: $C_{1-3}$alkyl, —OH, —$CH_2OH$, —COO($C_{1-4}$ alkyl), —$CH(CH_3)_2OH$, =O, F, —$CONHCH_3$, O($C_{1-3}$ alkyl), —$CONH_2$, —NHCOO($C_{1-4}$alkyl), $CF_3$, —CON($C_{1-3}$alkyl)$_2$, —C≡C—, —$SO_2CH_3$, —$CH_2COOH$, —$NHSO_2CH_3$, or phenyl. More preferred are compounds where G is unsubstituted or substituted by 1-2 groups independently selected from the group consisting of: $C_{1-3}$ alkyl, HO-alkyl, alkoxycarbonyl, mono- or dialkylaminocarbonyl, and $HO_2C$-alkyl. For compounds of formula III-A-a in each of the above embodiments, the (S) stereochemistry at the morpholine 3-position is preferred.

Another embodiment relates to compounds of formula III-A-aa:

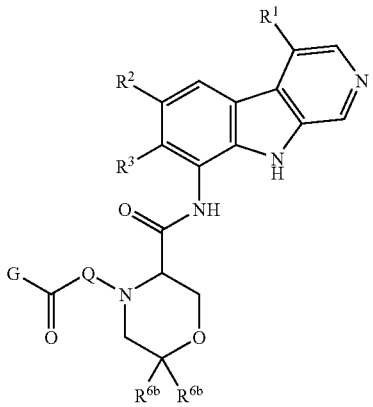

III-A-aa or a pharmaceutically acceptable salt thereof wherein,
Q is —CH$_2$— or —CH(R$^9$)—;
G is —NR$^4$R$^5$ or a 3-10 membered monocyclic or bicyclic heterocyclyl ring that is optionally substituted by 1-4 R$^{10}$;
R$^1$ is hydrogen, halo, C$_{1-2}$ alkyl, amino, or (C$_{1-2}$ alkyl)$_{1-2}$ amino;
R$^2$ is hydrogen, halo, C$_{1-4}$ aliphatic, C$_{1-2}$ alkoxy, or C$_{1-2}$ haloalkyl;
R$^3$ is hydrogen, halo, C$_{1-2}$ aliphatic, C$_{1-2}$ alkoxy, or C$_{1-2}$ haloalkyl;
R$^4$ is hydrogen or optionally substituted C$_{1-6}$ aliphatic;
R$^5$ is:
a) an optionally substituted group selected from aryl, heteroaryl, heterocyclyl, or carbocyclyl, or
b) a C$_{1-6}$ aliphatic group that is optionally substituted by: halo, —OR$^7$, —CN, —SR$^8$, —S(O)$_2$R$^8$, —C(O)R$^7$, —CO$_2$R$^7$, —N(R$^7$)$_2$, —C(O)N(R$^7$)$_2$, —N(R$^7$)C(O)R$^7$, —N(R$^7$)CO$_2$R$^8$, —SO$_2$N(R$^7$)$_2$, —NR$^7$SO$_2$R$^{7a}$, —N(R$^7$)C(O)N(R$^7$)$_2$, or an aryl, heteroaryl, heterocyclyl, or carbocyclyl group that is optionally further substituted by C$_{1-6}$aliphatic, —CF$_3$, halo, —OR$^7$, —CN, —SR$^8$, —S(O)$_2$R$^8$, —C(O)R$^7$, —CO$_2$R$^7$, —N(R$^7$)$_2$, —C(O)N(R$^7$)$_2$, —N(R$^7$)C(O)R$^7$, —N(R$^7$)CO$_2$R$^8$, —SO$_2$N(R$^7$)$_2$, —NR$^7$SO$_2$R$^{7a}$, —N(R$^7$)C(O)N(R$^7$)$_2$;
each R$^{6b}$ is independently selected from hydrogen or a C$_{1-6}$ aliphatic;
each R$^7$ is independently selected from hydrogen or an optionally substituted C$_{1-4}$ aliphatic, or two R$^7$ on the same nitrogen atom are taken together with the nitrogen to form an optionally substituted 3-6 membered heteroaryl or heterocyclyl ring;
each R$^{7a}$ is independently selected from hydrogen or an optionally substituted group selected from C$_{1-4}$ aliphatic, aryl, heteroaryl, heterocyclyl, or carbocyclyl, or two R$^{7a}$ on the same nitrogen atom are taken together with the nitrogen to form an optionally substituted 3-6 membered heteroaryl or heterocyclyl ring;
each R$^8$ is independently an optionally substituted C$_{1-4}$ aliphatic;
each R$^{8a}$ is independently an optionally substituted group selected from C$_{1-4}$ aliphatic, aryl, heteroaryl, heterocyclyl, or carbocyclyl;
R$^9$ is independently selected from a C$_{1-3}$ aliphatic;

each R$^{10}$ is independently selected from =O, R$^{11}$, T-R$^{11}$, or V-T-R$^{11}$, or two occurrences of R$^{10}$, taken together with the atom(s) to which they are bound, form an optionally substituted monocyclic or bicyclic 3-8-membered aryl, heteroaryl, heterocyclyl, or carbocyclyl ring;
each R$^{11}$ is independently selected from —CF$_3$, halo, —OR$^{7a}$, —CN, —SR$^{8a}$, —S(O)$_2$R$^{8a}$, —C(O)R$^{7a}$, —CO$_2$R$^{7a}$, —N(R$^{7a}$)$_2$, C(O)N(R$^{7a}$)$_2$, —N(R$^7$)C(O)R$^{7a}$, —N(R$^7$)CO$_2$R$^{7a}$, —SO$_2$N(R$^{7a}$)$_2$, —N(R$^7$)SO$_2$R$^{7a}$, —N(R$^7$)C(O)N(R$^{7a}$)$_2$ or an optionally substituted group selected from C$_{1-4}$ aliphatic, aryl, heteroaryl, heterocyclyl or carbocyclyl;
T is a straight or branched C$_{1-4}$alkylene chain; and
V is —O—, —N(R$^7$)—, —S—, —S(O)—, —S(O)$_2$—, —C(O)—, or —CO$_2$—.

Yet another embodiment relates to compounds of formula III-A-aa:

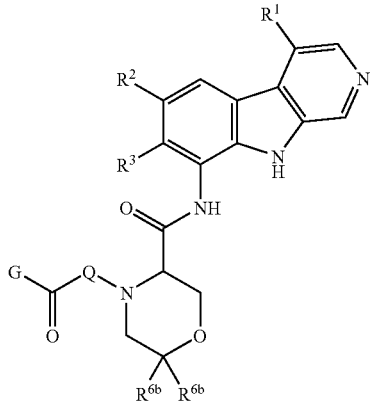

III-A-aa or a pharmaceutically acceptable salt thereof wherein,
Q is —CH$_2$— or —CH(R$^9$)—;
G is —NR$^4$R$^5$ or a 3-7 membered heterocyclyl ring that is optionally substituted by 1-4 R$^{10}$;
R$^1$ is hydrogen, halo, C$_{1-2}$ alkyl, amino, or (C$_{1-2}$ alkyl)$_{1-2}$ amino;
R$^2$ is hydrogen, halo, C$_{1-2}$ aliphatic, C$_{1-2}$ alkoxy, or C$_{1-2}$ haloalkyl;
R$^3$ is hydrogen, halo, C$_{1-2}$ aliphatic, C$_{1-2}$ alkoxy, or C$_{1-2}$ haloalkyl;
R$^4$ is hydrogen or C$_{1-6}$ aliphatic;
R$^5$ is a C$_{1-6}$ aliphatic group that is optionally substituted by halo, —OR$^7$, —CN, —SR$^8$, —S(O)$_2$R$^8$, —C(O)R$^7$, —CO$_2$R$^7$, —N(R$^7$)$_2$, —C(O)N(R$^7$)$_2$, —N(R$^7$)C(O)R$^7$, —N(R$^7$)CO$_2$R$^8$, or —N(R$^7$)C(O)N(R$^7$)$_2$;
each R$^{6b}$ is independently selected from hydrogen or a C$_{1-6}$ aliphatic;
each R$^7$ is independently selected from hydrogen or C$_{1-4}$ aliphatic, or two R$^7$ on the same nitrogen atom are taken together with the nitrogen to form a 5-6 membered heteroaryl or heterocyclyl ring;
R$^8$ is C$_{1-4}$ aliphatic;
R$^9$ is a C$_{1-3}$ aliphatic;
each R$^{10}$ is independently selected from =O, R$^{11}$, T-R$^{11}$, or V-T-R$^{11}$;
each R$^{11}$ is independently selected from C$_{1-6}$ aliphatic, —CF$_3$, halo, —OR$^7$, —CN, —SR$^8$, —S(O)$_2$R$^8$, —C(O)R$^7$, —CO$_2$R$^7$, —N(R$^7$)$_2$, —C(O)N(R$^7$)$_2$, —N(R$^7$)C(O)R$^7$, —N(R$^7$)CO$_2$R$^7$, or —N(R$^7$)C(O)N(R$^7$)$_2$;
T is a straight or branched C$_{1-4}$ alkylene chain; and
V is —O—, —N(R$^7$)—, —S—, —S(O)—, —S(O)$_2$—, —C(O)—, or —CO$_2$—.

Still another embodiment relates to compounds of formula III-A-aa:

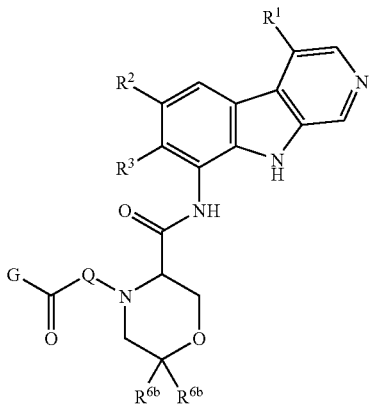

III-A-aa or a pharmaceutically acceptable salt thereof wherein,

Q is —CH$_2$—, or —CH(R$^9$)—;

G is —NR$^4$R$^5$ or a 3-7 membered heterocyclyl ring that is optionally substituted by 1-2 R$^{10}$;

R$^1$ is hydrogen, halo, C$_{1-2}$ alkyl, amino, or (C$_{1-2}$ alkyl)$_{1-2}$ amino;

R$^2$ is hydrogen, halo, C$_{1-2}$ aliphatic, C$_{1-2}$ alkoxy, or C$_{1-2}$ haloalkyl;

R$^3$ is hydrogen, halo, C$_{1-2}$ aliphatic, C$_{1-2}$ alkoxy, or C$_{1-2}$ haloalkyl;

R$^4$ is hydrogen or C$_{1-6}$ aliphatic;

R$^5$ is a C$_{1-6}$ aliphatic group that is optionally substituted by halo, —OR$^7$, —CN, —SR$^8$, —S(O)$_2$R$^8$, —C(O)R$^7$, —CO$_2$R$^7$, —N(R$^7$)$_2$, —C(O)N(R$^7$)$_2$, —N(R$^7$)C(O)R$^7$, —N(R$^7$)CO$_2$R$^8$, or —N(R$^7$)C(O)N(R$^7$)$_2$;

each R$^{6b}$ is independently selected from hydrogen or a C$_{1-6}$ aliphatic;

each R$^7$ is independently selected from hydrogen or C$_{1-4}$ aliphatic, or two R$^7$ on the same nitrogen atom are taken together with the nitrogen to form a 5-6 membered heteroaryl or heterocyclyl ring;

R$^8$ is C$_{1-4}$ aliphatic;

R$^9$ is independently selected from a C$_{1-3}$ aliphatic;

each R$^{10}$ is independently selected from R$^{11}$, T-R$^{11}$, or V-T-R$^{11}$;

each R$^{11}$ is independently selected from C$_{1-6}$ aliphatic, halo, —OR$^7$, —CN, —SR$^8$, —S(O)$_2$R$^8$, —C(O)R$^7$, —CO$_2$R$^7$, —N(R$^7$)$_2$, —C(O)N(R$^7$)$_2$, —N(R$^7$)C(O)R$^7$, —N(R$^7$)CO$_2$R$^7$ or —N(R$^7$)C(O)N(R$^7$)$_2$;

T is a straight or branched C$_{1-4}$ alkylene chain; and

V is —O—, —N(R$^7$)—, —S—, —S(O)—, —S(O)$_2$—, —C(O)—, or —CO$_2$—.

Yet another embodiment relates to compounds of formula III-A-aa where:

Q is —CH$_2$—;

G is —NR$^4$R$^5$ or a 5-6 membered heterocyclyl ring that is optionally substituted by 1-4 R$^{10}$;

R$^1$ is hydrogen, halo or methyl;

R$^2$ is hydrogen, halo, C$_{1-4}$ aliphatic, C$_{1-2}$ alkoxy, or C$_{1-2}$ haloalkyl;

R$^3$ is hydrogen;

R$^4$ is hydrogen or C$_{1-6}$ aliphatic;

R$^5$ is:

a) an optionally substituted group selected from aryl, heteroaryl, heterocyclyl, or carbocyclyl, or b) a C$_{1-6}$ aliphatic group that is optionally substituted by: halo, —OR$^7$, —CN, —SR$^8$, —S(O)$_2$R$^8$, —C(O)R$^7$, —CO$_2$R$^7$, —N(R$^7$)$_2$—C(O)N(R$^7$)$_2$, —N(R$^7$)C(O) R$^7$, —N(R$^7$)CO$_2$R$^8$, —SO$_2$N(R$^7$)$_2$, —NR$^7$SO$_2$R$^7$, —N(R$^7$)C(O)N(R$^7$)$_2$, or an aryl, heteroaryl, heterocyclyl, or carbocyclyl group that is optionally further substituted by C$_{1-6}$aliphatic, —CF$_3$, halo, —OR$^7$, —CN, —SR$^8$, —S(O)$_2$R$^8$, —C(O)R$^7$, —C$_2$R$^7$, —N(R$^7$)$_2$,—C(O)N(R$^7$)$_2$,—N(R$^7$)C(O)R$^7$,—N(R$^7$) CO$_2$R$^8$, —SO$_2$N(R$^7$)$_2$, —NR$^7$SO$_2$R$^7$, —N(R$^7$)C(O) N(R$^7$)$_2$;

each R$^{6b}$ is independently selected from hydrogen or a C$_{1-6}$ aliphatic;

each R$^7$ is independently selected from hydrogen or an optionally substituted C$_{1-4}$ aliphatic, or two R$^7$ on the same nitrogen atom are taken together with the nitrogen to form an optionally substituted 3-6 membered heteroaryl or heterocyclyl ring;

each R$^{7a}$ is independently selected from hydrogen or an optionally substituted group selected from C$_{1-4}$ aliphatic, aryl, heteroaryl, heterocyclyl, or carbocyclyl, or two R$^{7a}$ on the same nitrogen atom are taken together with the nitrogen to form an optionally substituted 3-6 membered heteroaryl or heterocyclyl ring;

each R$^8$ is independently an optionally substituted C$_{1-4}$ aliphatic;

each R$^{8a}$ is independently an optionally substituted group selected from C$_{1-4}$ aliphatic, aryl, heteroaryl, heterocyclyl, or carbocyclyl;

each R$^{10}$ is independently selected from =O, R$^{11}$, T-R$^{11}$, or V-T-R$^{11}$, or two occurrences of R$^{10}$, taken together with the atom(s) to which they are bound, form an optionally substituted monocyclic or bicyclic 3-8-membered aryl, heteroaryl, heterocyclyl, or carbocyclyl ring;

each R$^{11}$ is independently selected from —CF$_3$, halo, —OR$^7$, —CN, —SR$^8$, —S(O)$_2$R$^{8a}$, —C(O)R$^{7a}$, —CO$_2$R$^{7a}$, —N(R$^{7a}$)$_2$, C(O)N(R$^{7a}$)$_2$, —N(R$^7$)C(O)R$^{7a}$, —N(R$^7$) CO$_2$R$^{7a}$, —SO$_2$N(R$^{7a}$)$_2$, —N(R$^7$)SO$_2$R$^{7a}$, —N(R$^7$)C(O)N (R$^{7a}$)$_2$ or an optionally substituted group selected from C$_{1-6}$aliphatic, aryl, heteroaryl, heterocyclyl or carbocyclyl;

T is a straight or branched C$_{1-4}$ alkylene chain; and

V is —O—, —N(R$^7$)—, —S—, —S(O)—, —S(O)$_2$—, —C(O)—, or —CO$_2$—.

Another embodiment relates to compounds of formula III-A-aa where:

Q is —CH$_2$—;

G is —NR$^4$R$^5$ or a 5-6 membered heterocyclyl ring that is optionally substituted by 1-2 R$^{10}$;

R$^1$ is hydrogen, halo or methyl;

R$^2$ is hydrogen, halo, C$_{1-2}$ aliphatic, C$_{1-2}$ alkoxy, or C$_{1-2}$ haloalkyl;

R$^3$ is hydrogen;

R$^4$ is hydrogen or C$_{1-6}$ aliphatic;

R$^5$ is a C$_{1-6}$ aliphatic group that is optionally substituted by halo, —OR$^7$, —CN, —SR$^8$, —S(O)$_2$R$^8$, —C(O)R$^7$, —CO$_2$R$^7$, —N(R$^7$)$_2$, —C(O)N(R$^7$)$_2$, —N(R$^7$)C(O)R$^7$, —N(R$^7$)CO$_2$R$^8$, or —N(R$^7$)C(O)N(R$^7$)$_2$;

each R$^{6b}$ is independently selected from hydrogen or a C$_{1-6}$ aliphatic;

each R$^7$ is independently selected from hydrogen or C$_{1-4}$ aliphatic, or two R$^7$ on the same nitrogen atom are taken together with the nitrogen to form a 5-6 membered heteroaryl or heterocyclyl ring;

R$^8$ is C$_{1-4}$ aliphatic;

each R$^{10}$ is independently selected from R$^{11}$, T-R$^{11}$, or V-T-R$^{11}$;

each R$^{11}$ is independently selected from C$_{1-6}$ aliphatic, halo, —OR$^7$, —CN, —SR$^8$, —S(O)$_2$R$^8$, —C(O)R$^7$, —CO₂R⁷, —N(R⁷)₂, —C(O)N(R⁷)₂, —N(R⁷)C(O)R⁷, —N(R⁷)CO₂R⁷, or —N(R⁷)C(O)N(R⁷)₂;

T is a straight or branched $C_{1-4}$ alkylene chain; and

V is —O—, —N(R⁷)—, —S—, —S(O)—, —S(O)₂—, —C(O)—, or —CO₂—.

Preferred compounds of III-A-aa are compounds where:

Q is —CH₂—;

G is selected from an optionally substituted piperidinyl, piperazinyl, morpholinyl, pyrrolidinyl, or —NR⁴R⁵;

R¹ is hydrogen, halo or methyl;

R² is halo;

R³ is hydrogen;

R⁴ is hydrogen or $C_{1-6}$ aliphatic;

R⁵ is $C_{1-6}$ alkoxy, $C_{1-6}$ aliphatic, or $C_{1-6}$ hydroxyalkyl;

each $R^{6b}$ is independently selected from hydrogen or a $C_{1-3}$ aliphatic. Preferably, each $R^{6b}$ is hydrogen or methyl.

In preferred compounds of formula III-A-aa, G is a 3-7-membered nitrogen containing heterocyclyl ring that is optionally substituted by 1-4 R¹⁰. In other preferred embodiments, G is a 3-7-membered nitrogen containing heterocyclyl ring that is optionally substituted by 1-2 R¹⁰. In yet other preferred embodiments, the 3-7-membered nitrogen containing heterocyclyl ring is a 3-7-membered nitrogen containing N-linked heterocyclyl that is optionally substituted by 1-4 R¹⁰. In still other preferred embodiments, the 3-7-membered nitrogen containing heterocyclyl ring is a 3-7-membered nitrogen containing N-linked heterocyclyl that is optionally substituted by 1-2 R¹⁰.

In preferred compounds of formula III-A-aa, G is unsubstituted or substituted by 1-4 groups independently selected from: $C_{1-3}$ alkyl, —OH, —CH₂OH, —COO($C_{1-4}$alkyl), —CH(CH₃)₂OH, =O, F, —CONHCH₃, O($C_{1-3}$alkyl), —CONH₂, —NHCOO($C_{1-4}$alkyl), —CF₃, —CON($C_{1-3}$alkyl)₂, —C≡CH, —SO₂CH₃, —CH₂COOH, —NHSO₂CH₃, or phenyl. In other preferred embodiments, G is unsubstituted or substituted by 1-2 groups independently selected from the group consisting of: $C_{1-3}$ alkyl, HO-alkyl, alkoxycarbonyl, mono- or dialkylaminocarbonyl, and HO₂C-alkyl.

For compounds of formula III-A-aa in each of the above embodiments, the (S) stereochemistry is preferred at the three position of the Ring A morpholine.

Examples of specific formula I compounds are shown in Tables 3 and 4 below. For compounds in Table 3 and Table 4 (and compounds generally described and exemplified elsewhere in the specification) a methyl group may be represented by —CH₃, -Me, or by a single line (as exemplified in compounds 64-207) without the hydrogen atoms specifically exemplified.

TABLE 3

Specific examples of formula I compounds

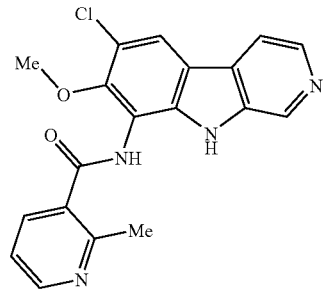

1

TABLE 3-continued

Specific examples of formula I compounds

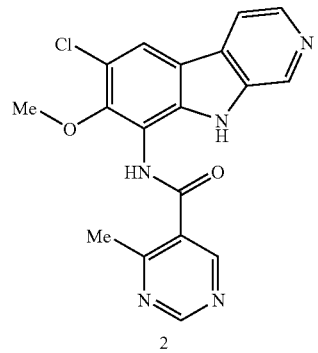

2

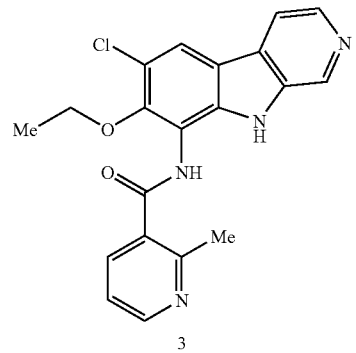

3

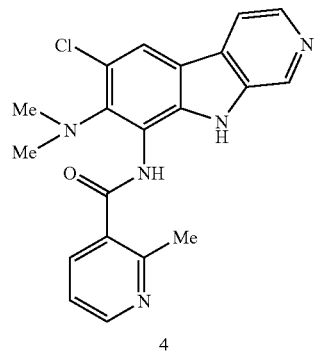

4

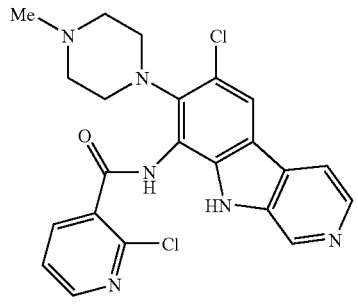

5

TABLE 3-continued
Specific examples of formula I compounds
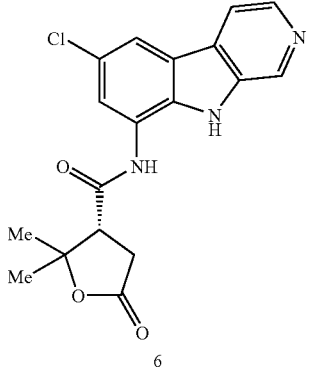
6
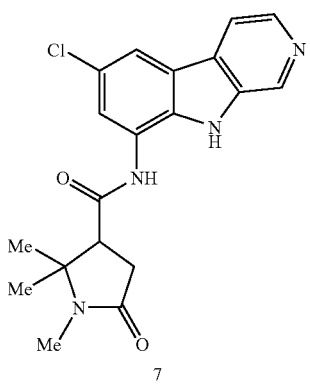
7
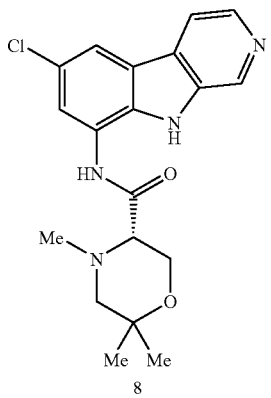
8
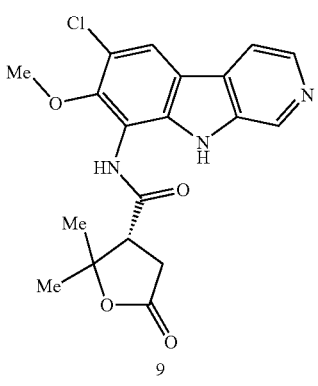
9
TABLE 3-continued
Specific examples of formula I compounds
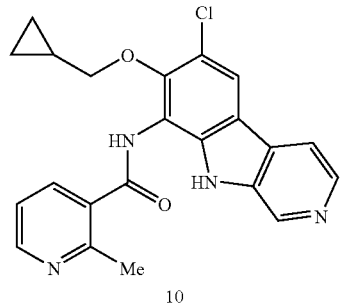
10
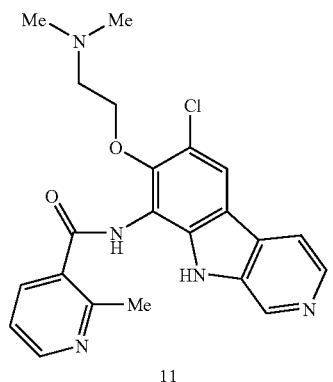
11
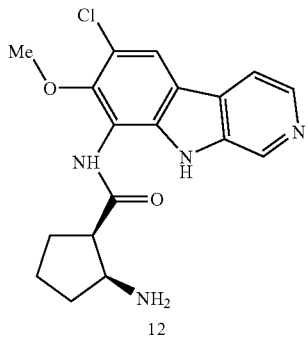
12
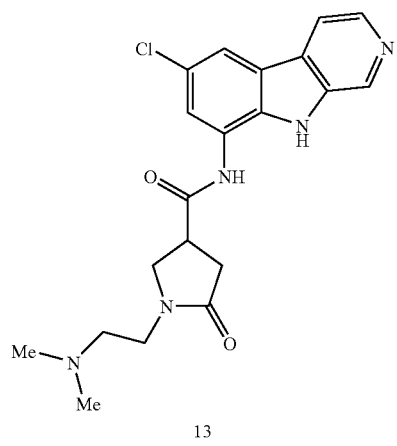
13

TABLE 3-continued
Specific examples of formula I compounds
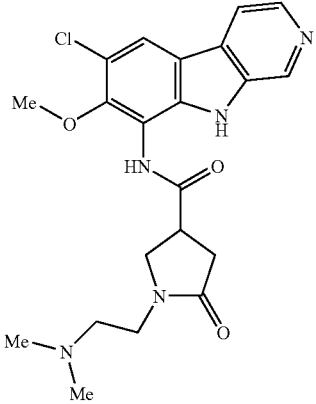
14
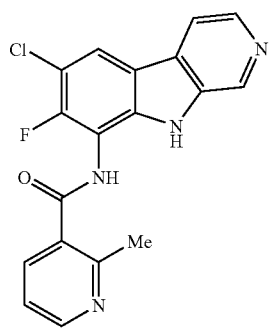
15
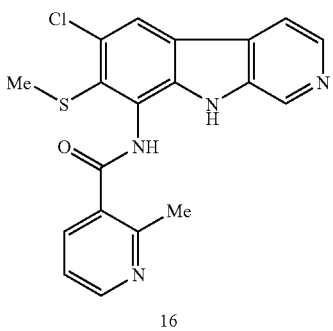
16
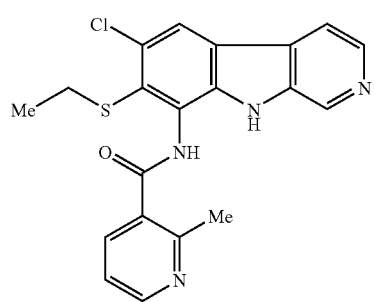
17
TABLE 3-continued
Specific examples of formula I compounds
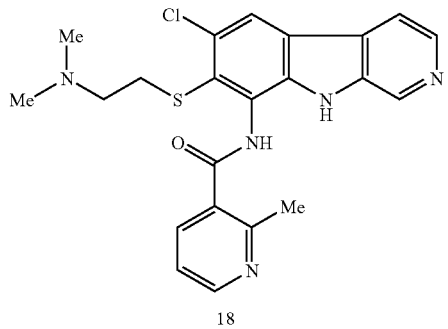
18
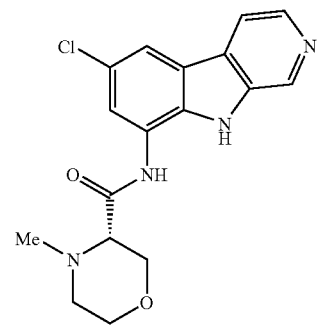
19
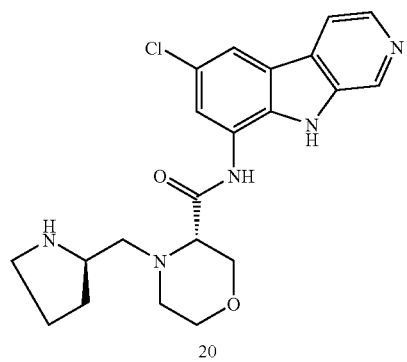
20
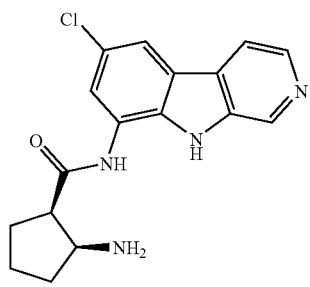
21

TABLE 3-continued
Specific examples of formula I compounds
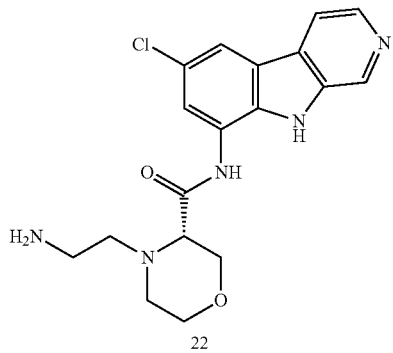
22
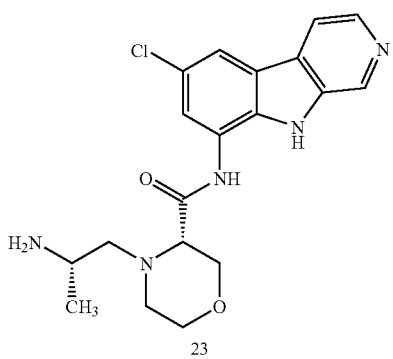
23
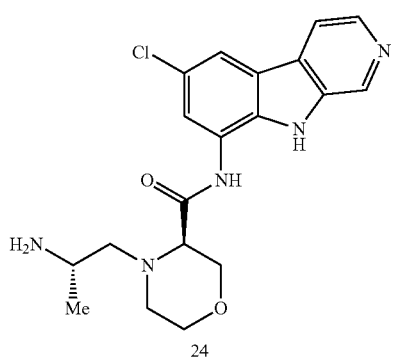
24
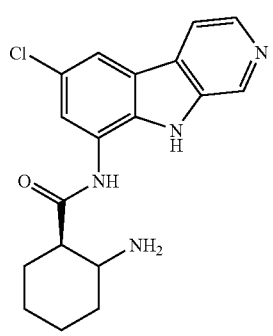
25
TABLE 3-continued
Specific examples of formula I compounds
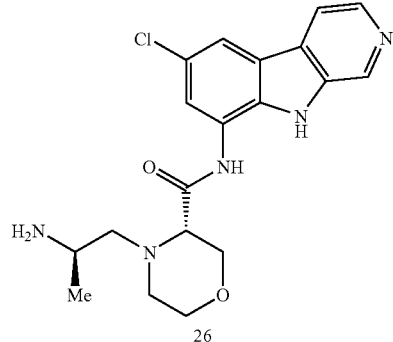
26
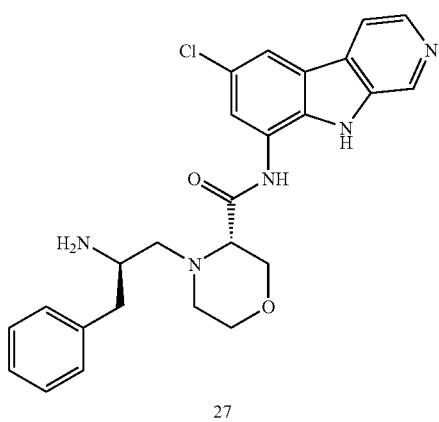
27
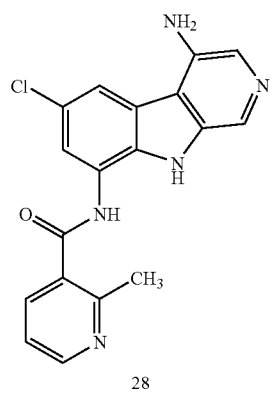
28
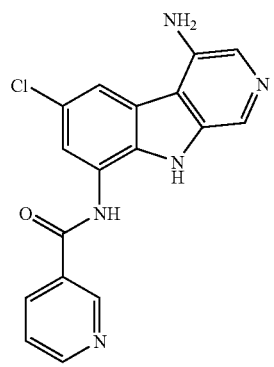
29

TABLE 3-continued
Specific examples of formula I compounds
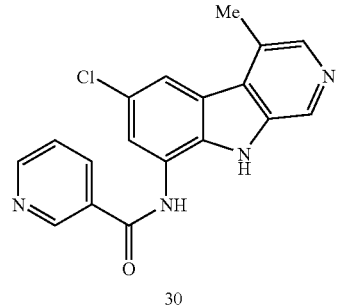
30
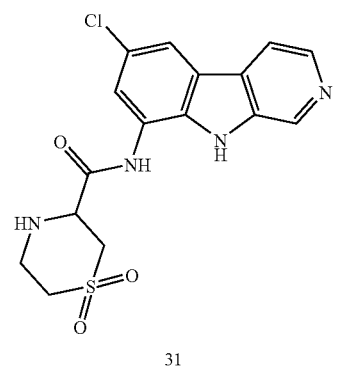
31
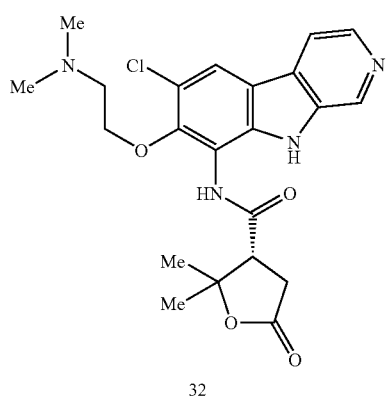
32
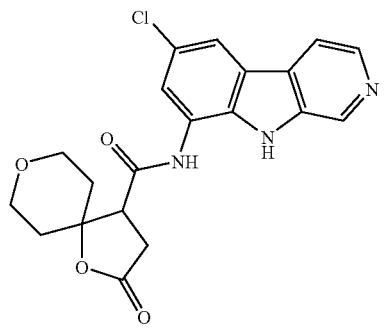
33
TABLE 3-continued
Specific examples of formula I compounds
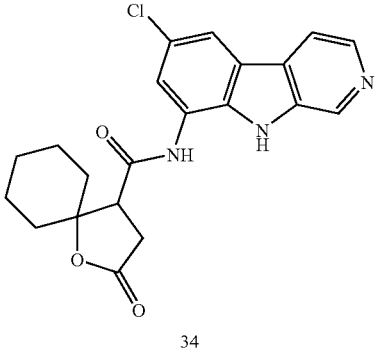
34
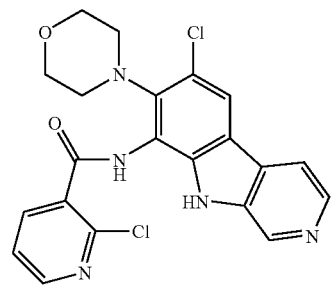
35
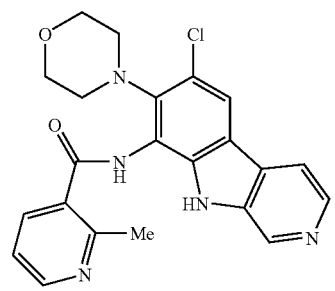
36
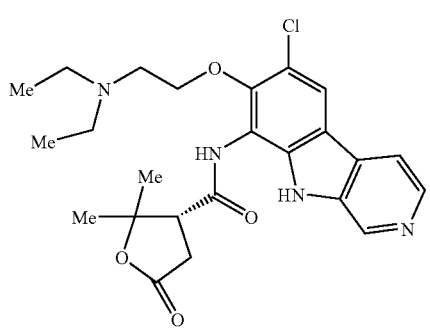
37

TABLE 3-continued

Specific examples of formula I compounds 38, 39, 40, 41, 42, 43, 44, 45

TABLE 3-continued

Specific examples of formula I compounds 46, 47, 48, 49, 50, 51, 52, 53

TABLE 3-continued
Specific examples of formula I compounds
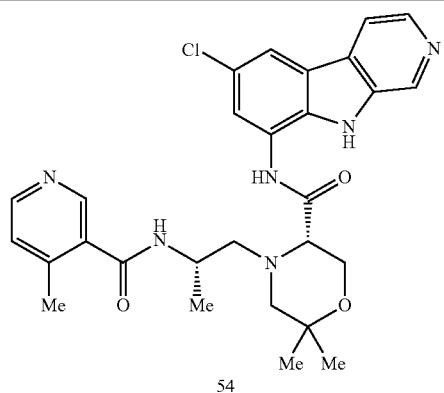
54
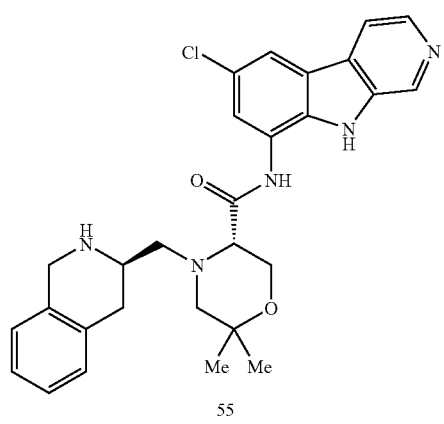
55
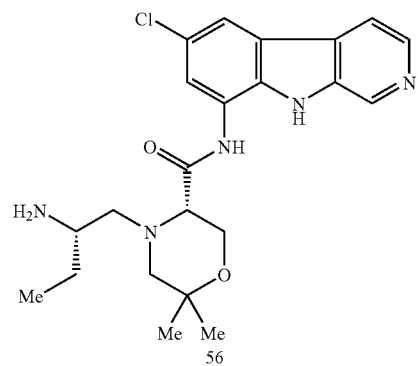
56
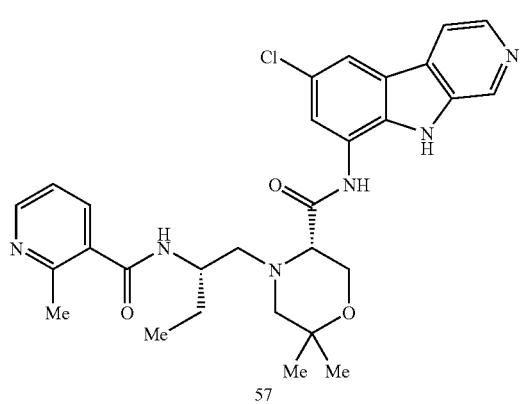
57
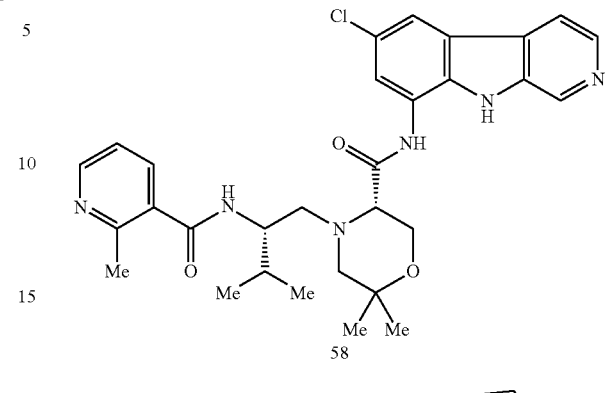
58
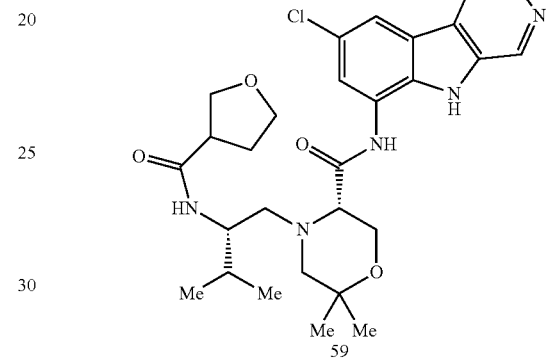
59
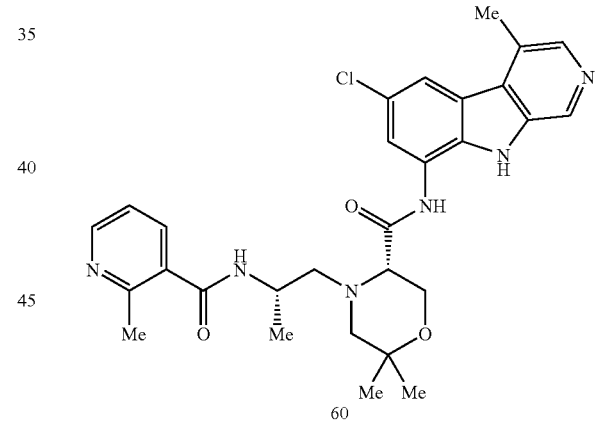
60
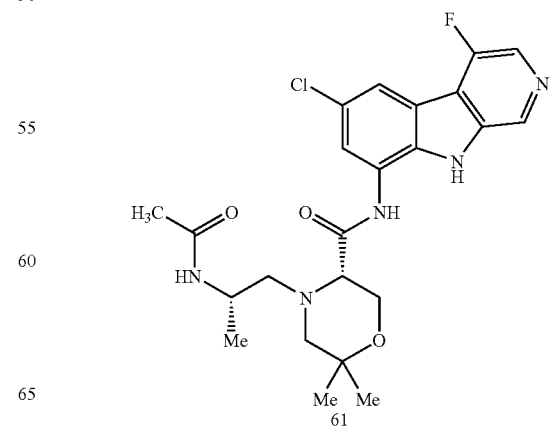
61

TABLE 3-continued
Specific examples of formula I compounds
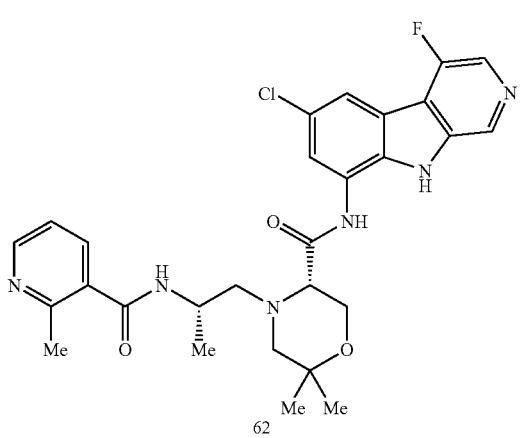
62
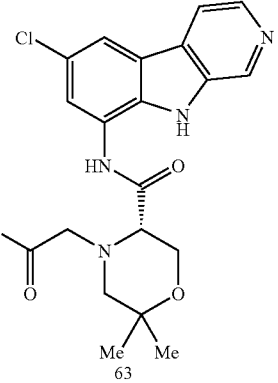
63
Table 4 below shows specific examples of III-A-aa compounds.
TABLE 4
Specific examples of formula III-A-aa compounds
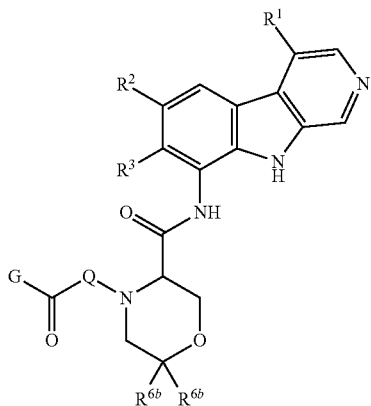
III-A-aa
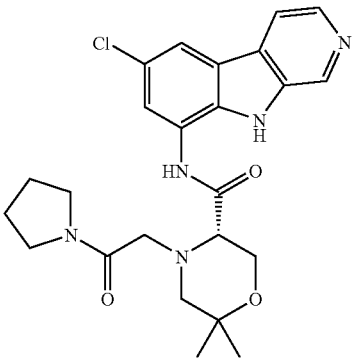
64

TABLE 4-continued
Specific examples of formula III-A-aa compounds
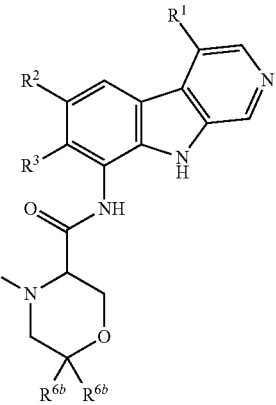
III-A-aa
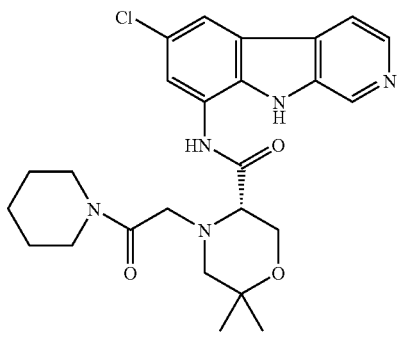
65
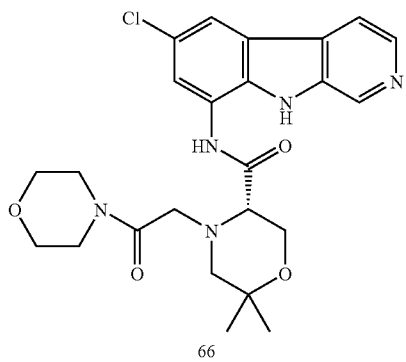
66
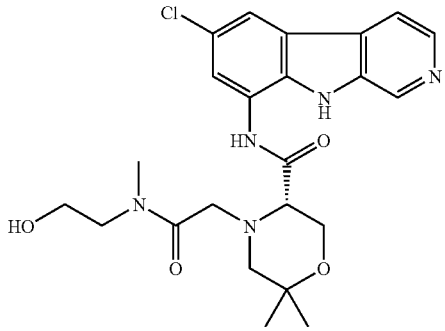
64

TABLE 4-continued
Specific examples of formula III-A-aa compounds
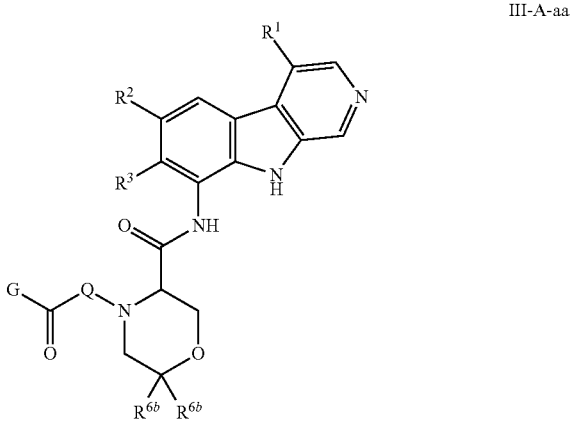
III-A-aa
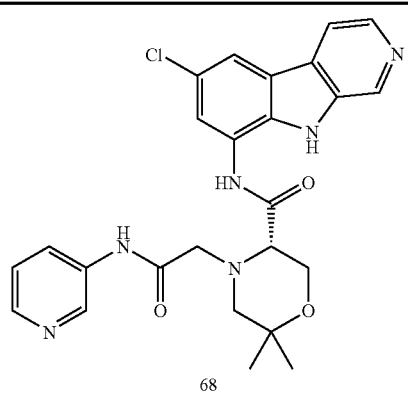
68
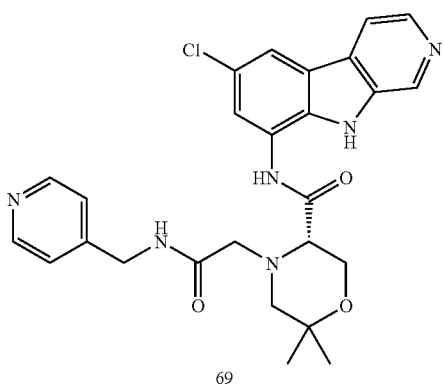
69
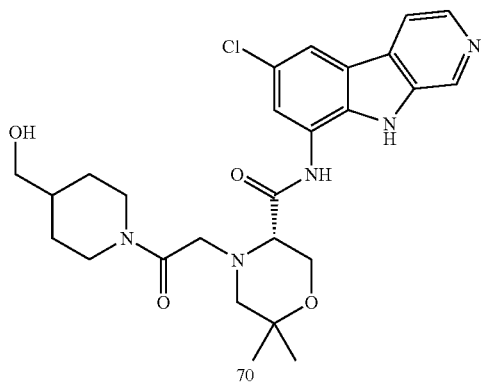
70

TABLE 4-continued
Specific examples of formula III-A-aa compounds
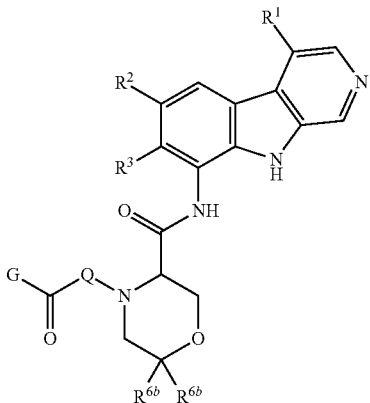
III-A-aa
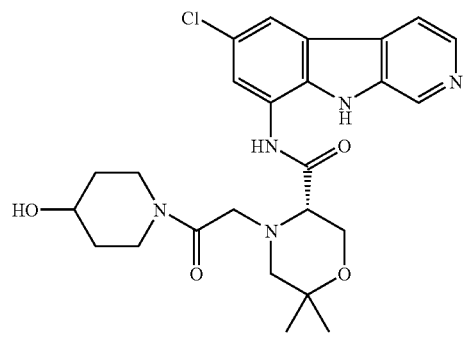
71
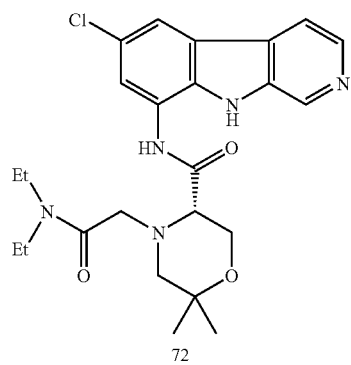
72
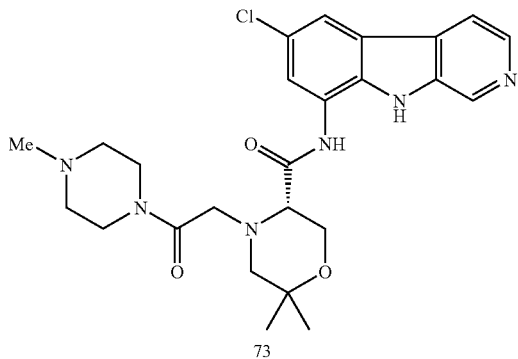
73

TABLE 4-continued
Specific examples of formula III-A-aa compounds
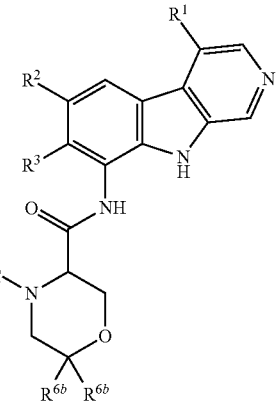
III-A-aa
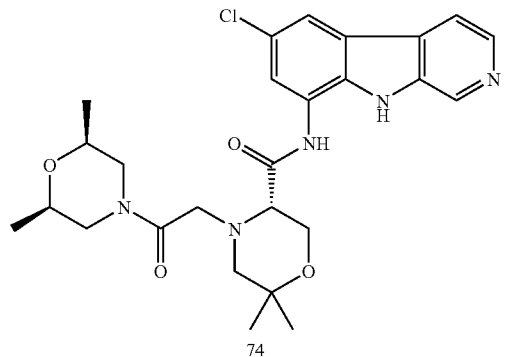
74
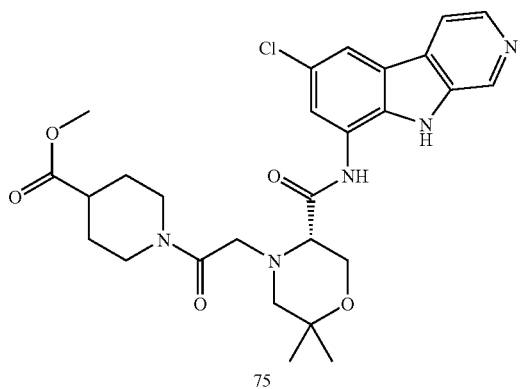
75
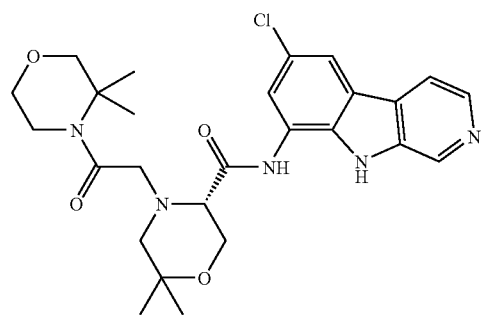
76

TABLE 4-continued
Specific examples of formula III-A-aa compounds
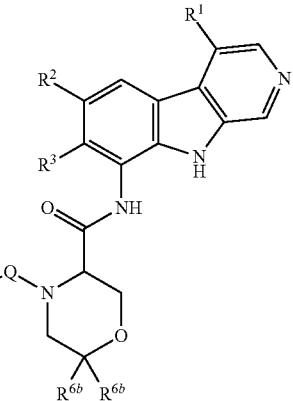
III-A-aa
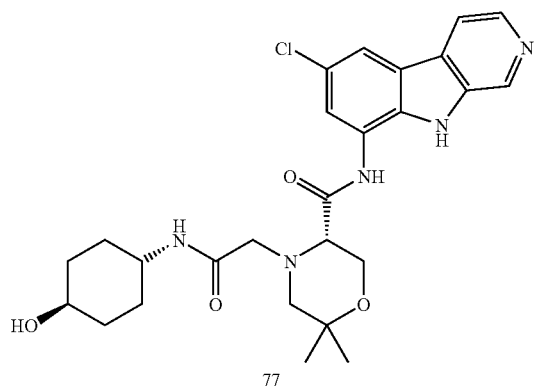
77
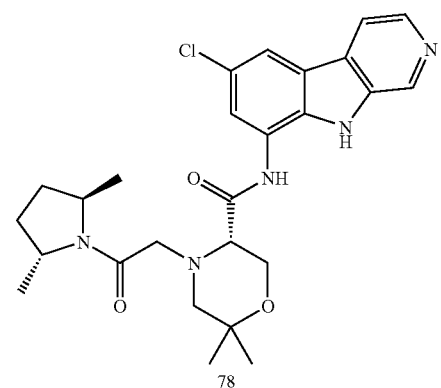
78
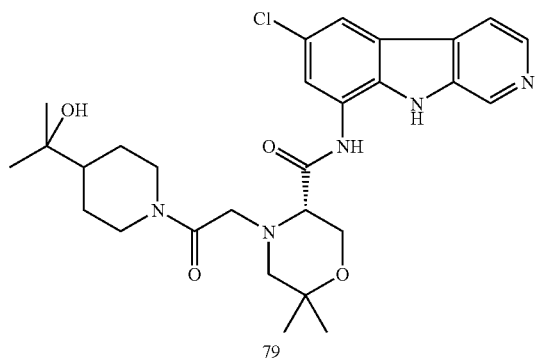
79

TABLE 4-continued
Specific examples of formula III-A-aa compounds
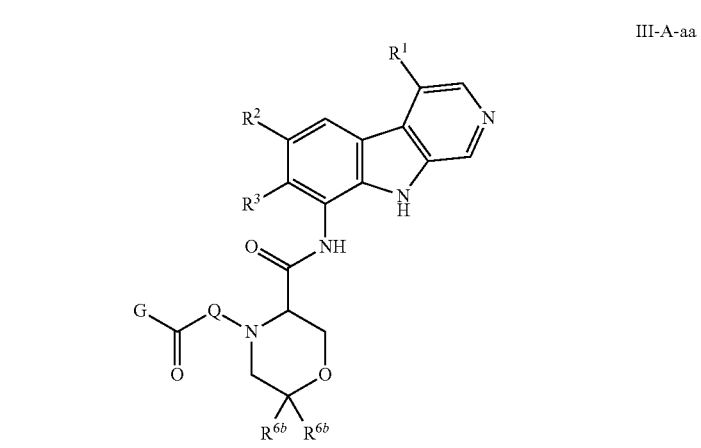
III-A-aa
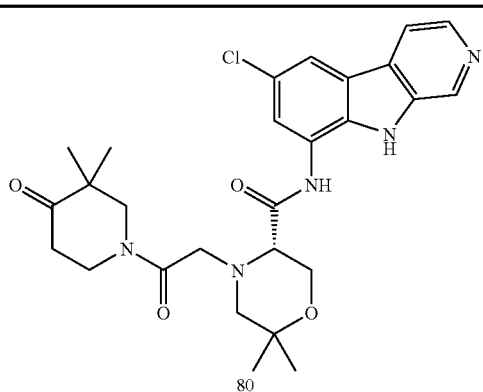
80
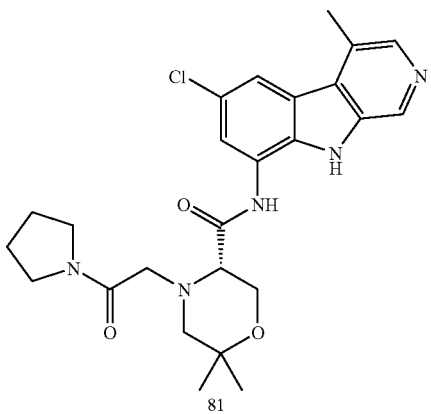
81
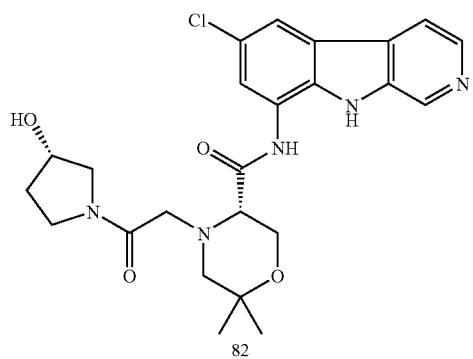
82

TABLE 4-continued
Specific examples of formula III-A-aa compounds
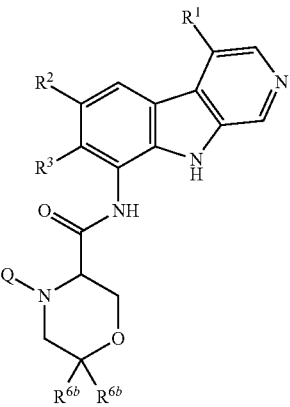
III-A-aa
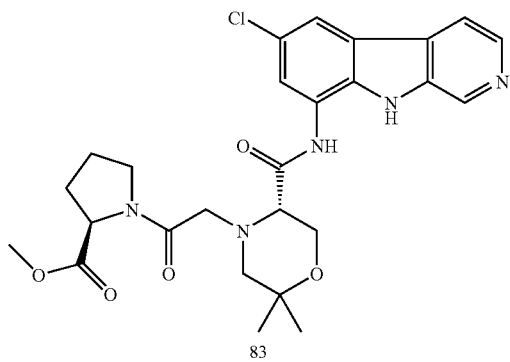
83
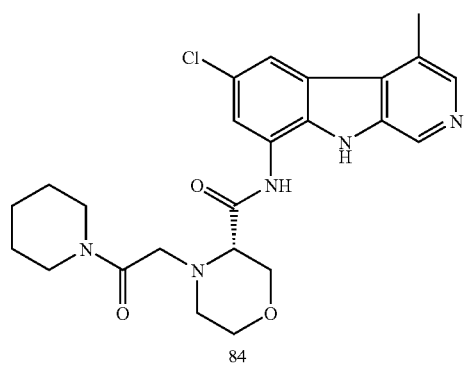
84
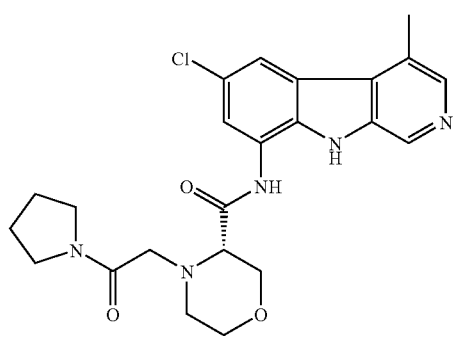
85

TABLE 4-continued
Specific examples of formula III-A-aa compounds
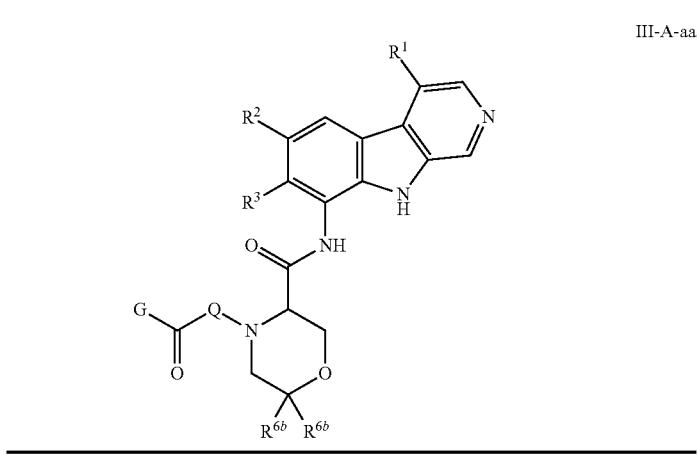
III-A-aa
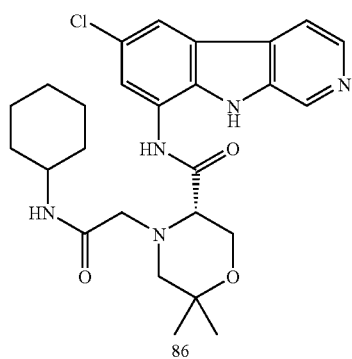
86
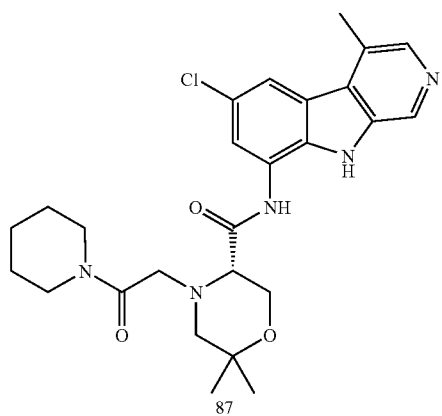
87
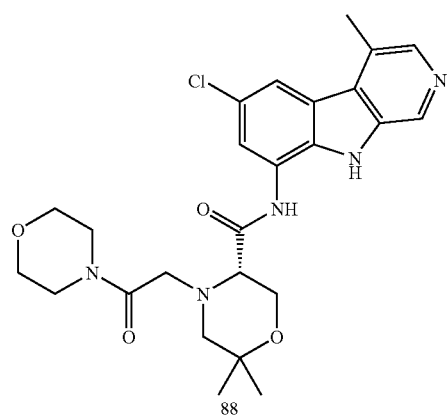
88

TABLE 4-continued
Specific examples of formula III-A-aa compounds
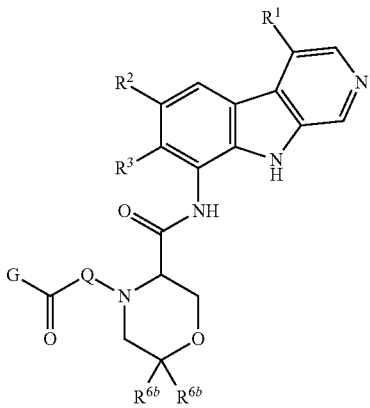
III-A-aa
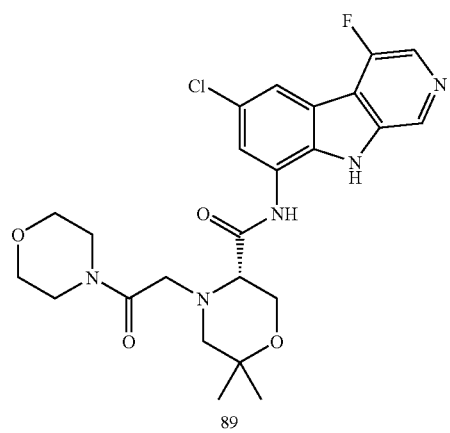
89
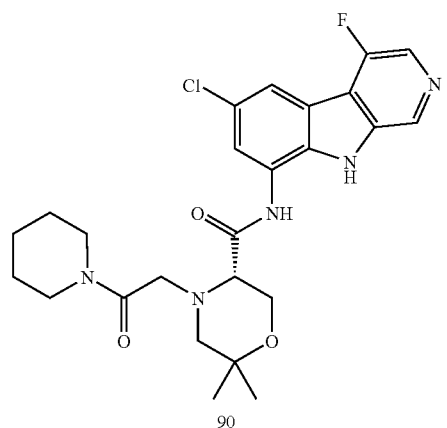
90

TABLE 4-continued
Specific examples of formula III-A-aa compounds
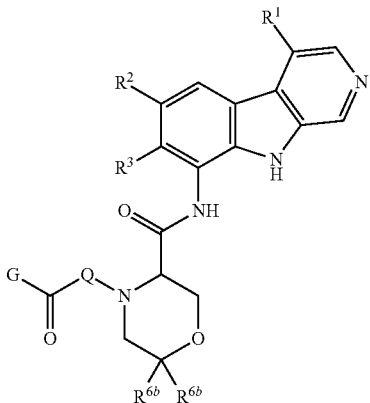
III-A-aa
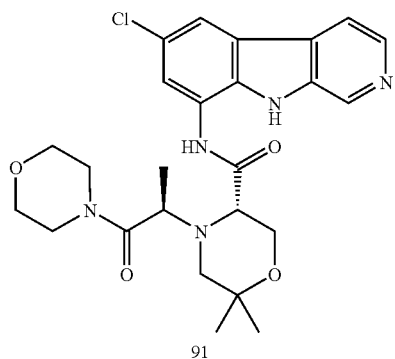
91
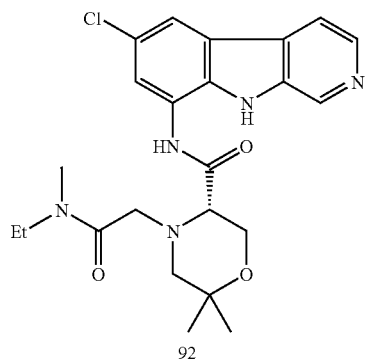
92
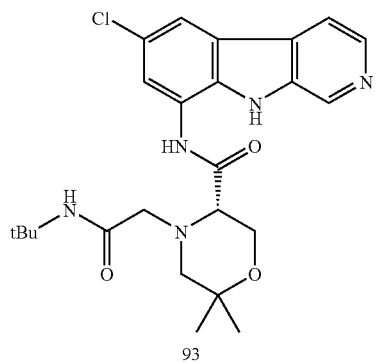
93

TABLE 4-continued
Specific examples of formula III-A-aa compounds
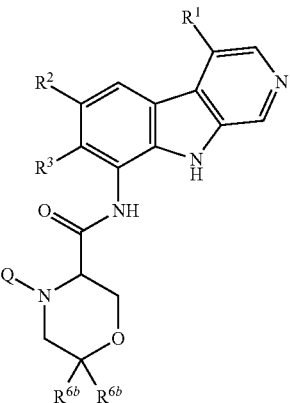
III-A-aa
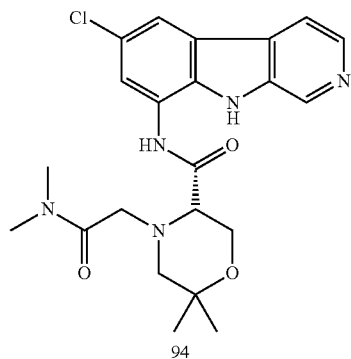
94
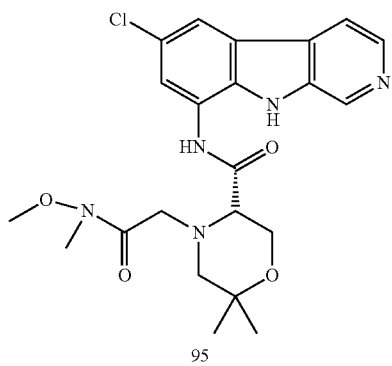
95
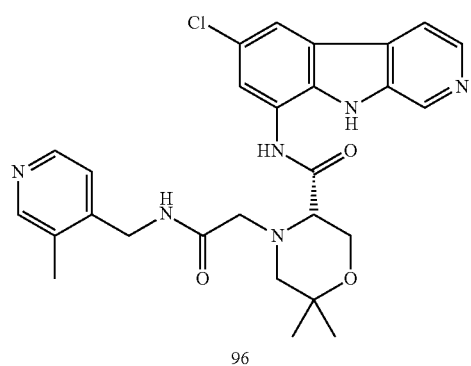
96

TABLE 4-continued
Specific examples of formula III-A-aa compounds
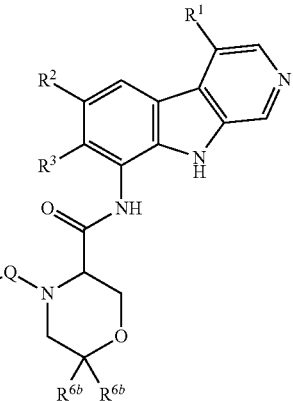
III-A-aa
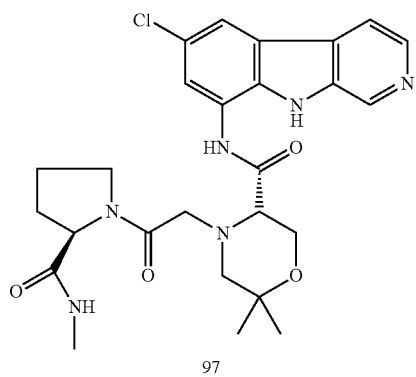
97
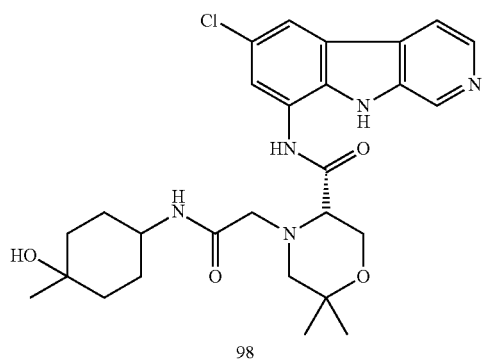
98
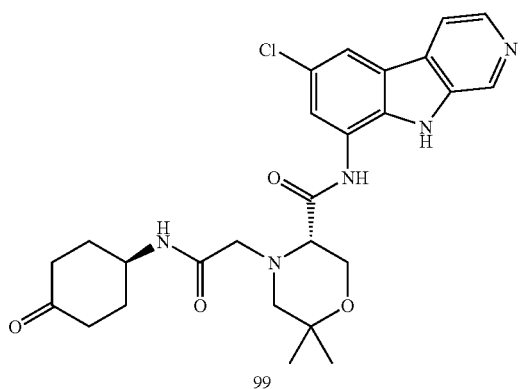
99

TABLE 4-continued
Specific examples of formula III-A-aa compounds
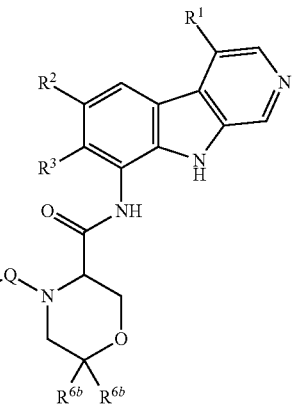
III-A-aa
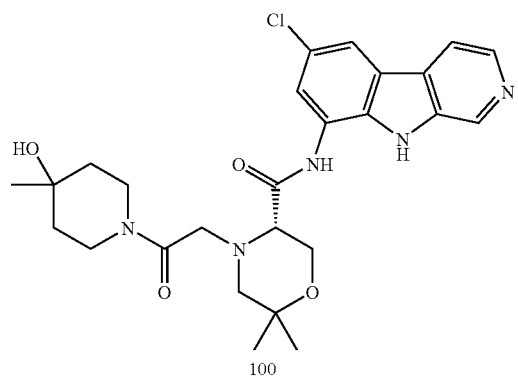
100
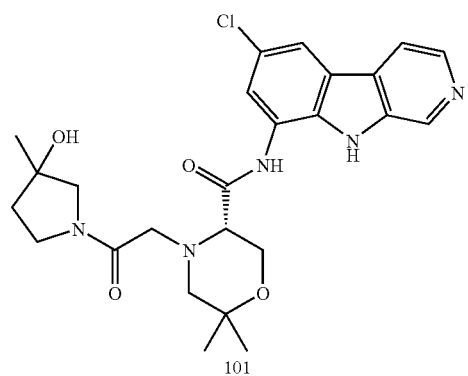
101
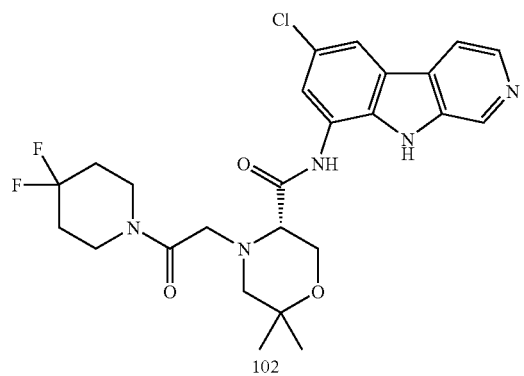
102

TABLE 4-continued
Specific examples of formula III-A-aa compounds
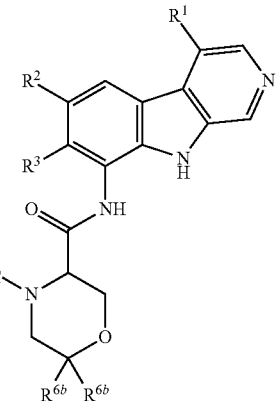
III-A-aa
103
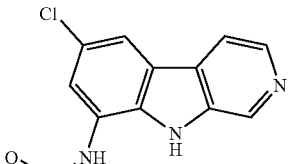
104
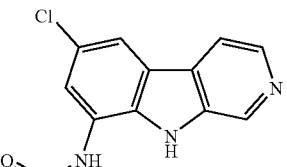
105

TABLE 4-continued
Specific examples of formula III-A-aa compounds
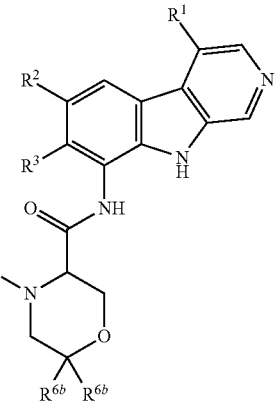
III-A-aa
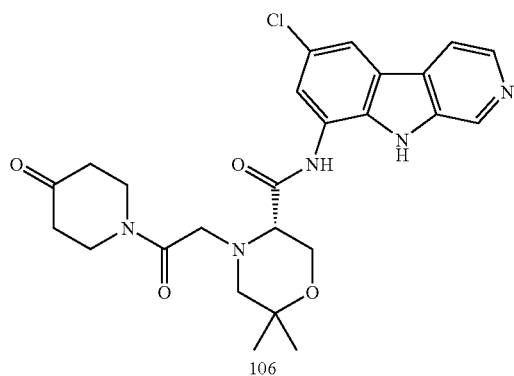
106
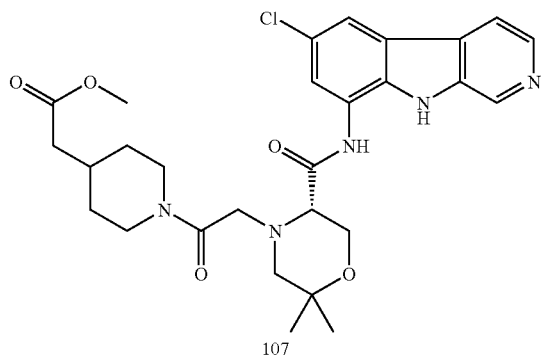
107
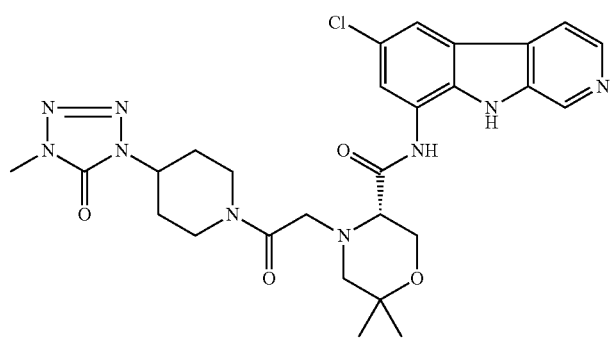
108

TABLE 4-continued
Specific examples of formula III-A-aa compounds
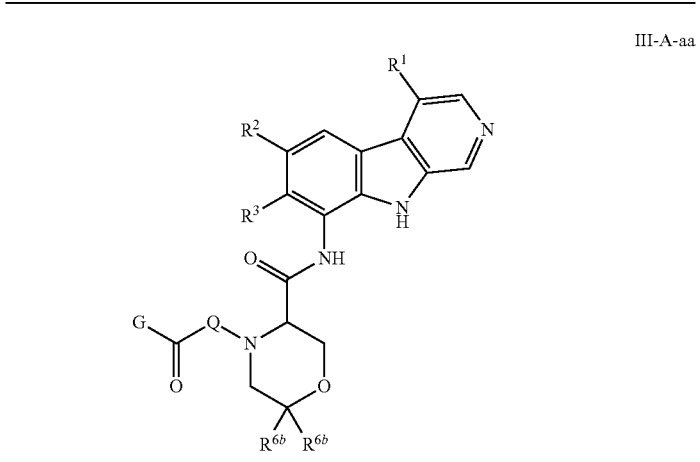
III-A-aa
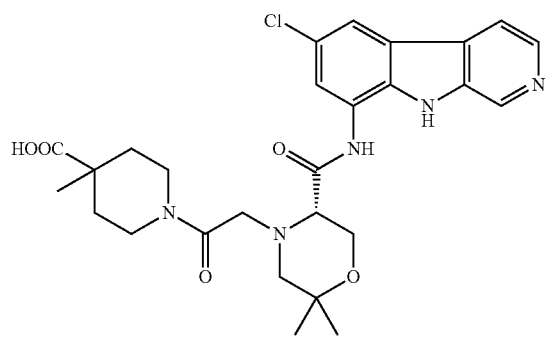
109
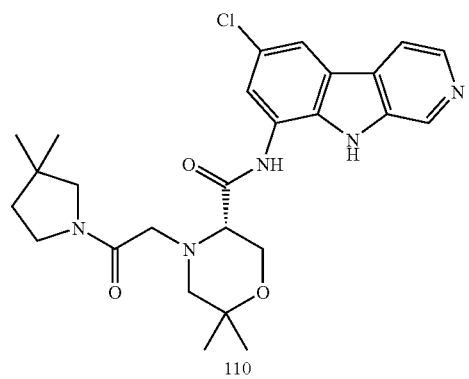
110
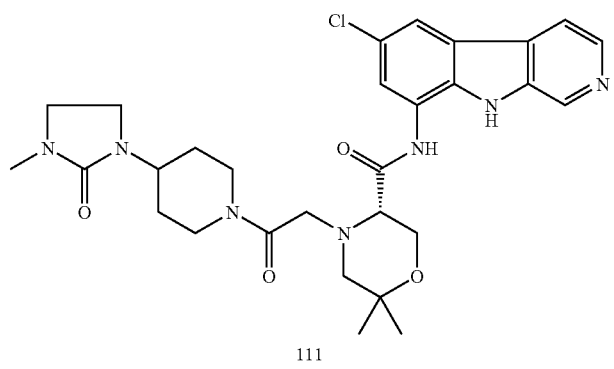
111

TABLE 4-continued
Specific examples of formula III-A-aa compounds
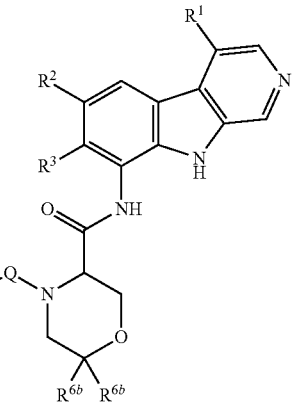
III-A-aa
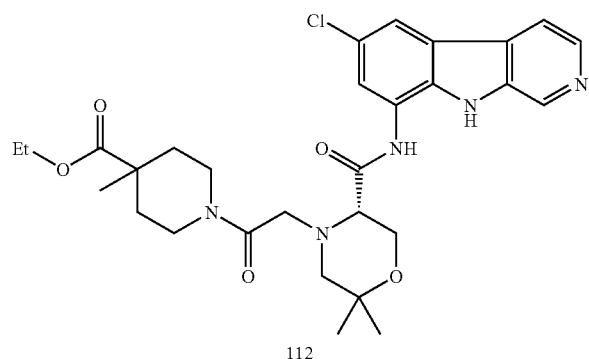
112
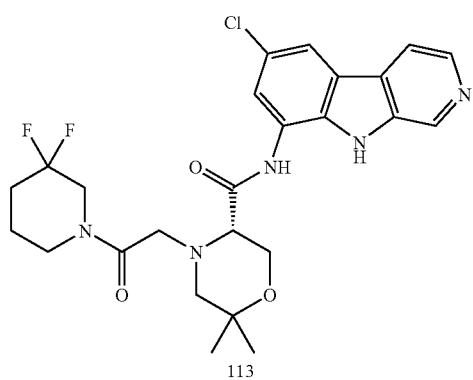
113
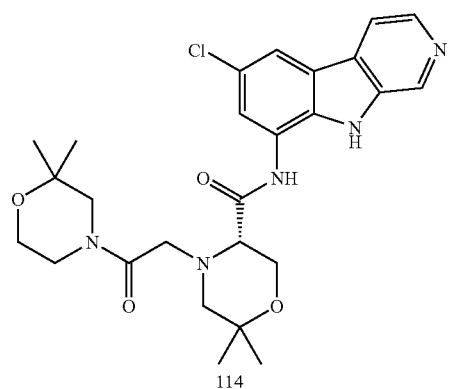
114

TABLE 4-continued
Specific examples of formula III-A-aa compounds
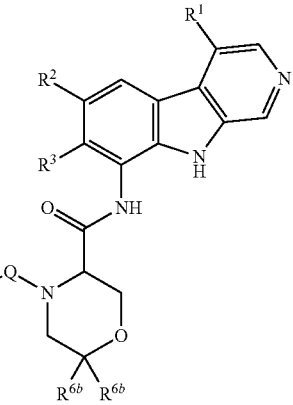
III-A-aa
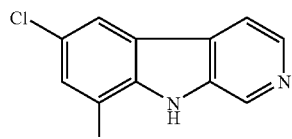
115
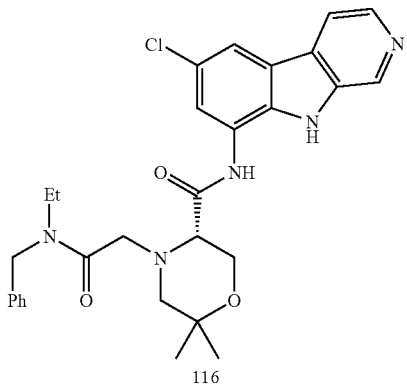
116
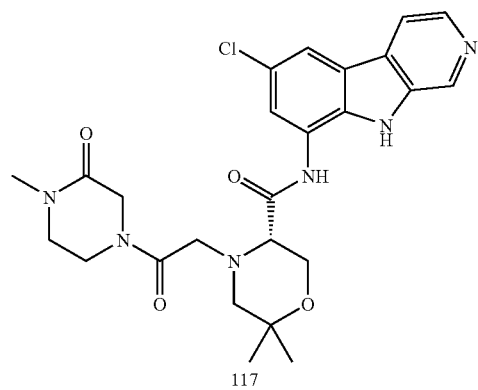
117

TABLE 4-continued
Specific examples of formula III-A-aa compounds
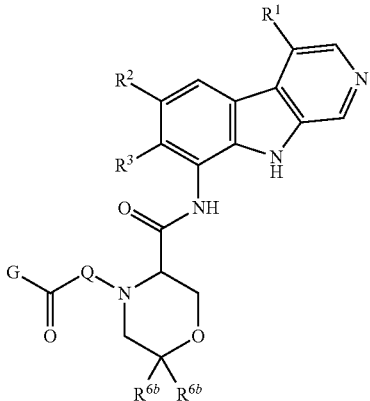
III-A-aa
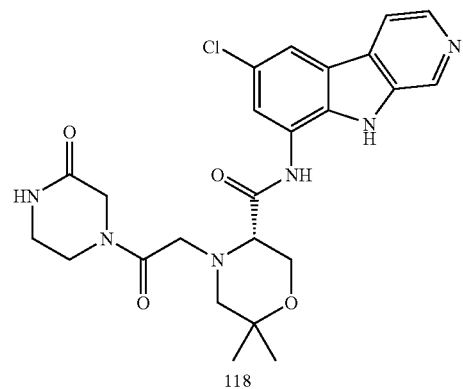
118
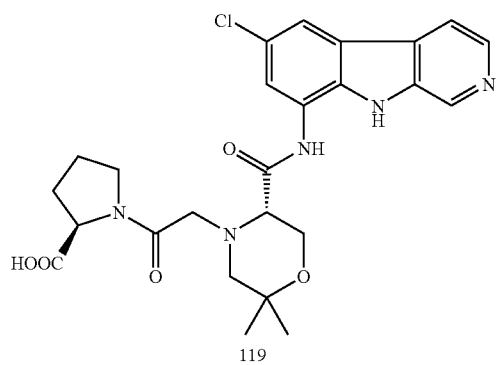
119
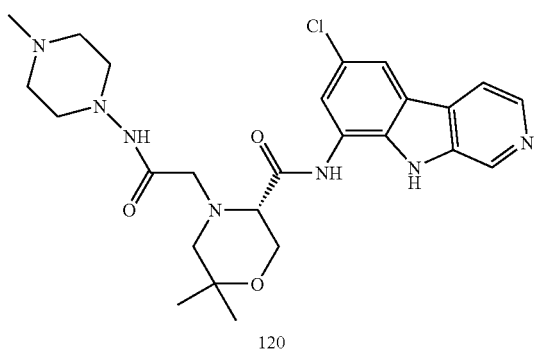
120

TABLE 4-continued
Specific examples of formula III-A-aa compounds
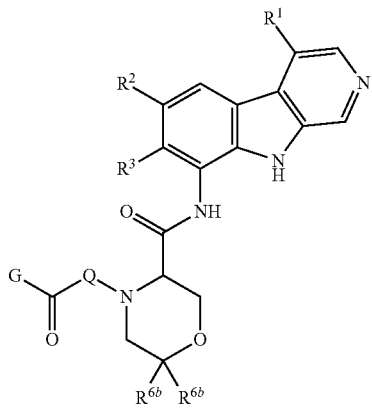
III-A-aa
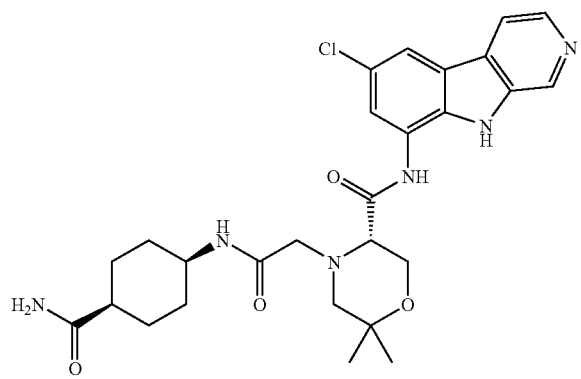
121
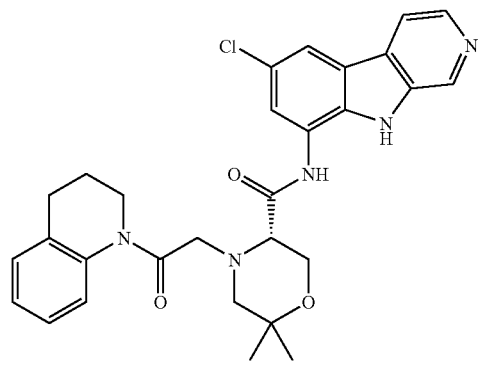
122

TABLE 4-continued
Specific examples of formula III-A-aa compounds
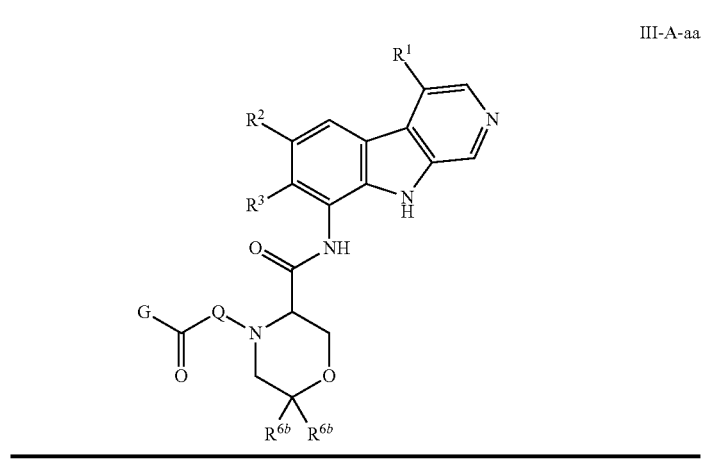
III-A-aa
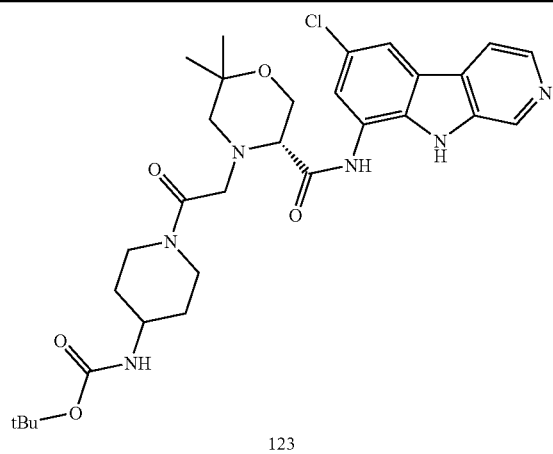
123
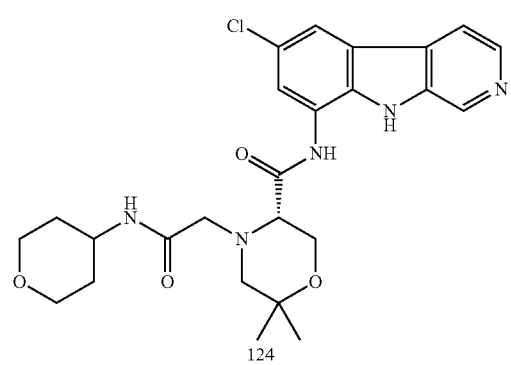
124
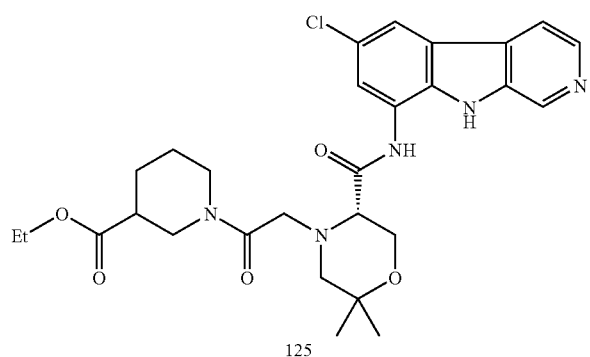
125

TABLE 4-continued
Specific examples of formula III-A-aa compounds
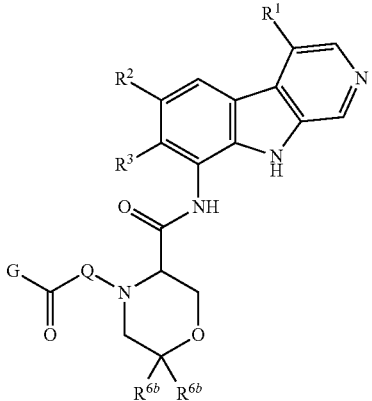
III-A-aa
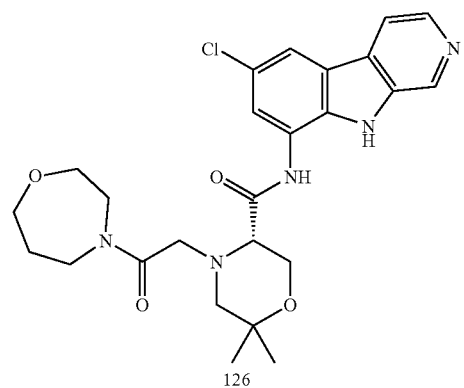
126
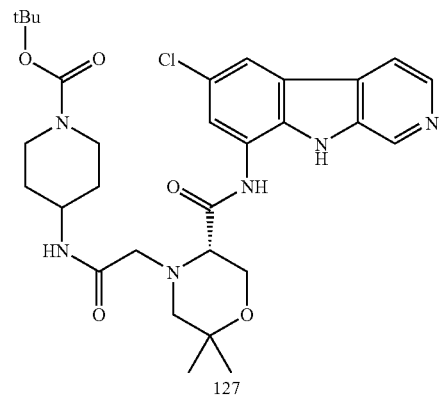
127
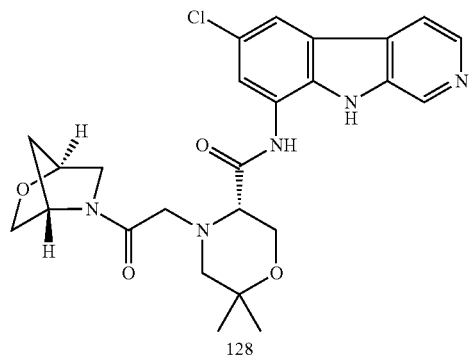
128

TABLE 4-continued
Specific examples of formula III-A-aa compounds
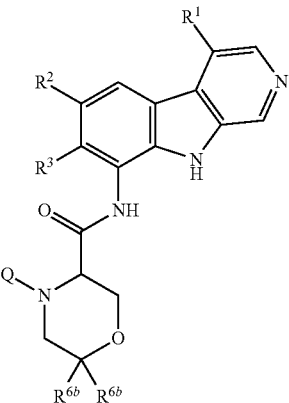
III-A-aa
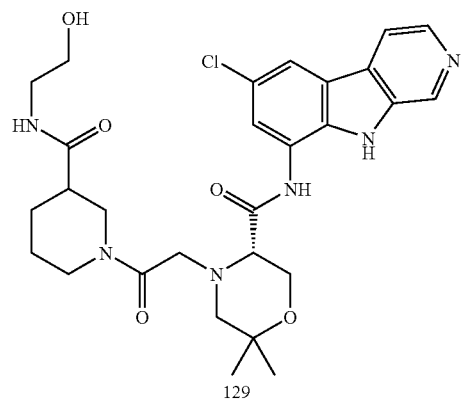
129
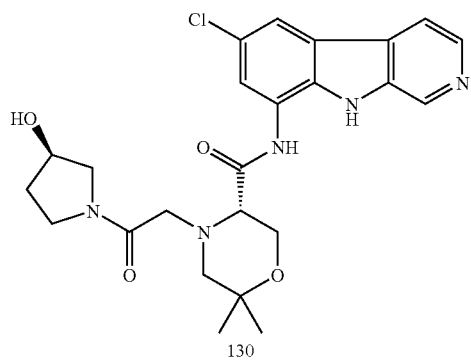
130
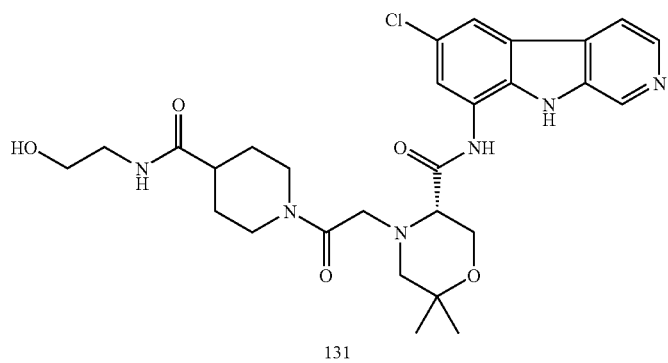
131

TABLE 4-continued
Specific examples of formula III-A-aa compounds
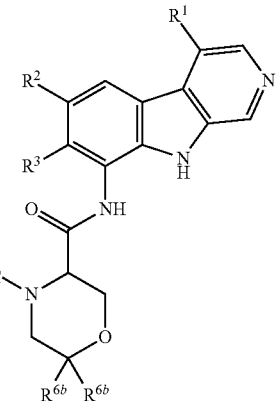
III-A-aa
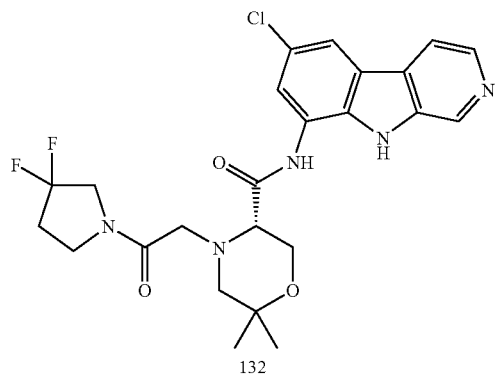
132
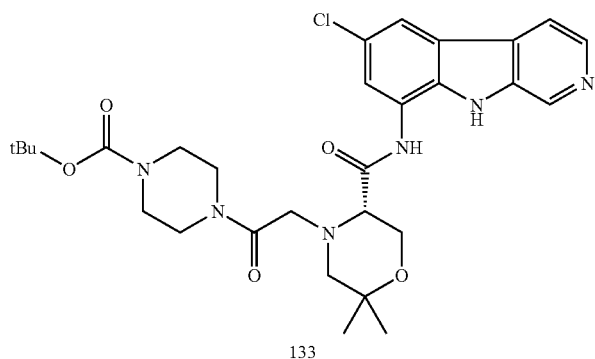
133
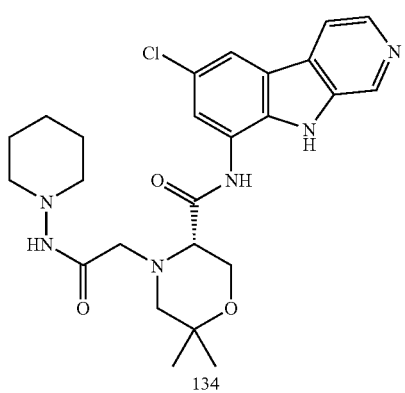
134

TABLE 4-continued
Specific examples of formula III-A-aa compounds
III-A-aa
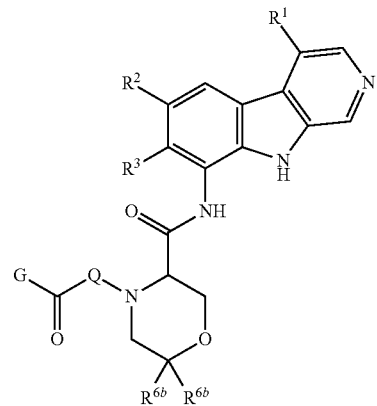
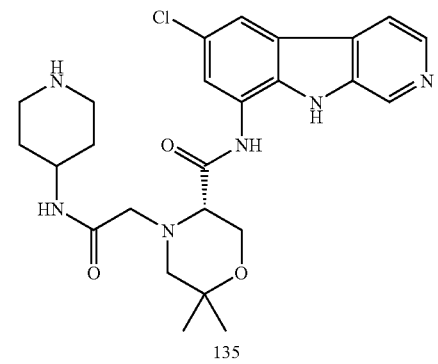
135
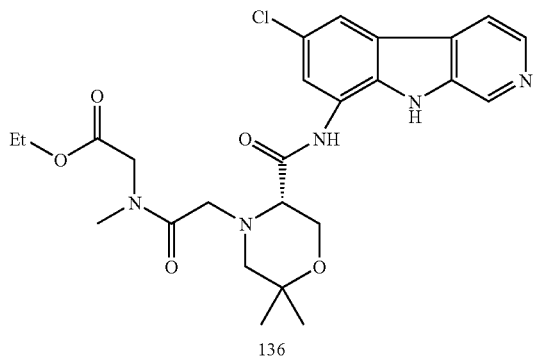
136
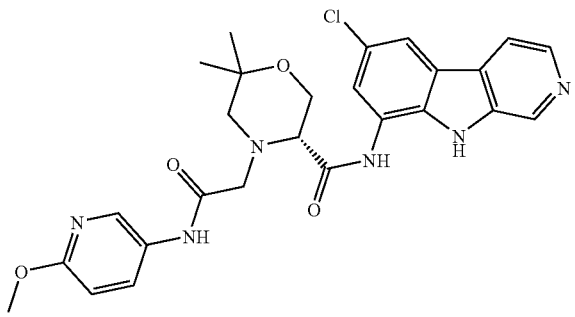
137

TABLE 4-continued
Specific examples of formula III-A-aa compounds
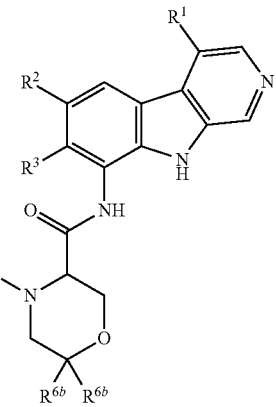
III-A-aa
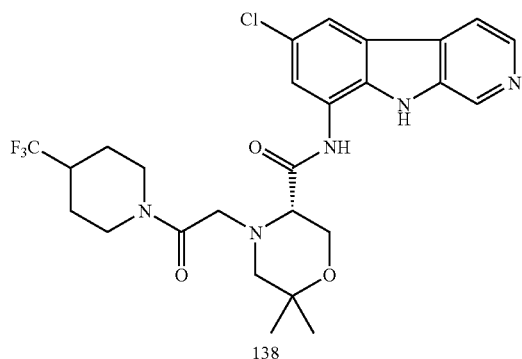
138
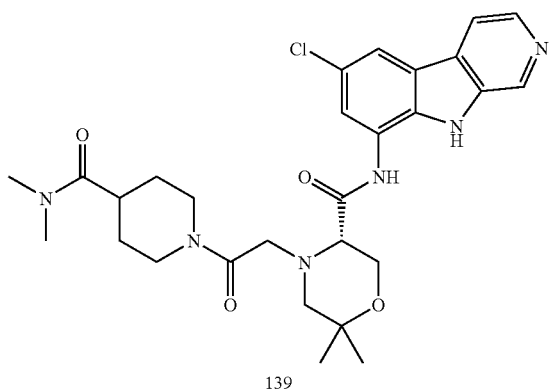
139
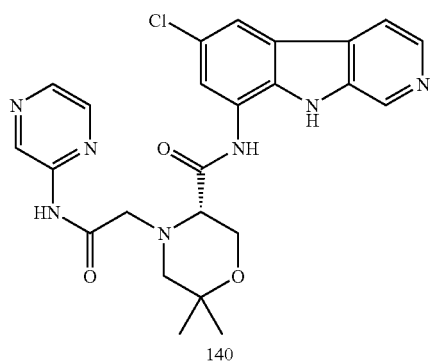
140

TABLE 4-continued
Specific examples of formula III-A-aa compounds
III-A-aa
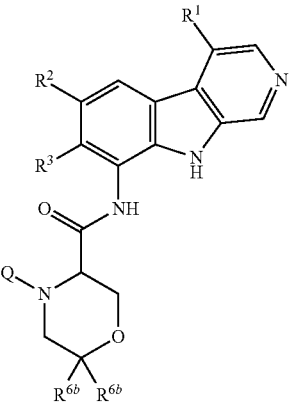
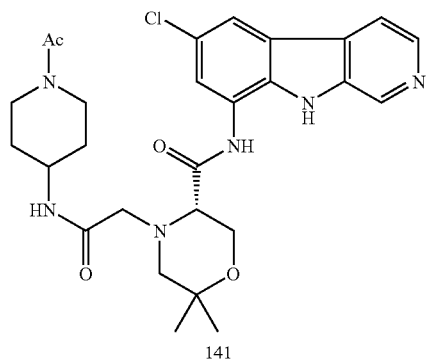
141
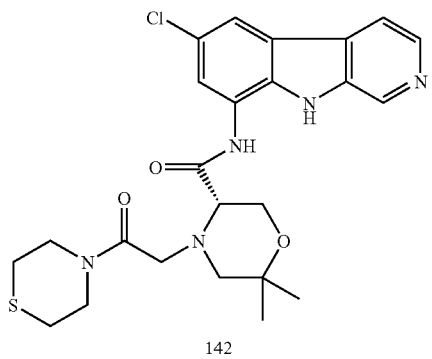
142
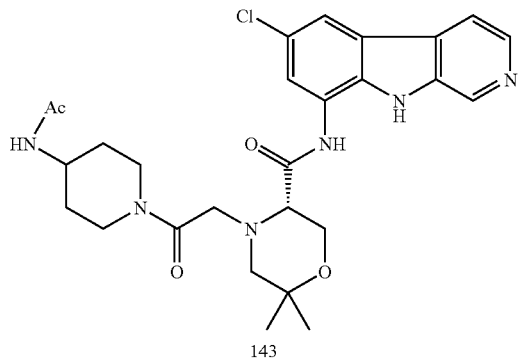
143

TABLE 4-continued
Specific examples of formula III-A-aa compounds
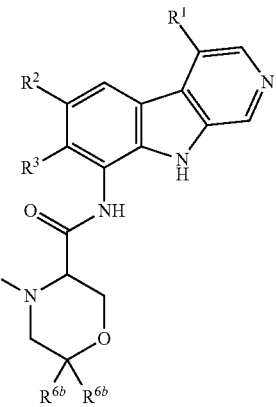
III-A-aa
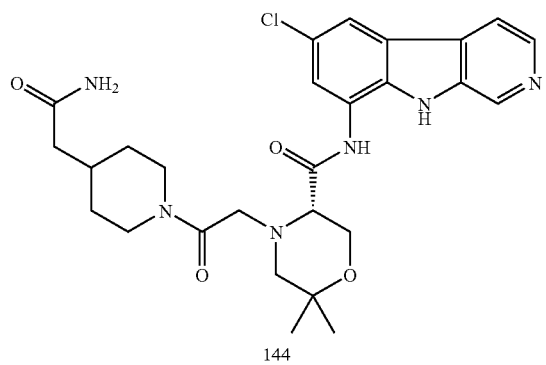
144
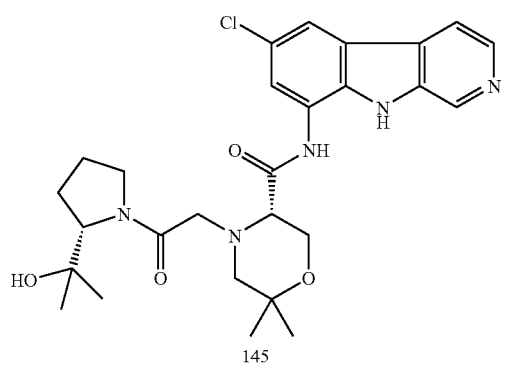
145
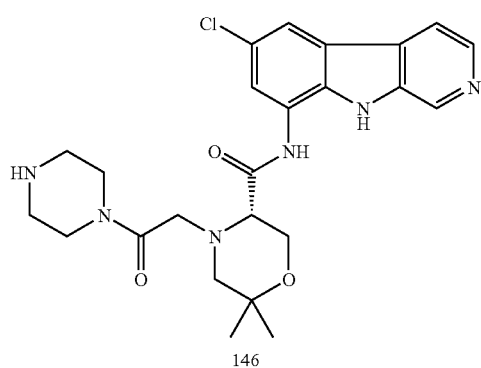
146

TABLE 4-continued
Specific examples of formula III-A-aa compounds
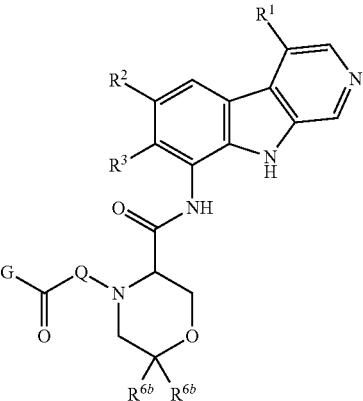
III-A-aa
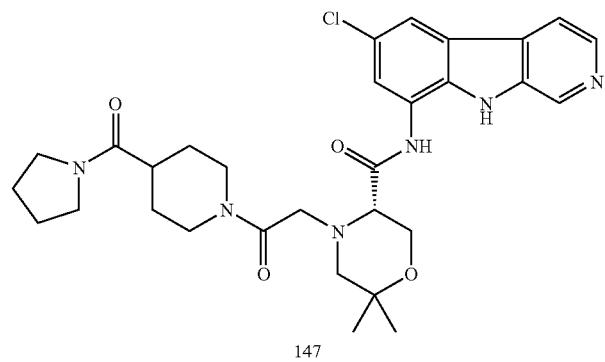
147
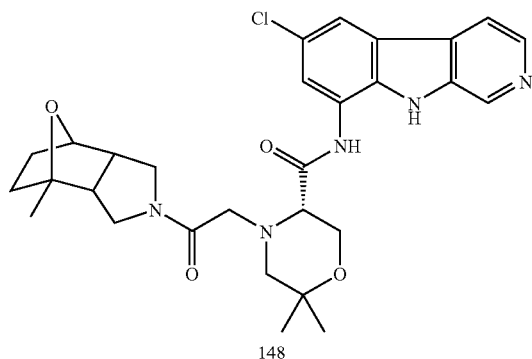
148
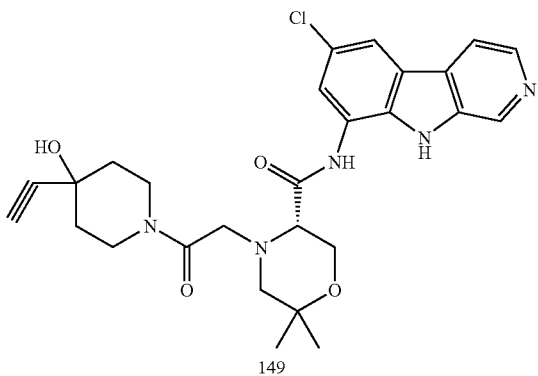
149

TABLE 4-continued
Specific examples of formula III-A-aa compounds
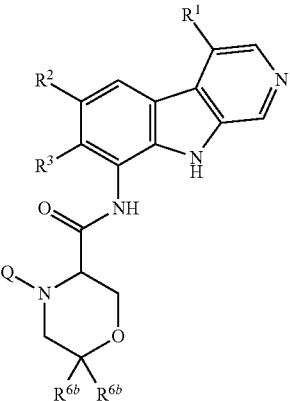
III-A-aa
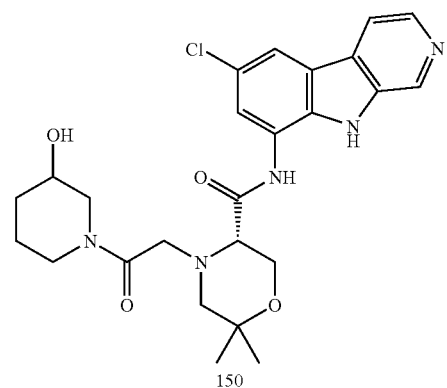
150
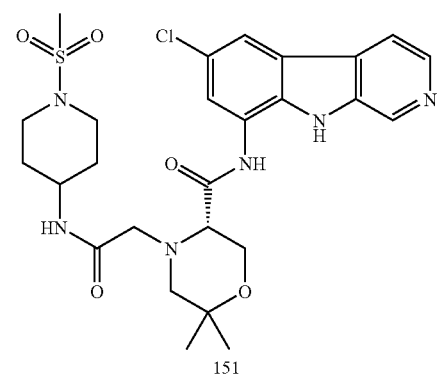
151
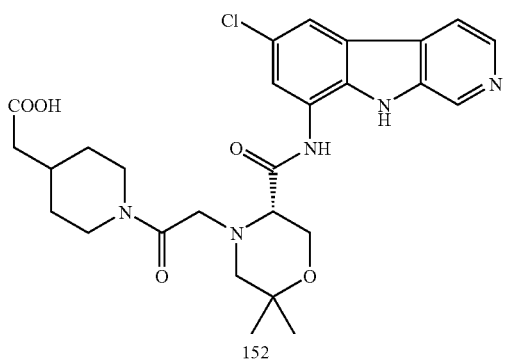
152

TABLE 4-continued
Specific examples of formula III-A-aa compounds
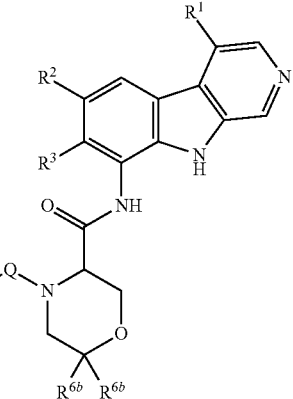
III-A-aa
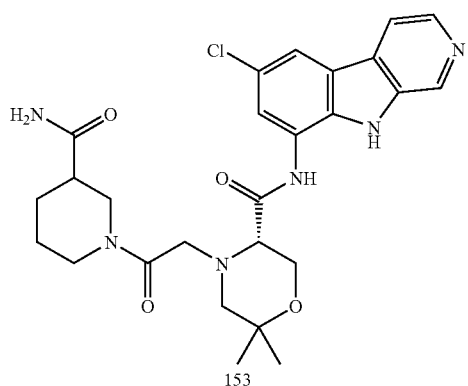
153
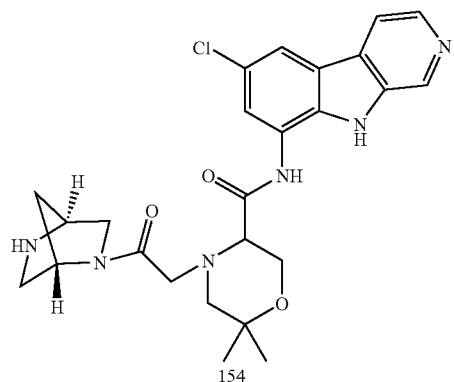
154
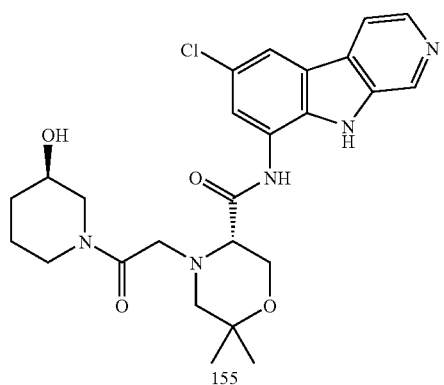
155

TABLE 4-continued
Specific examples of formula III-A-aa compounds
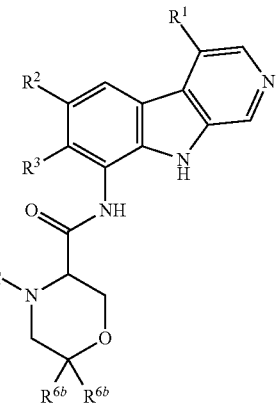
III-A-aa
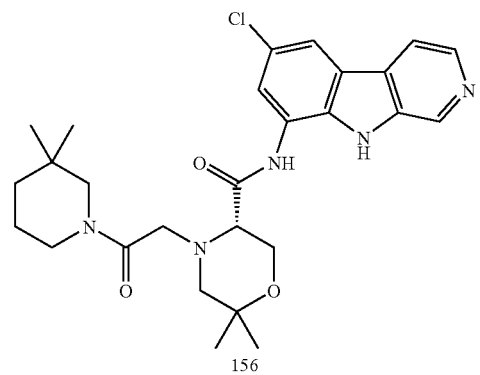
156
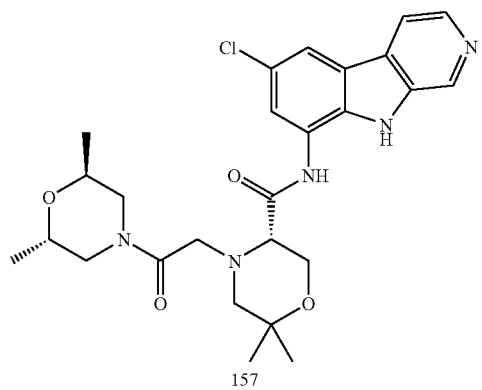
157
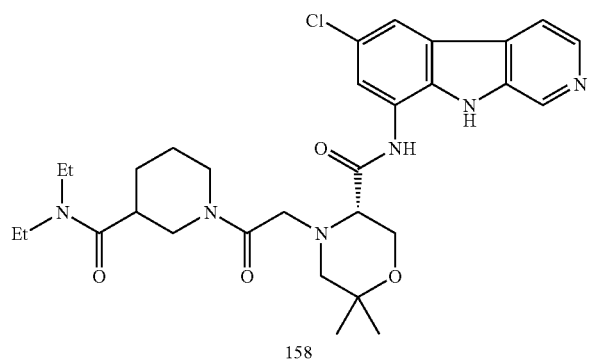
158

TABLE 4-continued
Specific examples of formula III-A-aa compounds
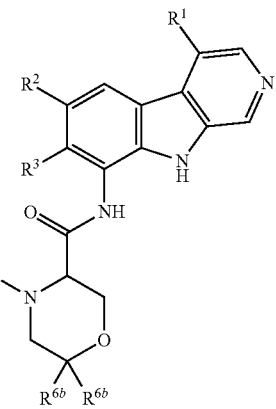
III-A-aa
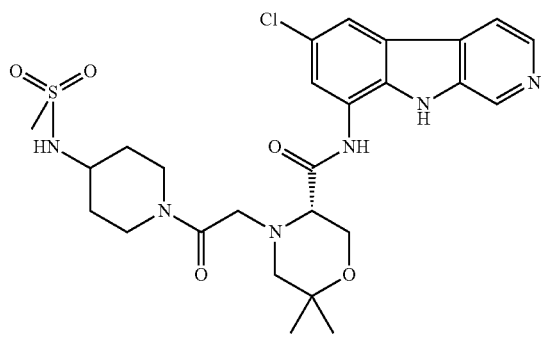
159
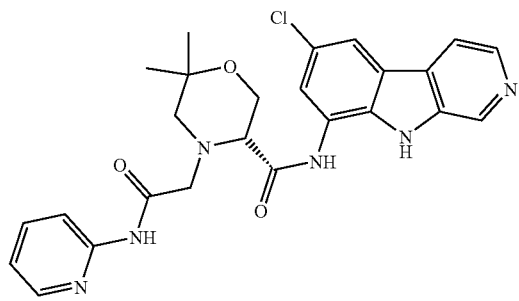
160
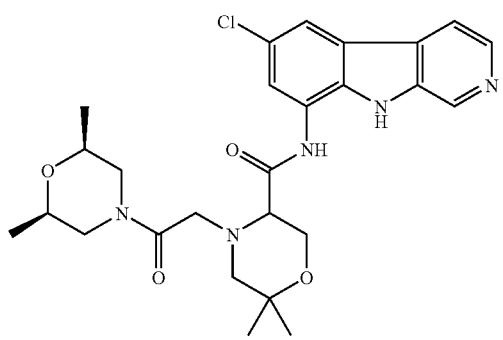
161

TABLE 4-continued
Specific examples of formula III-A-aa compounds
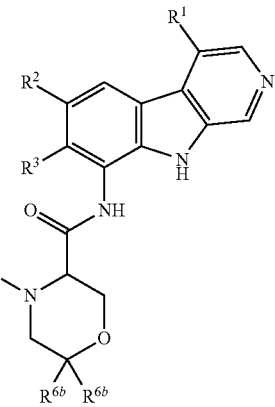
III-A-aa
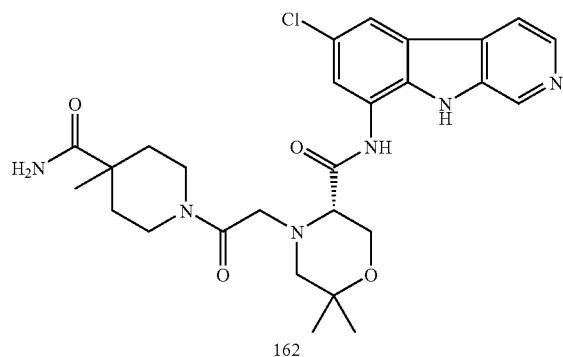
162
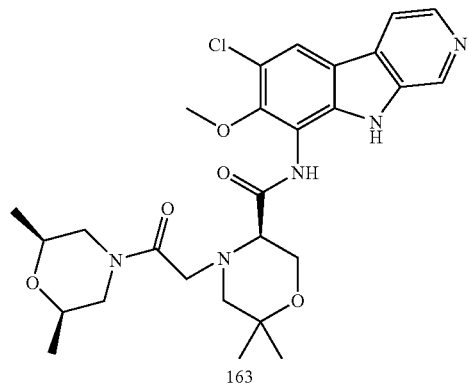
163
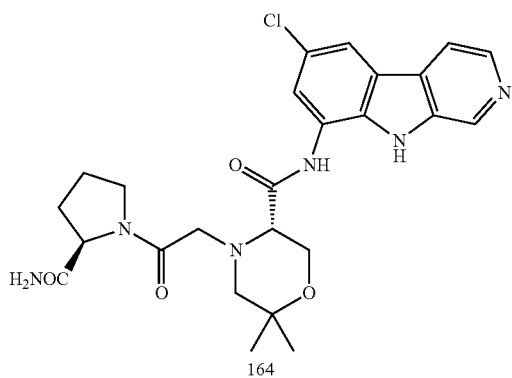
164

TABLE 4-continued
Specific examples of formula III-A-aa compounds
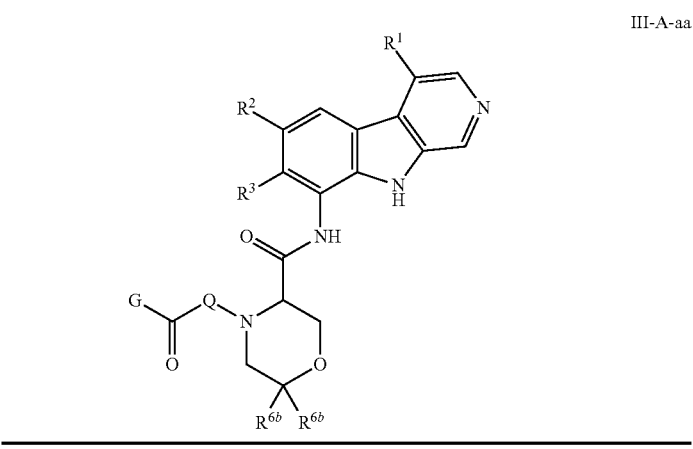
III-A-aa
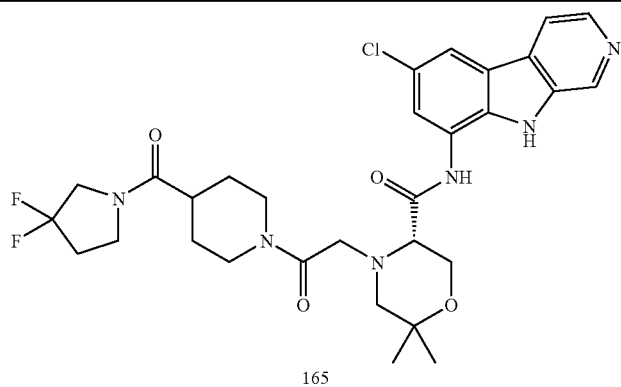
165
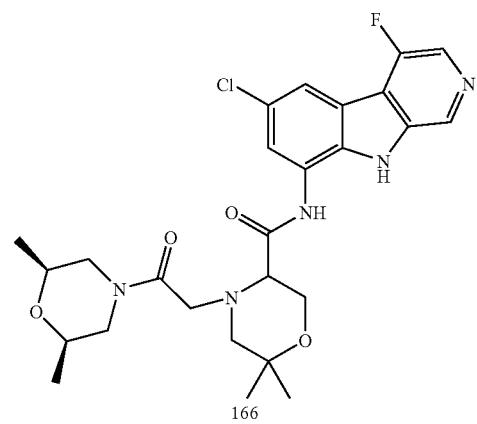
166
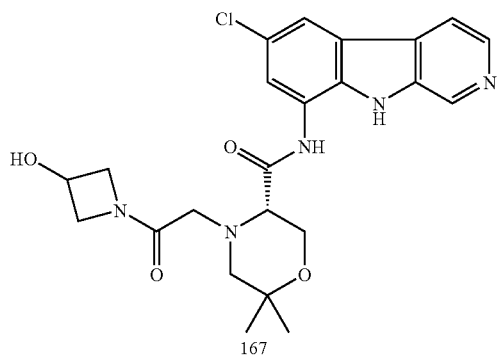
167

TABLE 4-continued
Specific examples of formula III-A-aa compounds
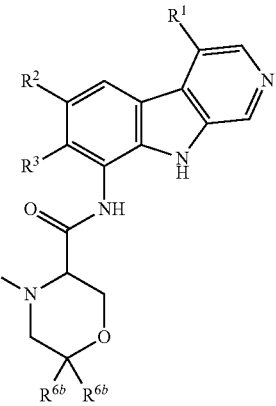
III-A-aa
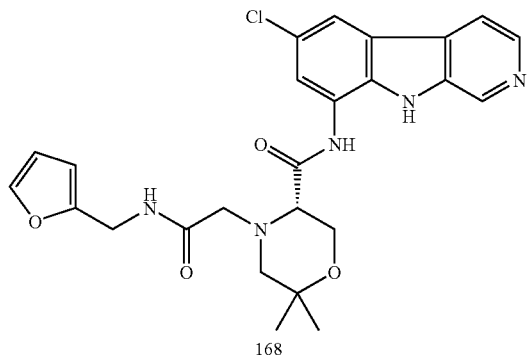
168
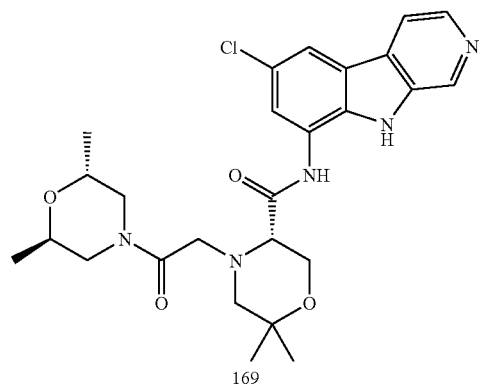
169
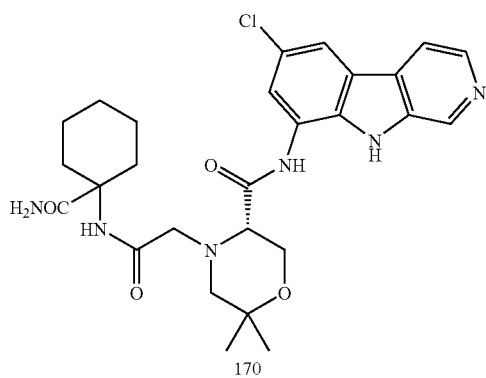
170

TABLE 4-continued
Specific examples of formula III-A-aa compounds
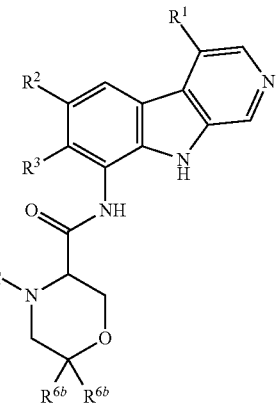
III-A-aa
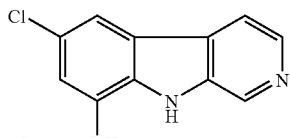
171
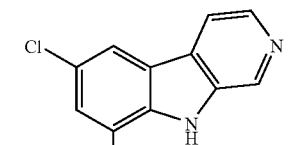
172
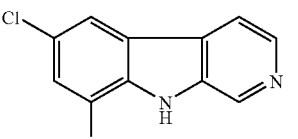
173

TABLE 4-continued
Specific examples of formula III-A-aa compounds
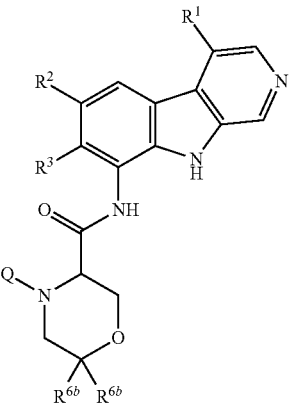
III-A-aa
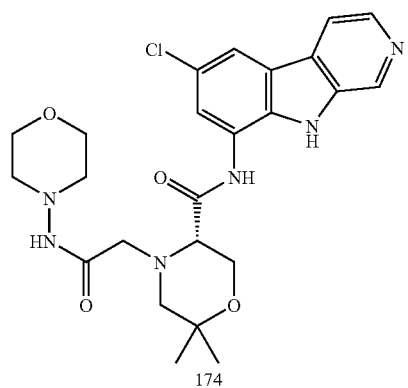
174
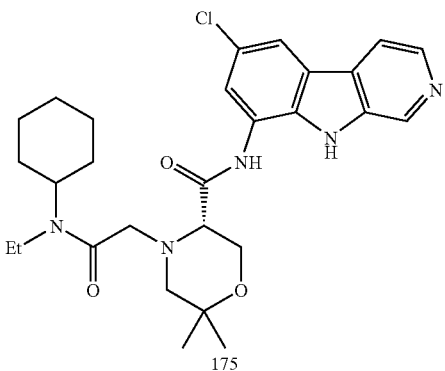
175
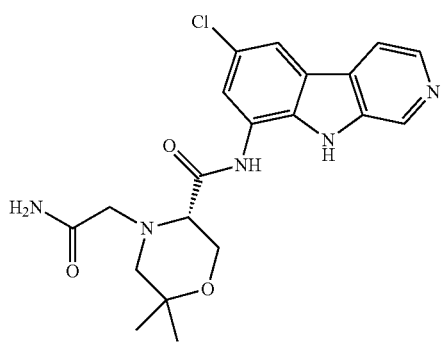
176

TABLE 4-continued
Specific examples of formula III-A-aa compounds
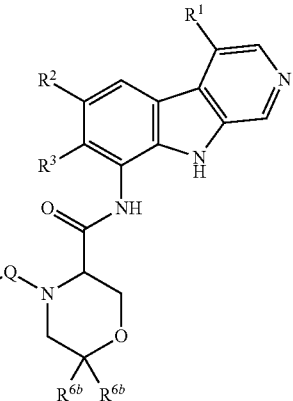
III-A-aa
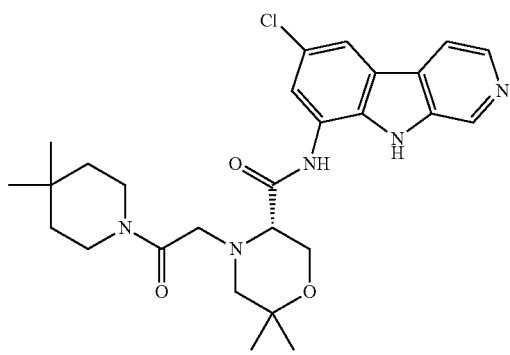
177
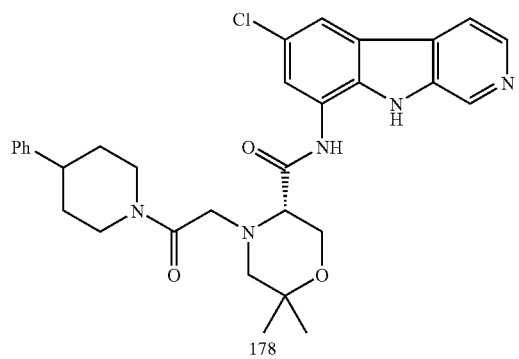
178
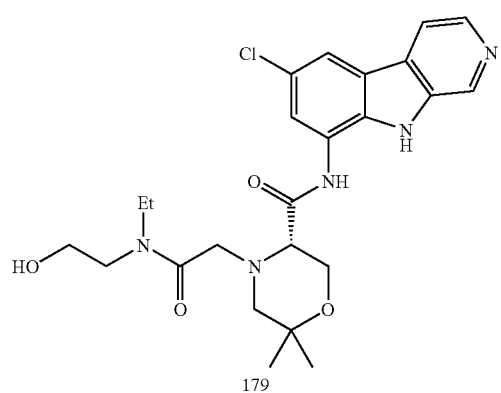
179

TABLE 4-continued
Specific examples of formula III-A-aa compounds
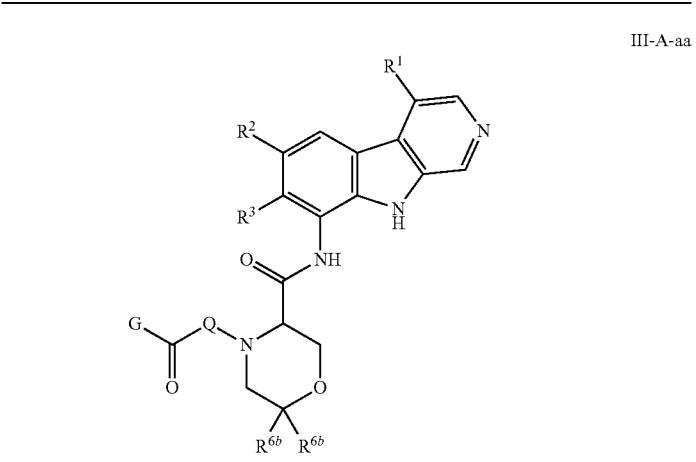
III-A-aa
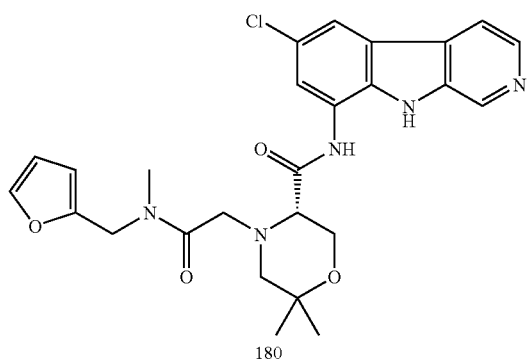
180
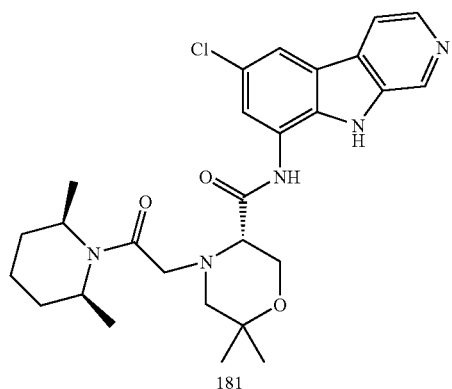
181
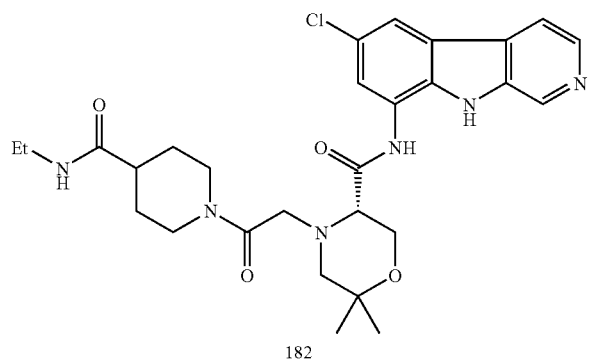
182

TABLE 4-continued
Specific examples of formula III-A-aa compounds
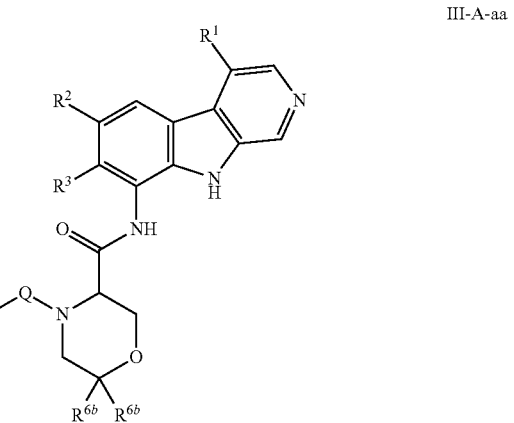
III-A-aa
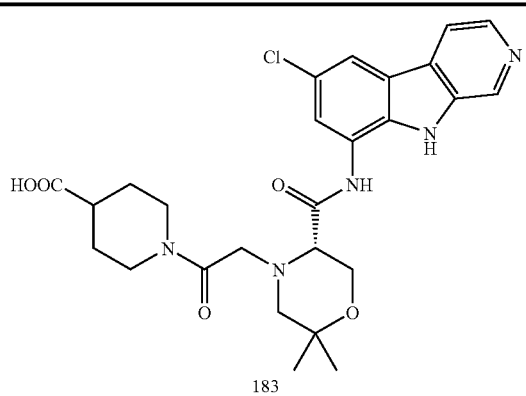
183
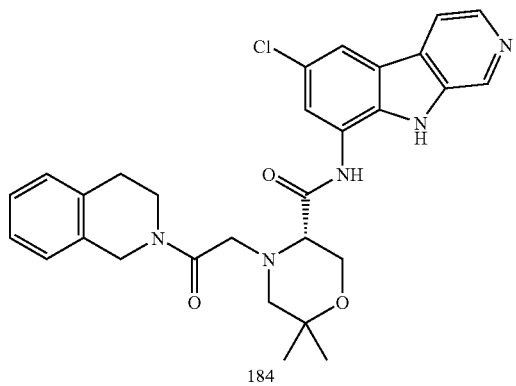
184
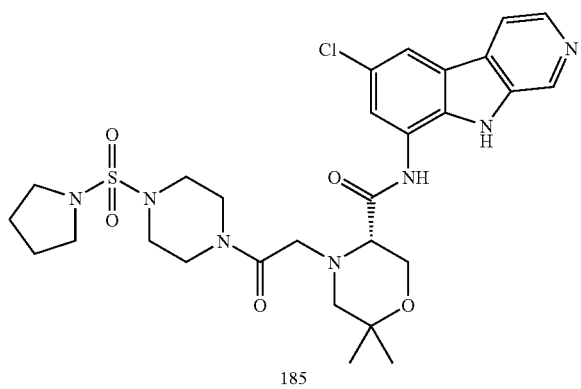
185

TABLE 4-continued
Specific examples of formula III-A-aa compounds
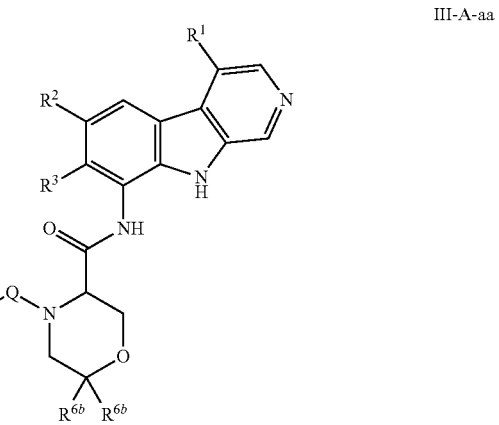
III-A-aa
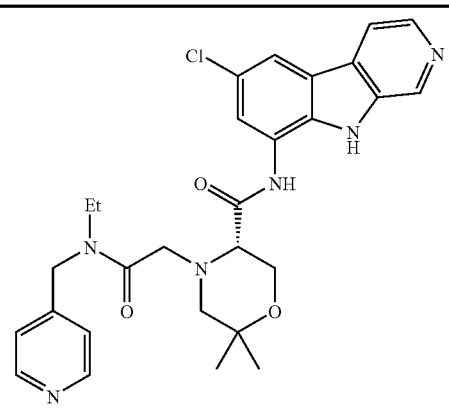
186
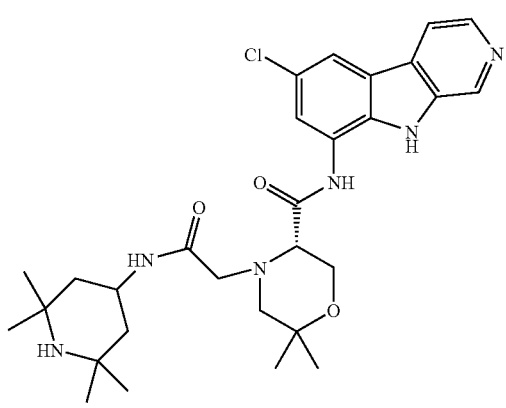
187
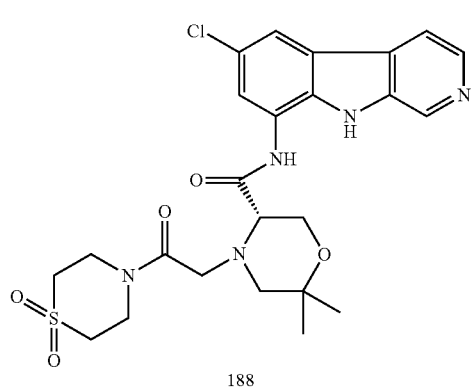
188

TABLE 4-continued
Specific examples of formula III-A-aa compounds
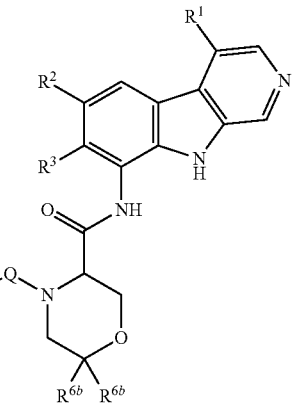
III-A-aa
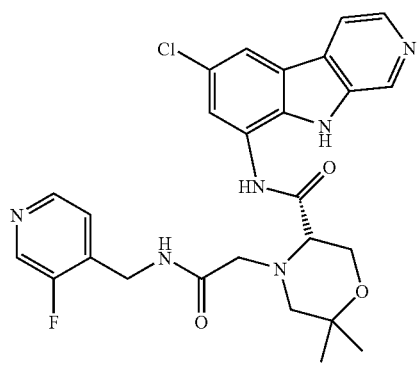
189
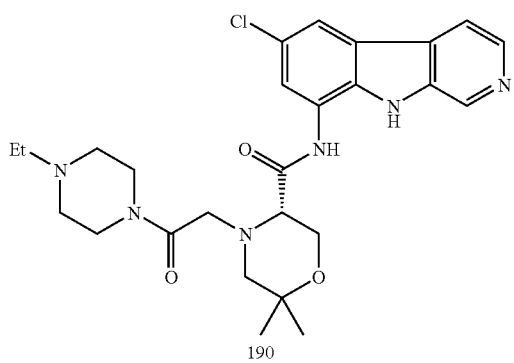
190
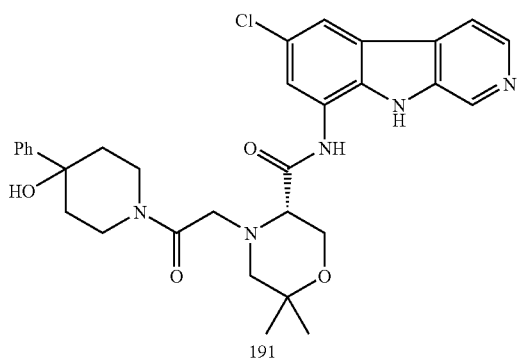
191

131 132
TABLE 4-continued
Specific examples of formula III-A-aa compounds
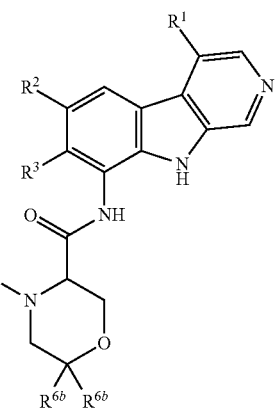
III-A-aa
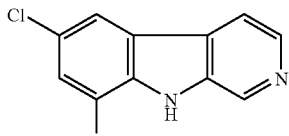
192
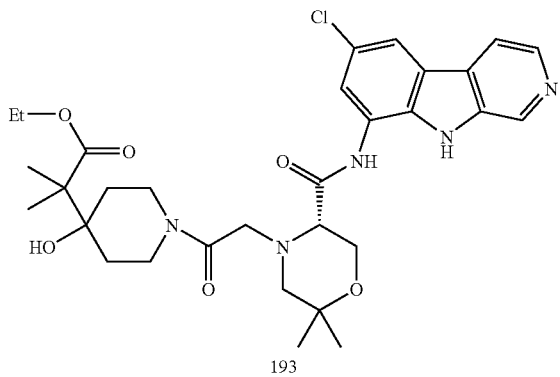
193
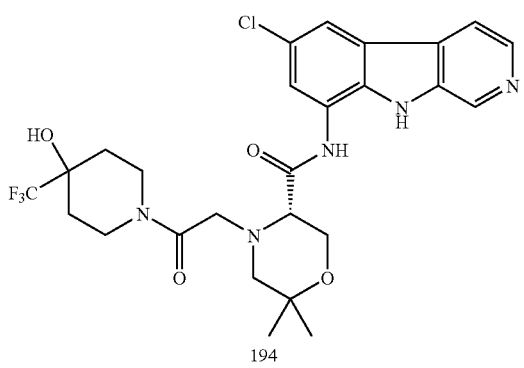
194

TABLE 4-continued
Specific examples of formula III-A-aa compounds
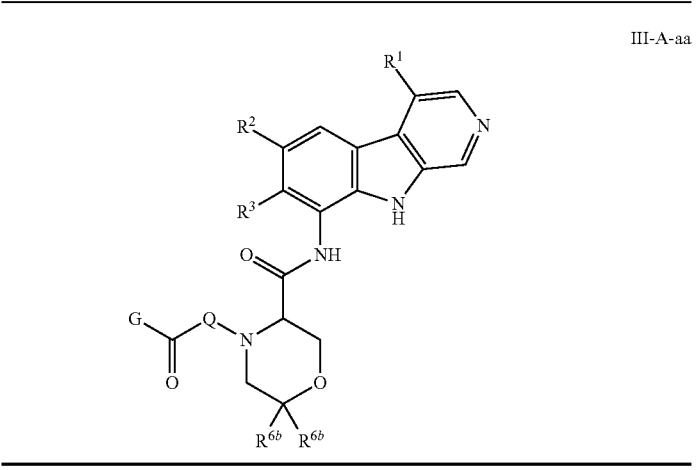
III-A-aa
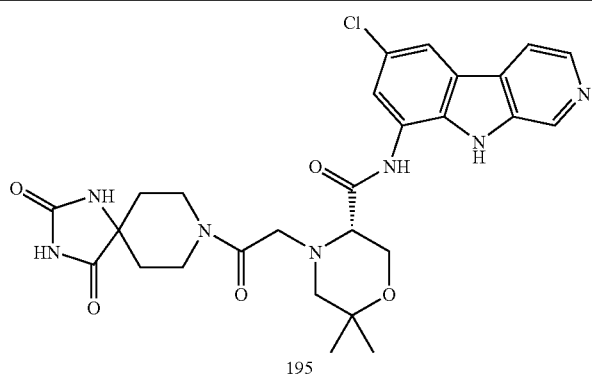
195
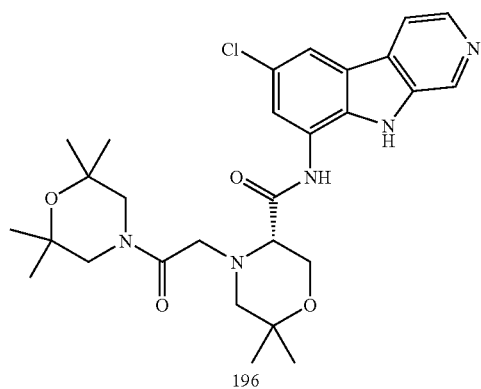
196
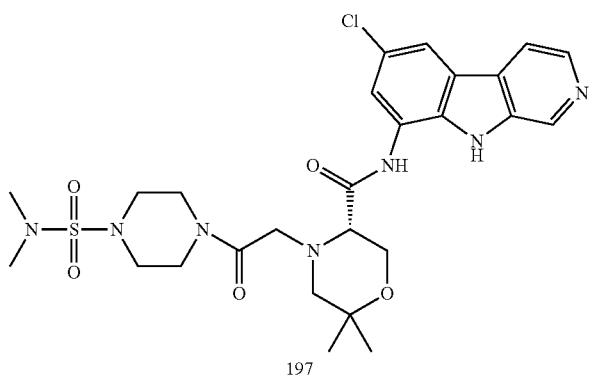
197

TABLE 4-continued
Specific examples of formula III-A-aa compounds
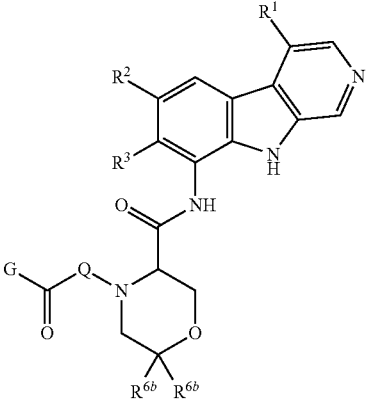
III-A-aa
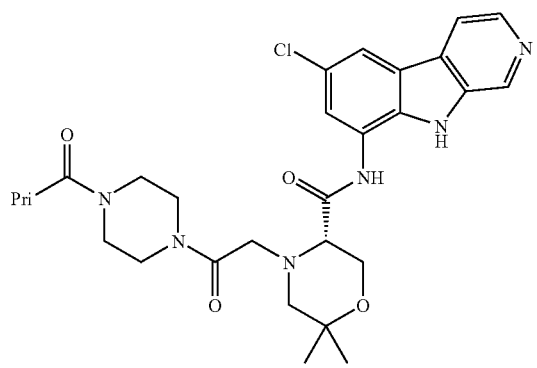
198
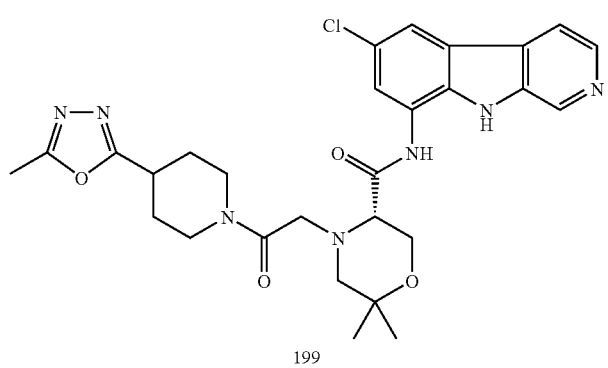
199
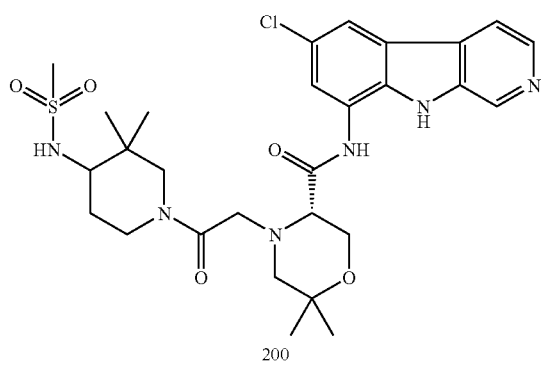
200

TABLE 4-continued
Specific examples of formula III-A-aa compounds
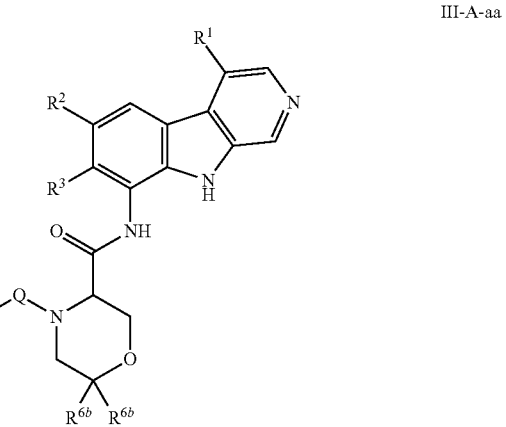
III-A-aa
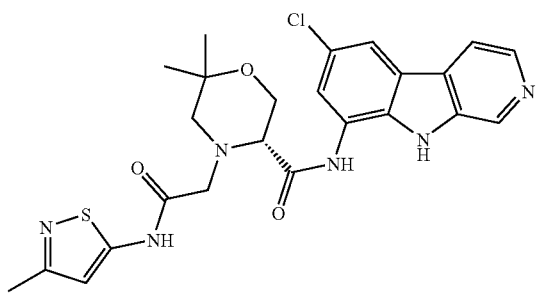
201
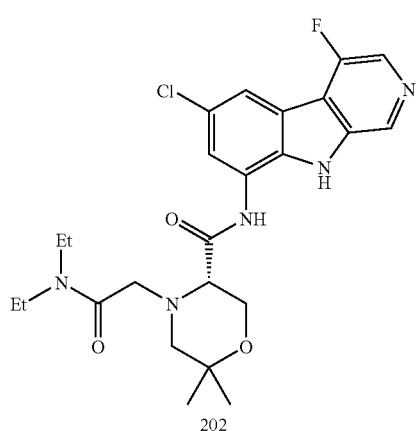
202
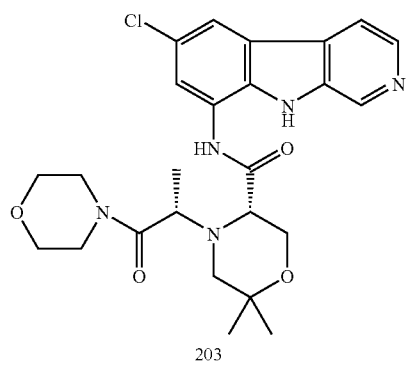
203

TABLE 4-continued
Specific examples of formula III-A-aa compounds
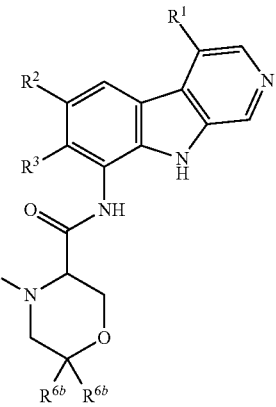
III-A-aa
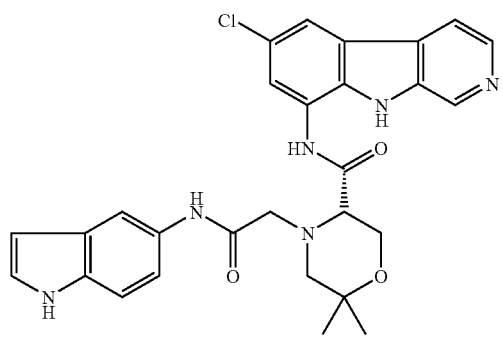
204
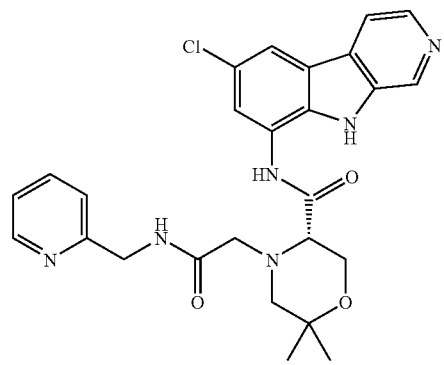
205
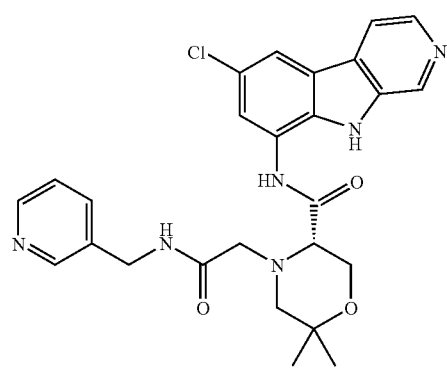
206

TABLE 4-continued

Specific examples of formula III-A-aa compounds

III-A-aa

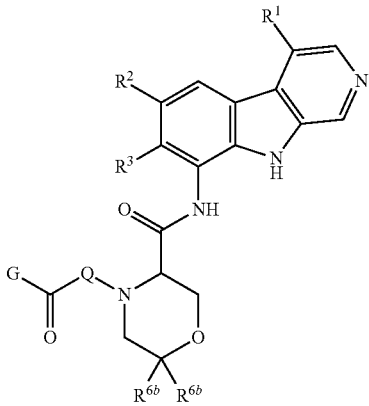

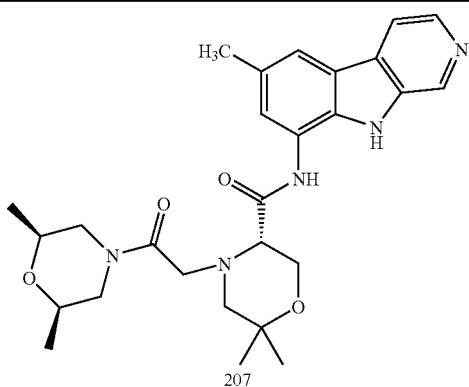

207

Based on their IκB kinase inhibitory properties and other pharmacological properties, compound example numbers 1-30, 39-62 and 64-206 are preferred. More preferred are compound example numbers 1, 2, 7, 10, 11, 13, 16, 17, 19-27, 39-62, 64-77, 79-180, 182-191, 193-201, and 204-207.

4 Uses, Formulation and Administration

Pharmaceutically Acceptable Compositions

The compounds of the present invention may be administered to humans or other mammals by a variety of routes, including oral dosage forms and injections (intravenous, intramuscular, intraperitoneal, subcutaneous, and the like). Numerous other dosage forms containing compounds of the invention can be readily formulated by one skilled in the art, utilizing the suitable pharmaceutical excipients (or carriers) as defined below.

Examples of pharmaceutically acceptable excipients (or carriers) and methods of manufacture for various compositions can be found in A. Gennaro (ed.), Remington: The Science and Practice of Pharmacy, 20$^{th}$ Edition, Lippincott Williams & Wilkins, Baltimore, Md. (2000), which is incorporated in its entirety by reference herein. Pharmaceutically acceptable excipients (or carriers) include flavoring agents, pharmaceutical-grade dyes or pigments, solvents, co-solvents, buffer systems, surfactants, preservatives, sweetener agents, viscosity agents, fillers, lubricants, glidants, disintegrants, binders and resins.

Conventional flavoring agents may be used, such as those described in Remington's Pharmaceutical Sciences, 18$^{th}$ Ed., Mack Publishing Co., pp. 1288-1300 (1990), which is incorporated in its entirety by reference herein. The pharmaceutical compositions of the invention generally contain from about 0 to 2% of flavoring agents.

Conventional dyes and/or pigments may also be used, such as those described in the Handbook of Pharmaceutical Excipients, by the American Pharmaceutical Association & the Pharmaceutical Society of Great Britain, pp. 81-90 (1986), which is incorporated in its entirety by reference herein. The pharmaceutical compositions of the invention generally contain from about 0 to 2% of dyes and/or pigments.

The pharmaceutical compositions of the invention generally contain from about 0.1 to 99.9% of solvent(s). A preferred solvent is water. Preferred co-solvents include ethanol, glycerin, propylene glycol, polyethylene glycol, and the like. The pharmaceutical compositions of the invention may include from about 0 to 50% of co-solvents.

Preferred buffer systems include acetic, boric, carbonic, phosphoric, succinic, maleic, tartaric, citric, acetic, benzoic, lactic, glyceric, gluconic, glutaric and glutamic acids and their sodium, potassium and ammonium salts. Particularly preferred buffers are phosphoric, tartaric, citric and acetic acids and salts thereof. The pharmaceutical compositions of the invention generally contain from about 0 to 5% of a buffer.

Preferred surfactants include polyoxyethylene sorbitan fatty acid esters, polyoxyethylene monoalkyl ethers, sucrose monoesters and lanolin esters and ethers, alkyl sulfate salts and sodium, potassium and ammonium salts of fatty acids. The pharmaceutical compositions of the invention generally contain from about 0 to 2% of surfactants.

Preferred preservatives include phenol, alkyl esters of parahydroxybenzoic acid, o-phenylphenol benzoic acid and salts thereof, boric acid and salts thereof, sorbic acid and salts thereof, chlorobutanol, benzyl alcohol, thimerosal, phenylmercuric acetate and nitrate, nitromersol, benzalkonium chloride, cetylpyridinium chloride, methyl paraben and propyl paraben. Particularly preferred preservatives are the salts of benzoic acid, cetylpyridinium chloride, methyl paraben and propyl paraben. The pharmaceutical compositions of the invention generally contain from about 0 to 2% of preservatives.

Preferred sweeteners include sucrose, glucose, saccharin, sorbitol, mannitol and aspartame. Particularly preferred sweeteners are sucrose and saccharin. Pharmaceutical compositions of the invention generally contain from about 0 to 5% of sweeteners.

Preferred viscosity agents include methylcellulose, sodium carboxymethylcellulose, hydroxypropyl-methylcellulose, hydroxypropylcellulose, sodium alginate, carbomer, povidone, acacia, guar gum, xanthan gum and tragacanth. Particularly preferred viscosity agents are methylcellulose, carbomer, xanthan gum, guar gum, povidone, sodium carboxymethylcellulose, and magnesium aluminum silicate. Pharmaceutical compositions of the invention generally contain from about 0 to 5% of viscosity agents.

Preferred fillers include lactose, mannitol, sorbitol, tribasic calcium phosphate, dibasic calcium phosphate, compressible sugar, starch, calcium sulfate, dextro and microcrystalline cellulose. Pharmaceutical compositions of the invention generally contain from about 0 to 75% of fillers.

Preferred lubricants/glidants include magnesium stearate, stearic acid and talc. Pharmaceutical compositions of the invention generally contain from about 0 to 7%, preferably, about 1 to 5% of lubricants/glidants.

Preferred disintegrants include starch, sodium starch glycolate, crospovidone and croscarmelose sodium and microcrystalline cellulose. Pharmaceutical compositions of the invention generally contain from about 0 to 20%, preferably, about 4 to 15% of disintegrants.

Preferred binders include acacia, tragacanth, hydroxypropylcellulose, pregelatinized starch, gelatin, povidone, hydroxypropylcellulose, hydroxypropylmethylcellulose, methylcellulose, sugar solutions, such as sucrose and sorbitol, and ethylcellulose. Pharmaceutical compositions of the invention generally contain from about 0 to 12%, preferably, about 1 to 10% of binders.

Additional agents known to a skilled formulator may be combined with the compounds of the invention to create a single dosage form. Alternatively, additional agents may be separately administered to a mammal as part of a multiple dosage form.

For preparing pharmaceutical compositions containing the inventive compounds, inert, pharmaceutically acceptable excipients or carriers can be either solid or liquid. Solid form preparations include powders, tablets, dispersible granules, capsules, cachets and suppositories. Generally, the powders and tablets may be comprised of from about 5 to 95 weight percent of active ingredient. Suitable solid carriers are known in the art, for example, magnesium carbonate, magnesium stearate, talc, sugar and lactose. Tablets, powders, cachets and capsules can be used as solid dosage forms suitable for oral administration. Examples of pharmaceutically acceptable carriers and methods of manufacture for various compositions may be found in Remington's Pharmaceutical Sciences, 18th Ed., Mack Publishing Co. (1990).

Liquid form preparations include solutions, suspensions and emulsions. Common liquid form preparations include water and water-propylene glycol solutions for parenteral injection or addition of sweeteners and opacifiers for oral solutions, suspensions and emulsions. Liquid form preparations may also include solutions for intranasal administration.

Aerosol preparations suitable for inhalation include solutions and solids in powder form, which may be combined with a pharmaceutically acceptable carrier, such as an inert compressed gas (e.g., nitrogen).

Also included are solid form preparations that may be converted, shortly before use, to liquid form preparations for either oral or parenteral administration. Such liquid forms include solutions, suspensions and emulsions.

The compounds of the invention may also be delivered transdermally. The transdermal compositions can take the form of creams, lotions, aerosols and emulsions and may be included in a transdermal patch of a matrix or reservoir type as is conventional in the art for this purpose.

The preferred mode of administering the compounds of the invention is oral. Preferably, the pharmaceutical preparation is in a unit dosage form. In such a form, the preparation is subdivided into suitable sized unit doses containing appropriate quantities of the active component, for example, an effective amount to achieve the desired purpose.

The quantity of active ingredient (compound) in a unit dose of preparation may be varied or adjusted from about 0.01 to 4,000 mg, preferably, from about 0.01 to 1,000 mg, more preferably, from about 0.01 to 500 mg, and even more preferably, from about 0.01 to 250 mg, according to the particular application. A typical recommended daily dosage regimen for oral administration will usually range from about 0.02 to 2,000 mg/day, in one to four divided doses. For convenience, the total daily dosage may be divided and administered in portions during the day as required. Typically, pharmaceutical compositions of the invention will be administered from about 1 to 5 times per day, or alternatively, as a continuous infusion. Such administration can be used for chronic or acute therapy. The amount of active ingredient that may be combined with excipient or carrier materials to produce a single dosage form will vary depending upon the host treated and the particular mode of administration. A typical preparation will usually contain from about 5 to 95% of active compound (w/w). Preferably, such preparations will contain from about 20 to 80 wt. % of active compound.

The pharmaceutically acceptable excipients or carriers employed in conjunction with the compounds of the invention are used at a concentration sufficient to provide a practical size to dosage relationship. The pharmaceutically acceptable excipients or carriers, in total, can comprise from about 0.1 to 99.9% by weight of the pharmaceutical compositions of the invention, preferably, from about 20 to 80% by weight.

Upon improvement of a patient's condition, a maintenance dose of a compound, composition or combination of the invention may be administered, if applicable. Subsequently, the dosage or frequency of administration, or both, may be reduced, as a function of the symptoms, to a level at which the improved condition is retained. When the symptoms have been alleviated to the desired level, treatment should cease. Patients may, however, require intermittent treatment on a long-term basis upon any recurrence of disease symptoms.

Specific dosage and treatment regimens for any particular patient may be varied and will depend upon a variety of factors, including the activity of the specific compound employed, the age, body weight, general health status, sex and diet of the patient, the time of administration, the rate of excretion, the specific drug combination, the severity and course of the symptoms being treated, the patient's disposition to the condition being treated and the judgment of the treating physician. Determination of the proper dosage regimen for a particular situation is within the skill of the art. The amount and frequency of the administration of compounds of the invention or their pharmaceutically acceptable salts may be regulated according to the judgment of the attending clinician, based on the factors recited above. As a skilled artisan will appreciate, lower or higher doses than those recited above may be required.

The inventive compounds are understood to provide efficacious treatment of a variety of diseases, symptoms and disorders, particularly, those which are inflammatory or immune-related in nature, including a reasonable time of onset upon administration, and a reasonable duration after administration. While food, diet, pre-existing conditions, alcohol and other systemic conditions could lengthen the time delay for an inventive drug to work after its administration, it is understood that optimum dosages will result in an efficacious drug treatment within and for a reasonable amount of time.

The term "effective amount", as used herein, is meant to describe an amount of a compound, composition, medicament or other active ingredient of the present invention producing the desired therapeutic effect, e.g., IKK-2 inhibition, and/or treating or lessening the severity of an inflammatory disease or disorder, and/or treating or lessening the severity of cancer.

The inventive compounds can exist in unsolvated as well as solvated forms, including hydrated forms. In general, the solvated forms, with pharmaceutically acceptable solvents, such as water, ethanol and the like, are equivalent to the unsolvated forms for purposes of this invention.

The inventive compounds may form pharmaceutically acceptable salts with organic and inorganic acids. Examples of suitable acids for salt formation are hydrochloric, sulfuric, phosphoric, acetic, citric, malonic, salicylic, malic, fumaric, succinic, ascorbic, maleic, methanesulfonic and other mineral and carboxylic acids well known to those skilled in the art. The salts are prepared by contacting the free base forms with a sufficient amount of the desired acid to produce a salt in a conventional manner. The free base forms may be regenerated by treating the salt with a suitable dilute aqueous base solution, such as dilute aqueous sodium hydroxide, potassium carbonate, ammonia or sodium bicarbonate. The free base forms may differ somewhat from their respective salt forms in certain physical properties, such as solubility in polar solvents, but the salts are otherwise equivalent to their respective free base forms for purposes of the invention.

On account of their pharmacological properties, the compounds according to the invention are suitable for the prophylaxis treatment and therapy of diseases, disorders and symptoms that involve increased activity of IkB kinase. These include, for example, joint inflammation (e.g., rheumatoid arthritis (RA), rheumatoid spondylitis, gouty arthritis, traumatic arthritis, rubella arthritis, psoriatic arthritis, osteoarthritis, and other arthritic conditions), acute synovitis, tuberculosis, atherosclerosis, muscle degeneration, cachexia, Reiter's syndrome, endotoxaemia, sepsis, septic shock, endotoxic shock, gram negative sepsis, gout, toxic shock syndrome, pulmonary inflammatory diseases (e.g., asthma, acute respiratory distress syndrome, chronic obstructive pulmonary disease, silicosis, pulmonary sarcoidosis, and the like), bone resorption diseases, reperfusion injuries, carcinoses, leukemia, sarcomas, lymph node tumors, skin carcinoses, lymphoma, apoptosis, graft versus host reaction, graft versus host disease (GVHD), allograft rejection and leprosy.

Furthermore, the inventive compounds may be used in the treatment of immune-related diseases, symptoms and disorders, for example, infections, such as viral infections (e.g., HIV, cytomegalovirus (CMV), influenza, adenovirus, the Herpes group of viruses, and the like), parasitic infections (e.g., malaria, such as cerebral malaria), and yeast and fungal infections (e.g., fungal meningitis). In addition, the inventive compounds can be useful for treating fever and myalgias due to infection, acquired immune deficiency syndrome (AIDS), AIDS related complex (ARC), cachexia secondary to infection or malignancy, cachexia secondary to AIDS or cancer, keloid and scar tissue formation, pyresis, diabetes, and inflammatory bowel diseases (IBD) (e.g., Crohn's disease and ulcerative colitis). The compounds of the invention are also useful in the treatment of diseases or injuries to the brain in which over-expression of TNF-α has been implicated, such as multiple sclerosis (MS), ischemic brain injury, e.g. cerebral infarction (stroke) and head trauma. The compounds of the invention are also useful in the treatment of psoriasis, Alzheimer's disease, carcinomatous disorders (potentiation of cytotoxic therapies), cardiac infarct, chronic obstructive pulmonary disease (COPD) and acute respiratory distress syndrome (ARDS).

In one embodiment the compounds of this invention are useful for treating cancer, especially for treating cancers where IKK activity is abnormally high. The cancer types that may be treated include lymphoma, such as diffuse large B-cell, primary mediastinal B-cell, and mantle cell; multiple myeloma; osteolytic bone metastasis; head and neck squamous cell cancer; prostate cancer; pancreatic cancer and non-small cell lung cancer. In one embodiment, the compounds are useful for ABC lymphoma. For the treatment of cancer, the compounds may be used as a single agent or in combination with other agents known to be useful for the treatment of cancer. Examples of such other agents include bortezomib; capecitibine; gemcitabine; irinotecan; fludarabine; 5-fluorouricil or 5-fluorouricil/leucovorin; taxanes, including, e.g., paclitaxel and docetaxel; platinum agents, including, e.g., cisplatin, carboplatin, and oxaliplatin; anthracyclins, including, e.g., doxorubicin and pegylated liposomal doxorubicin; mitoxantrone; dexamethasone; vincristine; etoposide; prednisone; thalidomide; Herceptin; temozolomide; and alkylating agents such as melphalan, chlorambucil, and cyclophosphamide.

The compounds of formula (I) are especially useful for treating inflammatory and immune-related diseases, disorders and symptoms, more especially, inflammatory ones such as RA, asthma, IBD, psoriasis, COPD and MS. It will be appreciated that the present compounds are useful for treating diseases, disorders or symptoms related to the activity of NF-κB, TNF-α, and other enzymes in pathways where IKK is known to modulate activity.

The compounds of this invention are also useful for treating a bone associated disease, symptom or disorder in which there is a deficit or deficiency of bone—either as a result of decreased new bone formation or an increase in bone resorption or a combination of both. Specific examples include osteoporosis, periodontal disease, osteomyelitis, rheumatoid arthritis, aseptic joint loosening and osteolytic lesions (typically cancer related). It is known that rheumatoid arthritis, which is characterized by inflammation of the joints, is also associated with destruction of cartilage and bone. Furthermore, it has been reported that an IKK inhibitor provided inhibition of cartilage and bone loss in a murine model of collagen-induced arthritis. See McIntyre et al., *Arthritis & Rheumatism* (2003), 48(9), 2652-2659.

Osteoporosis is a broad term applied to a number of distinct diseases in which there is decreased bone mass. These include primary osteoporosis (e.g., post-menopausal, senile osteoporosis and juvenile osteoporosis) and secondary osteoporosis. Examples of secondary osteoporosis would be those associated with chronic diseases (e.g., chronic renal disease, hepatic insufficiency, gastrointestinal malabsorption, chronic immobilization and chronic inflammatory diseases, including rheumatoid arthritis, osteoarthritis, periodontal disease and aseptic prosthetic joint loosening), endocrine dysfunction related diseases (e.g., diabetes, hyperthyroidism, hyperparathyroidism, hypogonadism and hypopituitarism), drug and substance related symptoms (e.g., corticosteroid, heparin, anticonvulsants, alcohol and immunosupressants), and hematological disorders (e.g., metastatic disease, myeloma, leukemia, gaucher's disease and anemia). Inhibition of either IkB directly or the NF-kB pathway indirectly has been reported to be useful for the treatment of osteoporosis and osteoarthritis. See, for example, PCT applications WO 2003104219, WO 2003103658, WO 2003029242, WO 2003065972, and WO 9965495. Accordingly, this invention also provides a method of treating or preventing bone loss in a patient in need thereof, comprising administering to the patient a compound of this invention. Also provided is a method of generating bone formation in a patient comprising administering a compound of this invention.

Another embodiment of the invention provides a method of inhibiting activation of NF-κB dependent gene expression associated with the inhibition of IKK catalytic activity and/or IκB phosphorylation, comprising administering to a patient in need thereof an amount of a compound of the invention or a pharmaceutically acceptable salt or solvate thereof, or a pharmaceutical composition thereof, which is effective to inhibit IKK catalytic activity and/or IκB phosphorylation, thereby inhibiting activation of NF-κB dependent gene expression.

In one embodiment of the invention, there is provided a method of treating an inflammatory or immune-related physiological disorder, symptom or disease in a patient in need of such treatment, comprising administering to the patient an amount of at least one compound of the invention, or a pharmaceutically acceptable salt or solvate thereof, or a pharmaceutical composition thereof, which is effective to treat the inflammatory or immune-related physiological disorder, symptom or disease. Preferably, the inflammatory disease, disorder or symptom is rheumatoid arthritis, asthma, psoriasis, psoriatic arthritis, chronic obstructive pulmonary disease (COPD), inflammatory bowel disease or multiple sclerosis.

In yet another embodiment of the invention, there is provided a method of treating cystic fibrosis in a patient in need of such treatment, comprising administering to the patient an amount of at least one compound of the invention, or a pharmaceutically acceptable salt or solvate thereof, or a pharmaceutical composition thereof.

The invention comprises a compound having the formula (I), a method for making an inventive compound, a method for making a pharmaceutical composition from at least one inventive compound and at least one pharmaceutically acceptable carrier or excipient, and a method of using one or more inventive compounds to treat a variety of disorders, symptoms and diseases, particularly ones that are inflammatory or immune-related in nature. The inventive compounds and their pharmaceutically acceptable salt and neutral compositions may be formulated together with a pharmaceutically acceptable excipient or carrier and the resulting composition may be administered in vivo to mammals, such as primates, e.g. chimpanzees and humans (e.g. males and females) and animals (e.g., dogs, cats, cows, horses, and the like), to treat a variety of disorders, symptoms and diseases. Furthermore, the inventive compounds can be used to prepare a medicament that is useful for treating a variety of disorders, symptoms and diseases.

While one or more of the inventive compounds may be used in an application of monotherapy to treat a disorder, disease or symptom, they also may be used in combination therapy, in which the use of an inventive compound or composition (therapeutic agent) is combined with the use of one or more other therapeutic agents for treating the same and/or other types of disorders, symptoms and diseases. Combination therapy includes administration of the therapeutic agents concurrently or sequentially. Alternatively, the therapeutic agents can be combined into one composition which is administered to the patient.

In one embodiment, the compounds of this invention are used in combination with other therapeutic agents, such as other inhibitors of IKK, other agents useful in treating NF-κB and TNF-α associated conditions, and agents useful for treating other disorders, symptoms and diseases. In particular, agents that induce apoptosis such as agents that disrupt cell cycle or mitochondrial function are useful in combination with the IKK inhibitors of this invention. Exemplary agents for combination with the IKK inhibitors include antiproliferative agents (e.g., methotrexate) and the agents disclosed in U.S. Pat. Application Publication No. U.S. 2003/0022898, p 14, para. [0173-0174], which is incorporated herein in its entirety. In some embodiments, a compound of the invention is administered in conjunction with a therapeutic agent selected from the group consisting of cytotoxic agents, radiotherapy, and immunotherapy. Non-limiting examples of cytotoxic agents suitable for use in combination with the IKK inhibitors of the invention include capecitibine; gemcitabine; irinotecan; fludarabine; 5-fluorouracil or 5-fluorouracil/leucovorin; taxanes, including, e.g., paclitaxel and docetaxel; platinum agents, including, e.g., cisplatin, carboplatin, and oxaliplatin; anthracyclins, including, e.g., doxorubicin and pegylated liposomal doxorubicin; mitoxantrone; dexamethasone; vincristine; etoposide; prednisone; thalidomide; herceptin; temozolomide; and alkylating agents such as melphalan, chlorambucil, and cyclophosphamide. It is understood that other combinations may be undertaken while remaining within the scope of the invention.

Another aspect of the invention relates to inhibiting IKK, activity in a biological sample or a patient, which method comprises administering to the patient, or contacting said biological sample with a compound of formula I or a composition comprising said compound. The term "biological sample", as used herein, generally includes in vivo, in vitro, and ex vivo materials, and also includes, without limitation, cell cultures or extracts thereof; biopsied material obtained from a mammal or extracts thereof; and blood, saliva, urine, feces, semen, tears, or other body fluids or extracts thereof.

Still another aspect of this invention is to provide a kit comprising separate containers in a single package, wherein the inventive pharmaceutical compounds, compositions and/or salts thereof are used in combination with pharmaceutically acceptable carriers to treat disorders, symptoms and diseases where IkB kinase plays a role.

5. General Synthetic Methods:

The compounds of this invention may be prepared by methods known to those skilled in the art for analogous compounds, as illustrated by the general schemes below, and by reference to the preparative examples shown below.

Scheme I

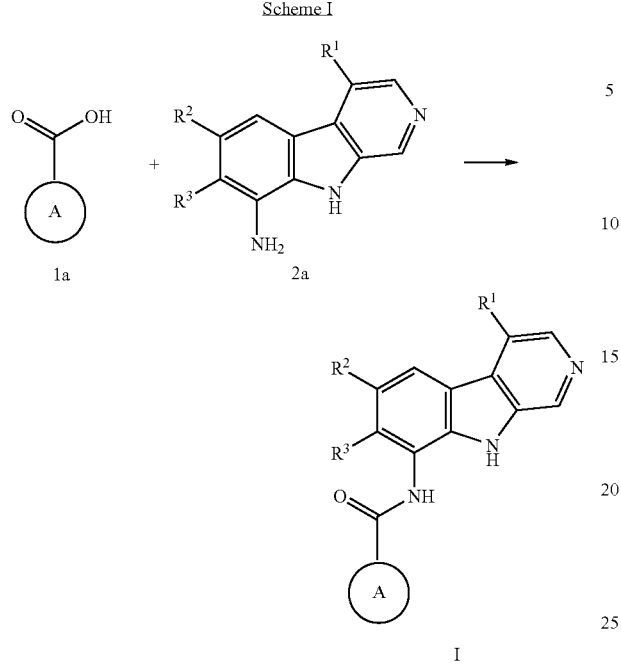

Scheme I above shows a general route for obtaining compounds of formula I. A Ring A carboxylic acid 1a may be coupled with the desired amino beta-carboline 2a to provide I. Many 1a intermediates that are useful for preparing compounds of this invention are readily available from known starting materials and chemical methods, especially in view of the synthetic examples detailed herein. Schemes II-IV describe routes for making the various β-carboline intermediates 2a.

Steps: (a) (i) $HCOCO_2H$ (ii) HCl (b) Pd/C (c) NCS (d) $NaNO_2$ (e) NaOMe (f) $Pt/H_2$ Scheme II above shows a route for making a beta-carboline moiety where $R^1$ is hydrogen, $R^2$ is chloro and $R^3$ is alkoxy. While the scheme is exemplified for $R^3$ being methoxy, it will be appreciated by one skilled in the art that beta-carbolines having other $R^3$ alkoxy groups may be obtained by replacing NaOMe in step (e) with other sodium or metal alkoxides.

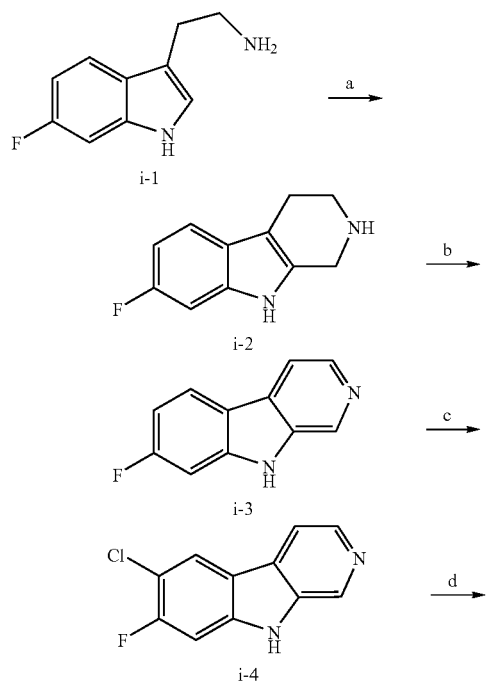

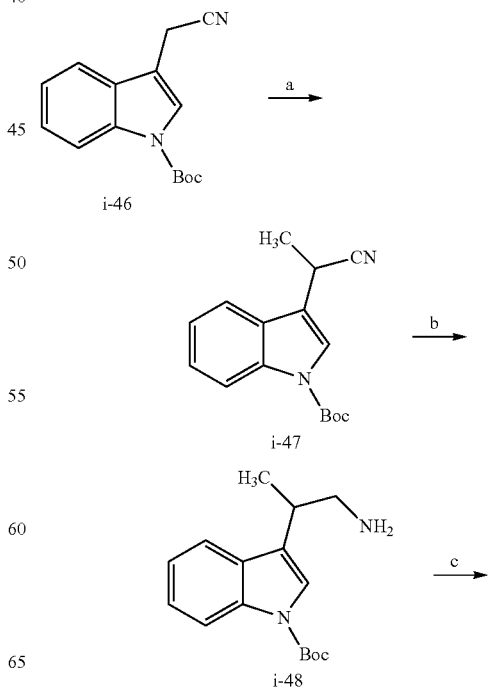

151

-continued

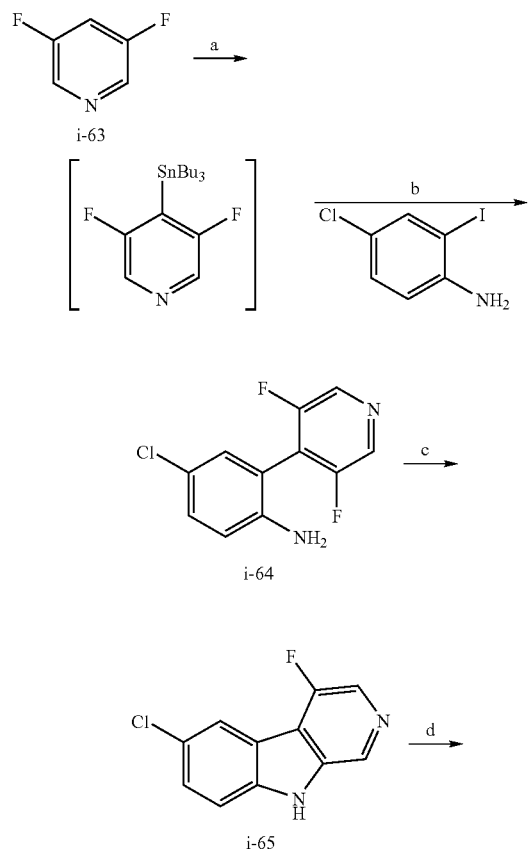

Steps: (a) NaHMDS, MeI (b) H$_2$, Raney Nickel, PtO (c) i. TFA ii. CHOCO$_2$H iii. HCl (d) Pd/C, xylenes, 160° C. (e) i. NCS, 1N HCl ii. NaNO$_2$, TFA iii. H$_2$, Pt Scheme III above shows a route for preparing a beta-carboline intermediate where R$^1$ is an alkyl such as methyl, R$^2$ is a halo such as chloro and R$^3$ is hydrogen. One skilled in the art will understand how the above scheme may be modified to obtain an R$^1$ alkyl group other than methyl or an R$^2$ halo group other than chloro.

152

-continued

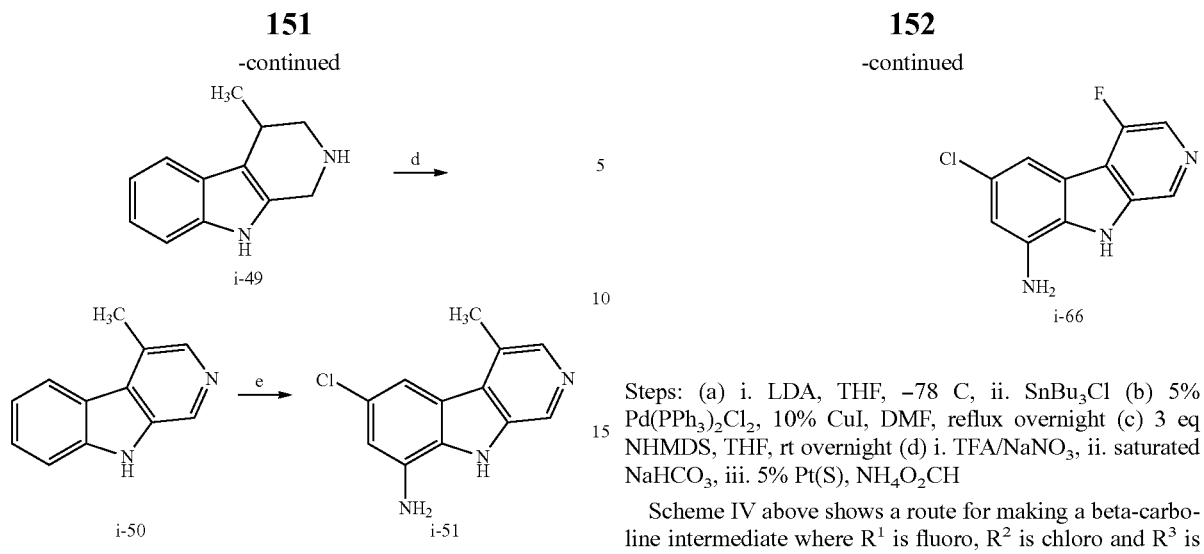

Steps: (a) i. LDA, THF, −78 C, ii. SnBu$_3$Cl (b) 5% Pd(PPh$_3$)$_2$Cl$_2$, 10% CuI, DMF, reflux overnight (c) 3 eq NHMDS, THF, rt overnight (d) i. TFA/NaNO$_3$, ii. saturated NaHCO$_3$, iii. 5% Pt(S), NH$_4$O$_2$CH Scheme IV above shows a route for making a beta-carboline intermediate where R$^1$ is fluoro, R$^2$ is chloro and R$^3$ is hydrogen. It will be appreciated that ready modification of this scheme will allow for the preparation of other intermediates. For example, another R$^2$ group may be introduced by replacing the 4-chloro-2-iodoaniline in step (b) with another 2-iodoaniline having a substituent other than chloro in the 4-position.

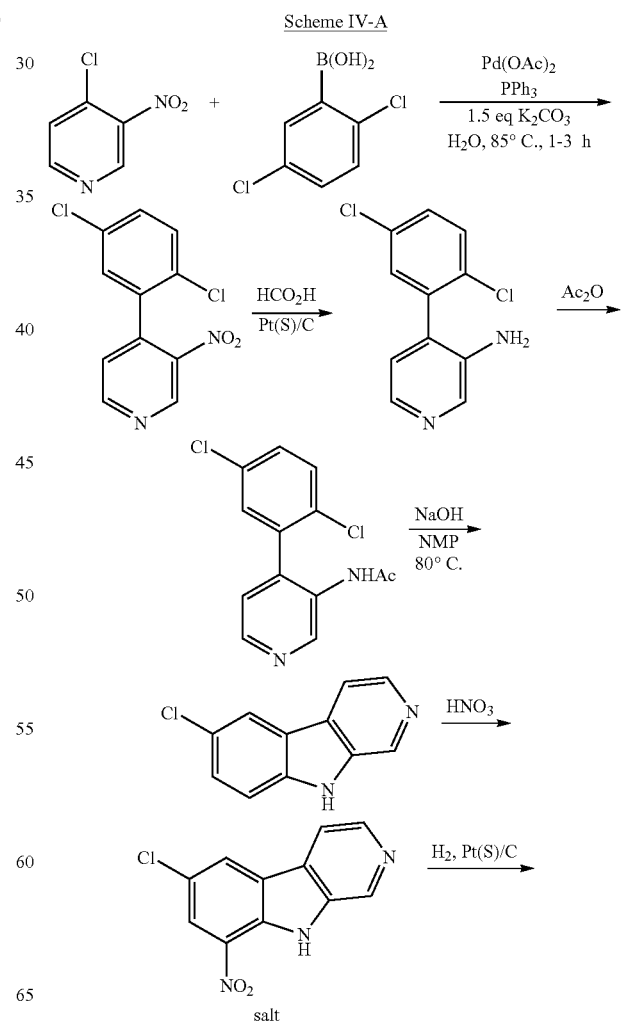

Scheme IVA above shows another route for making a beta-carboline intermediate where $R^1$ is hydrogen, $R^2$ is chloro and $R^3$ is hydrogen. It will be appreciated that ready modification of this scheme will allow for the preparation of other intermediates.

A particularly useful intermediate for making compounds of formula III-A-aa is intermediate 3a:

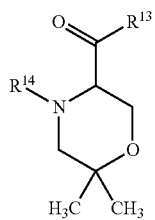

3a where $R^{13}$ is halo, OH, $OR^{15}$, or a carboxylic acid protecting group; $R^{14}$ is an amino protecting group, hydrogen or —W-G as defined above; and $R^{15}$ is an organic radical. Amino protecting groups are well-known in the art. Examples of suitable amino protecting groups include alkoxycarbonyl groups such as t-butoxycarbonyl (t-BOC) and benzyl groups such as benzyl and para-methoxybenzyl. The carboxylic acid group at the 3-position of the morpholine ring may be protected as any stable ester group such as a simple alkyl or aryl ester such as a methyl, ethyl, benzyl, or pentafluorophenyl ester. In one embodiment, $R^{14}$ is —W-G and $R^{13}$ is —OH, halo, or a carboxylic acid protecting group. Various protecting groups are described in detail in *Protecting Groups in Organic Synthesis*, Theodora W. Greene and Peter G. M. Wuts, $3^{rd}$ edition, 1999, published by John Wiley and Sons.

A preferred enantiomer of intermediate 3a is (S)-3a:

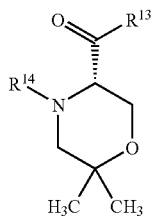

(S)-3a where $R^{13}$ and $R^{14}$ are as described above.

Intermediate 3a or (S)-3a, as the carboxylic acid or an activated form thereof (such as the acid chloride), may be coupled with an appropriate amino-beta-carboline as outlined in Scheme I above. When $R^{14}$ is an amino protecting group, the amide coupling reaction provides further useful intermediates, shown below as compounds of formula IV:

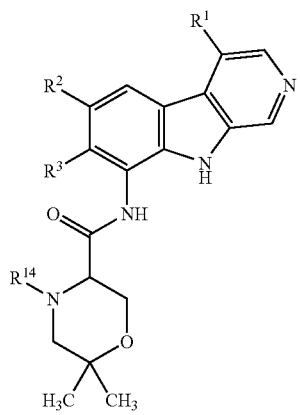

IV where $R^{14}$ is an amino protecting group and $R^1$, $R^2$ and $R^3$ are as described above. It will be appreciated by one of skill in the art that certain compounds of formula III-A-aa (where $R^{6b}$ is each methyl) may be prepared from compounds of formula IV by removing the $R^{14}$ protecting group and then attaching the —W-G portion using known methods. Alternatively, the compounds of formula III-A-aa may be prepared by first constructing intermediate 3a where $R^{14}$ is —W-G and $R^{13}$ is a carboxylic acid or derivative thereof. The amide coupling reaction with an appropriate amino-beta-carboline then provides the compounds of formula III-A-aa directly.

Scheme V

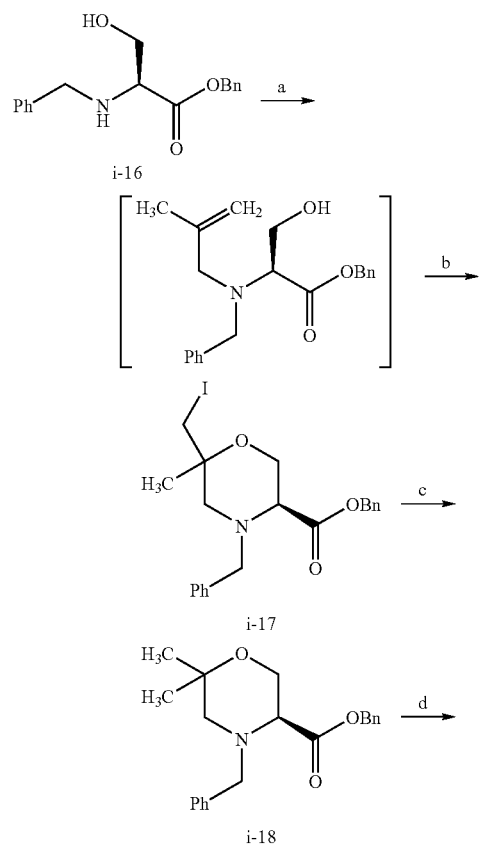

-continued

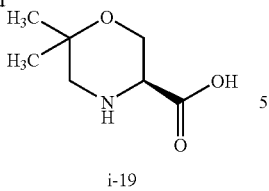

i-19

Steps: (a) K₂CO₃, KI, 3-Bromo-2-methyl-propene, MeCN (b) I₂, NaHCO₃, MeCN (c) Bu₃SnH, AIBN, toluene, 110° C. (d) H₂, 20% Pd(OH)₂/C, 10% AcOH/MeOH Scheme V above shows a route for making intermediates of formula 3a, including the unprotected i-19. The selective protection and deprotection of the amino and carboxylic acid groups in i-19 to provide various 3a intermediates will be within the knowledge of one skilled in the art.

Another useful intermediate for making compounds of formula III-A-aa is a compound of formula V, preferably (S)-V:

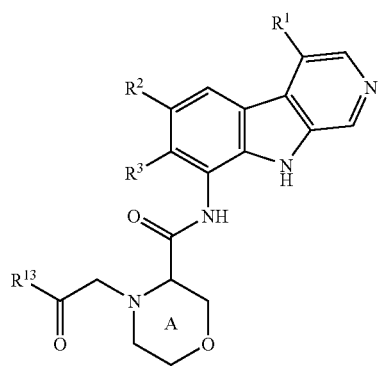

V

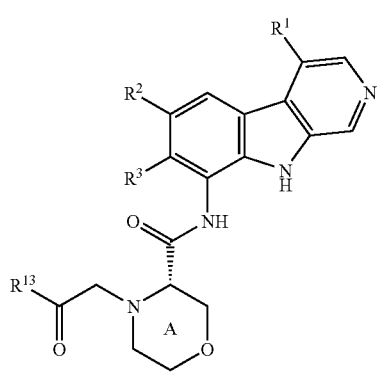

(S)-V where $R^{13}$ is halo or other leaving group, OH, $OR^{15}$, or a carboxylic acid protecting group, $R^{15}$ is an organic radical such as a $C_{1-6}$ aliphatic, aryl or benzyl, Ring A has 0-2 or 0-4 $R^{6b}$, and $R^1$, $R^2$ $R^3$, and $R^{6b}$ are as defined above.

Another useful intermediate for making compounds of this invention is VI, preferably (S)-VI:

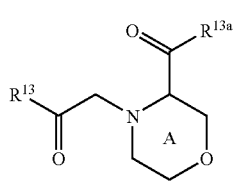

VI

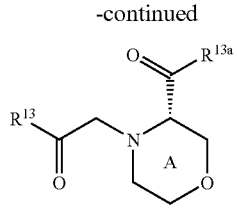

(S)-VI where one of $R^{13}$ and $R^{13a}$ is OH or a leaving group such as halo and the other is $OR^{15}$ or a carboxylic acid protecting group, $R^{15}$ is an organic radical such as a $C_{1-6}$ aliphatic, aryl or benzyl, Ring A has 0-2, and $R^{6b}$ is as defined above.

SYNTHESIS EXAMPLES

The following abbreviations are used in the methods of preparation: RT or rt is room temperature; h, hr or hrs is hour or hours; min is minutes; TFA is trifluoroacetic acid; DMSO is dimethylsulfoxide; NCS is N-chlorosuccinimide; EDCI is 1-(3-dimethylaminopropyl)-3-ethylcarbodiimide hydrochloride; EtOAc is ethyl acetate; DIEA is diisopropylethylamine; DCM is dichloromethane; DDQ is dichloro dicyano benzoquinone; mCPBA is meta-chloroperbenzoic acid; MeOH is methanol; EtOH is ethanol; MeCN is acetonitrile; TLC is thin layer chromatography; AIBN is azobisisobutyronitrile; NH₄OAc is ammonium acetate; NaOAc is sodium acetate; Et₂O is diethyl ether; AcOH is acetic acid; and DMF is dimethylformamide. TBTU is N,N,N',N'-tetramethyl-o-(benzotriazol-1-yl)uronium tetrafluoroborate.

Intermediate 1: 7-fluoro-2,3,4,9-tetrahydro-1H-β-carboline-1-carboxylic acid

To 10 g (46.6 mmol) of commercially available 6-fluorotryptamine hydrochloride was added 50 ml of 1M acetate buffer (pH 4.4) to give a suspension that was stirred at room temperature (RT). A suspension of glyoxylic acid monohydrate (1.1 eq, 51.28 mmol, 4.72 g) in ethyl acetate was then added to the stirred suspension in one portion. The suspension was stirred overnight (16 h) at RT and the precipitated solid was collected by filtration and washed with both H₂O and ethyl acetate. The sample was then dried in vacuo to give a light yellow solid in quantitative yield.

¹H-NMR (300 MHz, acetic acid-d₄): δ 3.04 (m, 2H), 3.56 (m, 1H), 3.83 (m, 1H), 6.80 (m, 1H), 7.13 (dd, 1H), 7.34 (dd, 1H). Retention Time (LC, method: ammonium acetate standard): 1.17 min. MS (M+H⁺): 235.0.

Intermediate 2:
7-fluoro-2,3,4,9-tetrahydro-1H-β-carboline 7-fluoro-2,3,4,9-tetrahydro-1H-β-carboline-1-carboxylic acid (5 g, 21.36 mmol) was suspended in 130 ml of 3N HCl in a 500 ml round-bottom flask and refluxed overnight (16 hr) with stirring. Upon cooling, a light brown solid precipitated out, which was collected by filtration and washed with H₂O. The salt obtained by filtration above was then dissolved in hot methanol (200 ml) and treated with 3M K₂CO₃ (5-10 ml) such that the pH is around 9. 100 ml of H₂O was added to this mixture, which was then allowed to stir at RT. The methanol was evaporated on a rotary evaporator to give a white aqueous suspension of the desired free base, which was collected by filtration (3.2 g, 79% yield). ¹H-NMR (300 MHz, methanol-d₄): δ 2.73 (t, 2H), 3.11 (t, 2H), 3.94 (s, 2H), 6.73 (m, 1H), 6.94 (m, 1H), 7.30 (dd, 1H). Retention Time (LC, method: ammonium acetate standard): 1.25 min. MS (M+H$^+$): 191.1.

Intermediate 3: 7-fluoro-9H-β-carboline 7-fluoro-2,3,4,9-tetrahydro-1H-β-carboline (3.5 g, 18.42 mmol) was suspended in xylenes (60 ml) in a 250 ml round-bottom flask equipped with a condenser that was open to the atmosphere, and heated. To this hot reaction mixture was added Pd/C (10 wt %, 0.2 eq, 700 mg) and the mixture refluxed in xylenes overnight (12-14 hours). The solution was then filtered through a pad of celite and the collected filtrate was then evaporated on a rotary evaporator to give the desired product as a brown/tan solid (3.0 g, 88% yield). $^1$H-NMR (300 MHz, DMSO-d$_6$): δ 7.10 (m, 1H), 7.37 (dd, 1H), 8.10 (d, 1H), 8.28 (dd, 1H), 8.35 (dd, 1H), 8.89 (s, 1H), 11.74 (s, 1H). Retention Time (LC, method: ammonium acetate standard): 1.88 min. MS (M+H$^+$): 187.1.

Intermediate 4: 6-chloro-7-fluoro-9H-β-carboline 7-fluoro-9H-β-carboline (2.15 g, 11.58 mmol) was suspended in 100 ml of 1N HCl. To this mixture was added NCS (1.85 g, 13.89 mmol, 1.2 eq) and the resulting mixture was stirred at RT overnight. The reaction mixture was then filtered to give a light yellow solid (2.1 g, 83% yield).
$^1$H-NMR (300 MHz, DMSO-d$_6$): δ 7.86 (d, 1H), 8.64 (d, 1H), 8.79 (d, 1H), 8.91 (d, 1H), 9.33 (s, 1H), 13.05 (s, 1H). Retention Time (LC, method: ammonium acetate standard): 2.19 min. MS (M+H$^+$): 221.1.

Intermediate 5:
6-chloro-7-fluoro-8-nitro-9H-β-carboline 6-chloro-7-fluoro-9H-β-carboline (2.1 g, 9.54 mmol) was taken in a round-bottom flask (250 ml) and NaNO$_3$ (1.136 g, 13.36 mmol, 1.4 eq) was added. TFA (48 ml) was then added to the flask and the resulting mixture refluxed overnight. The TFA is then removed on a rotary evaporator. The resulting slurry is suspended in water (50 ml) and sonicated thoroughly. The resulting suspension is then filtered to give a yellow solid (2.0 g, 80% yield). $^1$H-NMR (300 MHz, DMSO-d$_6$): δ 8.21 (d, 1H), 8.46 (d, 1H), 9.04 (m, 2H), 12.55 (s, 1H). Retention Time (LC, method: ammonium acetate standard): 2.24 min. MS (M+H$^+$): 266.2.

Intermediate 6:
6-chloro-7-methoxy-8-nitro-9H-β-carboline

Methanol (0.462 ml, 11.4 mmol) was added to a stirring suspension of NaH (684 mg, 17.1 mmol) in DMF (10 ml) under an argon atmosphere. The resulting solution was allowed to stir at RT for 20 min. 6-chloro-7-fluoro-8-nitro-9H-β-carboline (500 mg, 1.9 mmol) was added to the stirring solution and the resulting mixture was allowed to stir at RT. Upon addition of H$_2$O, a brown solid precipitated out which was filtered to give the desired 6-chloro-7-methoxy-8-nitro-9H-β-carboline (510 mg, 97% yield). $^1$H-NMR (300 MHz, DMSO-d$_6$): δ 4.02 (s, 3H), 8.52 (d, 1H), 8.60 (d, 1H), 9.05 (s, 1H), 9.12 (s, 1H), 12.78 (b, 1H). Retention Time (LC, method: ammonium acetate standard): 2.28 min. MS (M+H$^+$): 278.

Intermediate 7:
6-chloro-7-methoxy-9H-β-carboline-8-ylamine 6-chloro-7-methoxy-8-nitro-9H-β-carboline (510 mg, 1.84 mmol) was suspended in 50 ml of methanol and 100 mg of Pd/C (10%) was added. The flask was fitted with a balloon of hydrogen and the reaction mixture was stirred overnight at RT. Upon filtration through a pad of celite and evaporation of the methanol, a dark brown solid was obtained. This residue was suspended in methanol (15 ml) and added, with vigorous stirring, to a solution of saturated NaHCO$_3$ (100 ml). The light brown solid that precipitated out was collected by filtration and dried thoroughly in vacuo to give the desired product (512 mg, quantitative yield). $^1$H-NMR (300 MHz, methanol-d$_4$): 63.90 (s, 3H), 7.63 (s, 1H), 8.11 (d, 1H), 8.27 (d, 1H), 8.84 (s, 1H). Retention Time (LC, method: ammonium acetate standard): 1.12 min.
MS (M+H$^+$): 248.

Intermediate 8: 6-chloro-9H-β-carboline-8-ylamine

The target compound was prepared according to the procedures outlined for Intermediate 1 to Intermediate 7 where the starting material for Intermediate 1 was unsubstituted tryptamine. An alternative synthesis for 6-chloro-9H-β-carboline-8-ylamine is described on page 34, example 15 of PCT Application Publication No. WO 01/68648 A1, which is incorporated herein in its entirety.

Method A: Coupling Procedure for
6,7,8-SUBSTITUTED-β-CARBOLINES 6,7,8-substituted-9H-β-carboline (1 mmol), EDCI (1.6 mmol) and the appropriate carboxylic acid (1.2 mmol) were taken in a round-bottom flask and suspended in pyridine (5 ml). The resulting mixture was heated at 60° C. overnight. The pyridine was then removed by rotary evaporation and 5% Na$_2$CO$_3$ solution was added. The resulting solid that precipitated out was collected by filtration. Chromatographic purification gave the desired product.

Method B: Coupling Procedure for
6,8-SUBSTITUTED-β-CARBOLINES 6,8-substituted-9H-β-carboline (1.0 mmol), EDCI (1.6 mmol) and the carboxylic acid (1.2 mmol) to be coupled were taken in a round-bottom flask and suspended in pyridine (5 ml). The resulting mixture was stirred overnight. The pyridine was then removed by rotary evaporation and 5% Na$_2$CO$_3$ solution was added. The resulting solid that precipitated out was collected by filtration. Chromatographic purification gave the desired product.

Example 1

N-(6-chloro-7-methoxy-9H-β-carbolin-8-yl)-2-methyl-nicotinamide 6-chloro-7-methoxy-9H-β-carbolin-8-ylamine (100 mg, 0.4 mmol), EDCI (125 mg, 0.64 mmol) and 2-methyl nicotinic acid (66 mg, 0.48 mmol) were taken in a round-bottom flask and suspended in pyridine (2 ml). The resulting mixture was heated at 80° C. overnight. The pyridine was then removed by rotary evaporation and 5% Na$_2$CO$_3$ solution was added. The resulting solid that precipitated out was collected by filtration. Chromatographic purification gave the desired product in 50-70% yield. $^1$H-NMR (300 MHz, DMSO-d$_6$): δ 2.71 (s, 3H), 3.89 (s, 3H), 7.45 (dd, 1H), 8.15 (d, 1H), 8.21 (d, 1H), 8.38 (d, 1H), 8.45 (s, 1H), 8.61 (d, 1H), 8.92 (s, 1H), 10.33 (s, 1H), 11.57 (s, 1H). Retention Time (LC, method: ammonium acetate standard): 1.77 min. MS (M+H$^+$): 367.1.

Example 2

4-methyl-pyrimidine-5-carboxylic acid (6-chloro-7-methoxy-9H-beta-carbolin-8-yl)-amide The desired compound was prepared according to Method A from 6-chloro-7-methoxy-9H-beta-carbolin-8-ylamine and 4-methyl-5-pyrimidine carboxylic acid in 80% yield. $^1$H-NMR (300 MHz, DMSO-$d_6$): δ 2.75 (s, 3H), 3.92 (s, 3H), 8.19 (d, 1H), 8.41 (d, 1H), 8.50 (s, 1H), 8.96 (s, 1H), 9.20 (s, 1H), 9.25 (s, 1H), 10.63 (s, 1H), 11.67 (s,1H). Retention Time (LC, method: formic acid standard): 0.95 min. MS (M+H$^+$): 368.

Intermediate 9: 6-chloro-7-ethoxy-8-nitro-9H-β-carboline

Sodium ethoxide (232 mg, 3.4 mmol) was added to a solution of 6-chloro-7-fluoro-8-nitro-9H-β-carboline (200 mg, 0.76 mmol) in DMSO (4 ml) and the reaction mixture allowed to stir overnight. The reaction mixture was diluted with water and the pH of the solution was adjusted to about 4 by adding 1N HCl. The aqueous solution was extracted (3×) with EtOAc. The combined EtOAc layers were dried and evaporated. The crude product was purified by flash chromatography to give the desired product in 40-60% yield. $^1$H-NMR (300 MHz, DMSO-$d_6$): δ 1.44 (t, 3H), 4.24 (q, 2H), 8.21 (d, 1H), 8.46 (d, 1H), 8.91 (s, 1H), 9.02 (s, 1H). Retention Time (LC, method: ammonium acetate standard): 2.37 min. MS (M+H$^+$): 291.9.

Intermediate 10: 6-chloro-7-ethoxy-9H-β-carbolin-8-ylamine 6-chloro-7-ethoxy-8-nitro-9H-β-carboline (160 mg, 0.55 mmol) was suspended in 4 ml of methanol and 25 mg of Pd/C (10%) was added. The flask was fitted with a balloon of hydrogen and the reaction mixture was stirred overnight at RT. Upon filtration through a pad of celite and evaporation of the methanol, a dark brown solid was obtained and determined to be the desired 6-chloro-7-cyclopropylmethoxy-9H-β-carbolin-8-ylamine (80 mg, 55%). $^1$H-NMR (300 MHz, Methanol-$d_4$/CDCl$_3$): δ 1.26 (t, 3H), 3.91 (q, 2H), 7.34 (s, 1H), 7.71 (d, 1H), 8.02 (s, 1H), 8.56 (s, 1H). Retention Time (LC, method: formic acid standard): 1.16 min. MS (M+H$^+$): 262.0.

Example 3

N-(6-chloro-7-ethoxy-9H-β-carbolin-8-yl)-2-methyl-nicotinamide

The desired compound was prepared according to Method A from 6-chloro-7-ethoxy-9H-β-carbolin-8-ylamine and 2-methylnicotinic acid in 40% yield. $^1$H-NMR (300 MHz, MeOH-$d_4$): δ 1.39 (t, 3H), 2.76 (s, 3H), 4.14 (q, 2H), 7.43 (dd, 1H), 8.05 (d, 1H), 8.26 (m, 3H), 8.55 (d, 1H), 8.79 (s, 1H). Retention Time (LC, method: ammonium acetate standard): 1.98 min. MS (M+H$^+$): 381.3.

Intermediate 11: 6-chloro-7-(N,N)-dimethylamino-8-nitro-9H-β-carboline

N,N-dimethylamine hydrochloride (278 mg, 3.4 mmol) was added to a stirring solution of 6-chloro-7-fluoro-8-nitro-9H-β-carboline (300 mg, 1.13 mmol) in DMSO (8 ml) under an argon atmosphere. This was followed by the addition of DIEA (0.83 ml, 4.65 mmol) and the reaction mixture was heated at 60° C. overnight. After allowing the reaction mixture to cool to RT, water was added and a dark orange solid precipitated out. The solid was filtered, washed with water and dried to give the desired product (230 mg, 70% yield). $^1$H-NMR (300 MHz, DMSO-$d_6$): δ 4.06 (s, 6H), 7.23 (d, 1H), 7.53 (d, 1H), 7.66 (s, 1H), 8.05 (s, 1H). Retention Time (LC, method: ammonium acetate standard): 2.41 min. MS (M+H$^+$): 290.9.

Intermediate 12: 6-chloro-7-(N,N)-dimethylamino-9H-β-carboline-8-ylamine 6-chloro-7-(N,N)-dimethylamino-8-nitro-9H-β-carboline (828 mg, 2.86 mmol) was suspended in 30 ml of methanol and 166 mg of Pd/C (10%) was added. The flask was fitted with a balloon of hydrogen and the reaction mixture was stirred overnight at ambient temperature. Upon filtration through a pad of celite and evaporation of the methanol, a dark brown solid was obtained and determined to be the desired 6-chloro-7-(N,N)-dimethylamino-9H-β-carboline-8-ylamine (500 mg, 67% yield). $^1$H-NMR (300 MHz, DMSO-$d_6$): δ 2.80 (s, 6H), 5.42 (s, 2H), 7.45 (s, 1H), 7.95 (d, 1H), 8.23 (d, 1H), 8.86 (d, 1H). Retention Time (LC, method: ammonium acetate standard): 2.32 min. MS (M+H$^+$): 261.1.

Example 4

N-(6-chloro-7-7-(N,N)-dimethylamino-9H-β-carbolin-8-yl)-2-methyl-nicotinamide The desired compound was prepared according to Method A from 6-chloro-7-(N,N)-dimethylamino-9H-β-carboline-8-ylamine and 2-methylnicotinic acid in 40-60% yield. $^1$H-NMR (300 MHz, Methanol-$d_4$/CDCl$_3$): δ 2.82 (s, 3H), 2.94 (s, 6H), 7.33 (m, 1H), 8.02 (m, 3H), 8.34 (d, 1H), 8.61 (d, 1H), 8.95 (s, 1H). Retention Time (LC, method: ammonium acetate standard): 2.29 min. MS (M+H$^+$): 380.3.

Intermediate 13: 6-chloro-7-(4-methyl-piperazin-1-yl)-8-nitro-9H-β-carboline To a DMSO solution (4 ml) of 200 mg (0.755 mmol) of 6-chloro-7-fluoro-8-nitro-9H-β-carboline was added 1-methylpiperazine (226 mg, 2.26 mmol) and DIEA (400 mg, 3.09 mmol) via a syringe. The reaction was allowed to stir at RT overnight. Upon addition of water, an orange solid precipitated out. The solid was filtered, washed and dried to give 236 mg (91% yield) of the desired 6-chloro-7-(4-methyl-piperazin-1-yl)-8-nitro-9H-β-carboline. $^1$H-NMR (300 MHz, DMSO-$d_6$): δ 2.24 (s, 3H), 2.48 (m, 4H), 3.13 (m, 4H), 8.13 (d, 1H), 8.40 (d, 1H), 8.73 (s, 1H), 8.94 (s, 1H), 12.05 (s, 1H). Retention Time (LC, method: ammonium acetate standard): 1.72 min. MS (M+H$^+$): 346.

Intermediate 14: 6-chloro-7-(4-methyl-piperazin-1-yl)-8-amino-9H-β-carboline Suspended 236 mg of 6-chloro-7-(4-methyl-piperazin-1-yl)-8-nitro-9H-β-carboline in 100 ml of methanol and added 10% Pd/C (48 mg) under argon. The flask was flushed with hydrogen (3×) and the reaction mixture was stirred under a hydrogen atmosphere at RT overnight. The reaction mixture was filtered and Pd/C was removed using a pad of celite. The reaction mixture was evaporated to remove solvent and purified by flash chromatography to give 119 mg (55% yield) of the desired 6-chloro-7-(4-methyl-piperazin-1-yl)-8-amino- 9H-β-carboline. ¹H-NMR (300 MHz, methanol-d₄): δ 2.39 (s, 3H), 2.46 (m, 2H), 2.87 (m, 4H), 3.83 (m, 2H), 7.50 (s, 1H), 7.97 (d, 1H), 8.24 (d, 1H), 8.78 (s, 1H). Retention Time (LC, method: ammonium acetate polar): 1.32 min. MS (M+H⁺): 316.

Example 5

2-chloro-N-[6-chloro-7-(4-methyl-piperazin-1-yl)-9H-β-carbolin-8-yl]-nicotinamide The desired compound was prepared according to Method A from 6-chloro-7-(4-methyl-piperazin-1-yl)-8-amino-9H-β-carboline and 2-chloro-nicotinic acid in 25% yield. ¹H-NMR (300 MHz, DMSO-d₆): δ 2.21 (s, 3H), 2.33 (m, 2H), 2.54(m, 2H), 3.24 (m, 4H), 7.73 (dd, 1H), 8.12 (d, 1H), 8.35 (d, 1H), 8.37 (s, 1H), 8.48 (dd, 1H), 8.61 (dd, 1H), 8.91 (s, 1H), 10.40 (s, 1H), 11.33 (s, 1H). Retention Time (LC, method: ammonium acetate standard): 1.46 min. MS (M+H⁺): 455.

Intermediate 15: Resolution of rac-terebic acid

Terebic acid was dissolved in a 10:1 mixture of EtOAc-MeOH [10 g of terebic acid (17.7 g of salt) in 550 ml] and heated to 50-55° C., followed by addition of (S)-(−)-α-methyl-benzylamine. The reaction mixture was stirred for 2 minutes and then left at RT for 15 minutes. The reaction mixture was then seeded with enriched salt (prepared on a smaller scale using 3 recrystallization cycles), sonicated for 10-15 seconds and left at RT overnight. The solid was filtered off, washed with EtOAc and dried under vacuum. Recrystallization was done in the same solvent mixture by re-dissolving the salt (24 mg/ml). This mixture was then heated to a gentle reflux for a short period of time (few crystals remained in suspension). The mixture was left at RT over night. The solid was processed as previously described.

Enantiomeric excess was determined in a crude fashion using proton NMR of the corresponding amide obtained from TBTU coupling.

Regeneration of (R)-(+)-terebic acid: The salt was dissolved in water (320 mg/ml), heated to 65° C. and 1.2 equivalent of aqueous 6M HCl was added. The reaction mixture was then left at 4° C. overnight. The solid was filtered off, washed with small portions of cold water and dried under a high vacuum (yield of 25-30%). ¹H-NMR (300 MHz, DMSO-d₆): δ 1.30 (s, 3H), 1.52 (s, 3H), 2.74 (dd, 1H), 2.85 (dd, 1H), 3.25 (t, 1H). Retention Time (LC, method: ammonium acetate standard): 0.33 min. MS (M+H⁺): 159.0.

Example 6

2,2-dimethyl-5-oxo-tetrahydro-furan-3-carboxylic acid (6-chloro-9H-β-carbolin-8-yl)-amide The desired compound was prepared according to Method B from 6-chloro-9H-β-carboline-8-ylamine and (R)-terebic acid (Intermediate 15) in 80-90% yield. ¹H-NMR (300 MHz, DMSO-d₆): δ 1.44 (s, 3H), 1.59 (s, 3H), 2.91 (dd, 1H), 3.08 (dd, 1H), 3.38 (dd, 1H), 7.85 (m, 1H), 8.17 (d, 1H), 8.25 (d, 1H), 8.39 (d, 1H), 9.05 (s, 1H), 10.26 (s, 1H), 11.72 (s, 1H). Retention Time (LC, method: ammonium acetate standard): 1.22 min. MS (M+H⁺): 358.3.

Example 7

1,2,2-trimethyl-5-oxo-pyrrolidine-3-carboxylic acid (6-chloro-9H-β-carbolin-8-yl)-amide The desired compound was prepared according to Method B from 6-chloro-9H-β-carboline-8-ylamine and 1,2,2-trimethyl-5-oxo-pyrrolidine-3-carboxylic acid in 68% yield. ¹H-NMR (DMSO-d₆, 300 MHz) δ 1.23 (s, 3H), 1.45 (s, 3H), 2.59 (dd, 1H), 2.66(s, 3H), 2.70 (dd, 1H), 3.17 (t, 1H), 7.91 (m, 1H), 8.18 (d, 1H), 8.24 (d, 1H), 8.40 (d, 1H), 9.07 (s, 1H), 10.16 (s, 1H), 11.32 (s, 1H). Retention Time (LC, method: ammonium acetate standard): 1.17 min. MS (M+H⁺): 371.3.

Intermediate 16: N-benzyl-serine benzyl ester

To a mixture of L-serine-benzyl ester-HCl (2.3 g), benzaldehyde (1.05 eq.) and sodium acetate (1 eq.) in methanol was added sodium cyanoborohydride (1.0 eq.). The resulting mixture was stirred at ambient temperature for 15 hrs, then partitioned into ether and aqueous saturated sodium bicarbonate. The separated organic phase was extracted with 1M HCl (3×). Combined aqueous extracts were washed with ether, basified with aqueous 4.5M K₂CO₃ and extracted with ether. Combined organic extracts were washed with brine, dried over sodium sulfate and concentrated to dryness to give 2.32 g of the desired compound (waxy solid, 81% yield). ¹H-NMR (300 MHz, CDCl₃): δ 3.48 (dd, 1H), 3.64 (dd, 1H), 3.74 (d, 1H), 3.80 (dd, 1H), 3.88 (d, 1H), 5.18 (s, 2H), 7.25-7.39 (m, 10H). MS (M+H⁺): 286.

Intermediate 17: 4-benzyl-6-iodomethyl-6-methyl-morpholine-3-carboxylic acid benzyl ester To a solution of N-benzyl-serine benzyl ester (Intermediate 16, 6.35 g) in 90 ml of MeCN at ambient temperature was added 3-bromo-2-methyl-propene (5.6 ml), KI (740 mg) and K₂CO₃ (7.7 g). The reaction mixture was stirred at ambient temperature for 72 hrs. 1 ml of 3-bromo-2-methyl-propene was added and the reaction mixture was stirred for another 15 hrs. Only a small amount of starting material remained based on TLC (1:1; EtOAc-hexane). To the resulting mixture was added 11.2 g of iodine. After 4 hrs of stirring, TLC (10% EtOAc/hexane) showed complete conversion. The reaction mixture was partitioned into ether (300 ml) and 0.5 M Na₂S₂O₃ (100 ml). The separated organic phase was washed successively with water, saturated NaHCO₃ and brine, dried over MgSO₄, and concentrated to dryness. The residue was purified on silica (5% EtOAc/Hexane) to give 6.65 g (yellowish oil, 64% yield, about 4:1 mixture) of compound 4-benzyl-6-iodomethyl-6-methyl-morpholine-3-carboxylic acid benzyl ester. Major Component: ¹H-NMR (300 MHz, CDCl₃): δ 1.22 (s, 3H), 2.50 (d, 1H), 3.16-3.36 (m, 3H), 3.75-3.95 (m, 4H), 4.06 (dd, 1H), 5.16 (d, 1H), 5.21 (d, 1H), 7.28-7.36 (m, 10H).
MS (M+H⁺): 466.

Intermediate 18: 4-benzyl-6,6-dimethyl-morpholine-3-carboxylic acid benzyl ester To a solution of 4-benzyl-6-iodomethyl-6-methyl-morpholine-3-carboxylic acid benzyl ester (Intermediate 17, 1.23 g) and tributyltin hydride (1.8 ml, 2.5 eq.) in 11 ml of toluene under gentle reflux was added over 1.5 hr a solution of AIBN in toluene (25 mg/1 ml). The mixture was allowed to cool down and was concentrated to dryness. The residue was partitioned into 15% 1M HCl in acetonitrile and hexane. The separated hexane phase was extracted two times with the acetonitrile solution. The combined acetonitrile solutions were washed with hexane two times and concentrated. The residue was partitioned into ether and 1M $K_2CO_3$. The separated ether phase was washed successively with 0.4M $Na_2S_2O_3$ and brine, dried over $MgSO_4$ and concentrated. The residue was purified on silica (7.5% EtOAc/hexane) to give 760 mg (oil, 85% yield) of compound 4-benzyl-6,6-dimethyl-morpholine-3-carboxylic acid benzyl ester. $^1$H-NMR (300 MHz, CDCl$_3$): δ 1.21 (s, 3H), 1.24 (s, 3H), 2.12 (d, 1H), 2.84 (d, 1H), 3.29 (t, 1H), 3.58 (d, 1H), 3.95-4.05 (m, 2H), 5.15 (d, 1H), 5.21 (d, 1H), 7.28-7.36 (m, 10H). MS (M+H$^+$):340.

Intermediate 19:
6,6-dimethyl-morpholine-3-carboxylic acid

To a solution of 4-benzyl-6,6-dimethyl-morpholine-3-carboxylic acid benzyl ester (Intermediate 18, 1.25 g) in 40 ml of 10% AcOH/MeOH (under nitrogen) was added 250 mg of 20% Pd(OH)$_2$ on charcoal. The reaction mixture was purged with hydrogen (balloon) and was stirred at ambient temperature for 72 hrs. To the resulting gray mixture was added 4 ml of water to help dissolution. The catalyst was removed by filtration and the filtrate was concentrated to dryness. The residue was co-evaporated with ethanol (2×) and then triturated with EtOAc. The generated white solid was filtered off and dried under high vacuum to give 559 mg of 6,6-dimethyl-morpholine-3-carboxylic acid (95% yield). $^1$H-NMR (300 MHz, D$_2$O): δ 1.35 (s, 3H), 1.38(s, 3H), 3.11 (d, 1H), 3.32 (d, 1H), 3.81-3.87 (m, 1H), 4.05 (bt, 1H), 4.17 (bd, 1H). MS (M+H$^+$): 160.

Intermediate 20:
4,6,6-trimethyl-morpholine-3-carboxylic acid

To a suspension of 6,6-dimethyl-morpholine-3-carboxylic acid (Intermediate 19, 540 mg) in 17 ml of ethanol (under nitrogen) was added 100 mg of 10% Pd on charcoal and 830 ul (3 eq.) of 37% aqueous formaldehyde. The mixture was purged with hydrogen (balloon) and stirred at ambient temperature for 5 hrs. To the resulting gray mixture were added 4 ml of water and 4 ml of methanol to help dissolution. The catalyst was removed by filtration and the filtrate was concentrated to dryness. The residue was triturated with EtOAc. The generated white solid was filtered off and dried under high vacuum to give 574 mg of 4,6,6-trimethyl-morpholine-3-carboxylic acid (97% yield).
$^1$H-NMR (300 MHz, D$_2$O): δ 1.35 (s, 3H), 1.43(s, 3H), 2.94(s, 3H), 3.08 (d, 1H), 3.41 (d, 1H), 3.68 (dd, 1H), 3.96 (t, 1H), 4.14 (dd, 1H).
MS (M+H$^+$): 174.

Example 8

4,6,6-trimethyl-morpholine-3-carboxylic acid (6-chloro-9H-β-carbolin-8-yl)-amide The desired compound was prepared according to Method B from 6-chloro-9H-β-carboline-8-ylamine and 4,6,6-trimethyl-morpholine-3-carboxylic acid in 61% yield. $^1$H-NMR (DMSO-d$_6$, 300 MHz) δ 1.15 (s, 3H), 1.39 (s, 3H), 1.98 (d, 1H), 2.26 (s, 3H), 2.72 (d, 1H), 2.80 (dd, 1H), 3.79(m, 2H), 7.91 (s, 1H), 8.03-8.08 (m, 2H), 8.22 (d, 1H), 8.97 (s, 1H). Retention Time (LC, method: ammonium acetate standard): 1.33 min. MS (M+H$^+$): 373.2.

Example 9

2,2-Dimethyl-5-oxo-tetrahydro-furan-3-carboxylic acid (6-chloro-7-methoxy-9H-β-carbolin-8-yl)-amide The desired compound was prepared according to Method A from 6-chloro-7-methoxy-9H-β-carboline-8-ylamine and (R)-terebic acid in a 60-80% yield. $^1$H-NMR (300 MHz, DMSO-d$_6$): δ 1.48 (s, 3H), 1.61 (s, 3H), 3.03 (m, 2H), 3.51 (m, 1H), 3.86 (s, 3H), 8.16 (m, 1H), 8.37 (m, 1H), 8.43 (s, 1H), 8.94 (s, 1H), 10.10 (s, 1H), 11.33 (s, 1H). Retention Time (LC, method: ammonium acetate standard): 1.94 min. MS (M+H$^+$): 388.

Intermediate 21: 6-chloro-7-cyclopropylmethoxy-8-nitro-9H-β-carboline

Cyclopropylmethyl alcohol (0.921 ml, 11.4 mmol) was added to a stirring suspension of NaH (455 mg, 11.4 mmol) in DMF (20 ml) under an argon atmosphere. The resulting solution was allowed to stir at RT for 20 min. 6-chloro-7-fluoro-8-nitro-9H-β-carboline (500 mg, 1.9 mmol) was added to the stirring solution and the resulting mixture was allowed to stir at RT. Upon addition of H$_2$O, a brown solid precipitated out which was filtered to give the desired 6-chloro-7-cyclopropylmethyoxy-8-nitro-9H-β-carboline (510 mg, 85%). $^1$H-NMR (300 MHz, DMSO-d$_6$): δ 0.35 (m, 2H), 0.59 (m, 2H), 1.32 (m, 1H), 4.04 (d, 2H), 8.21 (d, 1H), 8.46 (d, 1H), 8.90 (s, 1H), 9.02 (s, 1H), 12.32 (b, 1H). Retention Time (LC, method: ammonium acetate standard): 2.63 min. MS (M+H$^+$): 318.

Intermediate 22: 6-chloro-7-cyclopropylmethoxy-9H-β-carbolin-8-ylamine 6-chloro-7-cyclopropylmethoxy-8-nitro-9H-β-carboline (510 mg, 1.61 mmol) was suspended in 12 ml of methanol and 100 mg of Pd/C (10%) was added. The flask was fitted with a balloon of hydrogen and the reaction mixture was stirred overnight at RT. Upon filtration through a pad of celite and evaporation of the methanol, a dark brown solid was obtained. This residue was suspended in methanol (10 ml) and added, with vigorous stirring, to a solution of saturated NaHCO$_3$ (100 ml). The light brown solid that precipitated out was collected by filtration and dried thoroughly in vacuo to give the desired 6-chloro-7-cyclopropylmethoxy-9H-β-carbolin-8-ylamine (371 mgs, 80% yield). $^1$H-NMR (300 MHz, methanol-d$_4$): δ 0.36 (m, 2H), 0.61 (m, 2H), 1.37 (m, 1H), 3.88 (d, 2H), 7.58 (s, 1H), 7.96(d, 1H), 8.23 (d, 1H), 8.76 (s, 1H). Retention Time (LC, method: ammonium acetate standard): 2.28 min. MS (M+H$^+$): 288.

Example 10

N-(6-chloro-7-cyclopropylmethoxy-9H-β-carbolin-8-yl)-2-methyl-nicotinamide

The desired compound was prepared according to Method A from 6-chloro-7-cyclopropylmethoxy-9H-β-carbolin-8-ylamine and 2-methylnicotinic acid in a 40-60% yield. $^1$H-NMR (300 MHz, MeOH-d$_4$): 60.29 (m, 2H), 0.55 (m, 2H), 1.29 (m, 1H), 2.78 (s, 3H), 3.95 (m, 2H), 7.46 (dd, 1H), 8.08 (m, 1H), 8.30 (m, 3H), 8.59 (m, 1H), 8.81 (s, 1H). Retention Time (LC, method: ammonium acetate standard): 2.18 min. MS (M+H$^+$): 405.

Intermediate 23: 6-chloro-7-(N,N)-dimethylaminoethoxy-8-nitro-9H-β-carboline N,N-dimethylaminoethyl alcohol (6.0 eq) was added to a stirring suspension of NaH (6.0 eq) in DMF under an argon atmosphere. The resulting solution was allowed to stir at RT for 20 min. 6-chloro-7-fluoro-8-nitro-9H-β-carboline (1.0 eq) was added to the stirring solution and the resulting mixture was allowed to stir at RT. Upon addition of $H_2O$, a brown solid precipitated out which was filtered to give the desired 6-chloro-7-(N,N)-dimethylaminoethoxy-8-nitro-9H-β-carboline (quantitative yield). $^1$H-NMR (300 MHz, DMSO-$d_6$): δ 2.23 (s, 6H), 2.74 (t, 2H), 4.28 (t, 2H), 8.21(d, 1H), 8.46 (d, 1H), 8.90 (s, 1H), 9.02 (s, 1H). Retention Time (LC, method: ammonium acetate standard): 1.26 min.
MS (M+H$^+$): 335.

Intermediate 24: 6-chloro-7-(N,N)-dimethylaminoethoxy-9H-β-carbolin-8-ylamine 6-chloro-7-(N,N)-dimethylaminoethoxy-8-nitro-9H-β-carboline (500 mg, 1.5 mmol) was suspended in 12 ml of methanol and 100 mg of Pd/C (10%) was added. The flask was fitted with a balloon of hydrogen and the reaction mixture was stirred overnight at RT. Upon filtration through a pad of celite and evaporation of the methanol, a dark brown solid was obtained. The residue was suspended in methanol (10 ml) and added, with vigorous stirring, to a solution of saturated $NaHCO_3$ (100 ml). The solid that precipitated out was collected by filtration and dried thoroughly in vacuo to give the desired 6-chloro-7-(N,N)-dimethylaminoethoxy-9H-β-carboline-8-ylamine (380 mgs, 83%). $^1$H-NMR (300 MHz, methanol-$d_4$): δ 2.43 (s, 6H), 2.84 (t, 2H), 4.11 (t, 2H), 7.47 (s, 1H), 7.88 (d, 1H), 8.20 (d, 1H), 8.72 (s, 1H). Retention Time (LC, method: ammonium acetate standard): 1.34 min. MS (M+H$^+$): 305.

Example 11

N-[6-cloro-7-(2-dimethylamino-ethoxy)-9H-β-carbolin-8-yl]-2-methyl-nicotinamide The desired compound was prepared according to Method A from 6-chloro-7-(N,N)-dimethylaminoethoxy-9H-β-carboline-8-ylamine and 2-methylnicotinic acid in a 40-60% yield. $^1$H-NMR (300 MHz, DMSO-$d_6$): δ 1.92 (s, 6H), 2.49 (m, 2H), 2.68 (s, 3H), 4.25 (m, 2H), 7.50 (dd, 1H), 8.16 (m, 2H), 8.38 (d, 1H), 8.42 (s, 1H), 8.66 (m, 1H), 9.00 (s, 1H), 11.27 (s, 1H), 11.78 (s, 1H). Retention Time (LC, method: ammonium acetate standard): 1.52 min. MS (M+H$^+$): 424.

Example 12

2-amino-cyclopentanecarboxylic acid (6-chloro-7-methoxy-9H-β-carbolin-8-yl)-amide 6-chloro-7-methoxy-9H-β-carboline-8-ylamine and 2-tert-butoxycarbonylamino-cyclopentanecarboxylic acid were reacted using Method A. To this product was added 5 ml of 4N HCl/dioxane and the resulting mixture was allowed to stir at RT. The reaction was followed by LC-MS until completion. Evaporation was allowed to remove all the solvent which gave a crude HCl salt. The desired product was then purified by preparative HPLC. $^1$H-NMR (300 MHz, DMSO-$d_6$): δ 1.68 (m, 1H), 1.84 (m, 2H), 2.06 (m, 2H), 2.20 (m, 1H), 3.46 (m, 1H), 3.67 (m, 1H), 3.89 (s, 3H), 8.24 (d, 2H), 8.61 (d, 1H), 8.72 (s, 1H), 8.78 (d, 1H), 9.19 (s, 1H), 10.58 (s, 1H), 13.20 (s, 1H). Retention Time (LC, method: ammonium acetate standard): 1.54 min. MS (M+H$^+$): 359.

Intermediate 25: 1-(2-dimethylamino-ethyl)-5-oxo-pyrrolidine-3-carboxylic acid A mixture of commercially available itaconic acid and N,N-dimethylethylenediamine was heated up to 160° C. for about 20-25 minutes. The mixture was allowed to cool to 100° C. and then diluted with MeOH to prevent solidification. The product was obtained in a 56% yield after crystallization from MeOH/EtOAc. $^1$H-NMR (300 MHz, $D_2O$): δ 2.63 (dd, 1H), 2.80 (dd, 1H), 2.95 (s, 6H), 3.15-3.25 (m, 1H), 3.32-3.44 (m, 1H), 3.44-3.76 (m, 4H), 3.82-3.94 (m, 1H). Retention Time (LC, method: ammonium acetate standard): 0.13 min. MS (M+H$^+$): 201.0.

Example 13

1-(2-Dimethylamino-ethyl)-5-oxo-pyrrolidine-3-carboxylic acid (6-chloro-9H-β-carbolin-8-yl)-amide Prepared according to Method B from 6-chloro-9H-β-carboline-8-ylamine and 1-(2-dimethylamino-ethyl)-5-oxo-pyrrolidine-3-carboxylic acid in 70-80% yield as the di-HCl salt. $^1$H-NMR (300 MHz, $D_2O$): δ 2.97 (dd, 1H), 3.03 (s, 6H), 3.08 (dd, 1H), 3.51 (t, 2H), 3.76-3.89 (m, 3H), 3.95 (dd, 1H), 4.01 (dd, 1H), 7.75 (d, 1H), 8.24 (d, 1H), 8.45 (dd, 1H), 8.52 (dd, 1H), 9.10 (bs, 1H). Retention Time (LC, method: ammonium acetate standard): 0.99 min. MS (M+H$^+$): 400.

Example 14

1-(2-dimethylamino-ethyl)-5-oxo-pyrrolidine-3-carboxylic acid (6-chloro-7-methoxy-9H-β-carbolin-8-yl)-amide Prepared according to Method A from 6-chloro-7-methoxy-9H-β-carboline-8-ylamine and 1-(2-dimethylamino-ethyl)-5-oxo-pyrrolidine-3-carboxylic acid in 60% yield following purification using a semi-preparative Chiralcel OD column with 85/7.5/7.5 hexane/EtOH/MeOH as the eluant. $^1$H-NMR (300 MHz, DMSO-$d_6$): δ 2.44 (s, 6H), 2.75 (t, 2H), 2.88 (d, 2H), 3.56 (t, 2H), 3.66 (m, 1H), 3.85 (m, 2H), 3.90 (s, 3H), 8.03 (d, 1H), 8.21 (s, 1H), 8.28 (d,1H), 8.79 (s,1H). Retention Time (LC, method: ammonium acetate standard): 1.42 min. MS (M+H$^+$): 430.

Intermediate 26: 6-chloro-7-fluoro-9H-β-carbolin-8-ylamine

A slurry of 6-chloro-7-fluoro-8-nitro-9H-β-carboline (500 mg, 1.88 mmol) in MeOH (25 ml) was degassed with argon. Palladium on charcoal (20% w/w on C, 50 mg) was added and the reaction vessel was flushed with hydrogen. The slurry was stirred under a balloon of hydrogen for 6 hr, then filtered through celite and concentrated under reduced pressure to yield 6-chloro-7-fluoro-9H-β-carbolin-8-ylamine (400 mg) as a brown solid. $^1$H-NMR (300 MHz, DMSO-$d_6$): δ 11.48 (br s, 1); 8.99-8.98 (m, 1); 8.37-8.35 (m, 1); 8.11-8.09 (m, 1); 7.74-7.72 (m, 1); 5.65 (br s, 2). HCOOH standard conditions. DAD $R_f$=1.00 min. MS (M+H$^+$): 236.

Example 15

N-(6-chloro-7-fluoro-9H-β-carbolin-8-yl)-2-methyl-nicotinamide

A solution of 6-chloro-7-fluoro-9H-β-carbolin-8-ylamine (100 mg, 0.424 mmol) in pyridine (2.5 ml) was stirred at RT.

2-methyl nicotinic acid (70 mg, 0.509 mmol) was added, followed by EDCI (130 mg, 0.678 mmol). The suspension was stirred at 100° C. for a day. The pyridine was removed under reduced pressure and the resulting dark oil was triturated with saturated aqueous $NaHCO_3$. The precipitate which formed was filtered and washed with MeOH. The material was treated with 2M HCl in $Et_2O$ to yield a gray solid, the di-HCl salt N-(6-chloro-7-fluoro-9H-β-carbolin-8-yl)-2-methyl-nicotinamide (110 mg). $^1$H-NMR (300 MHz, DMSO-$d_6$): δ 13.15 (s, 1); 11.03 (s, 1); 9.33 (s, 1); 8.99-8.97 (m, 1); 8.92-8.89 (m, 1); 8.79-8.73 (m, 2); 8.50 (m, 1); 7.70 (m, 1); 2.80 (s, 3). HCOOH standard conditions. DAD $R_f$=0.91 min. MS $(M+H^+)$: 355.

Intermediate 27: 6-chloro-7-methylsulfanyl-8-nitro-9H-β-carboline

A 250 ml round-bottom flask with magnetic stirrer was charged with 6-chloro-7-fluoro-8-nitro-β-carboline (Intermediate 5, 3.959 g, 14.9 mmol) and 100 ml anhydrous DMF. The resulting orange mixture was cooled to 0° C. (ice and water bath) and sodium thiomethoxide (1.809 g, 25.8 mmol) in powder form was added slowly thereto. The reaction mixture was stirred for 1 hr at 0° C., warmed to RT, and added slowly to a stirring mixture of 4:1$H_2O$/saturated aqueous sodium bicarbonate (500 ml). The precipitated solid was collected via suction filtration and air-dried to afford 4.017 g of 6-chloro-7-methylsulfanyl-8-nitro-9H-β-carboline as an orange powder. The crude material was used directly in subsequent steps. $^1$H-NMR (300 MHz, Methanol-$d_4$): δ 8.91 (1H, d) 8.63 (1H, s) 8.42 (1H, d) 8.17 (1H, dd) 2.54 (3H, s). LCMS (formic acid standard method) retention time=1.43 min. MS $(M+H^+)$: 294.

Intermediate 28: 6-chloro-7-methylsulfanyl-9H-β-carbolin-8-ylamine

A 500 ml round-bottom flask with magnetic stirrer was charged with 6-chloro-7-methylsulfanyl-8-nitro-9H-β-carboline (4.011 g, 13.6 mmol) and 200 ml anhydrous ethanol. To the resulting mixture was added aqueous ammonium chloride (75 ml of 0.33 M solution, 24.7 mmol), aqueous hydrochloric acid (10 ml of 1 M solution, 10 mmol), and iron powder (7.734 g, 138 mmol). The resulting mixture was heated to 60° C. (oil bath) and stirred vigorously for 3.5 hr. The reaction was cooled to RT, diluted with EtOAc (75 ml) and activated charcoal (ca. 2.5 g) was added. The resulting mixture was stirred at RT for an additional 1.5 hr, filtered through a pad of celite, and the resulting filtrate concentrated (rotavap, then vacuum pump) to afford 5.153 g of a yellowish-orange colored solid. The solid was redissolved in MeOH (50-100 ml) and slowly added to saturated aqueous sodium bicarbonate (500 ml) with stirring. The mixture was stirred at RT for 45 min and the resulting solid collected via suction filtration and air-dried to afford 3.476 g of 6-chloro-7-methylsulfanyl-9H-β-carbolin-8-ylamine as a tan solid which was used without further purification in subsequent steps.

$^1$H-NMR (300 MHz, Methanol-$d_4$): δ 8.87 (1H, s) 8.35-8.24 (1H, m) 8.16-8.06 (1H, m) 7.67 (1H, s) 2.32 (3H, s). LCMS (ammonium acetate standard method) retention time=2.12 min. MS $(M+H^+)$: 264.

Example 16

N-(6-chloro-7-methylsulfanyl-9H-β-carbolin-8-yl)-2-methyl-nicotinamide

A 250 ml round-bottom flask with magnetic stirrer was charged with 6-chloro-7-methylsulfanyl-9H-β-carbolin-8-ylamine (Intermediate 28, 2.336 g, 8.86 mmol) and 2-methylnicotinic acid (3.219 g, 23.4 mmol) in 80 ml anhydrous pyridine. To the resulting reaction mixture at RT was added solid 1-(3-dimethylaminopropyl)-3-ethylcarbodiimide hydrochloride (7.080 g, 36.9 mmol) and the reaction mixture was heated to 100° C. (oil bath) for 2 days. The resulting mixture was cooled to RT and concentrated (rotavap) to afford a brown residue. The residue was redissolved in MeOH (50 ml), slowly added to a stirring mixture of 5:1$H_2O$/saturated aqueous sodium bicarbonate (600 mlL) and stirred at RT for 18 hr. The precipitated solid was collected via suction filtration, washed with $Et_2O$ (2×150 ml), and air-dried to afford 3.036 g of crude N-(6-chloro-7-methylsulfanyl-9H-β-carbolin-8-yl)-2-methyl-nicotinamide as a brown solid. The crude material was purified via HPLC (yields=~40-60%). $^1$H-NMR (300 MHz, DMSO-$d_6$): δ 11.72 (1H, s) 10.50 (1H, s) 8.97 (1H, s) 8.62 (1H, dd) 8.57 (1H, s) 8.41 (1H, d) 8.33-8.27 (1H, m) 8.21 (1H, d) 2.73 (3H, s) 2.41 (3H, s). LCMS (ammonium acetate standard method) retention time=1.89 min. MS $(M+H^+)$: 383.

Intermediate 29: 6-chloro-7-ethylsulfanyl-8-nitro-9H-β-carboline

A 25 ml round-bottom flask with a magnetic stirrer was charged with 6-chloro-7-fluoro-8-nitro-9H-β-carboline (102 mg, 0.38 mmol) in 5 ml of anhydrous DMF. To the resulting orange mixture at RT was slowly added sodium thioethoxide (80% pure, 69.7 mg, 0.66 mmol) in powder form. The reaction mixture was stirred at RT for 45 minutes, then added drop-wise to a 5:1 mixture of $H_2O$/saturated sodium bicarbonate (30 ml). The resulting precipitated solid was collected by suction filtration, washed with 1:1 hexanes/diethyl ether (2×20 ml), and air-dried to afford 95.0 mg of 6-chloro-7-ethylsulfanyl-8-nitro-9H-β-carboline as an orange solid (79%). $^1$H-NMR (300 MHz, $CD_3OD$, ppm) δ 8.91 (1H, s) 8.63 (1H, s) 8.42 (1H, d) 8.18 (1H, d) 3.04 (2H, q) 1.20 (3H, t). Retention Time (LC, formic acid standard method): 1.71 min. MS $(M+H^+)$: 308.

Intermediate 30: 6-chloro-7-ethylsulfanyl-9H-β-carbolin-8-ylamine

A 50 ml round-bottom flask with magnetic stirrer was charged with 6-chloro-7-ethylsulfanyl-8-nitro-9H-β-carboline (85.0 mg, 0.28 mmol) in 10 ml anhydrous ethanol. To the resulting orange mixture at RT was added 0.33 M aqueous ammonium chloride (2.0 ml, 0.66 mmol) and iron powder (680 mg, 12.2 mmol). The reaction mixture was heated to 60° C. and stirred vigorously for 20 hr. Next, the mixture was cooled to RT, diluted with ethyl acetate (15 ml), and activated charcoal (180 mg) was added. The resulting mixture was filtered through a pad of celite and the filtrate was concentrated to afford 77.8 mg of 6-chloro-7-ethylsulfanyl-9H-β-carbolin-8-ylamine as a yellow solid (>99%). $^1$H-NMR (300 MHz, $CD_3OD$, ppm) δ 8.94 (1H, s) 8.33-8.29 (1H, m) 8.21-8.18 (1H, m) 7.73 (1H, s) 2.85 (2H, q) 1.21 (3H, t). LCMS (ammonium acetate standard method) retention time=2.13 min. $(M^+=278; M=276)$.

Example 17

N-(6-chloro-7-ethylsulfanyl-9H-β-carbolin-8-yl)-2-methyl-nicotinamide

A 25 ml round-bottom flask with magnetic stirrer was charged with 6-chloro-7-ethylsulfanyl-9H-β-carbolin-8- ylamine (37.2 mg, 0.13 mmol) and 2-methylnicotinic acid (36.2 mg, 0.26 mmol) in 3 ml anhydrous pyridine. To the resulting light-orange mixture at RT was added solid 1-(3-dimethylaminopropyl)-3-ethylcarbodiimide hydrochloride (73.2 mg, 0.38 mmol) and the resulting reaction mixture was heated to 80° C. for 5 days. Next, the reaction mixture was cooled to RT and concentrated to afford a brown, viscous syrup. The syrup was dissolved in a minimal amount of MeOH (~2 ml), slowly added to a 5:1 mixture of $H_2O$/saturated sodium bicarbonate (20 ml), and stirred at RT for 2.5 hr. The resulting precipitated solid was collected via suction filtration, washed with 1:1 hexanes/diethyl ether (2×20 ml), and air-dried to afford 21.0 mg of N-(6-chloro-7-ethylsulfanyl-9H-β-carbolin-8-yl)-2-methyl-nicotinamide as a tan solid (~38%). LCMS (ammonium acetate standard method) retention time=2.33 min. ($M^+$=397; $M^-$=395). $^1$H-NMR (300 MHz, $CD_3OD$, ppm) δ 8.89 (1H, s) 8.63-8.58 (1H, m) 8.44-8.38 (2H, m) 8.36 (1H, d) 8.15 (1H, d) 7.52-7.44 (1H, m) 2.98 (2H, q) 2.84 (3H, s) 1.20 (3H, t).

Intermediate 31: [2-(6-chloro-8-nitro-9H-β-carbolin-7-ylsulfanyl)-ethyl]-dimethyl-amine A 25 ml round-bottom flask with magnetic stirrer was charged with 6-chloro-7-fluoro-8-nitro-9H-β-carboline (98 mg, 0.37 mmol) in 2 ml of anhydrous DMF. A second 10 ml round-bottom flask with magnetic stirrer was charged with 2-dimethylamino-ethanethiol hydrochloride (100 mg, 0.70 mmol) in 2 ml anhydrous DMF. To the resulting suspension was added n-butyllithium (0.43 ml of 1.6 M solution in hexanes, 0.69 mmol) via syringe and the mixture was stirred for 5 min at RT. Next, the thioanion solution was added via syringe to 6-chloro-7-fluoro-8-nitro-9H-β-carboline, and the resulting red solution was stirred at RT for 30 min. The reaction mixture was slowly added to a 5:1 mixture of $H_2O$/saturated aqueous sodium bicarbonate (30 ml) and allowed to sit at RT for several hours. The resulting precipitated solid was collected via suction filtration and air-dried to afford 109 mg of [2-(6-chloro-8-nitro-9H-β-carbolin-7-ylsulfanyl)-ethyl]-dimethyl-amine as an orange solid (83%). LCMS (ammonium acetate standard method) retention time=1.35 min. ($M^+$=351; $M^-$=349). $^1$H-NMR (300 MHz, $CD_3OD$, ppm) δ 8.92 (1H, d, J=1.0 Hz) 8.66 (1H, s) 8.43 (1H, d) 8.19 (1H, dd) 3.18-3.13 (2H, m) 2.57-2.52 (2H, m) 2.21 (6H, s).

Intermediate 32: 6-chloro-7-(2-dimethylamino-ethylsulfanyl)-9H-β-carbolin-8-ylamine A 50 ml round-bottom flask with a magnetic stirrer was charged with [2-(6-chloro-8-nitro-9H-β-carbolin-7-ylsulfanyl)-ethyl]-dimethyl-amine (106 mg, 0.30 mmol) in 8 ml of anhydrous ethanol. To the resulting orange mixture at RT was added 0.33 M aqueous ammonium chloride (1.95 ml, 0.64 mmol) and iron powder (540 mg, 9.67 mmol). The reaction mixture was heated to 60° C. and stirred vigorously for 20 hr. Next, the mixture was cooled to RT, diluted with ethyl acetate (20 ml) and activated charcoal (ca. 150 mg) was added. The resulting mixture was filtered through a pad of celite and the resulting filtrate concentrated to afford 103 mg of 6-chloro-7-(2-dimethylamino-ethylsulfanyl)-9H-β-carbolin-8-ylamine as a yellow solid. The crude product was used directly in the coupling step.
LCMS (ammonium acetate standard method) retention time=1.34 min. ($M^+$=321; $M^-$=319). $^1$H-NMR (300 MHz, $CD_3OD$, ppm) δ 8.87 (1H, s) 8.30 (1H, d) 8.06 (1H, d) 7.75 (1H, s) 3.23-3.13 (4H, m) 2.84 (6H, s).

Example 18

N-[6-chloro-7-(2-dimethylamino-ethylsulfanyl)-9H-β-carbolin-8-yl]-2-methyl-nicotinamide A 25 ml round-bottom flask with magnetic stirrer was charged with 6-chloro-7-(2-dimethylamino-ethylsulfanyl)-9H-β-carbolin-8-ylamine (45.2 mg, 0.14 mmol) and 2-methylnicotinic acid (39.0 mg, 0.28 mmol) in 4.5 ml of anhydrous pyridine. To the resulting light-orange mixture at RT was added solid 1-(3-dimethylaminopropyl)-3-ethylcarbodiimide hydrochloride (95.0 mg, 0.49 mmol). The resulting reaction mixture was heated to 80° C. for 3 days. Next, the reaction was cooled to RT and concentrated to afford a brown, viscous syrup. The syrup was dissolved in a minimal amount of MeOH (2 ml), slowly added to a 5:1 mixture of $H_2O$ I saturated sodium bicarbonate (25 ml), and extracted with ethyl acetate (3×30 ml). The combined organic layers were washed with brine (1×30 ml), dried over $Na_2SO_4$, filtered and concentrated to afford a brown residue (79.6 mg). The residue was redissolved in MeOH (5 ml), and filtered through a cotton plug. To the resulting filtrate was added HCl in 1,4-dioxane (1.0 ml, 4.0 mmol), the resulting solution stirred at RT for 3 hr, and added drop-wise to diethyl ether (30 ml) with stirring. The resulting precipitated product was collected via suction filtration, washed with ether and air-dried to afford 36.3 mg of N-[6-chloro-7-(2-dimethylamino-ethylsulfanyl)-9H-β-carbolin-8-yl]-2-methyl-nicotinamide tris-hydrochloride as a yellow powder. $^1$H-NMR (300 MHz, $CD_3OD$, ppm) δ 8.95 (1H, s) 8.62 (1H, dd) 8.43 (1H, s) 8.38-8.34 (2H, m) 8.16 (1H, d) 7.50 (1H, dd) 3.09 (2H, t) 2.85 (3H, s) 2.30 (2H, t) 1.99 (6H, s). LCMS (ammonium acetate standard method) retention time=1.56 min. ($M^+$=440; $M^-$=438).

Intermediate 33: morpholine-3(S), 4-dicarboxylic acid 4-tert-butyl ester

A suspension of morpholine-3(S)-carboxylic acid (2.00 g, 15.3 mmol) in DMF (75 ml) was stirred at RT. Triethylamine (7.47 ml, 53.6 mmol) and di-tert-butyl dicarbonate ($BOC_2O$, 4.02 g, 18.4 mmol) were added. The suspension was stirred at RT for one hour, during which time the reaction formed a clear yellow solution. The solution was concentrated to a reduced volume (25 ml) and diluted with water (15 ml) and 1N HCl (15 ml). The mixture was poured into a separatory funnel, diluted further with water (100 ml) and brine (100 ml), and extracted with $Et_2O$ (3×100 ml). The organic layer was washed with brine, dried, filtered and concentrated to yield a white solid. The solid, which contained excess $BOC_2O$, was dissolved in $Et_2O$ (500 ml) and extracted with 1N NaOH (3×100 ml). The aqueous layer was acidified with 6N HCl to approximately a pH of 2, then extracted quickly with $Et_2O$ (3×100 ml). The $Et_2O$ layer was dried, filtered and concentrated to yield white solid (3.07 g). $^1$H-NMR (300 MHz, DMSO-$d_6$): δ 12.95 (br s, 1); 4.34-4.30 (m, 1); 4.18-4.10 (m, 1); 3.83-3.74 (m, 1); 3.59-3.51 (m, 2); 3.39-3.32 (m, 1); 3.21-2.95 (m, 1); 1.41-1.36 (m, 9). $NH_4OAc$ standard conditions. ELSD $R_f$=1.08 min. M-H=230.

Example 19

4-methyl-morpholine-3(S)-carboxylic acid (6-chloro-9H-β-carbolin-8-yl)-amide

A slurry of morpholine-3(S)-carboxylic acid (3.00 g, 22.9 mmol) in EtOH (115 ml) was stirred at RT. A solution of aqueous $CH_2O$ (3.42 ml, 45.8 mmol, 37% w/w in $H_2O$) was added, followed by Pd(OH)$_2$ (600 mg, 20% w/w on charcoal). The flask was charged with hydrogen (1 atm) and the grey slurry was stirred for 24 hr at RT under a balloon of hydrogen. The flask was purged with nitrogen and the black slurry was diluted with MeOH, filtered through filter paper and concentrated to a reduced volume. The pale grey solution was filtered through a 0.45 µm syringe filter to remove residual Pd(OH)$_2$ and concentrated to yield a clear colorless oil. The oil was placed under high vacuum for 24 hr and a white, solid foam was isolated. The foam was dissolved in pyridine (200 ml) and 6-chloro-9H-β-carbolin-8-ylamine (3.74 g, 17.2 mmol) was added, followed by EDCI (5.87 g, 30.6 mmol). The clear pale orange solution was stirred at RT for 24 hr. The solution was diluted with H$_2$O (300 ml) and poured into a separatory funnel containing EtOAc (300 ml). The mixture was shaken and the layers were separated. The aqueous layer was extracted with EtOAc (3×150 ml) and the combined organic layers were washed with H$_2$O and brine. The organic layer was dried, filtered and concentrated to yield a brown oil which was placed under high vacuum. The resulting brown foam was triturated with MeOH and the precipitate which formed was filtered and washed with MeOH. The resulting pale yellow solid was purified via chiral HPLC to yield a white solid (3.23 g). $^1$H-NMR (300 MHz, DMSO-d$_6$): δ 11.36 (s, 1); 10.02 (s, 1); 9.04 (s, 1); 8.38 (d, 1); 8.22-8.21 (m, 1); 8.15 (d, 1); 7.91-7.90 (m, 1); 4.00 (dd, 1); 3.85-3.81 (m, 1); 3.69-3.58 (m, 2); 2.99-2.95 (dd, 1); 2.89-2.85 (m, 1); 2.32 (s, 3); 2.32-2.24 (m, 1). NH$_4$OAc standard conditions. DAD R$_f$=1.89 min. M+H=345. Chiral preparative HPLC: 10% v/v EtOH/Hexanes. Chiralcel OD column. R$_f$=11.5-14 min. Enantiopurity of product≧99% ee.

Method C: Procedure for 4-MORPHOLINE Substituted Analogs

As outlined for Intermediate 34, Intermediate 35 and Example 20:

Intermediate 34: 3(S)-(6-chloro-9H-β-carbolin-8-ylcarbamoyl)-morpholine-4-carboxylic acid tert-butyl ester A solution of morpholine-3(S), 4-dicarboxylic acid 4-tert-butyl ester (2.83 g, 12.7 mmol) in pyridine (106 ml) was stirred at RT. 6-chloro-9H-β-carbolin-8-ylamine (2.30 g, 10.6 mmol) was added, followed by EDCI (4.06 g, 21.2 mmol). The clear orange-to-brown solution was stirred at RT for 14 hr. The solution was diluted with H$_2$O (120 ml) and poured into a separatory funnel containing EtOAc (200 ml), H$_2$O (100 ml) and brine (100 ml). The mixture was shaken and the layers were separated. The aqueous layer was extracted with EtOAc (2×50 ml) and the combined organic layers were washed with brine. The organic layer was dried, filtered and concentrated to a reduced volume, then added drop-wise to a stirring solution of 1:1 Et$_2$O/hexanes (500 ml). The precipitate which formed was filtered and washed with 1:1 Et$_2$O/Hexanes. The filtrate was concentrated to a reduced volume and a second crop of precipitate was collected. The solid product was placed under high vacuum for 2 hr to yield 3(S)-(6-chloro-9H-β-carbolin-8-ylcarbamoyl)-morpholine-4-carboxylic acid tert-butyl ester as a pale yellow to pale brown solid (4.36 g). $^1$H-NMR (300 MHz, DMSO-d$_6$): δ 11.30 (s, 1); 10.13 (s, 1); 9.06 (s, 1); 8.40-8.38 (m, 1); 8.19-8.16 (m, 2); 7.98 (s, 1); 4.67-4.47 (m, 2); 3.96-3.60 (m, 2); 3.64-3.39 (m, 3); 1.42 (s, 9). NH$_4$OAc standard conditions. DAD R$_f$=2.31 min. M+H=431.

Intermediate 35: 2(R)-[3(S)-(6-chloro-9H-β-carbolin-8-ylcarbamoyl)-morpholin-4-ylmethyl]-pyrrolidine-1-carboxylic acid tert-butyl ester A solution of 3(S)-(6-chloro-9H-β-carbolin-8-ylcarbamoyl)-morpholine-4-carboxylic acid tert-butyl ester (1.00 g, 2.32 mmol) in CH$_2$Cl$_2$ (6 ml) was stirred at RT. Trifluoroacetic acid (6 ml) was added and the solution was stirred at RT for 45 min, then concentrated to a residue. The residue was concentrated once more from CH$_2$Cl$_2$ to yield a yellow-brown solid which was dissolved in THF (13 ml) under argon. Gentle warming was sometimes needed to ensure complete dissolution. A solution of N-(tert-butoxycarbonyl)-D-prolinal (693 mg, 3.48 mmol) in THF (2 ml) was added, followed by sodium triacetoxyborohydride (738 mg, 3.48 mmol). The solution was stirred at RT for 30 min, then quenched via addition of 1N aqueous NaOH (30 ml). The mixture was poured into a separatory funnel containing EtOAc (100 ml), H$_2$O (100 ml), and brine (100 ml). The mixture was shaken and the layers were separated. The aqueous layer was extracted with EtOAc (2×50 ml) and the combined organic layers were washed with brine. The organic layer was dried, filtered and concentrated to yield a light brown solid. Column chromatography (2%-4% MeOH/CH$_2$Cl$_2$) yielded 2(R)-[3(S)-(6-Chloro-9H-β-carbolin-8-ylcarbamoyl)-morpholin-4-ylmethyl]-pyrrolidine-1-carboxylic acid tert-butyl ester as a white solid (915 mg). $^1$H-NMR (300 MHz, DMSO-d$_6$): δ 11.30 (s, 1); 9.88 (s, 1); 9.04 (s, 1); 8.39-8.37 (m, 1); 8.20-8.15 (m, 2); 7.95 (s, 1); 3.99-3.82 (m, 3); 3.69-3.63 (m, 2); 3.44-3.32 (m, 1); 3.27-3.11 (m, 3); 2.92-2.80 (m, 1); 2.44-2.32 (m, 1); 1.99-1.67 (m, 5); 1.33 (s, 9). HCOOH standard conditions. DAD R$_f$=1.39 min. M+H=514. Chiral HPLC.

The enantiopurity of the sample was checked. The samples were >97% ee. Chiralpak AD column. 15% v/v EtOH/Hexanes containing 0.1% Et$_2$NH.

Example 20

4-pyrrolidin-2(R)-ylmethyl-morpholine-3(S)-carboxylic acid (6-chloro-9H-β-carbolin-8-yl)-amide. HCl salt)

To a solution of 2(R)-[3(S)-(6-chloro-9H-β-carbolin-8-ylcarbamoyl)-morpholine-4-ylmethyl]-pyrrolidine-1-carboxylic acid tert-butyl ester (850 mg, 1.65 mmol) in MeOH (16 ml) was added concentrated aqueous HCl (13 ml). The solution was stirred at RT for 30-45 min, during which time a fine yellow precipitate formed. The reaction mixture was concentrated to yield 4-pyrrolidin-2(R)-ylmethyl-morpholine-3(S)-carboxylic acid (6-chloro-9H-β-carbolin-8-yl)-amide, HCl salt) as a pale yellow solid (755 mg). $^1$H-NMR (300 MHz, DMSO-d$_6$): δ 13.30 (s, 1); 11.56 (br s, 1); 9.63 (br s, 1); 9.46 (s, 1); 8.87-8.85 (m, 1); 8.66-8.57 (m, 2); 8.25 (s, 1); 4.38-4.26 (m, 1); 4.24-4.08 (m, 1); 4.04-3.86 (m, 2); 3.86-3.68 (m, 2); 3.57-3.39 (m, 1); 3.39-3.02 (m, 4); 2.99-2.76 (m, 1); 2.10-1.84 (m, 3); 1.75-1.56 (m, 1). HCOOH standard conditions. DAD R$_f$=0.81 min. M+H=414.

Intermediate 36: cis-2-(tert-butoxycarbonylamino)-cyclopentanecarboxylic acid (6-chloro-9H-carbolin-8-yl) amide A solution of cis-2-(tert-butoxycarbonylamino)-cyclopentane carboxylic acid (550 mg, 2.4 mmol) in pyridine (10 ml) was stirred at RT. 6-chloro-9H-β-carbolin-8-ylamine (436 mg, 2.0 mmol) was added, followed by EDCI (615 mg, 3.2 mmol), and the orange solution was stirred at RT for 1.5 hr.

The solution was diluted with H$_2$O (20 ml) and poured into a separatory funnel containing H$_2$O (50 ml) and EtOAc (100 ml). The mixture was shaken and the layers were separated. The aqueous layer was extracted with EtOAc (100 ml). The combined organic layers were washed with brine, dried over MgSO$_4$, filtered, and concentrated to orange oily solids which were subsequently triturated with 5% MeOH in Et$_2$O (20 ml) and captured by filtration to yield cis-2-(tert-butoxycarbonylamino)-cyclopentanecarboxylic acid (6-chloro-9H-carbolin-8-yl) amide as a light yellow solid (740 mg). $^1$H-NMR (300 MHz, DMSO-d$_6$): δ 11.17 (s, 1); 9.89 (s, 1); 9.04 (s, 1); 8.36 (d, 1); 8.18-8.08 (m, 2); 7.95 (s, 1); 6.92 (d, 1); 4.32-4.22 (m, 1); 3.16-3.09 (m, 1); 2.13-2.01 (m, 1); 1.96-1.75 (m, 3); 1.74-1.59 (m, 1); 1.58-1.42 (m, 1); 1.07 (s, 9). NH$_4$OAc standard conditions. DAD R$_f$=2.52 min. M+H=429.

Example 21 cis-2-amino-cyclonentanecarboxylic acid (6-chloro-9H-β-carbolin-8-yl)-amide

A solution of 2-(tert-butoxycarbonylamino)-cyclopentanecarboxylic acid (6-chloro-9H-β-carbolin-8-yl) amide (736 mg, 1.72 mmol) in trifluoroacetic acid (5 ml) was stirred at RT for 20 min, then concentrated to an orange oil. The oil was dissolved in MeOH (5 ml) and neutralized with a saturated aqueous sodium bicarbonate solution (25 ml). The resulting mixture was further diluted with H$_2$O (25 ml) and EtOAc (100 ml). The aqueous layer was removed and extracted with EtOAc (100 ml). The organic layers were combined, washed with brine, dried over MgSO$_4$, filtered and concentrated to yellow solids (507 mg). These solids were dissolved in MeOH (5 ml) and a solution of HCl in dioxane (4 M, 1.5 ml) was added. The bright yellow solution was stirred 30 min, then concentrated to yield cis-2-amino-cyclopentanecarboxylic acid (6-chloro-9H-β-carbolin-8-yl)-amide as a yellow powder (600 mg). $^1$H-NMR (300 MHz, DMSO-d$_6$): δ 9.29 (s, 1); 8.75 (d, 1); 8.53 (d, 1); 8.37 (s, 1); 8.02 (s, 1); 4.05-3.95 (m, 1); 3.42-3.34 (m, 1); 2.46-1.80 (m, 6). NH$_4$OAc standard conditions. DAD R$_f$=1.65 min. M+H=329.

Example 22

4-(2-amino-ethyl)-morpholine-3-carboxylic acid (6-chloro-9H-β-carbolin-8-yl)-amide, HCl salt Method C was followed using racemic morpholine-3-carboxylic acid reductively alkylated with 2-aminoacetaldehyde. $^1$H-NMR (300 MHz, MeOH-d$_4$): δ 9.37 (s, 1); 8.76 (d, 1); 8.55 (d, 1); 8.44 (d, 1); 8.06 (d, 1); 4.68-4.55 (m, 2); 4.17-3.99 (m, 3); 3.84-3.73 (m, 2); 3.57-3.39 (m, 4). NH$_4$OAc standard conditions. DAD R$_f$=1.69 min. M+H=374.

Example 23

4-(2(S)-amino-propyl)-morpholine-3(S)-carboxylic acid (6-chloro-9H-β-carbolin-8-yl)-amide. HCl salt (first eluting diastereomer)

Method C was followed using racemic morpholine-3-carboxylic acid reductively alkylated with the appropriate alanine aldehyde. The diastereomers were separated via column chromatography prior to the deprotection step. $^1$H-NMR (300 MHz, DMSO-d$_6$): δ 9.32 (s, 1); 8.76 (d); 8.55 (d, 1); 8.41 (s, 1); 8.08 (s, 1); 4.38 (d, 1); 4.32-4.21 (m, 1); 4.16-4.09 (m, 1); 4.04-3.95 (m, 2); 3.79-3.57 (m, 2); 3.47-3.40 (m, 1); 3.22-3.05 (m, 2); 1.44 (d, 3). NH$_4$OAc standard conditions. DAD R$_f$=1.38 min. M+H=388.

Example 24

4-(2(S)-amino-propyl)-morpholine-3(R)-carboxylic acid (6-chloro-9H-β-carbolin-8-yl)-amide, HCl salt (second eluting diastereomer)

Method C was followed using racemic morpholine-3-carboxylic acid reductively alkylated with the appropriate alanine aldehyde. The diastereomers were separated via column chromatography prior to the deprotection step. $^1$H-NMR (300 MHz, DMSO-d$_6$): δ 9.34 (s, 1); 8.77 (d, 1); 8.55 (d, 1); 8.42 (s, 1); 8.06 (s, 1); 4.42 (d, 1); 4.30-4.12 (m, 1); 4.07-3.92 (m, 3); 3.89-3.74 (m, 1); 3.65-3.49 (m, 1); 3.25-2.90 (m, 3); 1.36 (d, 3). NH$_4$OAc standard conditions. DAD R$_f$=1.57 min. M+H=388.

Example 25

2-amino-cyclohexanecarboxylic acid (6-chloro-9H-β-carbolin-8-yl)-amide

A solution of cis-2-(tert-butoxycarbonylamino)-cyclohexane carboxylic acid (255 mg, 1.05 mmol) in pyridine (10 ml) was stirred at RT. 6-chloro-9H-β-carbolin-8-ylamine (218 mg, 1.00 mmol) was added, followed by EDCI (315 mg, 1.64 mmol) and the slightly turbid pale orange solution was stirred at RT for 16 hr. The solution was diluted with H$_2$O (20 ml) and poured into a separatory funnel containing H$_2$O (50 ml) and EtOAc (50 ml). The mixture was shaken and the layers were separated. The aqueous layer was extracted with EtOAc (50 ml) and the combined organic layers were washed with brine. The organic layer was dried, filtered and concentrated to yield a yellow oil which was placed under high vacuum for 4 hr. The resulting yellow-brown glass was slurried in CH$_2$Cl$_2$ (10 ml) at RT. Trifluoroacetic acid (5 ml) was added and the slurry instantly dissolved to form a clear orange solution. The solution was stirred at RT for 45 min, then concentrated to a brown residue. The residue was azeotroped from toluene (3×10 ml) to yield a yellow solid. A solution of dilute aqueous Na$_2$CO$_3$ was prepared by adding a small volume of 10% aqueous Na$_2$CO$_3$ to H$_2$O (50 ml) until the aqueous solution reached a pH of 10. The yellow solid was dissolved in minimal MeOH and was added drop-wise to the aqueous solution with stirring. The precipitate which formed was filtered, washed with H$_2$O and placed under high vacuum to yield 2-amino-cyclohexanecarboxylic acid (6-chloro-9H-β-carbolin-8-yl)-amide as pale yellow solid (147 mg). $^1$H-NMR (300 MHz, DMSO-d$_6$): δ 9.00 (s, 1); 8.37-8.34 (m, 1); 8.16-8.13 (m, 2); 7.83 (m, 1); 5.66-5.00 (br s, 2); 3.42-3.40 (m, 1); 2.70-2.62 (m, 1); 2.02-1.90 (m, 1); 1.70-1.54 (m, 5); 1.42-1.29 (m, 2). NH$_4$OAc standard conditions. DAD R$_f$=1.46 min. M+H=343.

Example 26

4-(2(R)-amino-propyl)-morpholine-3(S)-carboxylic acid (6-chloro-9H-β-carbolin-8-yl)-amide, HCl salt Method C was followed using racemic morpholine-3-carboxylic acid reductively alkylated with the appropriate alanine aldehyde. The diastereomers were separated via column chromatography prior to the deprotection step. $^1$H-NMR (300 MHz, DMSO-d$_6$): δ 9.35 (s, 1); 8.77 (m, 1); 8.55 (m, 1); 8.43 (s, 1); 8.01 (s, 1); 4.45 (d, 1); 4.26 (m, 1); 4.09-3.91 (m, 3);

3.79 (m, 1); 3.63 (m, 1); 3.28-2.99 (m, 3); 1.37 (d, 3). NH$_4$OAc standard conditions. DAD R$_f$=1.39 min. M+H=388.

Example 27

4-(2(R)-amino-3-phenyl-propyl)-morpholine-3(S)-carboxylic acid (6-chloro-9H-β-carbolin-8-yl)-amide, HCl salt Method C was followed using racemic morpholine-3-carboxylic acid reductively alkylated with the appropriate alanine aldehyde. The diastereomers were separated via column chromatography prior to the deprotection step. $^1$H-NMR (300 MHz, DMSO-d$_6$): δ 9.34 (s, 1); 8.77 (d, 1); 8.55 (d, 1); 8.42 (s, 1); 8.04 (s, 1); 7.44-7.23 (m, 5); 4.39 (d, 1); 4.65-4.07 (m, 1); 4.40-3.82 (m, 4); 3.50-3.25 (m, 1); 3.30-3.14 (m, 1); 3.11-2.88 (m, 3); 2.85-2.69 (m, 1). NH$_4$OAc standard conditions. DAD R$_f$=1.90 min. M+H=464.

Method D: Chromatography Conditions

LCMS
Column type: Phenomenex Luna C18(2) columns, 5 um, size 50×4.6 mm
Run time: 5.00 minute run
  NH$_4$OAc Conditions:
Solvent A:
10 mM NH$_4$OAc
99% H$_2$O
1% MeCN
Solvent B:
10 mM NH$_4$OAc
5% H$_2$O
95% MeCN
  Standard Gradient:
Initial conditions—95% A, 5% B
3.5 minute gradient from 5%-100% B
3.5-4.3 minutes hold at 100% B
4.3-5 minutes initial conditions
  Polar Gradient:
Initial conditions—70% A, 30% B
3.5 minute gradient from 70%-100% B
3.5-4.3 minutes hold at 100% B
4.3-5 minutes initial conditions
  Nonpolar Gradient:
Initial conditions—100% A
3.5 minute gradient from 0%-50% B
3.5-4.3 minutes hold at 100% B
4.3-5 minutes initial conditions
  HCOOH Conditions:
Solvent C:
0.1% HCOOH
99% H$_2$O
1% MeCN
Solvent D:
0.1% HCOOH
5% H$_2$O
95% MeCN
  Standard Gradient:
Initial conditions—95% C, 5% D
3.5 minute gradient from 5%-100% D
3.5-4.3 minutes hold at 100% D
4.3-5 minutes initial conditions
  Polar Gradient:
Initial conditions—70% C, 30% D
3.5 minute gradient from 70%-100% D
3.5-4.3 minutes hold at 100% D
4.3-5 minutes initial conditions Nonpolar Gradient:
Initial conditions—100% C
3.5 minute gradient from 0%-50% D
3.5-4.3 minutes hold at 100% D
4.3-5 minutes initial conditions Intermediate 37:
6-chloro-2,3,4,9-tetrahydro-1H-β-carboline, HCl salt 5-chlorotryptamine hydrochloride (5 g, 20 mmol, 1 equiv.) was dissolved in 40 ml 3 M NaOAc buffer (pH=4.8) and 40 ml water. Glyoxalic acid (1.84 g, 20 mmol, 1 equiv.) was added in one portion and the solution was stirred at RT overnight. The resulting thick slurry was filtered and the light green solids were suspended in 100 ml 6N HCl and heated at 125° C. under a reflux condenser for 1 hour with intermittent additions of conc HCl (2 ml every 15 min). After cooling to RT, 4.38 g (90%) of 6-chloro-2,3,4,9-tetrahydro-1H-β-carboline, HCl salt as blue-grey solid was isolated by filtration. $^1$H-NMR (300 MHz, DMSO-d$_6$): δ 11.33 (br, 2H), 9.62 (br, 2H), 7.53 (d, 1), 7.39 (d, 1), 7.09 (dd, 1), 4.33 (br, 2H), 2.92 (t, 2). Formic acid standard conditions. DAD RT=1.56 min. M+H=207.

Intermediate 38: (6-chloro-1,3,4,9-tetrahydro-β-carbolin-2-yl)-phenyl-methanone 6-chloro-2,3,4,9-tetrahydro-1H-β-carboline, HCl salt (10.2 g, 42 mmol, 1 equiv.) was suspended in 100 ml of dry pyridine under N$_2$ and cooled to 0° C. in an ice water bath. Benzoyl chloride (7.3 ml, 63 mmol, 1.5 equiv.) was added drop-wise to the cold solution after which the reaction was removed from the ice bath and allowed to stir overnight at room temperature. The reaction was quenched by the addition of water until choked with solids. These solids were captured by filtration, washed with a saturated aqueous sodium bicarbonate solution, re-suspended in water, sonicated, and refiltered to give 1.27 g (94%) of (6-chloro-1,3,4,9-tetrahydro-β-carbolin-2-yl)-phenyl-methanone as crystalline orange solids. $^1$H-NMR (300 MHz, DMSO-d$_6$): δ 10.65-10.59 (br, 1H), 7.0-7.5 (m, 9H), 4.60-4.83 (br, 2H), 3.62-3.99 (br, 2H), 2.75 (br., 2H). Formic acid standard conditions. DAD RT=2.68 min. M+H=311.

Intermediate 39: 2-benzoyl-6-chloro-1,2,3,9-tetrahydro-β-carbolin-4-one (6-chloro-1,3,4,9-tetrahydro-β-carbolin-2-yl)-phenyl-methanone (1.76 g, 5.66 mmol, 1 equiv.) and DDQ (2.31 g, 10.2 mmol, 1.8 equiv.) were mixed as solids and cooled to −78° C. 15 ml of a 9:1 THF/H$_2$O solution was cooled to −78° C. and the resulting slurry was added to the cooled solids followed by an additional 15 ml of THF (also cooled to −78° C.). The deep blue solution was stirred at −78° C. for 2 hours and then gradually warmed to room temperature and stirred an additional two hours. The reaction was quenched by the addition of 1 N NaOH, and extracted with 3×150 ml EtOAc. The combined organic layers were washed with 2×100 ml 1 N HCl, 1×100 ml brine, dried over MgSO$_4$, filtered and concentrated to yield 1.38 g (75%) of 2-benzoyl-6-chloro-1,2,3,9-tetrahydro-β-carbolin-4-one as oily orange solids. $^1$H-NMR (300 MHz, DMSO-d$_6$): δ 12.11-12.48 (br, 1H), 7.29-7.88 (m, 8H), 4.93-5.18 (br, 2H), 4.60-4.46 (br, 2H). Exact Mass: 324.07. Formic acid standard conditions. DAD RT=2.15 min. M+H=325.

Intermediate 40: 4-amino-6-chloro β-carboline

Crude 2-benzoyl-6-chloro-1,2,3,9-tetrahydro-β-carbolin-4-one (4 g) was dissolved in 30 ml of anhydrous hydrazine and stirred at reflux (130° C. oil bath) under $N_2$ for 6 hours, after which the reaction mixture was allowed to cool to room temperature and sit overnight. The precipitated yellow solids were removed by filtration and washed with water, 2×5 ml, to yield 785 mg (30%) of 4-amino-6-chloro β-carboline as an off white solid. Additional water was added to the combined filtrates until no further precipitation occurred. These solids were also removed by filtration to give 1.056 g (39%) of 4-amino-6-chloro β-carboline as yellow solids, (69% total yield). $^1$H-NMR (300 MHz, DMSO-$d_6$): δ 11.48 (s, 1H), 8.44 (s, 1H), 8.13 (s, 1H), 7.77 (s, 1H), 7.42-7.52 (m, 2H), 5.86 (s, 2H). Formic acid standard conditions. DAD RT=1.68 min. M+H=218.

Intermediate 41: N-(6-chloro-9H-β-carbolin-4-yl)-2,2,2-trifluoro-acetamide 4-amino-6-chloro β-carboline (1.05 g, 4.82 mmol, 1 equiv.) was dissolved in 4 ml of anhydrous pyridine and 20 ml of THF and cooled to 0° C. under $N_2$. Trifluoroacetic anhydride (3.4 ml, 24 mmol, 5 equiv.) was added drop-wise to the cooled solution. Upon complete addition, the reaction was removed from the ice bath and stirred at room temperature for ~1.5 hours. The reaction was quenched by the slow addition of water (10 ml) and extracted 2×150 ml EtOAc, washed 2×100 ml saturated aqueous sodium bicarbonate, 1×100 ml brine, dried over $MgSO_4$, filtered and concentrated to orange solids. These solids were titurated by in 10-15 ml $Et_2O$ and captured by filtration to give 1.23 g (81%) of N-(6-chloro-9H-β-carbolin-4-yl)-2,2,2-trifluoro-acetamide as a yellow solid. $^1$H-NMR (300 MHz, DMSO-$d_6$): δ 12.11 (s, 1H), 11.89 (s, 1H), 8.92 (s, 1H), 8.33 (s, 1H), 7.82 (s, 1H), 7.60-7.70 (m, 2H). Formic acid standard conditions. DAD RT=2.12 min. M+H=314.

Intermediate 42: N-(6-chloro-8-nitro-9H-β-carbolin-4-yl)-2,2,2-trifluoro-acetamide N-(6-chloro-9H-β-carbolin-4-yl)-2,2,2-trifluoro-acetamide (125 mg, 0.4 mmol, 1 equiv.) was dissolved in 2 ml TFA and $NaNO_2$ (541 mg, 7.84 mmol, 2 equiv.) was added in one portion. The solution was stirred at room temperature for 4 hr. Volatiles were removed by rotovap, and the resulting oily orange solids were suspended in water, neutralized with a saturated aqueous sodium bicarbonate solution and filtered to give 132 mg (92%) of N-(6-chloro-8-nitro-9H-β-carbolin-4-yl)-2,2,2-trifluoro-acetamide. $^1$H-NMR (300 MHz, DMSO-$d_6$): δ 12.87 (s, 1H), 12.03 (s, 1H), 9.11 (s, 1H), 8.56 (s, 1H), 8.53 (s, 1H), 8.26 (s, 1H). Formic acid standard conditions. DAD RT=2.27 min. M+H=359.

Intermediate 43: N-(8-amino-6-chloro-9H-β-carbolin-4-yl)-2,2,2-trifluoro-acetamide The crude N-(6-chloro-8-nitro-9H-β-carbolin-4-yl)-2,2,2-trifluoro-acetamide (130 mg, 0.36 mmol) was dissolved in 7 ml of MeOH and the reaction vessel was vacuum purged 3× with $N_2$. Platinum (20 mg, 20% wt. on activated carbon) was added quickly, and the reaction vessel was again vacuum purged 3× with $N_2$, followed by 3 additional vacuum purge cycles with $H_2$. The reaction was allowed to stir under $H_2$ at 1 atm overnight. Upon completion, the reaction vessel was purged of $H_2$ and filtered over celite. The celite was washed several times with methanol until the filtrates were clear. The combined filtrates were concentrated to give N-(8-amino-6-chloro-9H-β-carbolin-4-yl)-2,2,2-trifluoro-acetamide as a yellow solid (112 mg, 95%). $^1$H-NMR (300 MHz, DMSO-$d_6$): δ 11.83 (s, 1H), 8.98 (s, 1H), 8.30 (s, 1H), 7.10 (s, 1H), 6.82 (s, 1H), 5.87 (br, 2H). Formic acid standard conditions. DAD RT=1.95 min. M+H=329.

Intermediate 44: N-[6-chloro-4-(2,2,2-trifluoro-acetylamino)-9H-β-carbolin-8-yl]-2-methyl-nicotinamide N-(8-amino-6-chloro-9H-β-carbolin-4-yl)-2,2,2-trifluoro-acetamide (90 mg, 0.274 mmol, 1 equiv.) and 2-methylnicotinic acid (45 mg, 0.329 mmol, 1.2 equiv.) were dissolved in 1.5 ml of anhydrous pyridine under $N_2$. EDCI (84 mg, 0.438 mmol, 1.6 equiv.) was added in one portion and the reaction mixture was stirred at room temperature for 2 hours. The reaction was quenched with water and the resulting dark solids captured by filtration. These solids were titurated in a 3:1 methanol—DMSO solution to give N-[6-chloro-4-(2,2,2-trifluoro-acetylamino)-9H-β-carbolin-8-yl]-2-methyl-nicotinamide as light yellow solids (41 mg, 3%). $^1$H-NMR (300 MHz, DMSO-$d_6$): δ 11.94 (br, 1H), 11.78 (s, 1H), 10.61 (s, 1), 9.00 (s, 1), 8.64 (d, 1), 8.38 (s, 1H), 8.13 (d, 1), 8.01 (s, 1H), 7.73 (s, 1H), 7.45 (m, 1H), 2.68 (s, 3H). Formic acid standard conditions. DAD RT=1.98 min. M+H=448.

Intermediate 45: N-[6-chloro-4-(2,2,2-trifluoro-acetylamino)-9H-β-carbolin-8-yl]-nicotinamide N-(8-amino-6-chloro-9H-β-carbolin-4-yl)-2,2,2-trifluoro-acetamide (90 mg, 0.274 mmol, 1 equiv.) and 2-methylnicotinic acid (40 mg, 0.329 mmol, 1.2 equiv.) were dissolved in 1.5 ml of anhydrous pyridine under $N_2$. EDCI (84 mg, 0.438 mmol, 1.6 equiv.) was added in one portion and the reaction mixture was stirred at room temperature 2 hours. The reaction was quenched and treated following the preceding protocol to obtain 38 mg (32%) of N-[6-chloro-4-(2,2,2-trifluoro-acetylamino)-9H-β-carbolin-8-yl]-nicotinamide. $^1$H-NMR (300 MHz, DMSO-$d_6$): δ 11.89 (br, 1H), 10.73 (s, 1), 9.28 (s, 1), 8.97 (s, 1), 8.84 (d, 1), 8.43 (d, 1), 8.37 (s, 1), 7.85 (s, 1), 7.76 (s, 1), 7.67 (m, 1). Formic acid standard conditions. DAD RT=1.94 min. M+H=434.

Example 28

N-(4-amino-6-chloro-9H-β-carbolin-8-yl)-2-methyl-nicotinamide

N-[6-chloro-4-(2,2,2-trifluoro-acetylamino)-9H-β-carbolin-8-yl]-nicotinamide (41 mg, 0.092 mmol, 1 equiv.) was suspended in 5 ml of MeOH and a 2 ml aqueous solution of $K_2CO_3$ (127 mg, 0.92 mmol, 10 equiv.) was added thereto. The resulting clear solution was heated at 60° C. for 16 hr and then allowed to cool to RT. Additional water was added producing fine solids that were captured by filtration, washed once with 10 ml of 5% MeOH in $Et_2O$, and dried under high vacuum to give 18 mg of N-(4-amino-6-chloro-9H-β-carbolin-8-yl)-2-methyl-nicotinamide as powdery yellow solids (56% yield). $^1$H-NMR (300 MHz, DMSO-$d_6$): δ 11.18 (s, 1H), 10.41 (s, 1H), 8.62 (d, J=3.6, 1H),), 8.32 (s, 1H), 8.20 (s, 1H), 8.11 (d, J=7.5, 1H), 7.91 (s, 1H), 7.79 (s, 1H), 7.43 (m, 1H), 5.91 (br, 2H), 2.66 (s, 3H). Formic acid standard conditions. DAD RT=1.63 min. M+H=352.

Example 29

N-(4-amino-6-chloro-9H-β-carbolin-8-yl)-nicotinamide

N-[6-chloro-4-(2,2,2-trifluoro-acetylamino)-9H-β-carbolin-8-yl]-nicotinamide (38 mg, 0.088 mmol, 1 equiv.) was suspended in 5 ml of MeOH and a 2 ml aqueous solution of $K_2CO_3$ (121 mg, 0.92 mmol, 10 equiv.) was added thereto. The resulting clear solution was heated at 60° C. for 11 hr. After cooling to RT, fine solids precipitated that were captured by filtration and washed with 10 ml of water to give 2.78 mg (10%) of N-(4-amino-6-chloro-9H-β-carbolin-8-yl)-nicotinamide. $^1$H-NMR (300 MHz, DMSO-$d_6$): δ 11.32 (s, 1H), 10.56 (s, 1H), 9.26 (s, 1H), 8.82 (d, 1), 8.42 (d, 1), 8.36 (s, 1H), 8.18 (s, 1H), 7.79 (s, 1H), 7.70 (s, 1H), 7.64 (m, 1H), 5.91 (br, 2H). Formic acid standard conditions. DAD RT=1.55 min. M+H=338.

Intermediate 46: 3-cyanomethyl-indole-1-carboxylic acid tert-butyl ester

A solution of 3-indoleacetonitrile (10 g, 64 mmol) in DMF (160 ml) was stirred at RT. $K_2CO_3$ (13.3 g, 96 mmol) and di-tert-butyl dicarbonate (15.35 g, 70 mmol) were added thereto and the reaction mixture was stirred at RT for 12 hr. $H_2O$ (100 ml) was added to the reaction mixture and the resulting precipitate was captured by filtration. The solids were dissolved in hot methanol (20 ml) and the solution was allowed to cool slowly, producing light orange solids that were isolated by filtration to give 3-cyanomethyl-indole-1-carboxylic acid tert-butyl ester (9.2 g). $^1$H-NMR (300 MHz, DMSO-$d_6$): δ 8.08 (d, 1); 7.70-7.66 (m, 2); 7.42-7.29 (m, 2); 4.12 (s, 2); 1.63 (3, 9). $NH_4OAc$ standard conditions. DAD $R_f$=3.31 min. M+H=257.

Intermediate 47: 3-(cyano-methyl-methyl)-indole-1-carboxylic acid tert-butyl ester A stirred solution of 3-cyanomethyl-indole-1-carboxylic acid tert-butyl ester (2.15 g, 8.39 mmol) in THF (40 ml) was cooled to −78° C. under an argon atmosphere. Sodium bis(trimethylsilyl)amide (1 M in THF, 10 ml, 10 mmol) was added thereto and the cold solution was stirred for 30 minutes. Iodomethane (627 uL, 10 mmol) was added thereto and the reaction mixture was stirred 1.5 hr while gradually warming to 0° C. $H_2O$ (100 ml) was added thereto and the solution was brought to RT and diluted with EtOAc (250 ml). The aqueous layer was removed and extracted with EtOAc (250 ml). The combined organic layers were washed with aqueous HCl (1N, 3×50 ml), followed by brine, then dried over $MgSO_4$, filtered, and concentrated to an orange oil. Purification via column chromatography (hexanes:ethyl acetate) gave 3-(cyano-methyl-methyl)-indole-1-carboxylic acid tert-butyl ester (1.8 g). $^1$H-NMR (300 MHz, DMSO-$d_6$): δ 8.09 (d, 1); 7.73 (d, 1); 7.69 (s, 1); 7.74-7.29 (m, 2); 4.56 (q, 1); 1.66 (d, J=7.2, 3); 1.63 (s, 9).

Intermediate 48: 3-(2-amino-1-methyl-methyl)-indole-1-carboxylic acid tert-butyl ester A solution of 3-(cyano-methyl-methyl)-indole-1-carboxylic acid tert-butyl ester (850 mg, 3.14 mol) in methanol (15 ml) was stirred at RT. A Raney-Nickel catalyst (50% g/wt suspension in $H_2O$, 1 ml) was added thereto and the reaction vessel was capped and vacuum purged 3 times with argon, followed similarly by hydrogen. The mixture was stirred 22 hr under 1 atm. of hydrogen, vacuum purged with argon and filtered through celite. The filtrate was concentrated to an oil (670 mg) and determined by LCMS to be composed mainly of the desired compound 3-(2-amino-1-methyl-methyl)-indole-1-carboxylic acid tert-butyl ester. $NH_4OAc$ standard conditions. DAD $R_f$=1.78 min. M+H=275.

Intermediate 49: 4-methyl-2,3,4,9-tetrahydro-1H-β-carboline-1-carboxylic acid Crude 3-(2-amino-1-methyl-methyl)-indole-1-carboxylic acid tert-butyl ester (670 mg, approx. 2.44 mmol) was dissolved in trifluoroacetic acid (2 ml) and stirred 30 min at RT, then concentrated to an oily solid under reduced pressure. The resulting oil was dissolved in a 3 M of NaOAc:AcOH buffer solution (pH=4.8, 12 ml) and $H_2O$ (6 ml) at RT. Glyoxalic acid (225 mg, 2.44 mmol) was added thereto and the reaction mixture was stirred for 4 hr at RT, then concentrated to dryness. The resulting solids were determined to be composed mainly of the desired compound 4-methyl-2,3,4,9-tetrahydro-1H-β-carboline-1-carboxylic acid by LCMS and used subsequently thereafter without purification. $NH_4OAc$ standard conditions. DAD $R_f$=1.24 min. M+H=231.

Intermediate 50: 4-methyl-2,3,4,9-tetrahydro-1H-β-carboline

Crude 4-methyl-2,3,4,9-tetrahydro-1H-β-carboline-1-carboxylic acid (approx. 2.44 mmol) was suspended in $H_2O$ (5 ml) and HCl (12 N, 5 ml) and the suspension was heated at 120° C. for 1 hr, then allowed to cool to RT. Dark orange-brown solids were removed by filtration and then dissolved in methanol (5 ml). A saturated sodium bicarbonate solution (20 ml) was added thereto, producing a thick yellow slurry. This reaction mixture was filtered to yield yellow solids composed mainly of 4-methyl-2,3,4,9-tetrahydro-1H-β-carboline (386 mg) as determined by LCMS. $NH_4OAc$ standard conditions. DAD $R_f$=1.23 min. M+H=187.

Intermediate 51: 4-Methyl-9H-β-carboline 4-methyl-2,3,4,9-tetrahydro-1H-β-carboline (214 mg, 1.17 mmol) was suspended in xylenes (10 ml). Pd (10% wt. on carbon, 21 mg) catalyst was added thereto and the reaction mixture was stirred at 160° C. for 24 hours, then cooled to RT and filtered through celite. The filtrate was concentrated to dryness to give 4-methyl-9H-β-carboline (210 mg). $^1$H-NMR (300 MHz, DMSO-d6): δ 11.73 (br s, 1); 8.78 (br s, 1); 8.19 (d, 1); 8.13 (s, 1); 7.62 (br s, 1); 7.53 (t, 1); 7.25 (t, 1); 2.78 (s, 3). $NH_4OAc$ standard conditions. DAD $R_f$=2.24 min. M+H=183.

Intermediate 52: 6-Chloro-4-methyl-9H-β-carboline 4-methyl-9H-β-carboline (97 mg, 0.532 mmol) was dissolved in HCl (1N, 4 ml) and stirred at RT. NCS (85 mg, 0.637 mmol) was added thereto and the reaction mixture was stirred for 5 hr. Saturated sodium bicarbonate solution (20 ml) was added thereto and the reaction mixture was extracted twice with EtOAc (100 ml). The combined organic layers were washed with brine, dried over $MgSO_4$, filtered, and concentrated to give 6-chloro-4-methyl-9H-β-carboline (108 mg) as an oil. $^1$H-NMR (300 MHz, DMSO-$d_6$): δ 8.67 (s, 1); 8.19 (s, 1); 8.11 (s, 1); 7.57-7.54 (m, 2); 2.82 (s, 3). $NH_4OAc$ standard conditions. DAD $R_f$=2.48 min. M+H=217.

Intermediate 53:
6-chloro-4-methyl-8-nitro-9H-β-carboline

A solution of 6-chloro-4-methyl-9H-β-carboline (100 mg, 0.462 mmol) in trifluoroacetic acid (10 ml) was stirred at RT. NaNO$_3$ (106 mg, 1.25 mmol) was added thereto and the reaction mixture was stirred 30 min., then concentrated to give an orange residue. The residue was dissolved in MeOH (5 ml) and neutralized by an addition of a saturated sodium bicarbonate solution (20 ml) causing the formation of yellow solids that were captured by filtration, washed with H$_2$O (10 ml) and Et$_2$O (2×10 ml) to give 6-chloro-4-methyl-8-nitro-9H-β-carboline (82 mg). $^1$H-NMR (300 MHz, DMSO-d$_6$): δ 8.90 (s, 1); 8.65 (s, 1); 8.55 (s, 1); 8.29 (s, 1); 2.89 (s, 3). NH$_4$OAc standard conditions. DAD R$_f$=3.00 min. M+H=262.

Intermediate 54:
6-chloro-4-methyl-9H-β-carbolin-8-ylamine

A solution of 6-chloro-4-methyl-8-nitro-9H-β-carboline (80 mg, 0.31 mmol) in MeOH (10 ml) was stirred at RT. Platinum (10% wt. on carbon, 24 mg) catalyst was added thereto and the reaction vessel was capped and vacuum purged 3 times with argon, followed similarly by hydrogen. The reaction mixture was stirred 1.5 hr under 1 atm hydrogen, then vacuum purged with argon, diluted with DCM (10 ml) and filtered through a 0.2 μM syringe filter. The filtrate was concentrated to yield 6-chloro-4-methyl-9H-β-carbolin-8-ylamine (67 mg) as a light brown oil. $^1$H-NMR (300 MHz, DMSO-d$_6$): δ 9.04 (s, 1); 8.29 (s, 1); 7.74 (d, 1); 7.10 (d, 1); 2.98 (s, 3). NH$_4$OAc standard conditions. DAD R$_f$=1.89 min. M+H=231.

Example 30

N-(6-chloro-4-methyl-9H-β-carbolin-8-yl)-nicotinamide

A solution of 6-chloro-4-methyl-9H-β-carbolin-8-ylamine (43 mg, 0.19 mmol) in pyridine (4 ml) was stirred at RT under an argon atmosphere. Nicotinoyl chloride hydrochloride (40 mg, 0.22 mmol) was added thereto and the reaction mixture was stirred for 12 hr. The solution was diluted with H$_2$O (5 ml) and poured into a separatory funnel containing H$_2$O (5 ml) and EtOAc (25 ml). The reaction mixture was shaken and the layers were separated. The aqueous layer was extracted with EtOAc (2×25 ml). The combined organic layers were washed with a saturated sodium bicarbonate solution (15 ml), followed by brine, then dried over MgSO$_4$, filtered, and concentrated to yield N-(6-chloro-4-methyl-9H-β-carbolin-8-yl)-nicotinamide (5.2 mg) as an orange viscous oil. $^1$H-NMR (300 MHz, DMSO-d$_6$): δ 11.67 (s, 1); 10.70 (s, 1); 9.27 (s, 1); 8.83 (s, 2); 8.45 (s, 1); 8.20-8.12 (m, 2); 7.83 (s, 1); 7.66 (s, 1); 2.80 (s, 3). NH$_4$OAc standard conditions. DAD R$_f$=1.92 min. M+H=337.

Intermediate 55: 1,1-Dioxo-1λ$^6$-thiomorpholine-3,4-dicarboxylic acid 4-tert-butyl ester Thiomorpholine-3,4-dicarboxylic acid 4-tert-butyl ester (120 mg, 0.485 mmol) was dissolved in Et$_2$O (8 ml). To the solution was added mCPBA (172 mg, 0.994 mmol), followed later by a second portion of mCPBA (84 mg, 0.485 mmol). The precipitate which formed was filtered, washed with Et$_2$O and dried to yield a white solid of 1,1-dioxo-1λ$^6$-thiomorpholine-3,4-dicarboxylic acid 4-tert-butyl ester (74 mg).

Example 31

1,1-Dioxo-1λ$^6$-thiomorpholine-3-carboxylic acid (6-chloro-9H-β-carbolin-8-yl)-amide A slurry of 6-chloro-7-fluoro-9H-β-carbolin-8-ylamine (43 mg, 0.198 mmol), 1,1-dioxo-1λ$^6$-thiomorpholine-3,4-dicarboxylic acid 4-tert-butyl ester (72 mg, 0.257 mmol), and EDCI (76 mg, 0.396 mmol) in pyridine (2 ml) was heated to 70° C. After 1 hr, the solvent was removed under reduced pressure and the resulting dark oil was dissolved in MeOH (1 ml). The MeOH solution was added drop-wise to a stirring solution of aqueous NaHCO$_3$ and a yellow precipitate was formed. The solid was filtered, dried, and dissolved in 2 M HCl in Et$_2$O. After stirring overnight the resulting yellow solid was filtered and dried to yield a yellow solid, the di-HCl salt of 1,1-Dioxo-1λ$^6$-thiomorpholine-3-carboxylic acid (6-chloro-9H-β-carbolin-8-yl)-amide (78 mg). $^1$H-NMR (300 MHz, MeOH-d$_4$): δ 9.26 (s, 1); 8.74 (d, 1); 8.54 (d, 1); 8.37 (d, 1); 7.94 (d, 1); 5.01 (dd, 1); 4.15-3.75 (m, 4); 3.64-3.58 (m, 2). NH$_4$OAc standard conditions. DAD R$_f$=1.57 min. M+H=379.

Intermediate 56:
6,6-Dimethyl-morpholine-3,4-dicarboxylic acid 4-tert-butyl ester To a suspension of 6,6-dimethyl-morpholine-3-carboxylic acid (5.56 g, 34.9 mmol) in dioxane (58 mL) was added aqueous potassium carbonate (1M, 58 mL). To the resulting clear colorless solution was added di-tert-butyl dicarbonate (9.14 g, 41.9 mmol). The solution was stirred at room temperature overnight. The reaction mixture was diluted with water (200 mL) and the pH of the solution was confirmed to be approximately 7. The reaction mixture was poured into a separatory funnel and extracted with Et$_2$O (2×100 mL) to remove excess di-tert-butyl dicarbonate. The aqueous layer was acidified by addition of 6N aqueous HCl with stirring until a pH of 3 was reached. The mixture was quickly extracted with Et$_2$O (2×200 mL) and the organic layers were combined, dried over magnesium sulfate, filtered, and concentrated to yield a clear colorless oil. The oil was dissolved in Et$_2$O (50 mL), triturated with hexanes (150 mL), and concentrated to yield a white solid. The solid product was placed on the high-vacuum pump for several hours, after which 8.85 g of 6,6-dimethyl-morpholine-3,4-dicarboxylic acid 4-tert-butyl ester was obtained (97% yield). $^1$H-NMR (300 MHz, DMSO-d$_6$): δ 12.95 (s, 1); 4.35 ("dd", 1); 3.98-3.83 (m, 2); 3.48 ("dd", 1); 2.81 ("dd", 1); 1.39 ("dd", 9); 1.15 (s, 3); 1.08 ("dd", 3). NH$_4$OAc standard conditions. DAD R$_f$=0.98 min. M-H=258.

Intermediate 57: (S)-5-(6-Chloro-9H-β-carbolin-8-ylcarbamoyl)-2,2-dimethyl-morpholine-4-carboxylic acid tert-butyl ester The desired compound was prepared according to Method C from 6-chloro-9H-β-carboline-8-ylamine and 6,6-dimethyl-morpholine-3,4-dicarboxylic acid 4-tert-butyl ester in 87% yield.
$^1$H-NMR (DMSO-d$_6$, 300 MHz) δ 11.33 (s, 1); 10.14 (s, 1); 9.05 (s, 1); 8.38 (d, 1); 8.21 (d, 1); 8.16 (d, 1); 7.94 (s, 1); 4.70-4.56 (m, 1); 4.25-4.14 (m, 1); 4.07 (dd, 1); 3.64-3.56 (m, 1); 3.30-3.14 (m, 1); 1.41 ("dd", 9); 1.21 (s, 3); 1.15 (s, 3). NH$_4$OAc standard conditions. DAD R$_f$=1.84 min. M+H=459.

Chiral HPLC: ≧95% ee. Chiralpak AD column. 15% v/v EtOH/Hexanes containing 0.1% Et$_2$NH.

Intermediate 58: [(S)-4-((S)-2-Amino-propyl)-6,6-dimethyl-morpholine-3-carboxylic acid (6-chloro-9H-beta-carbolin-8-yl)-amide trifluoroacetate salt The desired compound was prepared using the same procedure as for Intermediate 35 starting from (S)-5-(6-Chloro-9H-beta-carbolin-8-ylcarbamoyl)-2,2-dimethyl-morpholine-4-carboxylic acid tert-butyl ester and using Boc-alaninal in the reductive alkylation step in 60% yield. $^1$H-NMR (300 MHz, D$_2$O): δ 1.16 (d, 3H), 1.25 (s, 3H), 1.28 (s, 3H), 2.41 (d, 1H), 2.59 (dd, 1H), 2.89 (dd, 1H), 2.95 (d, 1H), 3.35-3.50 (m, 2H), 3.95-4.15 (m, 2H), 7.59 (d, 1H), 7.97 (d, 1H), 8.11 (d, 1H), 8.30 (d, 1H), 8.40 (d, 1H), 8.94 (s, 1H). Retention Time (LC, method: ammonium acetate standard): 1.57 min.
MS (M+H$^+$): 416.2.
METHOD E: Coupling procedure using [(S)-4-((S)-2-Amino-propyl)-6,6-dimethyl-morpholine-3-carboxylic acid (6-chloro-9H-beta-carbolin-8-yl)-amide trifluoroacetate salt [(S)-4-((S)-2-Amino-propyl)-6,6-dimethyl-morpholine-3-carboxylic acid (6-chloro-9H-beta-carbolin-8-yl)-amide trifluoroacetate salt (1.0 mmole), TBTU (1.2 mmoles), the acid (1.25 mmoles) to be coupled and Et$_3$N (4-6 mmoles, basic pH) were taken into acetonitrile (10 ml). The resulting mixture was stirred at ambient temperature for 4-15 hrs. The reaction mixture was then partitioned into EtOAc and 10% aqueous Na$_2$CO$_3$ solution. The separated aqueous phase was further extracted with EtOAc. The combined extracts were successively washed with 10% aqueous Na$_2$CO$_3$ solution and brine, dried over Na$_2$SO$_4$ and concentrated completely. The residue was purified on silica (2-7% MeOH/CH$_2$Cl$_2$) to give the corresponding product.

Example 39

6,6-Dimethyl-4-[2-(2,2,2-trifluoro-acetylamino)-propyl]-morpholine-3-carboxylic acid (6-chloro-9H-β-carbolin-8-yl)-amide 4-(2-Amino-propyl)-6,6-dimethyl-morpholine-3-carboxylic acid (6-chloro-9H-β-carbolin-8yl)-amide (3 CF$_3$COOH salt) (1.5 g) was suspended in dichloromethane (80 mL) along with 5 equivalents of triethylamine. Trifluoroacetic anhydride (56 μL, 2 equivalents) was added and the mixture stirred at room temperature for an hour. The solvent was removed by rotary evaporation. The product was purified by silica gel flash chromatography (5% methanol/dichloromethane, product R$_f$ 0.3) to afford 1 g. $^1$H-NMR (300 MHz, relative to CDCl$_3$ peak at 7.3 ppm) δ 10 (s, 1H), 9.7 (d, 1H), 8.7 (s, 1H), 8.6 (s, 1H), 8.2 (d, 1H), 7.6 (s, 2H), 6.6 (s, 1H), 4.3 (m, 1H), 3.9 (m, 1H), 3.8 (t, 1H), 3.2 (m, 1H), 2.7-2.9 (m, 2H), 2.5 (m, 1H), 2.2 (d, 1H), 1.4 (d, 3H), 1.3 (s, 3H), 1.2 (s, 3H). LCMS (ammonium acetate standard method) retention time=1.84 min. (M$^+$=512; M$^-$=510).

Example 40

4-((S)-2-Acetylamino-propyl)-6,6-dimethyl-morpholine-3-(S)-carboxylic acid (6-chloro-9H-b-carbolin-8-yl)-amide The desired compound was prepared according to the previous example from 4-(2-Amino-propyl)-6,6-dimethyl-morpholine-3-carboxylic acid (6-chloro-9H-β-carbolin-8yl)-amide (3 CF$_3$COOH salt) and acetic anhydride. $^1$H-NMR (300 MHz, methyl-d$_3$ alcohol-d): δ 1.15 (d, 3H), 1.23 (s, 3H), 1.39 (s, 3H), 1.98 (s, 3H), 2.24 (d, 1H), 2.38 (m, 1H), 2.68 (m, 1H), 2.92 (d, 1H), 3.24 (m, 1H), 3.98 (m, 2H), 4.22 (m, H), 7.78 (d, 1H), 7.98 (m, 2H), 8.27 (d, 1H), 8.84 (s, 1H). Retention Time (LC, method: ammonium acetate standard): 1.54 min. MS (M+H$^+$): 458.

Example 41

4-((S)-2-Methanesulfonylamino-propyl)-6,6-dimethyl-morpholine-3-(S)-carboxylic acid (6-chloro-9H-b-carbolin-8-yl)-amide The desired compound was prepared according to Method E. $^1$H-NMR (300 MHz, methyl-d$_3$ alcohol-d): δ 1.28 (s, 3H), 1.29 (d, 3H), 1.43 (s, 3H), 2.28 (d, 1H), 2.57 (m, 1H), 2.66 (m, 1H), 2.98 (s, 3H), 3.03 (d, 1H), 3.34 (m, 1H), 3.66 (m, 1H), 4.05 (m, 2H), 7.67 (d, 1H), 8.10 (m, 2H), 8.32 (d, 1H), 8.89 (s, 1H). Retention Time (LC, method: ammonium acetate standard): 1.54 min.
MS (M+H$^+$): 494.

Example 42

4-{2-[(-4,6-Dimethyl-pyrimidine-5-carbonyl)-amino]-propyl}-6,6-dimethyl-morpholine-3-carboxylic acid (6-chloro-9H-beta-carbolin-8-yl)-amide The desired compound was prepared using [4-(2-Amino-propyl)-6,6-dimethyl-morpholin-3-ylmethyl]-(6-chloro-9H-beta-carbolin-8-yl)-amine and 4,6-dimethylpyrimidine-5-carboxylic acid following Method E in 51% yield. $^1$H-NMR (300 MHz, DMSO): δ 11.27 (1H, s), 10.02 (1H, s), 9.0 (1H, s), 8.86 (1H, s), 8.5 (1H, d), 8.3 (1H, d), 8.22 (2H, m), 7.88 (1H, s), 4.1 (1H, m), 3.9 (2H, m), 2.99 (2H, m), 2.36 (6H, s), 2.1 (2H, m), 1.3 (3H, s), 1.24 (6H, m). Retention time (LC, method: ammonium acetate standard): 1.50 min. MS (M+H$^+$): 551

Example 43

(S)-6,6-Dimethyl-4-{(S)-2-[(2-methyl-pyridine-3carbonyl)amino]propyl}-morpholine-3-carboxylic acid (6-chloro-9H-beta-carbolin-8-yl)-amide The desired compound was prepared according to Method E from (S)-4-((S)-2-Amino-propyl)-6,6-dimethyl-morpholine-3-carboxylic acid (6-chloro-9H-beta-carbolin-8-yl)-amide trifluoroacetate salt and 2-methyl-nicotinic acid in 75% yield. $^1$H-NMR (300 MHz, DMSO-d$_6$): δ 1.21 (s,3H), 1.22 (d,3H), 1.36 (s,3H), 2.10 (d,1H), 2.42 (m,1H), 2.60 (m,1H), 2.99 (d,1H), 3.20 (m,1H), 3.92 (m,2H), 4.22 (m,1H), 7.22 (dd,1H), 7.65 (d,1H), 7.90 (s,1H), 8.16 (d,1H), 8.23 (s,1H), 8.31 (d,1H), 8.38 (d,1H), 8.45 (d,1H), 9.02 (s,1H), 10.04 (s,1H), 11.26 (s,1H). Retention Time (LC, method: ammonium acetate standard): 2.16 min. MS (M+H$^+$): 535.5.

Example 44

6,6-Dimethyl-4-{2-[(tetrahydro-pyran-4-carbonyl)-amino]-propyl}-morpholine-3-carboxylic acid (6-chloro-9H-b-carbolin-8-yl)-amide 4-(2-Amino-propyl)-6,6-dimethyl-morpholine-3-carboxylic acid (6-chloro-9H-β-carbolin-8-yl)-amide (3 CF$_3$COOH salt) (300 mg) was suspended in methylene chloride (12 mL) along with 3 equivalents of triethylamine. Morpholine-4-carbonyl chloride (70 mg, 1.3 equivalents) was added and the mixture stirred at room temperature overnight. The solvent was removed by rotary evaporation. The product was separated by preparative TLC on silica plates (10/90 methanol/ethyl acetate as eluent, product R$_f$ 0.4) Yield: 83 mg. $^1$H-NMR (300 MHz, relative to CD$_3$OD peak at 3.3 ppm) δ 8.8 (s, 1H), 8.27 (d, 1H), 7.9-7.99 (m, 3H), 3.95-4.15 (m, 2H), 3.85-3.95 (m, 2H), 3.5-3.6 (m, 5H), 3.3-3.45 (m, 2H), 3.15-3.3 (m, 2H), 2.85-2.95 (d, 1H), 2.6-2.72 m, 1H), 2.3-2.43 (m, 1H), 2.2-2.28 (d, 1H), 2.0 (s, 2H), 1.35-1.45 (d, 3H), 1.05-1.25 (m, 6H). LCMS (ammonium acetate standard method) retention time=2.39 min. (M$^+$=529; M$^-$=527).

Example 45

4-{(S)-2-[(1-Acetyl-pyrrolidine-2-(S)-carbonyl)-amino]-propyl}-6,6-dimethyl-morpholine-3-(S)-carboxylic acid (6-chloro-9H-b-carbolin-8-yl)-amide The desired compound was prepared according to Method E. $^1$H-NMR (300 MHz, methyl-d$_3$ alcohol-d): δ 1.21 (d, 3H), 1.28 (s, 3H), 1.39 (s, 3H), 1.95 (m, 3H), 2.05 (s, 3H), 2.17 (m, 1H), 2.28 (d, 1H), 2.51 (m, 1H), 2.74 (m, 1H), 3.05 (d, 1H), 3.30 (m, 1H), 3.55 (m, 1H), 3.61 (m, 1H), 4.05 (m, 2H), 4.18 (m, 1H), 4.34 (m 1H), 7.78 (d, 1H), 8.10 (m, 2H), 8.33 (d, 1H), 8.90 (s, 1H). Retention Time (LC, method: ammonium acetate standard): 2.07 min. MS (M+H$^+$): 555.

Example 46

6,6-Dimethyl-4-{-2-[(5-methyl-isoxazole-3-carbonyl)-amino]-propyl}-morpholine-3-carboxylic acid (6-chloro-9H-beta-carbolin-8-yl)-amide The desired compound was prepared using [4-(2-Amino-propyl)-6,6-dimethyl-morpholin-3-ylmethyl]-(6-chloro-9H-beta-carbolin-8-yl)-amine and 5-methylisoxazole carbonyl chloride following Method E in 61% yield. $^1$H-NMR (300 MHz, DMSO): δ 11.2 (1H, s), 9.98 (1H, s), 9.0 (1H, s), 8.7 (1H, d), 8.6 (1H, d), 8.2 (2H, m), 7.9 (1H, s). 6.47 (1H, s), 3.87 (2H, m), 3.17 (2H,m), 2.9 (1H, d), 2.7 (1H, m), 2.3 (4H), 2.1 (1H, d), 1.29 (3H, s), 1.15 (6H, m). Retention time (LC, method: ammonium acetate standard): 1.81 min. MS (M+H$^+$): 526

Example 47

6,6-Dimethyl-4-[2-(3-methyl-ureido)-proplyl]-morpholine-3-carboxylic acid (6-chloro-9H-β-carbolin-8-yl)-amide 4-(2-Amino-propyl)-6,6-dimethyl-morpholine-3-carboxylic acid (6-chloro-9H-β-carbolin-8yl)-amide (3 HCl salt) (300 mg) was suspended in dichloromethane (10 mL) triethyl amine (4 equivalents) and methyl isocyanate (2 equivalents) were added simultaneously. After one hour at room temperature solvent was removed by rotary evaporation. The product was purified by silica gel flash chromatography (5% methanol/dichloromethane, product R$_f$=0.3) to afford 200 mg. $^1$H-NMR (300 MHz, relative to CDCl$_3$ peak at 7.3 ppm) δ 12.3 (s, 1H), 10.2 (s, 1H), 8.9 (s, 1H), 8.6 (s, 1H), 8.4 (d, 1H), 7.9 (d, 1H), 7.8 (s, 1H), 5.4 (s, 1H), 5.2 (d, 1H), 4.2 (s, 1H), 3.8 (m, 2H), 3.2 (m, 1H), 2.6-3 (m, 7H), 2.3 (d, 1H), 2.2 (t, 1H), 1.4 (s, 3H), 1.2 (s, 3H), 1.1 (d, 3H) LCMS (ammonium acetate standard method) retention time=1.62 min. (M$^+$=473; M$^-$=471).

Example 49

{(S)-2-[(S)-5-(6-Chloro-9H-beta-carbolin-8-ylcarbamoyl)-2,2-dimethyl-morpholin-4-yl]-1-methyl-ethyl]-carbamic acid methyl ester To a solution of (S)-4-((S)-2-Amino-propyl)-6,6-dimethyl-morpholine-3 carboxylic acid (6-chloro-9H-beta-carbolin-8-yl)-amide hydrochloride salt (3.45 g, 6.59 mmole) in 68 ml of dry pyridine, was added in three portions over 1.5 hr, a 3M DCM solution of methyl chloroformate (9.2 ml, 27.6 mmole, 4.2 eq). After 2 h, 10 ml of water were added and the mixture was concentrated to dryness. The residue was partitioned into 150 ml Of EtOAc and 100 ml of an aqueous 0.5M solution of K$_2$CO$_3$. The separated aqueous phase was extracted with 50 ml of EtOAc. The combined organic extracts were successively washed with water (2×50 ml) and brine (50 ml), dried over Na$_2$SO$_4$ and concentrated to dryness. The residue was purified on silica (5% MeOH/CH$_2$Cl$_2$) to give 2.48 g (thick oil, 77% yield) of the desired product $^1$H-NMR (300 MHz, CDCl$_3$): δ 1.15 (d, 3H), 1.28 (s, 3H), 1.42 (s, 3H), 2.33 (dd, 1H), 2.42 (d, 1H), 2.78 (dd, 1H), 2.86 (d, 1H), 3.32 (dd, 1H), 3.86 (s, 3H), 3.92 (t, 1H), 4.01 (dd, 1H), 4.18 (m, 1H), 4.78 (d, 1H), 7.95 (d, 1H), 7.97 (s, 1H), 8.29 (s, 1H), 8.50 (d, 1H), 8.98 (s, 1H), 9.88 (s, 1H), 10.94 (s, 1H). Retention Time (LC, method: ammonium acetate standard): 1.70 min. MS (M+H$^+$): 474.1

Example 50

4-{2-[(2,4-Dimethyl-pyridine-3-carbonyl)-amino]-propyl}-6,6-dimethyl-morpholine-3-carboxylic acid (6-chloro-9H-beta-carbolin-8-yl)-amide The desired compound was prepared from [4-(2-Amino-propyl)-6,6-dimethyl-morpholin-3-ylmethyl]-(6-chloro-9H-beta-carbolin-8-yl)-amine nad 2,4-dimethyl nicotinic acid following Method E in 50% yield. $^1$H-NMR (300 MHz, DMSO): δ 11.27 (1H, s), 10 (1H, s), 8.9 (1H, s), 8.37 (2H, d), 8.24 (3H, m), 7.8 (1H, s), 7.04 (1H, d), 3.91 (2H, m), 3.1 (2H, m), 2.36 (4H, m), 2.1 (3H, m), 2.05 (1H, d), 1.3 (3H, s), 1.2 (6H, m). Retention time (LC, method: ammonium acetate standard): 1.53 min.

MS (M+H$^+$): 550

Example 51

6,6-dimethyl-4-{2-[(pyrazine-2-carbonyl)-amino]-propyl}-morpholine-3-carboxylic acid (6-chloro-9H-beta-carbolin-8-yl)-amide The desired compound was prepared from [4-(2-Amino-propyl)-6,6-dimethyl-morpholin-3-ylmethyl]-(6-chloro-9H-beta-carbolin-8-yl)-amine and 2-pyrazine carboxylic acid following Method E in 62% yield. $^1$H-NMR (300 MHz, DMSO): δ 12.9 (1H, s), 10.89 (1H, s), 9.42 (1H, s), 9.0 (1H, s), 8.8 (1H, d), 8.6 (1H, d), 8.4 (1H, s), 8.2 (1H, m), 4.5 (1H, m), 4.1 (2H, m), 3.1 (1H, m), 2.1 (4H, m), 1.23 (9H, m). Retention time (LC, method: ammonium acetate standard): 1.69 min. MS (M+): 522.2

Example 52

Pyridine-3,4-dicarboxylic acid 4-({2-[5-(6-chloro-9H-β-carbolin-8-ylcarbamoyl)-2,2-dimethyl-morpholin-4-yl}-1-methyl-ethyl}-amide}3-methylamide To a solution of [4-(2-Amino-propyl)-6,6-dimethyl-morpholin-3-ylmethyl]-(6-chloro-9H-beta-carbolin-8-yl)-amine (100 mg, 0.132 mmole) in 0.6 ml of dry acetonitrile, was added 3, 4-pyridinedicarboxylic anhydride (21 mg, 0.15 mmole) and triethylamine (102 ml, 0.8 mmole). The reaction mixture was stirred at ambient temperature for 1 h. The solvent was then removed under reduced pressure and the residue was taken up into pyridine (0.6 ml). To the resulting mixture was added 2M methylamine solution in THF (0.2 ml, 0.4 mmole) and EDCI (40 mg, 0.21 mmole). The reaction mixture was stirred for 4 hrs, the solvent was removed under reduce pressure and the residue was partitioned into EtOAc and 1M aqueous $K_2CO_3$. The separated aqueous phase was extracted twice with EtOAc. The combined organic phases were successively washed with water and brine, dried over $MgSO_4$, and concentrated completely. The residue was purified on silica gel (10% MeOH—$CH_2Cl_2$) to give the title compound as a white solid in 36% yield. $^1$H-NMR (300 MHz, DMSO): δ 9.24 (1H, s), 8.17 (1H,s), 7.81 (2H, m), 7.5 (3H, m), 7.3 (1H, s), 7.0 (1H, s) 6.5 (1H, d), 3.08 (2H, d), 3.35 (1H, m), 2.4 (3H, m), 1.86 (4H, m), 0.5 (3H, s), 0.37 (6H, m). Retention time (LC, method: ammonium acetate standard): 1.46 min. MS (M+H$^+$): 579

Example 53

6,6-Dimethyl-4-{(4-methyl-pyrimidine-5-carbonyl)-amino)-propyl}-morpholine-3-carboxylic acid (6-chloro-9H-beta-carbolin-8-yl)-amide The desired compound was prepared according to Method E from [4-(2-Amino-propyl)-6,6-dimethyl-morpholin-3-yl-methyl]-(6-chloro-9H-beta-carbolin-8-yl)-amine and 4-methyl-pyrimidine-5-carboxylic acid in 55% yield. $^1$H-NMR (300 MHz, DMSO): δ 11.26 (1H, s), 10.04 (1H, s) 9.04 (2H, m), 8.66 (1H, d) 8.3 (2H, m) 8.22-8.17 (2H, m), 7.9 (1H, s), 4.2 (1H, m), 3.93 (2H, m), 3.2 (1H, m), 2.98 (2H, m), 2.6 (3H, m), 2.1 (2H, m), 1.36 (3H, s), 1.23 (6H, m). Retention time (LC, method: ammonium acetate standard): 1.55 min. MS (M+H$^+$): 537

Example 54

(S)-6,6-Dimethyl-4-{(S)-2-[(4-methyl-pyridine-3-carbonyl)-amino]-propyl}-morpholine-3-carboxylic acid (6-chloro-9H-beta-carbolin-8-yl)-amide The desired compound was prepared according to Method E from (S)-4-((S)-2-Amino-propyl)-6,6-dimethyl-morpholine-3-carboxylic acid (6-chloro-9H-beta-carbolin-8-yl)-amide trifluoroacetate salt and 4-methyl-nicotinic acid in 79% yield. $^1$H-NMR (300 MHz, DMSO-d$_6$): δ 1.21 (s,3H), 1.22 (d,3H), 1.36 (s,3H), 2.10 (d,1H), 2.40 (m,1H), 2.62 (m,1H), 2.99 (d,1H), 3.22 (m,1H), 3.94 (m,2H), 4.23 (m,1H), 7.26 (d,1H), 7.90 (s,1H), 8.16 (d,1H), 8.23 (s,1H), 8.34-8.46 (m,3H), 9.02 (s,1H), 10.04 (s,1H), 11.27 (s,1H). Retention Time (LC, method: ammonium acetate standard): 2.22 min. MS (M+H$^+$): 535.5.

Example 47

4-[2-(2-Amino-2-methyl-propionyl)]-6,6-dimethyl-morpholine-3-carboxylic acid (6-chloro-9H-β-carbolin-8yl)-amide A solution of {2-[5-(6-Chloro-9H-β-carbolin-8-ylcarbamoyl) 2,2-dimethyl-morpholin-4-yl]-1-methyl-ethyl}-carbamic acid tert-butyl ester (70.2 mg, 0.14 mmol) in TFA (2 mL) was stirred at room temperature. After 15 min, the reaction was concentrated and the crude product was azeotroped with $CH_2Cl_2$ (2×5 mL). A mixture of the crude intermediate, TBTU (54.0 mg, 0.17 mmol), triethylamine (0.2 mL, 1.43 mmol) and 2-tert-butoxycarbonylamino-2-methyl-propionic acid (45.0 mg, 0.22 mmol) in MeCN (1 mL) was stirred at room temperature for 18 h. The solution was diluted with $H_2O$ (20 mL) and poured into a separatory funnel containing EtOAc (50 mL), and brine (50 mL). The mixture was shaken and the layers were separated. The aqueous layer was extracted with EtOAc (2×50 mL). The combined organic layers were dried, filtered and concentrated. The crude product was purified by flash chromatography to yield a yellow solid (51.0 mg, 62%) which was shown by NMR and LCMS to be 4-[2-(2-amino-2-methyl-propionyl]-6,6-dimethyl-morpholine-3-carboxylic acid (6-chloro-9H-β-carbolin-8yl)-amide.
$^1$H-NMR (300 MHz, DMSO-d$_6$): δ 12.94 (br s, 1); 11.36 (br s, 1); 10.16 (s, 1); 9.06 (s, 1); 8.39 (d, 1); 8.22 (d, 1); 8.19 (d, 1); 7.95 (s, 1); 4.77-4.52 (m, 1); 4.28-4.13 (m, 1); 4.13-4.00 (m, 1); 3.68-3.52 (m, 1); 3.22-3.12 (m, 1); 1.44 (s, 3); 1.41-1.38 (m, 6); 1.28-1.24 (m, 2); 1.22 (s, 3); 1.25 (s, 3); 1.11-1.07 (m, 1). NH$_4$OAc standard conditions. DAD R$_f$=1.31 min. M+H=501.

Example 55

6,6 Dimethyl-4-(1,2,3,4-tetrahydroisoquinolin-3-ylmethyl)-morpholine-3-carboxylic acid (6-chloro-9H-beta-carbolin-8-yl)amide The desired compound was made following the procedure outlined in Method C using 6,6-dimethyl morpholine-3-carboxylic acid and (s)-tetrahydroisoquinoline aldehyde. $^1$H-NMR (300 MHz, D$_2$O): δ 9.1 (1H, s), 8.68 (1H, d), 8.52 (1H, d), 8.41 (1H, d), 7.68 (1H, d), 7.27 (1H, d), 7.06 (1H, m), 6.97 (1H, d), 6.84 (1H, m), 4.31 (2H, m), 4.09 (2H, m), 3.68 (1H, m), 3.56 (1H, t), 3.2 (2H, m), 3.06 (2H, m), 2.7 (2H, m) 1.48 (3H, s), 1.32 (3H, s) Retention time (LC, method: ammonium acetate standard): 2.43 min. MS (M+H$^+$): 505

Intermediate 59: 6,6-Dimethyl-morpholine-3-carboxylic acid (6-chloro-9H-β-carbolin-8-yl)-amide, HCl salt To a clear brown solution of 5-(6-chloro-9H-β-carbolin-8-ylcarbamoyl)-2,2-dimethyl-morpholine-4-carboxylic acid tert-butyl ester (10.4 g, 22.7 mmol) in methanol (41 mL) was added HCl in dioxane (4M, 91 mL). The reaction was stirred for 30 minutes at room temperature, during which time a pale brown precipitate began to form. The mixture was poured into a 250-mL volume of vigorously stirring Et$_2$O. The resulting slurry was stirred at room temperature for 15 minutes, then filtered to yield a pale orange solid. The solid was placed on the high-vacuum pump overnight, after which 9.71 g of 6,6-dimethyl-morpholine-3-carboxylic acid (6-chloro-9H-β-carbolin-8-yl)-amide was obtained (99% yield). $^1$H-NMR (DMSO-d$_6$, 300 MHz) δ 13.47 (s, 1); 11.77 (s, 1); 9.42 (s, 1); 8.86 (d, 1); 8.66 (d, 1); 8.58 (d, 1); 8.25 (d, 1); 4.41-4.37 (m, 2); 4.05 (dd, 1); 3.32-3.28 (m, 1); 3.04-3.00 (m, 1); 1.34 (s, 3); 1.30 (s, 3). NH$_4$OAc standard conditions. DAD R$_f$=1.48 min. M+H=359.

Example 56

4-(2-Amino-butyl)-6,6-dimethyl-morpholine-3-carboxylic acid (6-chloro-9H-β-carbolin-8-yl)-amide (also INTERMEDIATE 60)

Method C was followed, using 5-(6-chloro-9H-β-carbolin-8-ylcarbamoyl)-2,2-dimethyl-morpholine-4-carboxylic acid tert-butyl ester and the appropriate aldehyde, (1-formyl-propyl)-carbamic acid tert-butyl ester.

$^1$H-NMR (DMSO-d$_6$, 300 MHz) δ 9.06 (s, 1); 8.37 (d, 1); 8.19 (d, 1); 8.15 (d, 1); 7.85 (d, 1); 6.75 (br s, 2); 3.96-3.85 (m, 2); 3.17-3.13 (m, 1); 2.89 (d, 1); 2.78-2.74 (m, 1); 2.67-2.59 (m, 1); 2.26-2.20 (m, 1); 2.14 (d, 1); 1.58-1.50 (m, 1); 1.32 (s, 3); 1.32-1.23 (m, 1); 1.18 (s, 3); 0.87 (t, 3). NH$_4$OAc standard conditions. DAD R$_f$=1.27 min. M+H=430.

Example 57

6,6-Dimethyl-4-{2-[(2-methyl-pyridine-3-carbonyl)-amino]-butyl}-morpholine-3-carboxylic acid (6-chloro-9H-β-carbolin-8-yl)-amide, HCl salt To a solution of 4-(2-amino-butyl)-6,6-dimethyl-morpholine-3-carboxylic acid (6-chloro-9H-β-carbolin-8-yl)-amide (100 mg, 0.233 mmol) in pyridine (4 mL) was added 2-methyl-nicotinic acid (38.4 mg, 0.280 mmol) and EDCI (71.5 mg, 0.373 mmol). The solution was stirred overnight at room temperature, then diluted with water (5 mL). The mixture was poured into a separatory funnel and diluted further with water (20 mL). The mixture was extracted with EtOAc (2×20 mL), then the combined organic layers were washed with brine. The organic layer was dried over magnesium sulfate, filtered, and concentrated to yield a yellow-brown oil which was purified via column chromatography. The resulting yellow solid was dissolved in methanol (2 mL) and HCl in Et$_2$O (2M, 2 mL) was added. The mixture was stirred for 5 minutes, then concentrated to yield 103 mg of 6,6-dimethyl-4-{2-[(2-methyl-pyridine-3-carbonyl)-amino]-butyl}-morpholine-3-carboxylic acid (6-chloro-9H-β-carbolin-8-yl)-amide (71% yield). $^1$H-NMR (DMSO-d$_6$, 300 MHz) δ 13.31 (br s, 1); 11.41 (br s, 1); 11.14 (br s, 1); 9.44 (s, 1); 8.85 (d, 1); 8.73-8.64 (m, 3); 8.52 (s, 1); 8.32 (s, 1); 7.72 (s, 1); 4.64-3.55 (m, 6); 3.24-3.06 (m, 1); 2.95-2.81 (m, 1); 2.71 (s, 3); 1.89-1.74 (m, 1); 1.55-1.41 (m, 1); 1.32 (s, 3); 1.23 (s, 3); 0.93 (t, 3). NH$_4$OAc standard conditions. DAD R$_f$=1.66 min. M+H=549.

Intermediate 61: 4-(2-Amino-3-methyl-butyl)-6,6-dimethyl-morpholine-3-carboxylic acid (6-chloro-9H-β-carbolin-8-yl)-amide Method C was followed, using 5-(6-chloro-9H-β-carbolin-8-ylcarbamoyl)-2,2-dimethyl-morpholine-4-carboxylic acid tert-butyl ester and the appropriate aldehyde, (1-formyl-2-methyl-propyl)-carbamic acid tert-butyl ester. $^1$H-NMR (DMSO-d$_6$, 300 MHz) δ 9.05 (s, 1); 8.37 (d, 1); 8.21 (d, 1); 8.16 (dd, 1); 7.90 (d, 1); 6.71 (br s, 2); 3.93-3.86 (m, 2); 3.18-3.14 (m, 1); 2.91 (d, 1); 2.70-2.65 (m, 2); 2.21 (dd, 1); 2.15 (d, 1); 1.74-1.66 (m, 1); 1.31 (s, 3); 1.19 (s, 3); 0.85 (d, 3); 0.80 (d, 3). NH$_4$OAc standard conditions. DAD R$_f$=1.27 min. M+H=444.

Example 58

6,6-Dimethyl-4-{3-methyl-2-[(2-methyl-pyridine-3-carbonyl)-amino]-butyl}-morpholine-3-carboxylic acid (6-chloro-9H-β-carbolin-8-yl)-amide To a solution of 4-(2-amino-3-methyl-butyl)-6,6-dimethyl-morpholine-3-carboxylic acid (6-chloro-9H-β-carbolin-8-yl)-amide (1.47 g, 3.31 mmol) in pyridine (35 mL) was added 2-methyl-nicotinic acid (544 mg, 3.97 mmol) and EDCI (1.02 g, 5.30 mmol). The solution was stirred 6.5 hours at room temperature, then diluted with water (100 mL). The mixture was poured into a separatory funnel and diluted further with water (50 mL) and EtOAc (150 mL). The layers were shaken and separated. The aqueous layer was extracted with EtOAc (3×50 mL), then the combined organic layers were washed with brine. The organic layer was dried over magnesium sulfate, filtered, and concentrated to yield an orange semi-solid residue which was purified via column chromatography. The resulting yellow solid was placed on the high-vacuum pump overnight, after which 1.43 g of 6,6-dimethyl-4-{3-methyl-2-[(2-methyl-pyridine-3-carbonyl)-amino]-butyl}-morpholine-3-carboxylic acid (6-chloro-9H-β-carbolin-8-yl)-amide was obtained (77% yield). $^1$H-NMR (DMSO-d$_6$, 300 MHz) δ 11.32 (s, 1); 10.08 (s, 1); 9.02 (s, 1); 8.46 (dd, 1); 8.38 (d, 1); 8.21-8.14 (m, 3); 7.97 (d, 1); 7.64 (dd, 1); 7.23 (dd, 1); 4.23-4.14 (m, 1); 3.99-3.87 (m, 2); 3.22-3.19 (m, 1); 3.02 (d, 1); 2.85 (dd, 1); 2.52 (s, 3); 2.30 (dd, 1); 2.11 (d, 1); 2.05-1.95 (m, 1); 1.32 (s, 3); 1.21 (s, 3); 0.93 (d, 3); 0.86 (d, 3). NH$_4$OAc standard conditions. DAD R$_f$=1.67 min. M+H=563.

Example 59

6,6-Dimethyl-4-{3-methyl-2-(S)-[(tetrahydro-furan-3-carbonyl)-amino]-butyl}-morpholine-3-(S)-carboxylic acid (6-chloro-9H-b-carbolin-8-yl)-amide The desired compound was prepared following Method E from Intermediate 61 and the appropriate acid. $^1$H-NMR (300 MHz, methyl-d$_3$ alcohol-d): δ 0.87 (m, 6H), 1.25 (d, 3H), 1.37 (d, 3H), 1.81 (m, 1H), 2.10-2.47 (m, 4H), 2.93 (m, 2H), 3.10 (m, 1H), 3.26 (m, 1H), 3.80 (m, 1H), 3.86-4.07 (m, 6H), 7.86 (d, 1H), 8.10 (m, 2H), 8.32 (d, 1H), 8.89 (s, 1H). Retention Time (LC, method: ammonium acetate standard): 1.73 min. MS (M+H$^+$): 542.

Intermediate 62: {(S)-2-[(S)-5-(6-Chloro-4-methyl-9H-β-carbolin-8-ylcarbamoyl)-2,2-dimethyl-morpholin-4-yl]-1-methyl-ethyl]-carbamic acid tert-butyl ester A solution of (S)-4-((S)-2-tert-butoxycarbonylamino-propyl)-6,6-dimethyl-morpholine-3-carboxylic acid (3.316 g, 10.5 mmol) (prepared by reductively alkylating (S)-6,6-dimethyl-morpholine-3-carboxylic acid with N-(tert-butoxycarbonyl)-L-alanal) in anhydrous pyridine (75 mL) was stirred at room temperature. 6-chloro-4-methyl-9H-β-carbolin-8-ylamine (1.869 g, 8.09 mmol) was added, followed by EDCI (2.894 g, 15.1 mmol). The reaction was stirred at room temperature for 14-18 hours under argon. The reaction was partially concentrated, diluted with H$_2$O (20 mL) and transferred to a separatory funnel. The mixture was diluted with brine (50 mL) and extracted with EtOAc (3×100 mL). The combined organic layers were washed with brine, dried, filtered and concentrated to afford a dark residue. Column chromatography (0-8% MeOH/CH$_2$Cl$_2$) yielded ((S)-2-[(S)-5-(6-Chloro-4-methyl-9H-β-carbolin-8-ylcarbamoyl)-2,2-dimethyl-morpholin-4-yl]-1-methyl-ethyl)-carbamic acid tert-butyl ester as a light tan solid (2.688 g). $^1$H-NMR (300 MHz, DMSO-d$_6$): δ 11.25 (s, 1) 9.94 (s, 1) 8.88 (s, 1) 8.18 (s, 1) 8.02 (s, 1) 7.92 (s, 1) 6.73 (d, 1) 3.95-3.85 (m, 2) 3.66 (br s, 1) 3.16-3.08 (m, 1) 2.88 (d, 1) 2.76 (s, 3) 2.51-2.40 (m, 1) 2.23 (dd, 1) 1.99 (d, 1) 1.34 (br s, 12) 1.17 (s, 3) 1.08 (d, 3). NH$_4$OAc standard conditions. ELSD R$_f$=2.07 min. M+H=530.

Example 60

(S)-6,6-Dimethyl-4-{(S)-2-[(2-methyl-pyridine-3-carbonyl)-amino]-propyl}-morpholine-3-carboxylic acid (6-chloro-4-methyl-9H-β-carbolin-8-yl)-amide A solution of {(S)-2-[(S)-5-(6-Chloro-4-methyl-9H-β-carbolin-8-ylcarbamoyl)-2,2-dimethyl-morpholin-4-yl]-1-methyl-ethyl}-carbamic acid tert-butyl ester (2.688 g, 5.08 mmol) in EtOH (60 mL) was stirred at room temperature.

Concentrated HCl (10 mL) was added and the reaction stirred for 14 hours at room temperature under argon. The reaction was concentrated to afford a yellow solid (2.84 g). The solid was dissolved in anhydrous pyridine (40 mL) and stirred at room temperature under argon. Triethylamine (2.20 mL, 15.7 mmol) and EDCI (1.39 g, 7.28 mmol) were added. The reaction mixture was stirred at room temperature for 10 minutes and 2-methyl-nicotinic acid (0.868 g, 6.33 mmol) was added. The reaction was stirred at room temperature for 14-18 hours and diluted with $H_2O$ (40 mL). The mixture was poured into a separatory funnel containing $H_2O$ (40 mL), brine (40 mL), and EtOAc (40 mL). The mixture was shaken and the layers were separated. The aqueous layer was extracted with EtOAc (2×40 mL) and the combined organic layers washed with brine. The organic layer was dried, filtered, and concentrated. The resulting residue was dissolved in EtOAc (10-20 mL) and added dropwise to a stirring solution of 4:1 hexanes/$Et_2O$ (300 mL). The precipitate which formed was collected via filtration and air dried to yield (S)-6,6-Dimethyl-4-{(S)-2-[(2-methyl-pyridine-3-carbonyl)-amino]-propyl}-morpholine-3-carboxylic acid (6-chloro-4-methyl-9H-β-carbolin-8-yl)-amide as a tan solid (3.151 g). $^1$H-NMR (300 MHz, DMSO-$d_6$): δ 11.28 (s, 1) 9.98 (s, 1) 8.81 (s, 1) 8.45-8.39 (m, 1) 8.26 (d, 1) 8.13 (s, 1) 7.97 (s, 1) 7.89 (s, 1) 7.64-7.56 (m, 1) 7.24-7.12 (m, 1) 4.25-4.10 (m, 1) 3.91-3.82 (m, 2) 3.20-3.10 (m, 1) 2.94 (d, 1) 2.71 (s, 3) 2.61-2.49 (m, 1) 2.37 (s, 3) 2.06-2.02 (m, 2) 1.30 (s, 3) 1.16 (d, 3) 1.15 (s, 3). $NH_4OAc$ standard conditions. ELSD $R_f$=1.57 min. M+H=549.

Intermediate 63:
3,5-Difluoro-4-tributylstannanyl-pyridine n-Butyl lithium (1.0 eq, 76 mmol, 47.6 mL, 1.6 M in hexanes) was added via dropping funnel to a solution of diisopropylamine (1.05 eq, 80 mmol, 11.2 mL) in THF (300 mL) at −78° C. under nitrogen ($N_2$). The solution was stirred for 30 min at −78° C., then a solution of 3,5-difluoropyridine (1.05 eq, 80 mmol, 9.2 g) in THF (20 mL) was added dropwise via syringe. A beige precipitate was observed to form. The reaction stirred at −78° C. for 90 min then tributyltin chloride (1.0 eq, 76 mmol, 20.7 mL) was added dropwise via syringe and the resulting solution allowed to warm to RT over 2 h. Water (5 mL) was added, then roughly 250 mL of THF was removed on a rotary evaporator. The resulting material was diluted with diethyl ether (350 mL) and washed successively with water (2×200 mL), saturated sodium chloride solution (1×150 mL), dried over magnesium sulfate, filtered and concentrated in vacuo to afford the 3,5-Difluoro-4-tributylstannanyl-pyridine as a colourless oil (27.5 g, 88%). This material was used crude without further purification. Retention Time (LC, method: ammonium acetate standard): 3.35 min. MS (M+H$^+$): 406.

Intermediate 64:
4-Chloro-2-(3,5-difluoro-pyridin-4-yl)-phenylamine

Stille coupling: A dimethyl formamide (256 mL) solution of crude Intermediate 63 (1.1 eq, 70 mmol, 27.5 g) and 2-iodo-4-chloro-phenylamine (1.0 eq, 64 mmol, 16.2 g) was degassed with $N_2$ for 15 min. Dichlorobis(triphenylphosphine)palladium (II) (0.05 eq, 3.2 mmol, 2.2 g) and copper (I) iodide (0.1 eq, 6.4 mmol, 1.2 g) were added and the suspension heated at reflux for 15 h under $N_2$. The mixture was cooled to RT, filtered through a short plug of celite® and the dimethyl formamide removed on a rotary evaporator. The crude material was dissolved in acetonitrile (300 mL), washed with hexanes (2×200 mL) then concentrated in vacuo. The material was then dissolved in ethyl acetate (400 mL) and washed successively with water (2×200 mL), saturated sodium bicarbonate solution (1×200 mL), saturated sodium chloride solution (200 mL), dried over magnesium sulfate, filtered and concentrated in vacuo. The resulting solid was triturated with diethyl ether (50 mL) to remove the dark colour, then dissolved in the minimum volume of methanol, filtered to remove an insoluble impurity and concentrated in vacuo to afford the 4-Chloro-2-(3,5-difluoro-pyridin-4-yl)-phenylamine as a tan solid (12.3 g, ~80%,) which was used in the subsequent step without further purification. $^1$H-NMR (300 MHz, dmso-$d_6$): δ 5.28 (s, 2H), 6.77 (d, 1H), 7.08 (d, 1H), 7.19 (dd, 1H) and 8.58 (s, 2H). Retention Time (LC, method: ammonium acetate standard): 1.70 min. MS (M+H$^+$): not observed.

Intermediate 65: 6-Chloro-4-fluoro-9H-β-carboline

Sodium bis(trimethylsilyl)amide (3.0 eq, 130 mmol, 130 mL, 1.0M in THF) was added via dropping funnel to a solution of crude Intermediate 64 (1.0 eq, 43 mmol, 10.4 g) in THF at RT under $N_2$. After stirring for 15 h the excess base was quenched by the cautious addition of saturated ammonium chloride solution (100 mL) and the majority of the THF removed on a rotary evaporator. The resulting slurry was extracted with ethyl acetate (400 mL then 2×200 mL), then the combined organics were washed successively with saturated sodium bicarbonate solution (300 mL), saturated sodium chloride solution (300 mL), dried over sodium sulfate and filtered. Silica gel was added and the slurry concentrated on a rotary evaporator. The material was purified using a Biotage Flash 75 purification system (short column) eluting with 96:4 dichloromethane/methanol to afford the 6-Chloro-4-fluoro-9H-β-carboline as an off-white solid (7.8 g, 82%). $^1$H-NMR (300 MHz, dmso-$d_6$): δ 7.71-7.61 (m, 3H), 8.11 (d, 1H) and 12.16 (s, 1H). Retention Time (LC, method: ammonium acetate standard): 1.70 min. MS (M+H$^+$): 221.

Intermediate 66:
6-chloro-4-fluoro-9H-β-carbolin-8-ylamine

Sodium nitrate (1.5 eq, 53 mmol, 4.5 g) was added portionwise to a solution of Intermediate 65 (1.0 eq, 35 mmol, 7.8 g) in trifluoroacetic acid (200 mL) and the resulting mixture heated at 70° C. for 3 h. After cooling to RT the trifluoroacetic acid was removed on a rotary evaporator to afford a crude solid which was suspended in a small volume of methanol and added dropwise to a vigorously stirred mixture of saturated sodium bicarbonate solution (500 mL). The resulting slurry was stirred for 15 min then the precipitated solids were collected by suction filtration, washed with water (300 mL) and then dried in vacuo to afford 6-chloro-4-fluoro-8-nitro-9H-β-carboline (about 9.5 g) which was used in the subsequent step without further purification. Retention Time (LC, method: ammonium acetate standard): 1.79 min. MS (M+H$^+$): 266

Sulfated platinum (0.1 eq, 1 g) was added to a suspension of 6-chloro-4-fluoro-8-nitro-9H-β-carboline (1.0 eq, 35 mmol, 9.3 g) and ammonium formate (3.0 eq, 105 mmol, 6.6 g) in ethanol (175 mL) and the resulting mixture heated at 75° C. for 4 h. After cooling to RT the mixture was filtered through a short plug of Celite® washing with copious amounts of methanol, and then the filtrate concentrated in vacuo to afford a beige solid. The solid was suspended in the minimum volume of methanol and added dropwise to a vigorously stirred mixture of saturated sodium bicarbonate solution and saturated sodium chloride solution. After stirring for 15 min the precipitated solids were collected by suction filtration, washed with water (200 mL) and dried in vacuo to afford 6-chloro-4-fluoro-9H-β-carbolin-8-ylamine (5.8 g, 70% 2 steps) as a beige powder. $^1$H-NMR (300 MHz, dmso-d$_6$): δ 5.76 (s, 2H), 6.81 (d, 1H), 7.29 (d, 1H), 8.24 (d, 1H), 8.82 (d, 1H), and 11.71 (s, 1H). Retention Time (LC, method: ammonium acetate standard): 1.59 min. MS (M+H$^+$): 236.

Example 61

4-(2-Acetylamino-propyl)-6,6-dimethyl-morpholine-3-carboxylic acid (6-chloro-4-fluoro-9H-b-carbolin-8-yl)-amide The desired compound was prepared from Intermediate 66 and acetic anhydride. $^1$H-NMR (300 MHz, dmso-d$_6$): δ 11.70 (s, 1H), 10.17 (s, 1H), 8.92 (s, 1H), 8.34 (d, 1H), 7.95 (s, 2H), 7.81 (d, 1H), 4.05-3.95 (m, 1H), 3.92-3.83 (m, 2H), 3.18-3.12 (m, 1H), 2.87 (d, 1H), 2.55-2.47 (m, 1H), 2.40-2.31 (m, 1H), 2.03 (d, 1H), 1.78 (s, 3H), 1.32 (s, 3H), 1.63 (s, 3H) and 1.08 (d, 3H). Retention Time (LC, method: ammonium acetate standard): 1.73 min. MS (M+H$^+$): 474.

Example 62

6,6-Dimethyl-4-{2-[(2-methyl-pyridine-3-carbonyl)-amino]-propyl}-morpholine-3-carboxylic acid (6-chloro-4-fluoro-9H-β-carbolin-8-yl)-amide The desired compound was prepared according to Method E from Intermediate 66 and methylnicotinic acid. $^1$H-NMR (300 MHz, dmso-d$_6$): δ 11.63 (s, 1H), δ 10.10 (s, 1H), δ 8.90 (s, 1H), δ 8.44 (d, 1H), δ 8.34 (s, 1H), δ 8.29 (d, 1H), 7.94 (s, 2H), 7.65 (d, 1H), 7.21 (dd, 1H), 4.25-4.15 (m, 1H), 3.97-3.88 (m, 2H), 3.24-3.15 (m, 1H), 2.99 (d, 1H), 2.59 (t, 1H), 2.49 (s, 3H), 2.40 (dd, 1H), 2.09 (d, 1H), 1.35 (s, 3H), 1.21 (d, 3H) and 1.20 (s, 3H). Retention Time (LC, method: ammonium acetate standard): 1.67 min. MS (M+H$^+$): 553.

Example 63

[(S)-5-(6-Chloro-9H-beta-carbolin-8-Ylcarbamoyl)-2,2-dimethyl-morpholin-4-yl]-acetic acid To a suspension of (S)-6,6-Dimethyl-morpholine-3-carboxylic acid (6-chloro-9H-beta-carbolin-8-yl)-amide (2.6 g, 6.0 mmoles) in 60 ml of methanol was added 1.7 ml of triethylamine (2.0 eq.), sodium cyanoborohydride (575 mg, 9.1 mmoles) and glyoxylic acid (780 mg, 8.5 mmoles). The reaction mixture was stirred at ambient temperature for 1.5 hrs. Water was added (5 ml) and the mixture was concentrated to a thick yellow slurry. More water was then added (30 ml) and the resulting slurry was stirred at ambient temperature for 10 min. and was filtered. The collected yellow solid was washed with water and dried under high vacuum to give 1.80 g (71%) of the desired product. $^1$H-NMR (300 MHz, DMSO-d$_6$): δ 1.17 (s,3H), 1.30 (s,3H), 2.81 (d,1H), 3.34 (d,1H), 3.46 (d,1H), 3.56 (dd,1H), 3.84-3.90 (m,2H), 7.92 (s,1H), 8.15 (d,1H), 8.21 (s,1H), 8.36 (d,1H), 9.01 (s,1H), 10.28 (s,1H), 11.40 (s,1H). Retention Time (LC, method: ammonium acetate standard): 1.26 min. MS (M+H$^+$): 417.1.

Method F: Coupling Procedure for Reverse Amides from [(S)-5-(6-Chloro-9H-beta-carbolin-8-ylcarbamoyl)-2,2-dimethyl-morpholin-4-yl]-acetic acid

[(S)-5-(6-Chloro-9H-beta-carbolin-8-ylcarbamoyl)-2,2-dimethyl-morpholin-4-yl]-acetic acid (1.0 mmol), EDCI (1.6 mmol) and the amine (1.2 mmol) to be coupled were taken in a round-bottom flask and suspended in pyridine (5 ml). The resulting mixture was stirred overnight. The pyridine was then removed under reduced pressure and the residue was partitioned in EtOAc and 5% aqueous Na$_2$CO$_3$ solution. The separated aqueous phase was further extracted with EtOAc. The combined extracts were successively washed with water and brine, dried over Na$_2$SO$_4$ and concentrated completely. The residue was purified on silica to give the desired product.

Example 64

(S)-6,6-Dimethyl-4-(2-oxo-2-pyrrolidin-1-yl-ethyl)-morpholine-3-carboxylic acid (6-chloro-9H-beta-carbolin-8-yl)-amide The desired compound was prepared according to Method F from [(S)-5-(6-Chloro-9H-beta-carbolin-8-ylcarbamoyl)-2,2-dimethyl-morpholin-4-yl]-acetic acid and pyrrolidine in 82% yield. $^1$H-NMR (300 MHz, DMSO-d$_6$): δ 1.21 (s,3H), 1.29 (s,3H), 1.75-1.92 (m,4H), 2.46 (d,1H), 2.77 (d,1H), 3.35-3.68 (m,7H), 3.94 (m,2H), 8.08 (s,1H), 8.19 (d,1H), 8.23 (s,1H), 8.41 (d,1H), 9.05 (s,1H), 10.71 (s,1H), 11.51 (s,1H). Retention Time (LC, method: ammonium acetate standard): 1.75 min. MS (M+H$^+$): 470.3.

Example 65

(S)-6,6-Dimethyl-4-(2-oxo-2-piperidin-1-yl-ethyl) morpholine-3-carboxylic acid (6-chloro-9H-beta-carbolin-8-yl)-amide The desired compound was prepared according to Method F from [(S)-5-(6-Chloro-9H-beta-carbolin-8-ylcarbamoyl)-2,2-dimethyl-morpholin-4-yl]-acetic acid and piperidine in 90% yield. $^1$H-NMR (300 MHz, DMSO-d$_6$): δ 1.17 (s,3H), 1.29 (s,3H), 1.35-1.60 (m,6H), 2.25 (d,1H), 2.71 (d,1H), 3.15 (d,1H), 3.26 (dd,1H), 3.37 (dd,1H), 3.45-3.65 (m, 2H), 3.65 (d, 1H), 3.70 (m, 1H), 3.89 (m, 2H) 7.95 (d,1H), 8.15 (d,1H), 8.20 (d,1H), 8.37 (d,1H), 9.01 (s,1H), 10.43 (s,1H), 11.32 (s,1H). Retention Time (LC, method: ammonium acetate standard): 1.86 min. MS (M+H$^+$): 484.3.

Example 66

(S)-6,6-Dimethyl-4-(2-morpholin-4-yl-2-oxo-ethyl)-morpholine-3-carboxylic acid (6-chloro-9H-beta-carbolin-8-yl)-amide The desired compound was prepared according to Method F from [(S)-5-(6-Chloro-9H-beta-carbolin-8-ylcarbamoyl)-2,2-dimethyl-morpholin-4-yl]-acetic acid and morpholine in 86% yield. $^1$H-NMR (300 MHz, DMSO-d$_6$): δ 1.17 (s,3H), 1.30 (s,3H), 2.19 (d,1H), 2.71 (d,1H), 3.03 (d,1H), 3.16 (d,1H), 3.22 (dd,1H), 3.45-3.72 (m,7H), 3.80-3.98 (m, 3H), 7.94 (d,1H), 8.15 (d,1H), 8.21 (d,1H), 8.37 (d,1H), 9.03 (s,1H), 10.35 (s,1H), 11.28 (s,1H). Retention Time (LC, method: ammonium acetate standard): 1.56 min. MS (M+H$^+$): 486.3.

Example 67

(S)-4-1[(2-Hydroxy-ethyl)-methyl-carbamoyl]-methyl}-6,6-dimethyl-morpholine-3-carboxylic acid (6-chloro-9H-beta-carbolin-8-yl)-amide The desired compound was prepared according to Method F from [(S)-5-(6-Chloro-9H-beta-carbolin-8-ylcarbamoyl)-

2,2-dimethyl-morpholin-4-yl]-acetic acid and 2-methylamino-ethanol in 55% yield. $^1$HNMR (300 MHz, DMSO-d$_6$): δ1.21 (s, 3H), 1.30 (s, 3H), 2.39 (m,1H), 2.75 (bd,1H), 2.96 (s,1.5H), 3.17 (s,1.5H), 3.50-3.65 (m,2.5H), 3.70-3.85 (m,1.5H), 3.93 (m, 2H), 4.69 (m, 0.5H), 4.94(m, 0.5H), 8.05 (d,1H), 8.18-8.25 (m, 2H), 8.42 (d,1H), 9.06 (s,1H), 10.68 (s,1H), 11.38 (s,1H). Retention Time (LC, method: ammonium acetate standard): 1.47 min. MS (M+H$^+$): 474.

Example 68

(S)-6,6-Dimethyl-4-(pyridin-3-ylcarbamoylmethyl)-morpholine-3-carboxylic acid (6-chloro-9H-beta-carbolin-8-yl)-amide The desired compound was prepared according to Method F from [(S)-5-(6-Chloro-9H-beta-carbolin-8-ylcarbamoyl)-2,2-dimethyl-morpholin-4-yl]-acetic acid and 3-aminopyridine. The product was isolated as hydrochloride salt in 55% yield. $^1$HNMR (300 MHz, D$_2$O): δ 1.34 (s, 3H), 1.54 (s, 3H), 2.60 (d,1H), 3.4 (d, 1H), 3.50 (d, 1H), 3.70 (t, 1H), 3.81 (d, 1H) 4.23 (d, 2H), 7.69 (d, 1H), 7.98 (d, 1H), 8.01 (d, 1H), 8.17(d, 1H), 8.42 (d, 1H), 8.48-8.55 (m, 3H), 9.09 (s,1H), 9.30 (d, 1H). Retention Time (LC, method: ammonium acetate standard): 1.56 min. MS (M+H$^+$): 493.2.

Example 69

(S)-6,6-Dimethyl-4-{[(pyridin-4-ylmethyl)-carbamoyl]-methyl}-morpholine-3-carboxylic acid (6-chloro-9H-beta-carbolin-8-yl)-amide The desired compound was prepared according to Method F from [(S)-5-(6-Chloro-9H-beta-carbolin-8-ylcarbamoyl)-2,2-dimethyl-morpholin-4-yl]-acetic acid and 4-(aminomethyl)pyridine. The product was isolated as hydrochloride salt in 53% yield. $^1$HNMR (300 MHz, D$_2$O): δ 1.34 (s, 3H), 1.49 (s, 3H), 2.64 (d, 1H), 3.03 (d, 1H), 3.48 (d, 1H), 3.72 (t, 1H), 3.74 (d, 1H), 4.15-4.25 (m, 2H), 7.66 (d, 1H), 7.88 (s, 1H), 7.91 (s, 1H), 8.21(d, 1H), 8.44 (d,1H), 8.53 (d, 1H), 8.56 (s, 1H), 8.58 (s, 1H), 9.08 (s, 1H). Retention Time (LC, method: ammonium acetate standard): 1.47 min. MS (M+H$^+$): 507.3.

Example 70

4-[2-(4-Hydroxymethyl-piperidin-1-yl)-2-oxo-ethyl]-6,6-dimethyl-morpholine-3-carboxylic acid (6-chloro-9H-beta-carbolin-8-yl)-amide

[5-(6-Chloro-9H-beta-carbolin-8-ylcarbamoyl)-2,2-dimethyl-morpholin-4-yl]-acetic acid (200 mg, 0.48 mmol) and piperidin-4-yl-methanol (111 mg, 0.96 mmol) were dissolved in pyridine (4 mL). The resulting yellow solution was stirred at room temperature for 10 min and then EDC (184 mg, 0.96 mmol) was added in a single portion. The reaction mixture was allowed to stir overnight (16 h). Water (4 mL) was added and the mixture was concentrated under reduced pressure. The resulting residue was partitioned between ethyl acetate (50 mL) and 1 M aqueous potassium carbonate. The aqueous layer was back-extracted with ethyl acetate (3×50 mL) and the combined extracts were washed with water and brine, dried over sodium sulfate, filtered, and concentrated. The crude residue was purified by silica gel chromatography (methylene chloride and methanol gradient) to afford pure 4-[2-(4-hydroxymethyl-piperidin-1-yl)-2-oxo-ethyl]-6,6-dimethyl-morpholine-3-carboxylic acid (6-chloro-9H-beta-carbolin-8-yl)-amide as a yellow foam (152 mg, 62%). The bis-HCl salt was prepared by adding 2 equivalents of conc. HCl to an ethanolic solution of the freebase. Concentration, followed by ether trituration afforded the salt as a free-flowing, yellow powder. $^1$H-NMR (freebase, 300 MHz, CDCl$_3$) δ: 11.03 (d, 1H), 10.51 (d, 1H), 8.97-8.80 (m, 1H), 8.47-8.27 (m, 2H), 7.94-7.76 (m, 2H), 4.84 (d, 1H), 4.16-3.77 (m, 3H), 3.68-3.26 (m, 5H), 3.08 (ddd, 1H), 2.89-2.64 (m, 2H), 2.50-2.37(m, 2H), 1.98-1.70 (m, 3H), 1.38 (s, 3H), 1.25 (s, 3H), 1.19-0.97 (m, 1). MS (NH$_4$OAc standard conditions, ES+) e/z=514 (M+H)+DAD R$_f$=1.51 min Example 71

4-[2-(4-Hydroxy-piperdin-1-yl)-2-oxo-ethyl]-6,6-dimethyl-morpholine-3-carboxylic acid (6-chloro-9H-beta-carbolin-8-yl)-amide The desired compound was synthesized using [5-(6-Chloro-9H-beta-carbolin-8-ylcarbamoyl)-2,2-dimethyl-morpholin-4-yl]-acetic acid and 4-hydroxypiperazine following Method F in 31% yield. $^1$H-NMR (300 MHz, D$_2$O): δ 8.85 (1H,s), 8.19 (2H, s), 7.82 (1H, s), 7.44 (1H, s), 4.15 (2H, m), 3.9-3.75 (4H, m), 3.6 (2H, m), 3.56 (2H, m), 3.12 (1H, m), 2.9 (3H, m), 2.8 (1H, m), 1.7 (2H, m) 1.34 (3H, s), 1.19 (3H, s). Retention time (LC, method: ammonium acetate standard): 1.5 min
MS (M+H$^+$): 501

Example 72

4-Diethylcarbamoylmethyl-6,6-dimethyl-morpholine-3-carboxylic acid (6-chloro-9H-beta-carbolin-8-yl)-amide The desired compound was made using of [5-(6-Chloro-9H-beta-carbolin-8-ylcarbamoyl)-2,2-dimethyl-morpholin-4-yl]-acetic acid and diethylamine following Method F in 60% yield. $^1$H-NMR (300 MHz, D$_2$O): δ 8.87 (1H, s), 8.26 (2H, m), 7.8 (1H, s), 7.52 (1H, s), 4.1 (3H, m), 3.8 (2H, m), 3.22 (2H, m), 3.0 (1H, d), 2.7 (1H, d), 1.3 (3H, s), 1.19 (3H, s), 0.09 (6H, m).
Retention time (LC, method: ammonium acetate standard): 1.96 min. MS (M+H$^+$): 472

Example 73

6,6-dimethyl-4-[-2-(4-methyl-piperazin-1-yl)-2-oxo-ethyl]-morpholine-3-carboxylic acid (6-chloro-9H-beta-carbolin-8-yl)-amide The desired compound was prepared using [5-(6-Chloro-9H-beta-carbolin-8-ylcarbamoyl)-2,2-dimethyl-morpholin-4-yl]-acetic acid and 1-methyl piperazine following Method F in 12% yield.
$^1$H-NMR (DMSO) δ 11.28 (1H, s), 10.35 (1H, s), 9.01 (1H,s), 8.37 (1H, s), 8.21-8.15 (2H, m), 7.9 (1H, s), 3.89 (2H, m), 3.7 (5H, m), 3.1 (2H, m), 2.85 (2H, m), 2.49 (3H, s), 2.4 (3H, m), 1.2 (3H, s), 1.16 (3H, s). Retention time (LC, method: ammonium acetate standard): 1.34 min. MS (M+H$^+$): 500

Example 74

4-[2-(2,6-Dimethyl-morpholin-4-yl)-2-oxo-ethyl]-6,6-dimethyl-morpholine-3-carboxylic acid (6-chloro-9H-β-carbolin-8-yl)-amide The desired compound was prepared using [5-(6-Chloro-9H-beta-carbolin-8-ylcarbamoyl)-2,2-dimethyl-morpholin-4-yl]-acetic acid and 2,6-dimethyl morpholine following Method F. Chromatographic purification gave the desired product in 70-80% yield. $^1$H-NMR (300 MHz, CDCl$_3$): δ 9.31 (s, 1H), 8.75 (d, 1H), 8.55 (d, 1H), 8.37 (d, 1H), 8.14 (m, 1H), 4.73 (m, 2H), 4.96 (m, 1H), 4.37 (m, 2H), 3.69 (m, 2H), 3.57 (m, 4H), 2.82 (t, 1H), 2.47 (t, 1H), 1.50 (d, 3H), 1.42 (d, 3H), 1.18 (m, 6H). Retention Time (LC, method: formic acid standard): 1.14 min (Diode Array).

MS (M+H$^+$): 514, (M−H$^+$): 512

Example 75

1-{2-[5-(6-Chloro-9H-beta-carbolin-8-ylcarbamoyl)-2,2-dimethyl-morpholin-4-yl]-acetyl}-piperidine-4-carboxylic acid methyl ester

[5-(6-Chloro-9H-beta-carbolin-8-ylcarbamoyl)-2,2-dimethyl-morpholin-4-yl]-acetic acid (200 mg, 0.48 mmol) and methyl isonipecotate (137 mg, 130 uL, 0.96 mmol) were dissolved in pyridine (4 mL) and stirred at room temperature 10 min. EDC was added and the reaction mixture was allowed to stir at room temperature over night (16 h). Additional methyl isonipecotate (137 uL, 0.96 mmol) was added and the mixture was stirred an additional 24 h. Water (4 mL) was added and the mixture concentrated. The crude residue was partitioned between ethyl acetate (75 mL) and 1 M aqueous potassium carbonate (50 mL). The aqueous phase was back-extracted with additional ethyl acetate (75+50 mL). The combined extracts were washed with water and brine, dried over sodium sulfate, filtered, concentrated and purified by silica gel chromatography (methylene chloride/methanol gradient) to afford the freebase as a yellow foam (150 mg, 57%). The bis-HCl salt was prepared by adding 2 equivalents of conc. HCl to an ethanolic solution of the freebase. Concentration, followed by ether trituration afforded the salt as a free-flowing, yellow powder. $^1$H-NMR (freebase, 300 MHz, CDCl$_3$) δ 11.04 (d, 1H), 10.48 (d, 1H), 8.95 (s, 1H), 8.48-8.31 (m, 2 H), 7.96-7.79 (m, 2H), 4.48 (dd, 1H), 4.13-3.92 (m, 2H), 3.88-2.97 (m, 9H), 2.84-2.35 (m, 3H), 2.09-1.90 (m, 2H), 1.85-1.52 (m, 2H), 1.38 (s, 3H), 1.23 (s, 3H). MS (NH$_4$OAc standard conditions, ES+) e/z=542 (M+H)$^+$. DAD R$_f$=1.72 min

Example 76

(S)-4-[2-(3,3-Dimethyl-morpholin-4-yl)-2-oxo-ethyl]-6,6-dimethyl-morpholine-3-carboxylic acid (6-chloro-9H-beta-carbolin-8-yl)-amide-bis-hydrochloride salt 2,2-Dimethylmorpholine (3.0 g, 26.1 mmol) (prepared according to the procedure of Cottle, D. L., et al. *J. Org. Chem.* 1946, 11, 286-291) was dissolved in dichloromethane (60 mL). Triethylamine (3.6 mL, 2.66 g, 26.1 mmol) was added and the reaction was cooled to −10° C. Bromoacetyl chloride (2.2 mL, 4.08 g, 26.1 mmol) was added dropwise and the solution was warmed slowly to room temperature. The reaction was concentrated to dryness in vacuo, redissolved in ethyl acetate and passed through a plug of silica gel. The eluant was concentrated to a yellow oil (3.45 g, 56%) that was carried to the next step. Retention Time (LC, method: ammonium acetate standard): 1.20 min. MS (M+H$^+$): 237.

Intermediate 59 (60 mg, 0.14 mmol) was suspended in dichloromethane (3 mL). A solution of 1M potassium carbonate (0.5 mL) was added. The organic layer was separated, dried over MgSO$_4$ and concentrated to dryness. The free base was dissolved in DMF (1 mL) and stirred at room temperature. 2-Bromo-1-(3,3-dimethyl-morpholin-4-yl)-ethanone (30 mg, 0.13 mmol) was dissolved in DMF (1 mL) and added dropwise. The reaction was stirred for 3 hours at room temperature and concentrated to dryness in vacuo. Flash column chromatography (93:7 dichloromethane:methanol) afforded a yellow oil, which was dissolved in 4N HCl/dioxane (2 mL). Concentration in vacuo afforded the title compound as a yellow solid (22 mg, 29%). $^1$HNMR (300 MHz, MeOH-d$_4$): δ 1.35 (s, 3H), 1.41 (s, 3H), 1.43 (s, 6H), 2.98 (m, 1H), 3.45 (m, 4H), 3.56 (m, 1H), 3.76 (m, 3H), 4.30 (m, 4H), 8.04 (s, 1H), 8.39 (s, 1H), 8.52 (d, 1H), 8.73 (d, 1H), 9.24 (s, 1H). Retention Time (LC, method: ammonium acetate standard): 1.16 min. MS (M+H$^+$): 514

Example 77

4-[(Trans-4-hydroxy-cyclohexylcarbamoyl)-methyl]-6,6-dimethyl-morpholine-3-carboxylic acid (6-chloro-9H-beta-carbolin-8-yl)-amide

[5-(6-Chloro-9H-beta-carbolin-8-ylcarbamoyl)-2,2-dimethyl-morpholin-4-yl]-acetic acid (200 mg, 0.48 mmol), trans-4-aminocyclohexanol hydrochloride (145 mg, 0.96 mmol) and diisopropylethylamine (124 mg, 167 uL, 0.96 mmol) were dissolved in pyridine (4 mL) and stirred at room temperature 10 min. EDC (184 mg) was added and the reaction was stirred at room temperature over night (16 h). Water (2 mL) was added and the resulting mixture was concentrated under reduced pressure. The resulting residue was diluted with 50 mL 1 M aqueous potassium carbonate and extracted with ethyl acetate (75+2×50 mL). The combined extracts were washed with water and brine, dried over sodium sulfate, filtered and concentrated. The crude residue was purified by silica gel chromatography (methanol/methylene chloride gradient) to afford pure 4-[(trans-4-hydroxy-cyclohexylcarbamoyl)-methyl]-6,6-dimethyl-morpholine-3-carboxylic acid (6-chloro-9H-beta-carbolin-8-yl)-amide (148 mg, 59%) as a yellow foam. The bis-HCl salt was prepared by adding 2 equivalents of conc. HCl to an ethanolic solution of the freebase. Concentration, followed by ether trituration afforded the salt as a free-flowing, yellow powder. $^1$H-NMR (freebase, 300 MHz, CDCl$_3$) δ 11.71 (br s, 1H), 10.21 (s, 1H), 9.06 (s, 1H), 8.45-8.27 (m, 2H), 8.08-7.84 (m, 2H), 6.36 (br s, 1H), 4.13-3.81 (m, 3H), 3.72-3.56 (m, 1H), 3.51-3.37 (m, 2H), 3.03 (d, 1H), 2.79-2.26 (m, 5H), 2.16-1.94 (m, 4H), 1.54-1.30 (m, 5H), 1.22 (s, 3H). MS (NH$_4$OAc standard conditions, ES+) e/z=514 (M+H)$^+$. DAD R$_f$=1.39 min.

Example 78

(S)-4-[2-((2R,5R)-2,5-Dimethyl-pyrrolidin-1-yl)-2-oxo-ethyl]-6,6-dimethyl-morpholine-3-carboxylic acid (6-chloro-9H-beta-carbolin-8-yl)-amide-bis-hydrochloride salt (2R,5R)-2,5-Dimethyl-pyrrolidine hydrochloride (270 mg, 2.0 mmol) (prepared using the procedure of Masamune, S., et al. *J. Org. Chem.* 1989, 54, 1756) was dissolved in dichloromethane (3 mL) and cooled to 0° C. Triethylamine (405 mg, 0.56 mL, 4.0 mmol) was added. Chloroacetyl chloride (226 mg, 0.16 mL, 2.0 mmol) was dissolved in dichloromethane (1 mL) and added dropwise. The mixture was warmed to room temperature and stirred an additional 30 minutes. The reaction was diluted with dichloromethane (5 mL), extracted with 1N HCl and brine, then dried over MgSO$_4$. The organic layer was concentrated to a brown oil. Wt.: 242 mg (82%). Retention Time (LC, method: ammonium acetate standard): 1.24 min. MS (M+H$^+$): 176.5. The material was carried to the next step without further purification.

Intrmediate 59 (495 mg, 1.15 mmol) was dissolved in a mixture of acetonitrile (8 mL) and water (2 mL). Potassium carbonate (477 mg, 3.45 mmol) was added and the reaction was warmed to 40° C. 2-Chloro-1-((2R,5R)-2,5-dimethyl-pyrrolidin-1-yl)-ethanone (242 mg, 1.38 mmol) (prepared as described above) was dissolved in acetonitrile (1 mL) and added dropwise. The reaction was warmed to 80° C. and stirred overnight. The reaction was cooled to 40° C. Sodium iodide (207 mg, 1.38 mmol) was dissolved in acetone (1 mL) and added in one portion. The reaction was stirred overnight at 40° C. The reaction was concentrated in vacuo and diluted with ethyl acetate (40 mL). The organic layer was extracted twice with water, brine then dried over MgSO$_4$. The organic layer was filtered, and concentrated to an orange foam in vacuo. Flash column chromatography (95:5 dichloromethane:methanol) afforded a yellow solid, which was dissolved in 4N HCl/dioxane (1 mL) and concentrated to dryness. Trituration with ether afforded the title compound as a yellow solid (18 mg, 3%). $^1$H-NMR (300 MHz, MeOH-d$_4$): δ 1.23 (dd, 6H), 1.38 (s, 3H), 1.48 (s, 3H), 1.65 (m, 2H), 2.23 (m, 2H), 3.18 (m, 1H), 3.50 (m, 1H), 3.66 (m, 1H), 4.18 (m, 2H), 4.35 (m, 4H), 8.15 (s, 1H), 8.42 (s, 1H), 8.55 (d, 1H), 8.78 (d, 1H), 9.29 (s, 1H). Retention Time (LC, method: ammonium acetate standard): 2.02 min. MS (M+H$^+$): 498.

Example 79

4-{2-[4-(1-Hydroxy-1-methyl-ethyl)-piperidin-1-yl]-2-oxo-ethyl}-6,6-dimethyl-morpholine-3-carboxylic acid (6-chloro-9H-b-carbolin-8-yl)-amide A solution of 1-{2-[5-(6-chloro-9H-β-carbolin-8-ylcarbamoyl)-2,2-dimethyl-morpholin-4-yl]-acetyl}-piperidine-4-carboxylic acid methyl ester (62 mg, 0.11 mmol) in a mixture of anhydrous ether and toluene (1 ml: 1 ml) was stirred at 0° C. under N$_2$. To this solution was slowly added methlymagnesium bromide (3.0 M in ether, 306 µL, 0.917 mmol). The reaction mixture was stirred at room temperature overnight, and then quenched by adding saturated aqueous sodium bicarbonate. The resulting mixture was further diluted with water (10 ml) and ethyl acetate (30 ml). The aqueous layer was removed and extracted with ethyl acetate (30×2 ml). The organic layers were combined, washed with brine, dried over magnesium sulfate, filtered and concentrated to afford a yellow solid (85 mg). The residue was purified by HPLC, to afford the pure product (13 mg, 20%). $^1$H-NMR (300 MHz, (CDCl$_3$): δ 10.94 (d, 1H), 10.47 (d, 1H), 8.94 (s, 1H), 8.41 (d, 1H), 8.32 (d, 1H), 7.89-7.81 (m, 2H), 4.91 (d, 1H), 4.04-3.91 (m, 2H); 3.64-3.57 (m, 1H), 3.43 (s, 1H), 3.37-3.31 (m, 1H), 3.15-2.90 (m, 1H), 2.77-2.58 (m, 2H), 2.47-2.41 (m, 1H), 2.00-1.86 (m, 2H), 1.53-1.03 (m, 17H). NH$_4$OAc standard conditions. DAD R$_f$=1.85 min. M+H=542.

Example 80

4-[2-(3,3-Dimethyl-4-oxo-piperidin-1-yl)-2-oxo-ethyl]-6,6-dimethyl-morpholine-3-carboxylic acid (6-chloro-9H-beta-carbolin-8-yl)-amide 4-Oxo-piperidine-1-carboxylic acid tert-butyl ester (5 g, 25 mmol) was dissolved in tetrahydrofuran (100 mL) and the resulting solution was cooled to 0° C. Sodium hydride (60% in mineral oil, 2.10 g, 53 mmol) was added to the cooled solution in a single portion, and the resulting cloudy mixture was allowed to stir 10 min. Methyl iodide was subsequently added and the mixture was allowed to warm to room temperature over several hours. Stirring continued over night (12 h). The light orange mixture was concentrated under reduced pressure. The residue was partitioned between ether and water. The aqueous phase was back-extracted with additional ether. The combined extracts were washed with water and brine, dried over sodium sulfate, filtered and concentrated to a pale yellow solid. The solid was triturated with 4% ethyl acetate in hexanes (50 mL) to afford 3,3-dimethyl-4-oxo-piperidine-1-carboxylic acid tert-butyl ester as a cream-colored solid (1.8 g, 32%). $^1$H-NMR (CDCl$_3$, 300 MHz) δ 3.73 (t, 2H), 3.43 (br s, 2H), 2.49 (t, 2H), 1.49 (s, 9H), 1.13(s, 6H).

The 3,3-dimethyl-4-oxo-piperidine-1-carboxylic acid tert-butyl ester thus prepared (450 mg, 1.97 mmol) was dissolved in methylene chloride (10 mL). Trifluoroacetic acid was added (305 uL) and the resulting solution stirred at room temperature 2 h. Additional trifluoroacetic acid was added (300 uL) and the reaction stirred at room temperature 3 days. The pale yellow solution was concentrated to afford an oily residue, which was triturated with ether. The solids were collected by suction filtration and dried in vacuo. 3,3-Dimethyl-piperidin-4-one was isolated and used as its trifluoroacetic acid salt (381 mg, 80%). $^1$H-NMR (d$_6$-DMSO, 300 MHz) δ 3.44-3.33 (m, 4H), 2.63-2.57 (m, 2H), 1.11 (s, 6H).

[5-(6-Chloro-9H-beta-carbolin-8-ylcarbamoyl)-2,2-dimethyl-morpholin-4-yl]-acetic acid (100 mg, 0.24 mmol), 3,3-dimethyl-piperidin-4-one trifluoroacetatic acid salt (116 mg, 0.48 mmol) and diisopropylethylamine (62 mg, 85 µL) were dissolved in pyridine (3 mL) and stirred 10 min. EDC (92 mg, 0.48 mmol) was added and the mixture was stirred at room temperature 4 days. Water was added (3 mL) and the quenched reaction was concentrated. The residue was partitioned between ethyl acetate (50 mL) and 1 M aqueous sodium carbonate (50 mL). The aqueous phase was extracted with additional ethyl acetate (50 mL), and the extracts were combined. The extracts were then washed with water and brine, dried over sodium sulfate, filtered, dried and concentrated under reduced pressure. The resulting residue was purified by silica gel chromatography (chloroform, ethyl acetate, methanol gradient), affording 4-[2-(3,3-dimethyl-4-oxo-piperidin-1-yl)-2-oxo-ethyl]-6,6-dimethyl-morpholine-3-carboxylic acid (6-chloroa-9H-beta-carbolin-8-yl)-amide as a yellow foam (91 mg, 73%). The bis-HCl salt was prepared by adding 2 equivalents of conc. HCl to an ethanolic solution of the freebase. Concentration, followed by ether trituration afforded the salt as a free-flowing, yellow powder. $^1$H-NMR (CDCl$_3$, 300 MHz) δ 10.67 (s, 1H), 10.37 (d, 1H), 8.93 (s, 1H), 8.41 (d, 1H), 8.15 (dd, 1H), 7.82 (d, 1H), 7.71 (d, 1H), 4.07-3.92 (m, 3H), 3.83-3.89 (m, 6H), 2.79-2.68 (m, 1H), 2.62-2.40 (m, 3H), 1.41-1.36 (m, 3H), 1.27-1.22 (m, 3H), 1.18-1.13 (m, 3H), 1.07-0.99 (m, 3H). MS (NH$_4$OAc standard conditions, ES+) e/z=526 (M+H)$^+$. DAD R$_f$=1.79 min.

Example 81

6,6-Dimethyl-4-(2-oxo-2-pyrrolidin-1-yl-ethyl)-morpholine-3-carboxylic acid (6-chloro-4-methyl-9H-β-carbolin-8-yl)-amide The desired compound was prepared according to Methods C, E and F from 6-chloro-4-methyl-9H-β-carbolin-8-ylamine (Intermediate 54) and pyrrolidine. $^1$H-NMR (300 MHz, MeOD-d$_4$) δ 9.17 (s, 1) 8.39 (s, 1) 8.26 (d, 1) 8.17 (d, 1) 4.74-4.52 (m, 3) 4.47-4.30 (m, 1) 3.80-3.52 (m, 3) 3.48-3.34

(m, 4) 3.01 (s, 3) 1.76-1.55 (m, 4) 1.50 (s, 3) 1.43 (s, 3). NH$_4$OAc standard conditions ELSD R$_f$=2.01 min. M+H=498.

It will be appreciated that compounds of the invention as exemplified generally above and specifically in Tables 3 and 4 herein may be prepared according to the methods described above.

Experimental data for certain exemplary compounds has been provided below in Table 5.

TABLE 5

LCMS data for Exemplary Compounds:

| Compound Number | LCMS M + 1 values (unless otherwise noted) |
|---|---|
| 64 | 470 |
| 107 | 556 |
| 72 | 472 |
| 108 | 582 |
| 109 | 542 |
| 110 | 498 |
| 111 | 582 |
| 112 | 570 |
| 113 | 520 |
| 66 | 486 |
| 100 | 514 |
| 71 | 500 |
| 114 | 514 |
| 115 | 557 |
| 116 | 534 |
| 117 | 513 |
| 118 | 499 |
| 119 | 514 |
| 120 | 514 |
| 121 | 541 |
| 122 | 532 |
| 123 | 599 |
| 76 | 514 |
| 124 | 500 |
| 125 | 556 |
| 126 | 500 |
| 127 | 599 |
| 77 | 514 |
| 74 | 514 |
| 128 | 498 |
| 129 | 571 |
| 130 | 486 |
| 131 | 571 |
| 70 | 514 |
| 65 | 484 |
| 73 | 499 |
| 132 | 506 |
| 133 | 585 |
| 67 | 474 |
| 134 | 499 |
| 135 | 499 |
| 136 | 516 |
| 137 | 523 |
| 138 | 552 |
| 139 | 555 |
| 140 | 494 |
| 141 | 541 |
| 142 | 502 |
| 143 | 541 |
| 144 | 541 |
| 145 | 528 |
| 146 | 485 |
| 147 | 581 |
| 148 | 552 |
| 149 | 524 |
| 150 | 500 |
| 151 | 577 |
| 152 | 542 |
| 153 | 527 |
| 154 | 497 |
| 102 | 520 |
| 155 | 500 |
| 156 | 512 |
| 157 | 514 |
| 158 | 583 |
| 159 | 577 |
| 79 | 542 |
| 160 | 493 |
| 161 | 514 |
| 83 | 528 |
| 162 | 541 |
| 163 | 544 |
| 164 | 513 |
| 165 | 617 |
| 166 | 532 |
| 167 | 472 |
| 168 | 496 |
| 78 | 498 |
| 169 | 514 |
| 170 | 541 |
| 171 | 553 |
| 80 | 526 |
| 172 | 527 |
| 173 | 499 |
| 174 | 501 |
| 175 | 526 |
| 176 | 416 |
| 177 | 512 |
| 178 | 560 |
| 179 | 488 |
| 180 | 510 |
| 181 | 512 |
| 182 | 555 |
| 183 | 528 |
| 184 | 532 |
| 185 | 618 |
| 186 | 535 |
| 187 | 555 |
| 82 | 486 |
| 75 | 542 |
| 188 | 534 |
| 189 | 523 (M − 1) |
| 95 | 460 |
| 190 | 513 |
| 191 | 576 |
| 192 | 500 |
| 193 | 614 |
| 194 | 568 |
| 195 | 568 |
| 99 | 512 |
| 196 | 542 |
| 197 | 592 |
| 198 | 555 |
| 199 | 566 |
| 200 | 605 |
| 201 | 513 |
| 86 | 498 |
| 202 | 490 |
| 90 | 502 |
| 89 | 504 |
| 88 | 500 |
| 81 | 484 |
| 87 | 498 |
| 91 | 500 |
| 203 | 500 |
| 93 | 472 |
| 92 | 458 |
| 94 | 444 |
| 97 | 527 |
| 204 | 531 |
| 69 | 507 |
| 205 | 507 |
| 206 | 507 |
| 68 | 493 |

Biological Testing

Compounds of this invention are effective inhibitors of IκB kinase (IKK), and therefore, are useful for treating conditions caused or aggravated by the activity of this kinase. The in vitro and in vivo IκB kinase inhibitory activities of the compounds of formula I may be determined by various procedures known in the art. The potent affinities for IκB kinase exhibited by the inventive compounds can be measured as an $IC_{50}$ value (in nM), which is the concentration (in nM) of compound required to provide 50% inhibition of IκB kinase.

Following are examples of assays that can be useful for evaluating and selecting a compound that modulates IKK.

Assay for Measuring IκB Kinase Enzyme Inhibition

An in vitro assay for detecting and measuring inhibition activity against IκB kinase complex by candidate pharmacological agents can employ a polypeptide spanning both $Ser^{32}$ and $Ser^{36}$ of IκB (SwissProt Accession No. P25963, Swiss Institute of Bioinformatics, Geneva, Switzerland) and an agent for detection of the phosphorylated product, e.g. a specific antibody binding only to the phosphorylated form of the polypeptide, being either monoclonal or polyclonal (e.g., commercially-available anti-phospho-serine$^{32}$ IκB antibodies). In the example of detecting the phosphorylated product by an anti-phosphoserine$^{32}$ IκB antibody, once the antibody-phospho-polypeptide complex is formed, the complex can be detected by a variety of analytical methods (e.g., radioactivity, luminescence, fluorescence, or optical absorbance). For the use of the DELFIA (Dissociation Enhancement Lanthanide Fluorescence Immunoassay) method (time-resolved fluorometry, Perkin Elmer Life and Analytical Sciences Inc., Boston, Mass.), the complex can be immobilized either onto a biotin-binding plate (e.g., Neutravidin coated plate) and detected with a secondary antibody conjugated to Europium, or onto an antibody-binding plate (e.g., Protein-A coated plate) and detected with biotin-binding protein conjugated to Europium (e.g., Streptavidin-Europium). The level of activity can be correlated with a standard curve using synthetic phosphopeptides corresponding to the substrate polypeptide. How to prepare materials for and conduct this assay are described in more detail below.

Isolation of the IκB Kinase Complex

An IκB-α kinase complex was prepared by first diluting 10 ml of HeLa S3 cell-extracts S100 fraction (Lee et al. (1997) Cell 88:213-222) with 40 ml of 50 mM HEPES pH 7.5. Then, 40% ammonium sulfate was added and incubated on ice for 30 minutes. The resulting precipitated pellet was redissolved with 5 ml of SEC buffer (50 mM HEPES pH 7.5, 1 mM DTT, 0.5 mM EDTA, 10 mM 2-glycerophosphate), clarified by centrifugation at 20,000×g for 15 min., and filtrated through a 0.22 μm filter unit. The sample was loaded onto a 320 ml SUPEROSE-6 gel filtration FPLC column (Amersham Biosciences AB, Uppsala, Sweden) equilibrated with a SEC buffer operated at 2 ml/min flow rate at 4° C. Fractions spanning the 670-kDa molecular-weight marker were pooled for activation. A kinase-containing pool was then activated by incubation with 100 nM MEKK1Δ (Lee et al. (1997) Cell 88:213-222), 250 μM MgATP, 10 mM $MgCl_2$, 5 mM DTT, 10 mM 2-glycerophosphate, 2.5 μM Microcystin-LR, for 45 minutes at 37° C. The activated enzyme was stored at −80° C. until further use.

Measurement of IκB Kinase phospho-transferase Activity

At the per well of a 96 well plate, compounds of various concentrations in 5 μL of 20% DMSO were preincubated for 30 minutes at 25° C. with 40 μL of activated enzyme diluted 1:25 with assay buffer (50 mM Hepes pH 7.5, 5 mM DTT, 10 mM $MgCl_2$, 10 mM 2-glycerophosphate, 2 μM Microcystin-LR, 0.1% Bovine Serum Albumin). 5 μL of peptide substrate (biotin-$(CH_2)_6$-DRHDSGLD(phosphoS)MKD-$CONH_2$) at 200 μM+500 μM ATP were added to each well and incubated for 1 hour before quenching with 50 μL of 50 mM Hepes pH 7.5, 0.1% BSA, 100 mM EDTA. 5 μL of quenched kinase reaction were transferred to a Protein A plate (Pierce Biotechnology, Inc., Rockford, Ill., USA) containing 90 μL of anti-phospho IκB S32/S36 antibody (Cell Signaling Technologies Beverly, Mass., USA) at 2 μg/ml. Samples were incubated for 2 hours with shaking. Following 3 washes with PBS+0.05% Tween20, 90 μL of streptavidin linked europium chelate (Perkin Elmer Life and Analytical Sciences, Boston, Mass., USA) at 0.1 μg/ml were added to each well and incubated for 1 hour with shaking. Following 3 washes with PBS+0.05% Tween20, 100 μL of DELFIA Enhancement Solution (Perkin Elmer Life and Analytical Sciences, Boston, Mass., USA) were added to each well. An europium signal was read with an excitation of 330 nM and emission of 615 nM on a Wallac Victor plate reader (Perkin Elmer Life and Analytical Sciences, Boston, Mass.). As the assay was previously shown to be linear with respect to enzyme concentration and time for the enzyme dilution tested, levels of europium signal were used to determine the inhibition activity of candidate pharmacological agents.

The compounds of the invention were active inhibitors of the IKK complex. It will be appreciated that compounds of this invention can exhibit IκB kinase inhibitor activities of varying degrees. Following assay procedures such as the in vitro and cell-based assays described herein, the IκB kinase inhibition average $IC_{50}$ values for the inventive compounds were generally below about 10 micromolar, preferably, below about 1.0 micromolar and more preferably below about 100 nanomolar. The inventive compounds were also selective for inhibiting IKK-2 as opposed to IKK-1.

Cellular Assays

Multiple Myeloma (MM) Cell Lines and Patient-Derived MM Cells Isolation

RPMI 8226 and U266 human MM cells were obtained from American Type Culture Collection (Manassas, Va.). All MM cell lines were cultured in RPMI-1640 containing 10% fetal bovine serum (FBS, Sigma-Aldrich Co., St. Louis, Mo.), 2 mM L-glutamine, 100 U/mL penicillin (Pen) and 100 μg/mL streptomycin (Strep) (GIBCO brand cell culture products available from Invitrogen Life Technologies, Carlsbad, Calif.). Patient-derived MM cells were purified from patient bone marrow (BM) aspirates using ROSETTESEP (B cell enrichment kit) separation system (StemCell Technologies, Vancouver, Canada). The purity of MM cells was confirmed by flow cytometry using PE-conjugated anti-CD138 antibody (BD Biosciences, Bedford, Mass.).

Bone Marrow Stroma Cell Cultures

Bone marrow (BM) specimens were obtained from patients with MM. Mononuclear cells (MNCs) separated by Ficoll-Hipaque density sedimentation were used to established long-term BM cultures as previously described (Uchiyama et al., *Blood* 1993, 82:3712-3720). Cells were harvested in Hank's Buffered Saline Solution (HBSS) containing 0.25% trypsin and 0.02% EDTA, washed, and collected by centrifugation.

Cell Proliferation Via Measurement of DNA-Synthesis Rate

Proliferation was measured as previously described (Hideshima et al., *Blood* 96:2943 (2000)). MM cells ($3 \times 10^4$ cells/well) were incubated in 96-well culture plates (Corning Life Sciences, Corning, N.Y.) in the presence of media or an IKK inhibitor of this invention for 48 h at 37° C. DNA synthesis was measured by [$^3$H]-thymidine ([$^3$H]-TdR, New England Nuclear division of Perkin Elmer Life and Analytical Sciences, Boston, Mass.) incorporation into dividing cells.

Cells were pulsed with [$^3$H]TdR (0.5 µCi/well) during the last 8 h of 48 h cultures. All experiments were performed in triplicate.

MTT Cell Viability Assay

The inhibitory effect of the present compounds on MM growth was assessed by measuring the reduction of yellow tetrazolium MTT (3-(4,5-dimethylthiazolyl-2)-2,5-diphenyltetrazolium bromide) by metabolically active cells (J. Immunol. Methods 174: 311-320, 1994). Cells from 48 h cultures were pulsed with 10 µL of 5 mg/mL MTT to each well for the last 4 h of the 48 h cultures, followed by 100 µL isopropanol containing 0.04N HCl. Absorbance was measured at 570 nm using a spectrophotometer (Molecular Devices Corp., Sunnyvale Calif.).

NF-κB Activation Via Electrophoretic Mobility Shift Assay

Electrophoretic mobility shift analyses (EMSA) were carried out as previously described (Hideshima et al., Oncogene 2001, 20:4519). Briefly, MM cells were pre-incubated with an IKK inhibitor of this invention (10 µM for 90 min) before stimulation with TNF-α (5 ng/mL) for 10 to 20 min. Cells were then pelleted, resuspended in 400 mL of hypotonic lysis buffer (20 mM HEPES, pH 7.9, 10 mM KCl, 1 mM EDTA, 0.2% Triton X-100, 1 mM Na$_3$VO$_4$, 5 mM NaF, 1 mM PMSF, 5 µg/mL leupeptin, 5 µg/mL aprotinin), and kept on ice for 20 min. After centrifugation (14000 g for 5 min) at 4° C., the nuclear pellet was extracted with 100 µL hypertonic lysis buffer (20 mM HEPES, pH 7.9, 400 mM NaCl, 1 mM EDTA, 1 mM Na$_3$VO$_4$, 5 mM NaF, 1 mM PMSF, 5 µg/mL leupeptin, 5 µg/mL aprotinin) on ice for 20 min. After centrifugation (14000 g for 5 min) at 4° C., the supernatant was collected as nuclear extract. Double-stranded NF-κB consensus oligonucleotide probe (5'-GGGGACTTTCCC-3', Santa Cruz Biotechnology Inc., Santa Cruz Calif.) was end-labeled with [($^{32}$P)ATP (50 µCi at 222 TBq/mM; New England Nuclear division of Perkin Elmer Life and Analytical Sciences, Boston, Mass.). Binding reactions containing 1 ng of oligonucleotide and 5 µg of nuclear protein were conducted at room temperature for 20 min in a total volume of 10 µL of binding buffer (10 mM Tris-HCl, pH 7.5, 50 mM NaCl, 1 mM MgCl$_2$, 0.5 mM EDTA, 0.5 mM DTT, 4% glycerol (v/v), and 0.5 µg poly (dI-dC) (Amersham Biosciences AB, Uppsala, Sweden). For supershift analysis, 1 µg of anti-p65 NF-κB Ab was added 5 min before the reaction mixtures, immediately after addition of radiolabeled probe. The samples were loaded onto a 4% polyacrylamide gel, transferred to Whatman paper (Whatman International, Maidstone, U.K.), and visualized by autoradiography.

Diffuse Large B-Cell Lymphoma (DLBCL) Cell Proliferation Assay

ABC-like (LY3 and Ly10) and GCB-like (Ly7 and Ly19) DLBCL cell lines (Alizadeh et al (2000) Nature 403:503-511; Davis et al. (2001) J. Exp. Med. 194:1861-1874) were maintained in growth medium (GM, Iscove's DMEM+10% FBS) by passaging cells twice per week. Cells were starved overnight in Iscove's DMEM medium+0.5% FBS overnight before plated in proliferation assay. On the day of the assay, cells were counted and viability was checked using Trypan Blue staining. For the Ly3 and Ly10 cells, 5000 cell were plated in GM per well in a 96-well plate. The Ly7 and Ly19 cells were plated at 10,000 cells per well. IKK inhibitors were first dissolved in DMSO and then diluted in GM to reach the final concentrations of 80 µM-0.01 µM. Each concentration was plated in triplicate. Cell viability was determined using a standard WST-1 cell viability assay (Roche Applied Science, Indianapolis, Ind.).

Human Peripheral Blood Monocyte (PBMC) Cytokine Release Assay

Human PBMC was purified from normal donor whole blood by Ficoll gradient method. After a PBS wash, PBMC were re-suspended in AIM-V medium. Serially diluted IKK inhibitors of this invention in 100% DMSO was added at 1 µl to the bottom of a 96-well plate and mixed with 180 g 4.5×10$^5$ PBMC in AIM-V media per well. After preincubating PBMC with inhibitor at 37° C. for 40 min, cells were stimulated with 20 µl of either with LPS (100 ng/ml) or with anti-CD3 (0.25 µg/ml) and anti-CD28 (0.25 µg/ml) (Pharmingen division of BD Biosciences, Bedford, Mass.) at 37° C. for 5 hours. The supernatants were collected and assessed for IL-1β or TNF-α release using standard commercially available ELISA kits.

Human Chondrocyte Matrix Metalloproteases (MMPs) Release Assay

Human chondrocyte cell line SW1353 (ATCC, Manassas, Va.) was cultured containing 10% fetal bovine serum (Hyclone, Logan, Utah), 2 mM L-glutamine (GIBCO brand cell culture products available from Invitrogen Life Technologies, Carlsbad, Calif.) and 1% Pen/Strep (GIBCO). Cells were seeded in 96-well Poly-D-Lysine plate (BD BIOCOAT, Black/Clear bottom, BD Biosciences, Bedford, Mass.). Serially diluted IKK inhibitors at 1 µl were added to each well of 96-well plates and mixed with 180 µl 4.5×10$^5$ chondrocytes per well. After pre-incubating cells with compounds for 1 hr at 37° C., cells were stimulated with 20 µl IL-1β (10 ng/mL, R&D Systems Inc.) at 37° C. for 24 hrs. The supernatants were then collected and assessed for production of matrix metalloproteinases (MMPs) using commercially available ELISA kits.

Human Fibroblast Like Synoviocyte (HFLS) Assay

HFLS isolated from RA synovial tissues obtained at joint replacement surgery was provided by Cell Applications Inc. (San Diego, Calif.). IKK inhibitors of the invention were tested for their ability to block the TNF- or IL-1β-induced release of IL-6 or IL-8 from these cells using commercially available ELISA kits. Cell culture conditions and assay methods were described in Aupperle et al., Journal of Immunology, 163:427-433 (1999).

Human Cord Blood Derived Mast Cell Assay

Human cord blood was obtained from Cambrex (Walkersville, Md.). Mast cells were differentiated and cultured in a manner similar to that described by Hsieh et al., J. Exp. Med., 193:123-133 (2001). IKK inhibitors of the invention were tested for their ability to block the IgE- or LPS-induced TNFα release using commercially available ELISA kits.

Osteoclast Differentiation and Functional Assays

Human osteoclast precursors were obtained as cryopreserved form from Cambrex (Walkersville, Md.). The cells were differentiated in culture based on instructions from the manufacturer. IKK inhibitors of the invention were tested for their ability to block the differentiation, bone resorption and collagen degradation as described previously (see Khapli, S. M., Journal of Immunol, 171:142-151 (2003); Karsdal, M. A., J Biol Chem, 278:44975-44987 (2003); and Takami, M., Journal of Immunol, 169:1516-1523 (2002)).

Rat Models for Rheumatoid Arthritis

Certain compounds of this invention were found to be active in one or more rat models for rheumatoid arthritis. Such testing is known in the literature and include a standard rat LPS model as described in Conway et al., "Inhibition of Tumor Necrosis Factor-α (TNF-α) Production and Arthritis in the Rat by GW3333, a Dual Inhibitor of TNF—Converting Enzyme and Matrix Metalloproteinases", *J. Pharmacol. Exp. Ther.* 298(3), 900-908 (2001); a rat adjuvant induced arthritis model as described in Pharmacological Methods in the Control of Inflammation (1989) p 363-380 "Rat Adjuvant Arthritis: A Model of Chronic Inflammation" Barry M. Weichman author of book chapter {Alan R. Liss Inc Publisher}; and a rat collagen induced arthritis model as described in Pharmacological Methods in the Control of Inflammation (1989) p 395-413 "Type II Collagen Induced Arthritis in the Rat" DE Trentham and RA Dynesuis-Trentham authors of book chapter {Alan R. Liss Inc Publisher}. See also, "Animal Models of Arthritis: Relevance to Human Disease" (1999) by A. Bendele, J. McComb, T. Gould, T. McAbee, G. Sennello, E. Chlipala and M. Guy. Toxicologic Pathology Vol 27 (1) 134-142.

Based on the results of one or more rat models such as the ones described above, compounds of formula II-C were found to be surprisingly superior compared to other compounds where Ring A is a pyridine ring. Also in the rat models, compounds of formula III-A-a, especially compounds of formula III-A-aa, were found to be surprisingly superior compared to other compounds where Ring A is a morpholine ring.

While we have described a number of embodiments of this invention, it is apparent that our basic examples may be altered to provide other embodiments, which utilize the compounds and methods of this invention. Therefore, it will be appreciated that the scope of this invention is to be defined by the appended claims rather than by the specific embodiments, which have been represented by way of example.

The invention claimed is:
1. A compound of formula III-A-aa:

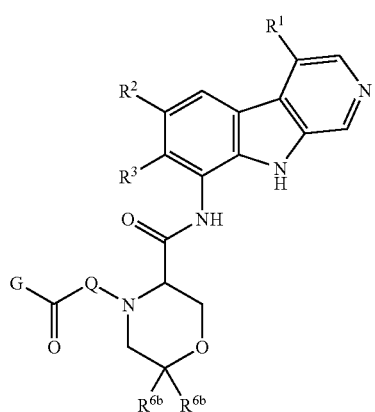

III-A-aa or a pharmaceutically acceptable salt thereof wherein,
Q is —CH$_2$— or CH(R$^9$);
G is morpholinyl optionally substituted by 1-2 R$^{10}$;
R$^1$ is hydrogen, halo, C$_{1-2}$alkyl, amino, or (C$_{1-2}$alkyl)$_{1-2}$amino;
R$^2$ is hydrogen, halo, C$_{1-2}$aliphatic, C$_{1-2}$alkoxy, or C$_{1-2}$haloalkyl;
R$^3$ is hydrogen, halo, C$_{1-2}$aliphatic, C$_{1-2}$alkoxy, or C$_{1-2}$haloalkyl;
each R$^{6b}$ is independently methyl;

each R$^7$ is independently selected from hydrogen or C$_{1-4}$aliphatic, or two R$^7$ on the same nitrogen atom are taken together with the nitrogen to form a 5-6 membered heteroaryl or heterocyclyl ring;
each R$^8$ is independently C$_{1-4}$ aliphatic;
each R$^9$ is independently selected from a C$_{1-3}$aliphatic;
each R$^{10}$ is independently selected from R$^{11}$, T-R$^{11}$, or V-T-R$^{11}$;
each R$^{11}$ is independently selected from C$_{1-6}$ aliphatic, halo, —OR$^7$, —CN, —SR$^8$, —S(O)$_2$R$^8$, —C(O)R$^7$, —CO$_2$R$^7$, —N(R$^7$)$_2$, —C(O)N(R$^7$)$_2$, —N(R$^7$)C(O)R$^7$, —N(R$^7$)CO$_2$R$^7$, or —N(R$^7$)C(O)N(R$^7$)$_2$;
T is a straight or branched C$_{1-4}$ alkylene chain; and
V is —O—, —N(R$^7$)—, —S—, —S(O)$_2$—, —C(O)—, or —CO$_2$—.

2. The compound of claim 1, wherein the compound has the (S) stereochemistry and is represented by the structure (S)-III-A-aa:

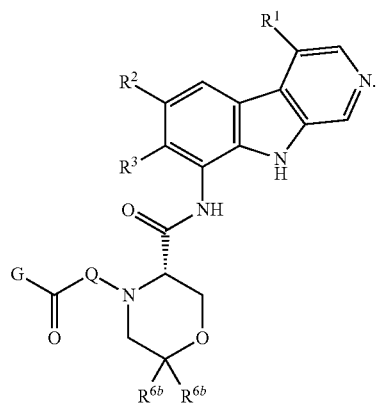

3. The compound of claim 2, wherein the optionally substituted morpholinyl group is N-morpholinyl.

4. The compound of claim 3 where:
G is unsubstituted or is substituted by 1-2 groups independently selected from: C$_{1-3}$ alkyl, HO-alkyl, alkoxycarbonyl, mono- or dialkylaminocarbonyl, or HO$_2$C-alkyl; and
R$^{6b}$ is methyl.

5. A compound selected from:

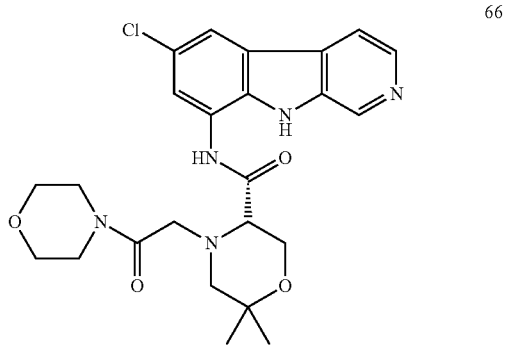

66

74
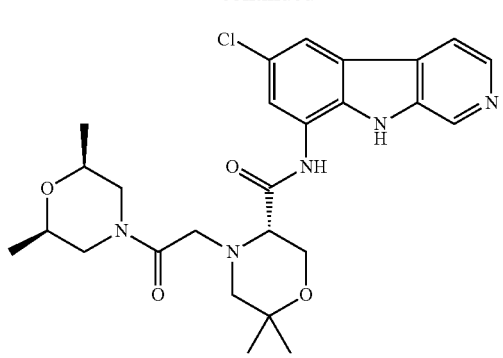
76
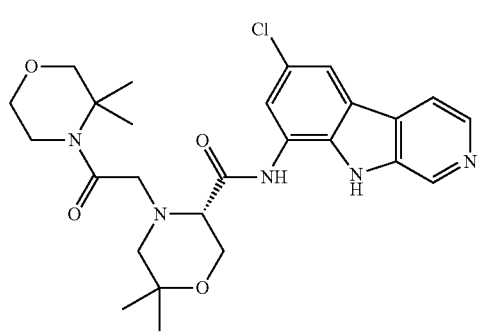
88
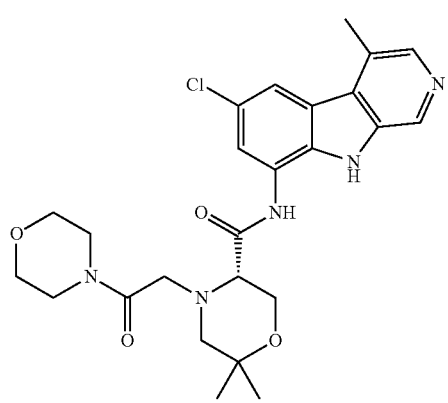
89
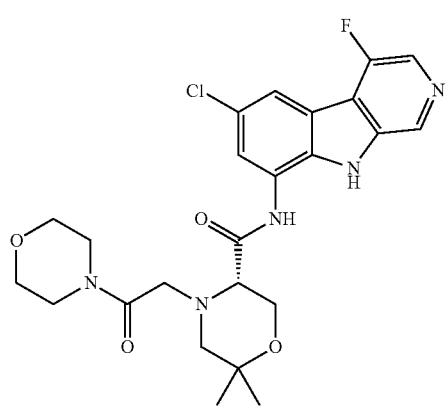
91
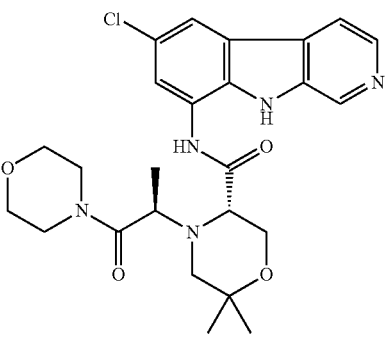
114
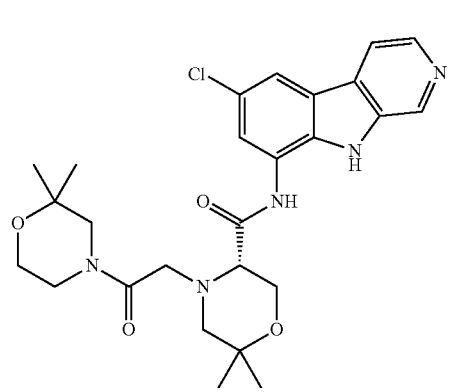
157
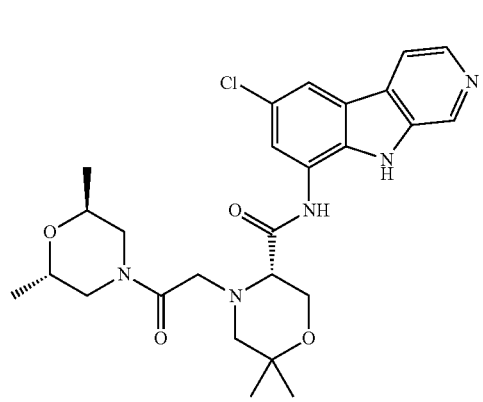
161
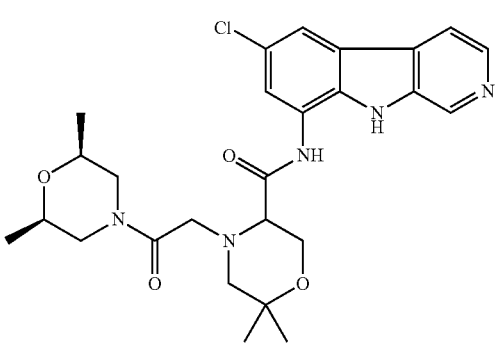

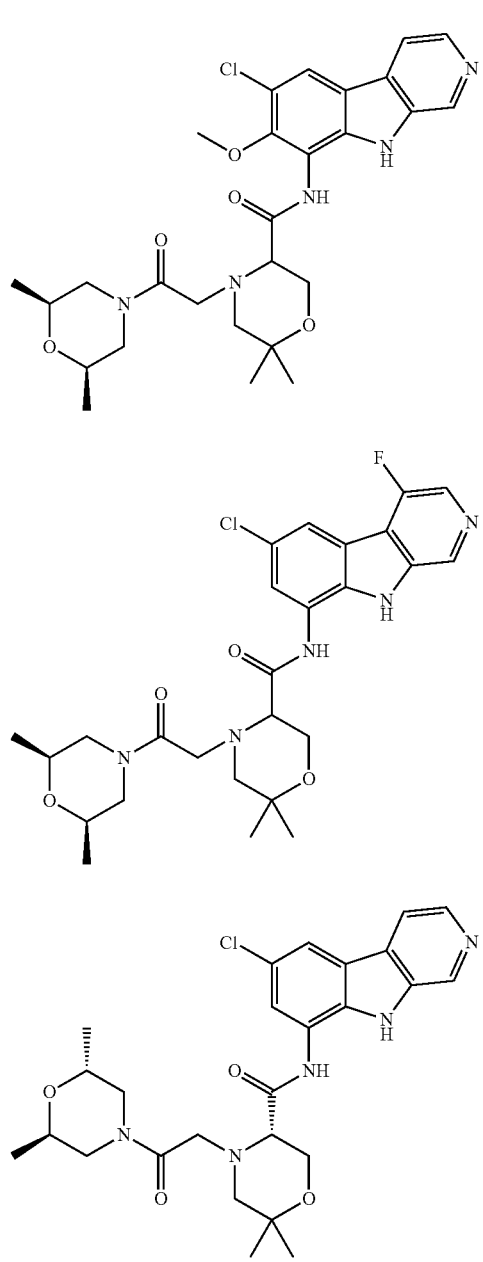
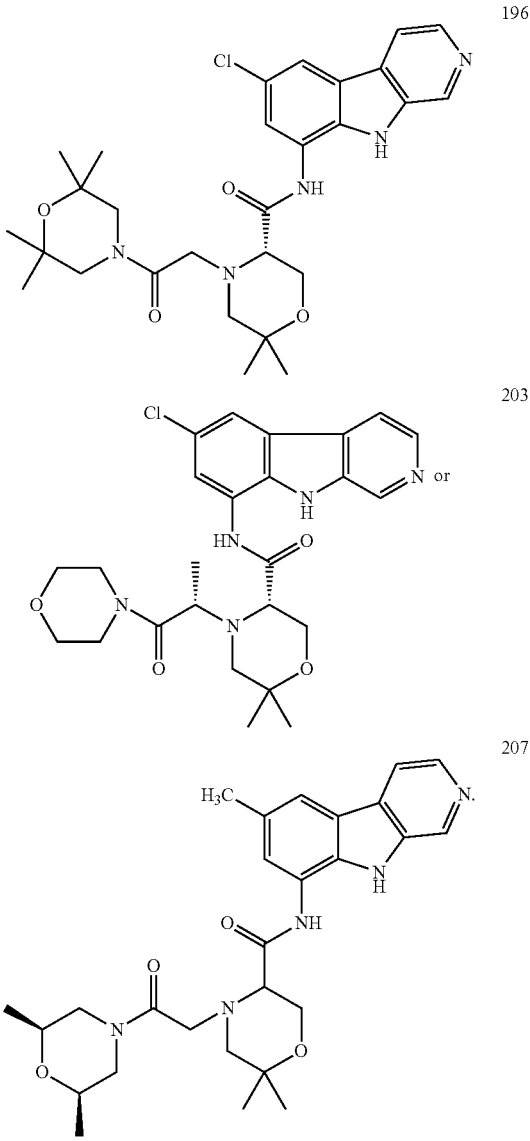
6. A pharmaceutical composition comprising a compound of claim 1, 2, 3, 4, or 5, and a pharmaceutically acceptable carrier.
* * * * *

UNITED STATES PATENT AND TRADEMARK OFFICE
CERTIFICATE OF CORRECTION

| | | |
|---|---|---|
| PATENT NO. | : 7,951,801 B2 | Page 1 of 1 |
| APPLICATION NO. | : 11/101998 | |
| DATED | : May 31, 2011 | |
| INVENTOR(S) | : Michael E. Hepperle et al. | |

It is certified that error appears in the above-identified patent and that said Letters Patent is hereby corrected as shown below:

Please make the following corrections to the claims:

CLAIMS

In Column 208, Claim 1, Line 16, please delete "V is –O-, -N($R^7$)-, -S-, -,S(O)$_2$-, -C(O)-, or –C(O)$_2$-" and replace with -- V is –O-, -N($R^7$)-, -S-, -S(O)-, -S(O)$_2$-, -C(O)-, or -C(O)$_2$- --

Signed and Sealed this
First Day of July, 2014

Michelle K. Lee
*Deputy Director of the United States Patent and Trademark Office*